(12) United States Patent
Fernandez et al.

(10) Patent No.: US 9,880,088 B2
(45) Date of Patent: Jan. 30, 2018

(54) FORCE-CLAMP SPECTROMETER WITH FUNCTIONALIZED CANTILEVER TIP

(71) Applicant: THE TRUSTEES OF COLUMBIA UNIVERSITY IN THE CITY OF NEW YORK, New York, NY (US)

(72) Inventors: Julio M. Fernandez, New York, NY (US); Raul Perez-Jimenez, New York, NY (US); Pallav Kosuri, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 837 days.

(21) Appl. No.: 13/741,208

(22) Filed: Jan. 14, 2013

(65) Prior Publication Data
US 2013/0143248 A1    Jun. 6, 2013

Related U.S. Application Data

(63) Continuation-in-part of application No. PCT/US2011/044084, filed on Jul. 14, 2011.
(Continued)

(51) Int. Cl.
*G01N 29/22* (2006.01)
*G01N 21/01* (2006.01)
(Continued)

(52) U.S. Cl.
CPC .............. *G01N 21/01* (2013.01); *B82Y 35/00* (2013.01); *G01N 19/04* (2013.01); *G01N 29/022* (2013.01); *G01Q 60/42* (2013.01)

(58) Field of Classification Search
CPC .............. Y10S 977/869; Y10S 977/724; Y10S 977/86; Y10S 977/861; Y10S 977/873;
(Continued)

(56) References Cited

U.S. PATENT DOCUMENTS 5,969,345 A    10/1999    Williams et al.
6,323,903 B1   11/2001    Poulsen et al.
(Continued)

FOREIGN PATENT DOCUMENTS

WO    WO-2008021543 A2    2/2008

OTHER PUBLICATIONS

Carrion-Vazquez et al. "Protein Nanomechanics—as Studied by AFM Single-Molecule Force Spectroscopy", Chapter 8 from Advanced Techniques in Biophysics, ed. Arrondo and Alonso, 2006, pp. 163-245.*
(Continued)

*Primary Examiner* — Yelena G Gakh
(74) *Attorney, Agent, or Firm* — Leason Ellis LLP

(57) ABSTRACT

The disclosed subject matter relates to a force-clamp spectrometer that enables operation in constant force mode and allows for automated data acquisition and analysis, using feedback electronics and software. The disclosed subject matter also relates to methods of using the force-clamp spectrometer for the measurement of the dynamics of chemical reactions. The methods may include, but are not limited to, the measurement of the dynamics of substrate folding and unfolding, as well as bond cleavage and bond formation.

5 Claims, 40 Drawing Sheets
(38 of 40 Drawing Sheet(s) Filed in Color)

Related U.S. Application Data

(60) Provisional application No. 61/364,208, filed on Jul. 14, 2010, provisional application No. 61/364,640, filed on Jul. 15, 2010.

(51) Int. Cl.
  *G01N 29/02* (2006.01)
  *B82Y 35/00* (2011.01)
  *G01N 19/04* (2006.01)
  *G01Q 60/42* (2010.01)

(58) Field of Classification Search
  CPC ............. Y10S 977/881; Y10S 977/732; Y10S 977/85; Y10S 977/932; Y10S 977/853; Y10S 977/863; Y10S 977/951; C12Q 2523/303; G01N 29/022
  See application file for complete search history.

(56) References Cited

U.S. PATENT DOCUMENTS

| | | | |
|---|---|---|---|
| 2003/0015653 | A1 | 1/2003 | Hansma et al. |
| 2004/0042097 | A1 | 3/2004 | Murnan et al. |
| 2004/0052810 | A1 | 3/2004 | Nesbit et al. |
| 2007/0180889 | A1 | 8/2007 | Murayama et al. |
| 2009/0092582 | A1 | 4/2009 | Bogin et al. |
| 2010/0257643 | A1* | 10/2010 | Reifenberger ......... G01Q 60/38 850/6 |

OTHER PUBLICATIONS

Graves et al. "Optical neuronal guidance in three-dimensional matrices", J. Neurosci. Methods, May 15, 2009; v. 179, No. 2, pp. 1-16.*

Abbondanzieri, E. A. et al., "Direct observation of base-pair stepping by RNA polymerase," Nature, vol. 438, No. 7067, pp. 460-465 (Nov. 24, 2005).

Adam, G. et al., "Reduction of Dimensionality in Biological Diffusion Processes," Structural Chemistry and Molecular Biology, vol. 4, pp. 198-215, 20 pages (1968).

Ainavarapu, S. R. et al., "Contour length and refolding rate of a small protein controlled by engineered disulfide bonds," Biophysical Journal, vol. 92, pp. 225-233 (Jan. 2007).

Ainavarapu, S. R. K. et al., "Single-Molecule Force Spectroscopy Measurements of Bond Elongation during a Bimolecular Reaction," J. Am. Chem. Soc., vol. 130, pp. 6479-6487, 11 pages (2008).

Ainavarapu, S. R. et al., "A Single-Molecule Assay to Directly Identify Solvent-Accessible Disulfide Bonds and Probe Their Effect on Protein Folding," J. Am. Chem. Soc., vol. 130, pp. 436-437 (2008).

Aktah, D. et al., "Breaking Bonds by Mechanical Stress: When Do Electrons Decide for the Other Side?," J. Am. Chem. Soc., vol. 124, pp. 3402-3406 (2002).

Alegre-Cebollada, J. et al., "Direct observation of disulfide isomerization in a single protein," Nature Chemistry, vol. 3, pp. 882-887 (Nov. 2011).

Alegre-Cebollada, J. et al., "Isopeptide Bonds Block the Mechanical Extension of Pili in Pathogenic *Streptococcus pyogenes*," The Journal of Biological Chemistry, vol. 285, No. 15, pp. 11235-11242 (Apr. 9, 2010).

Alegre-Cebollada, J. et al., "Single-molecule Force Spectroscopy Approach to Enzyme Catalysis," The Journal of Biological Chemistry, vol. 285, No. 25, pp. 18961-18966 (Jun. 18, 2010).

Antikainen, N. M. et al., "Conformation Coupled Enzyme Catalysis: Single-Molecule and Transient Kinetics Investigation of Dihydrofolate Reductase," Biochemistry, vol. 44, pp. 16835-16843 (2005).

Arner, E. S. et al., "Physiological functions of thioredoxin and thioredoxin reductase," Eur. J. Biochem., vol. 267, No. 20, pp. 6102-6109 (2000).

Asbury, C. L. et al., "Kinesin moves by an asymmetric hand-over-hand mechanism," Science, vol. 302, pp. 2130-2134 (Dec. 19, 2003).

Aslund, F. et al., "Redox potentials of glutaredoxins and other thiol-disulfide oxidoreductases of the thioredoxin superfamily determined by direct protein-protein redox equilibria," The Journal of Biological Chemistry, vol. 272, No. 49, pp. 30780-30786 (Dec. 5, 1997).

Avval, F. Z. et al., "Molecular Mechanisms of Thioredoxin and Glutaredoxin as Hydrogen Donors for Mammalian S Phase Ribonucleotide Reductase*," The Journal of Biological Chemistry, vol. 284, No. 13, pp. 8233-8240 (Mar. 27, 2009).

Baker-Austin, C. et al., "Life in acid: pH homeostasis in acidophiles," Trends in Microbiology, vol. 15, No. 4, pp. 165-171 (2007).

Barford, David, "The role of cysteine residues as redox-sensitive regulatory switches," Curr. Opin. Struct. Biol., vol. 14, pp. 679-686 (2004).

Bechtluft, P. et al., "Direct observation of chaperone-induced changes in a protein folding pathway," Science, vol. 318, pp. 1458-1461 (Nov. 30, 2007).

Bell, George I., "Models for the specific adhesion of cells to cells," Science, vol. 200, pp. 618-627 (May 12, 1978).

Benkovic, S. J. et al., "A Perspective on Enzyme Catalysis," Science, vol. 301, pp. 1196-1202 (Aug. 29, 2003).

Benkovic, S. J. et al., "Free-Energy Landscape of Enzyme Catalysis," Biochemistry, vol. 47, pp. 3317-3321 (2008).

Benner, S. A. et al., "Molecular Paleoscience: Systems Biology From the Past," Advances in Enzymology and Related Areas of Molecular Biology, vol. 75, pp. 1-132 (2007).

Berg, O. G. et al., "Association Kinetics with Coupled Diffusion III. Ionic-Strength Dependence of the Lac Repressor-Operator Association," Biophysical Chemistry, vol. 8, No. 4, pp. 271-280, 12 pages (1978).

Berg, O. G. et al., "Diffusion-Driven Mechanisms of Protein Translocation on Nucleic-Acids 1. Models and Theory," Biochemistry, vol. 20, No. 24, pp. 6929-6948 (1981).

Berkovich, R. et al., "Collapse Dynamics of Single Proteins Extended by Force," Biophysical Journal, vol. 98, pp. 2692-2701 (Jun. 2010).

Beyer, M. K. et al., "Mechanochemistry: The Mechanical Activation of Covalent Bonds," Chemical Reviews, vol. 105, No. 8, pp. 2921-2948 (2005).

Beyer, Martin K., "Coupling of Mechanical and Chemical Energy: Proton Affinity as a Function of External Force," Angew. Chem. Int. Ed., vol. 42, pp. 4913-4915, 28 pages (2003).

Beyer, Martin K., "The mechanical strength of a covalent bond calculated by density functional theory," The Journal of Checmical Physics, vol. 112, pp. 7307-7312, 7 pages (2000).

Beynon, R. J. et al., "Proteolytic enzymes: a practical approach," Practical Approach Series Second Edition, Oxford University Press, New York, 355 pages (2001).

Bhasin, N. et al., "Chemistry on a Single Protein, Vascular Cell Adhesion Molecule-1, during Forced Unfolding," The Journal of Biological Chemistry, vol. 279, No. 44, pp. 45865-45874 (Oct. 29, 2004).

Bloom, J. D. et al., "Inferring stabilizing mutations from protein phylogenies: application to influenza hemagglutinin," PLoS Comput. Biol., vol. 5, No. 4, e1000349, pp. 1-19 (Apr. 2009).

Boehr, D. D. et al., "The Dynamic Energy Landscape of Dihydrofolate Reductase Catalysis," Science, vol. 313, pp. 1638-1642 (Sep. 15, 2006).

Boggon, T. J. et al., "C-Cadherin Ectodomain Structure and Implications for Cell Adhesion Mechanisms," Science, vol. 296, pp. 1308-1313, 7 pages (May 17, 2002).

Boucher, I. W. et al., "Structural and biochemical characterization of a mitochondrial peroxiredoxin from Plasmodium falciparum," Molecular Microbiology, vol. 61, No. 4, pp. 948-959 (2006).

Boussau, B. et al., "Parallel adaptations to high temperatures in the Archaean eon," Nature, vol. 456, pp. 942-945, 59 pages (Dec. 25, 2008).

(56) References Cited

OTHER PUBLICATIONS

Brockwell, D. J. et al., "Pulling geometry defines the mechanical resistance of a β-sheet protein," Nature Structural Biology, vol. 10, No. 9, pp. 731-737 (Sep. 2003).
Brujic, J. et al., "Dwell-Time Distribution Analysis of Polyprotein Unfolding Using Force-Clamp Spectroscopy," Biophysical Journal, vol. 92, pp. 2896-2903 (Apr. 2007).
Brujic, J. et al., "Single-molecule force spectroscopy reveals signatures of glassy dynamics in the energy landscape of ubiquitin," Nature Physics, vol. 2, pp. 282-286 (Apr. 2006).
Bustanji, Y. et al., "The Mechanical Properties of Human Angiostatin Can Be Modulated by Means of Its Disulfide Bonds: A Single-Molecule Force-Spectroscopy Study," Angew. Chem. Int. Ed., vol. 41, No. 9, pp. 1546-1548 (2002).
Capitani, G. et al., "Crystal structures of two functionally different thioredoxins in spinach chloroplasts," J. Mol. Biol., vol. 302, pp. 135-154 (2000).
Carl, P. et al., "Forced unfolding modulated by disulfide bonds in the Ig domains of a cell adhesion molecule," PNAS, vol. 98, No. 4, pp. 1565-1570 (Feb. 13, 2001).
Carrion-Vazquez, M. et al., "Mechanical and chemical unfolding of a single protein: A comparison," Proc. Natl. Acad. Sci. USA, vol. 96, pp. 3694-3699 (Mar. 1999).
Carrion-Vazquez, M. et al., "Review: Mechanical design of proteins studied by single-molecule force spectroscopy and protein engineering," Progress in Biophysics & Molecular Biology, vol. 74, pp. 63-91 (2000).
Carrion-Vazquez, M. et al., "The mechanical stability of ubiquitin is linkage dependent," Nature Structural Biology, vol. 10, No. 9, pp. 738-743 (Sep. 2003).
Carvalho, A. T. et al., "Mechanism of Thioredoxin-Catalyzed Disulfide Reduction. Activation of the Buried Thiol and Role of the Variable Active-Site Residues," J. Phys. Chem. B, vol. 112, pp. 2511-2523 (2008).
Cecconi, C. et al., "Protein-DNA chimeras for single molecule mechanical folding studies with the optical tweezers," Eur. Biophys. J., vol. 37, No. 6, pp. 729-738 (Jul. 2008).
Chang, B.S. et al., "Recreating a functional ancestral archosaur visual pigment," Mol. Biol. Evol., vol. 19, pp. 1483-1489 (2002).
Chen, S. et al., "Selectin receptor-ligand bonds: Formation limited by shear rate and dissociation governed by the Bell model," PNAS, vol. 98, No. 3, pp. 950-955 (Jan. 30, 2001).
Cheng, Z. et al., "The relationship of the redox potentials of thioredoxin and thioredoxin reductase from *Drosophila melanogaster* to the enzymatic mechanism: reduced thioredoxin is the reductant of glutathione in *Drosophila*," Biochemistry, vol. 46, No. 26, pp. 7875-7885 (2007).
Chivers, P.T. et al., "General acid/base catalysis in the active site of *Escherichia coli* thioredoxin," Biochemistry, vol. 36, No. 50, pp. 15810-15816, 9 pages (1997).
Chivers, P.T. et al., "The CXXC motif: imperatives for the formation of native disulfide bonds in the cell," The EMBO Journal, vol. 15, No. 11, pp. 2659-2667 (1996).
Cipriano, D. J. et al., "Tethering polypeptides through bifunctional PEG cross-linking agents to probe protein function: application to ATP synthase," Proteins, vol. 73, No. 2, pp. 458-467 (2008).
Conti, M. et al., "How Strong Is the Coordination Bond between a Histidine Tag and Ni-Nitrilotraiacetate? An Experiment of Mechanochemistry on Single Molecules," Angew. Chem. Int. Ed., vol. 39, pp. 215-218 (2000).
Copley, S. D. et al., "Divergence of Function in the Thioredoxin Fold Suprafamily: Evidence for Evolution of Peroxiredoxins from a Thioredoxin-like Ancestor," Biochemistry, vol. 43, pp. 13981-13995 (2004).
Corey, David R., "Synthesis of oligonucleotide-peptide and oligonucleotide-protein conjugates," Methods Mol. Biol., vol. 283, pp. 197-206 (2004).
Costentin, C. et al., "Competition between SN2 and single electron transfer reactions as a function of steric hindrance illustrated by the model system alkylCl+NO$^-$," J. Am. Chem. Soc., vol. 122, pp. 2329-2338 (2000).
Crankshaw, M. W. et al., "Modification of cysteine," Curr. Protoc. Protein Sci., Chapter 15, pp. 15.1.1-15.1.18 (1996).
Csaszar, P. et al., "Breaking and making of the S-S linkage via nucleophilic substitution: An ab initio study," Journal of Molecular Structure (Theochem), vol. 455, pp. 107-122 (1998).
Culotta, V. C. et al., "Activation of superoxide dismutases: Putting the metal to the pedal," Biochim. Biophys. Acta., vol. 1763, No. 7, pp. 747-758 (Jul. 2006).
Dai, S. et al., "Structural snapshots along the reaction pathway of ferredoxin-thioredoxin reductase," Nature, vol. 448, pp. 92-96 (Jul. 5, 2007).
Damdimopoulos, A. E. et al., "Human mitochondrial thioredoxin: Involvement in mitochondrial membrane potential and cell death," The Journal of Biological Chemistry, vol. 277, No. 36, pp. 33249-33257 (Sep. 6, 2002).
Darby, N. J. et al., "Identifying and characterizing a structural domain of protein disulfide isomerase," Biochemistry, vol. 35, pp. 10517-10528 (1996).
del Rio, A. et al., "Stretching single talin rod molecules activates vinculin binding," Science, vol. 323, No. 5914, pp. 638-641, 6 pages (Jan. 30, 2009).
Di Jeso, B. et al., "Mixed-disulfide folding intermediates between thyroglobulin and endoplasmic reticulum resident oxidoreductases ERp57 and protein disulfide isomerase," Molecular and Cellular Biology, vol. 25, No. 22, pp. 9793-9805 (Nov. 2005).
Dietz, H. et al., "Exploring the energy landscape of GFP by single-molecule mechanical experiments," PNAS, vol. 101, No. 46, pp. 16192-16197 (Nov. 16, 2004).
Dougan, L. et al., "A Single-Molecule Perspective on the Role of Solvent Hydrogen Bonds in Protein Folding and Chemical Reactions," Chemphyschem, vol. 9, pp. 2836-2847 (2008).
Dudko, O. K. et al., "Intrinsic Rates and Activation Free Energies from Single-Molecule Pulling Experiments," Physical Review Letters, vol. 96, No. 108101, pp. 1-4 (Mar. 17, 2006).
Dyson, H. J. et al., "Effects of buried charged groups on cysteine thiol ionization and reactivity in *Escherichia coli* thioredoxin: structural and functional characterization of mutants of Asp 26 and Lys 57," Biochemistry, vol. 36, pp. 2622-2636, 17 pages (1997).
Edgar, Robert C., "Muscle: multiple sequence alignment with high accuracy and high throughput," Nucleic Acids Research, vol. 32, pp. 1792-1797 (2004).
Efron, Bradley, "The Jackknife, the Bootstrap, and Other Resampling Plans," Department of Statistics, Stanford University, Society for Industrial and Applied Mathematics (SIAM), Philadelphia, 9 pages (1982).
Eisenmesser, E. Z. et al., "Intrinsic dynamics of an enzyme underlies catalysis," Nature, vol. 438, pp. 117-121 (Nov. 2005).
Eklund, H., "Structural and functional relations among thioredoxins of different species," Proteins, vol. 11, pp. 13-28 (1991).
English, B. P. et al., "Ever-fluctuating single enzyme molecules: Michaelis-Menten equation revisited," Nature Chemical Biology, vol. 2, No. 2, pp. 87-94 (Feb. 2006).
Erlandsson, M. et al., "Metallic zinc reduction of disulfide bonds between cysteine residues in peptides and proteins," International Journal of Peptide Research and Therapeutics, vol. 11, No. 4, pp. 261-265 (2005).
Evans, E. et al., "Dynamic Strength of Molecular Adhesion Bonds," Biophysical Journal, vol. 72, pp. 1541-1555 (Apr. 1997).
Evans, Evan, "Probing the Relation Between Force-Lifetime-and Chemistry in Single Molecular Bonds," Annu. Rev. Biophys. Biomol. Struct., vol. 30, pp. 105-128 (2001).
Extended European Search Report mailed on Dec. 10, 2013 for co-pending EP Application No. 11807607.4; 7 pages.
Falkowski, Paul G., "Evolution: Tracing oxygen's imprint on earth's metabolic evolution," Science, vol. 311, pp. 1724-1725 (Mar. 24, 2006).
Farver, O. et al., "Low activation barriers characterize intramolecular electron transfer in ascorbate oxidase," Proc. Natl. Acad. Sci. USA, vol. 89, pp. 8283-8287 (Sep. 1992).

(56) References Cited

OTHER PUBLICATIONS

Fernandes, P. A. et al., "Theoretical insights into the mechanism for thiol/disulfide exchange," Chem. Eur. J., vol. 10, pp. 257-266 (2004).
Fernandez, J. M. et al., "Force-clamp spectroscopy monitors the folding trajectory of a single protein," Science, vol. 303,, No. 5664, pp. 1674-1678, 7 pages (Mar. 12, 2004).
Florin, E. L. et al., "Sensing Specific Molecular-Interactions with the Atomic-Force Microscope," Biosensors & Bioelectronics, vol. 10, pp. 895-901 (1995).
Foloppe, N. et al., "The glutaredoxin—C—P—Y—C—motif: influence of peripheral residues," Structure, vol. 12, pp. 289-300 (Feb. 2004).
Forman-Kay, J. D. et al., "High-resolution three-dimensional structure of reduced recombinant human thioredoxin in solution," Biochemistry, vol. 30, pp. 2685-2698 (1991).
Frey, P. A. et al., "Enzymatic reaction mechanisms," Oxford University Press 852 pages (2007).
Furuike, S. et al., "Mechanical unfolding of single filamin A (ABP-280) molecules detected by atomic force microscopy," FEBS Letters, vol. 498, pp. 72-75 (2001).
Garcia-Manyes, S. et al., "Contrasting the individual reactive pathways in protein unfolding and disulfide bond reduction observed within a single protein," Journal of the American Chemical Society, vol. 133, No. 9, pp. 3104-3113, 20 pages (Mar. 9, 2011).
Garcia-Manyes, S. et al., "Direct observation of an ensemble of stable collapsed states in the mechanical folding of ubiquitin," Proc. Natl. Acad. Sci. USA, vol. 106, No. 26, pp. 10534-10539 (Jun. 30, 2009).
Garcia-Manyes, S. et al., "Force-activated reactivity switch in a biomolecular chemical reaction," Nature Chemistry, vol. 1, pp. 236-242 (Jun. 2009).
Garcia-Manyes, S. et al., "Force-Clamp Spectroscopy of Single-Protein Monomers Reveals the Individual Unfolding and Folding Pathways of I27 and Ubiquitin," Biophysical Journal, vol. 93, pp. 2436-2446 (Oct. 2007).
Garcia-Manyes, S. et al., "Osmolyte-induced separation of the mechanical folding phases of ubiquitin," PNAS, vol. 106, No. 26, pp. 10540-10545 (Jun. 30, 2009).
Gaucher, E. A. et al., "Inferring the palaeoenvironment of ancient bacteria on the basis of resurrected proteins," Nature, vol. 425, No. 6955, pp. 285-288 (Sep. 18, 2003).
Gaucher, E. A. et al., "Palaeotemperature trend for Precambrian life inferred from resurrected proteins," Nature, vol. 451, pp. 704-707 (Feb. 2008).
Gelhaye, E. et al., "The plant thioredoxin system," Cell. Mol. Life Sci., vol. 62, pp. 24-35 (2005).
Godoy-Ruiz, R. et al., "Natural selection for kinetic stability is a likely origin of correlations between mutational effects on protein energetics and frequencies of amino acid occurrences in sequence alignments," J. Mol. Biol., vol. 362, pp. 966-978 (2006).
Gogarten-Boekels, M. et al., "The effects of heavy meteorite bombardment on the early evolution—the emergence fo the three domains of life," Orig. Life Evol. Biosph., vol. 25, pp. 251-264, 17 pages (1995).
Gorman, J. et al., "Dynamic basis for one-dimensional DNA scanning by the mismatch repair complex Msh2-Msh6," Mol. Cell, vol. 28, No. 3, pp. 359-370 (Nov. 9, 2007).
Grandbois, M. et al., "How strong is a covalent bond?," Science, vol. 283, pp. 1727-1730 (Mar. 12, 1999).
Graves, B. J. et al., "Insight into E-selectin/ligand interaction from the crystal structure and mutagenesis of the Iec/EGF domains," Nature, vol. 367, pp. 532-538 (Feb. 10, 1994).
Green, N. S. et al., "Quantitative evaluation of the lengths of homo bifunctional protein cross-linking reagents used as molecular rulers," Protein Science, vol. 10, No. 7, pp. 1293-1304 (2001).
Grosberg, A. Y. et al., "Statistical Physics of Macromolecules," American Institute of Physics (AIP), New York, 5 pages (1994).

Halford, S. E. et al., "How do site-specific DNA-binding proteins find their targets?," Nucleic Acids Research, vol. 32, No. 10, pp. 3040-3052 (2004).
Hall, Barry G., "Simple and accurate estimation of ancestral protein sequences," Proc. Natl. Acad. Sci. USA, vol. 103, No. 14, pp. 5431-5436 (Apr. 4, 2006).
Hammes-Schiffer, S. et al., "Relating protein motion to catalysis," Annu. Rev. Biochem., vol. 75, pp. 519-541 (2006).
Hansen, R. E. et al., "Increasing the Reactivity of an Artificial Dithiol-Disulfide Pair through Modification of the Electostatic Milieu," Biochemistry, vol. 44, pp. 5899-5906 (2005).
Hatahet, F. et al., "Protein disulfide isomerase: a critical evaluation of its function in disulfide bond formation," Antioxid Redox Signal, vol. 11, pp. 2807-2850 (2009).
Hazzard, J. T. et al., "Direct measurement by laser flash photolysis of intramolecular electron transfer in the three-electron reduced form of ascorbate oxidase from zucchini," Biochim. Biophys. Acta, vol. 1208, pp. 166-170 (1994).
Hedges, S. B. et al., "The Timetree of Life," Oxford University Press, 19 pages (2009).
Henzler-Wildman, K. A. et al., "A hierarchy of timescales in protein dynamics is linked to enzyme catalysis," Nature, vol. 450, pp. 913-918 (Dec. 6, 2007).
Henzler-Wildman, K. A. et al., "Intrinsic motions along an enzymatic reaction trajectory," Nature, vol. 450, pp. 838-844 (Dec. 2007).
Heras, B. et al., "DSB proteins and bacterial pathogenicity," Nature Reviews: Microbiology, vol. 7, pp. 215-225 (Mar. 2009).
Hermans, Rodolfo I., "Experimental Study of Single Protein Mechanics and Protein Rates of Unfolding," Thesis—Submitted in partial fulfillment of the Requirements for the degree of Doctor of Philosophy in the Graduate School of Arts and Sciences, Columbia University, 19 pages (2010).
Hogg, Philip J., "Disulfide bonds as switches for protein function," Trends in Biochemical Science, vol. 28, No. 4, pp. 210-214 (Apr. 2003).
Holm, R. H., "Structural and functional aspects of metal sites in biology," Chem. Rev., vol. 96, pp. 2239-2314 (1996).
Holmgren, Arne, "Reduction of disulfides by thioredoxin: Exceptional reactivity of insulin and suggested functions of thioredoxin in mechanism of hormone action," The Journal of Biological Chemistry, vol. 254, No. 18, pp. 9113-9119 (Sep. 25, 1979).
Holmgren, Arne, "Thioredoxin and glutaredoxin systems," J. Biol. Chem., vol. 264, No. 24, pp. 13963-13966 (Aug. 25, 1989).
Holmgren, Arne, "Thioredoxin catalyzes the reduction of insulin disulfides by dithiothreitol and dihydrolipoamide," The Journal of Biological Chemistry, vol. 254, No. 19, pp. 9627-9632 (Oct. 10, 1979).
Holmgren, Arne, "Thioredoxin structure and mechanism: conformational changes on oxidation of the active-site sulfhydryls to a disulfide," Structure, vol. 3, pp. 239-243 (Mar. 15, 1995).
Holmgren, Arne, "Tryptophan fluorescence study of conformational transitions of the oxidized and reduced form of thioredoxin," The Journal of Biological Chemistry, vol. 247, No. 7, pp. 1992-1998 (Apr. 10, 1972).
Holmgren, Arne, "Thioredoxin," Ann. Rev. Biochem., vol. 54, pp. 237-271 (1985).
Houk, J. et al., "Measurement of Thiol-Disulfide Interchange Reactions and Thiol pKa Values," Methods in Enzymology, vol. 143, pp. 129-140 (1987).
Hutter, J. L. et al., "Calibration of atomic-force microscope tips," AIP: Review of Scientific Instruments, vol. 64, pp. 1868-1873, 7 pages (1993).
Ibarra-Molero, B. et al., "Thermal versus guanidine-induced unfolding of ubiquitin. An analysis in terms of the contributions from charge-charge interactions to protein stability," Biochemistry, vol. 38, pp. 8138-8149 (1999).
International Search Report issued by the International Searching Authority for International Application No. PCT/US11/44275 mailed on Dec. 13, 2011 (4 pages).
Iozzi, M. F. et al., "Influence of External Force on Properties and Reactivity of Disulfide Bonds," The Journal of Physical Chemistry A, vol. 115, pp. 2308-2315 (2011).

(56) References Cited

OTHER PUBLICATIONS

Jackel, C., "Protein Design by Directed Evolution," Annu. Rev. Biophys., vol. 37, pp. 153-173 (2008).
Ji, T. H. et al., "Bifunctional reagents," Methods in Enzymology, vol. 91, Part I, pp. 580-609, 32 pages (1983).
Jones, P. R. et al., "A new member of plant CS-lyases: A ysteine lyase from Arabidopsis thaliana," The Journal of Biological Chemistry, vol. 278, No. 12, pp. 10291-10296 (Mar. 21, 2003).
Kadokura, H. et al., "Detecting folding intermediates of a protein as it passes through the bacterial translocation channel," Cell, vol. 138, No. 6, pp. 1164-1173 (Sep. 18, 2009).
Kadokura, H. et al., "Snapshots of DsbA in action: detection of proteins in the process of oxidative folding," Science, vol. 303, pp. 534-537 (Jan. 23, 2004).
Kadokura, H., "Protein Disulfide Bond Formation in Prokaryotes," Annu. Rev. Biochem., vol. 72, pp. 111-135 (2003).
Kaganman, Irene, "Resurrected Enzymes," Research Highlights, Nature Methods, vol. 8, No. 6, p. 452 (Jun. 2011).
Kappler, U. et al., "Molecular basis of intramolecular electron transfer in sulfiteoxidizing enzymes is revealed by high resolution structure of a heterodimeric Complex of the catalytic molybdopterin subunit and a c-type cytochrome subunit," The Journal of Biological Chemistry, vol. 280, No. 26, pp. 24999-25007 (Jul. 1, 2005).
Karala, A. R. et al., "Modulation of an active-site cysteine pKa allows PDI to act as a catalyst of both disulfide bond formation and isomerization," J. Mol. Biol., vol. 396, pp. 883-892 (2010).
Karplus, M. et al., "Dynamics of Proteins: Elements and Function," Annu. Rev. Biochem., vol. 53, pp. 263-300 (1983).
Katti, S. K. et al., "Crystal structure of thioredoxin from *Escherichia coli* at 1.68 A resolution," J. Mol. Biol., vol. 212, pp. 167-184 (1990).
Kern, D. et al., "Enzyme Dynamics During Catalysis Measured by NMR Spectroscopy," Methods in Enzymology, vol. 394, pp. 507-524 (2005).
Kice, John L., "Nucleophilic Substitution at Different Oxidation States of Sulfur," Progress in Inorganic Chemistry, Inorganic Reaction Mechanisms, Part II, pp. 148-206, 64 pages (1972).
Kirschvink, J. L. et al., "Palaeoproterozoic ice houses and the evolution of oxygen-mediating enzymes: the case for a late origin of photosystem II," Phil. Trans. R. Soc. B., vol. 363, pp. 2755-2765 (2008).
Knauth, L. P. et al., "High Archean climatic temperature inferred from oxygen isotope geochemistry of cherts in the 3.5 Ga Swaziland Supergroup, South Africa," The Geological Society of America, vol. 115, No. 5, pp. 566-580, 18 pages (May 2003).
Koch, Arthur L., "Shrinkage of growing *Escherichia coli* cells by osmotic challenge," Journal of Bacteriology, vol. 159, No. 3, pp. 919-924 (Sep. 1984).
Kosuri, P. et al., "Protein folding drives disulfide formation," Cell, vol. 151, No. 4, pp. 794-806, 23 pages (Nov. 9, 2012).
Koti Ainavarapu, S. R. et al., "Single-molecule force spectroscopy measurements of bond elongation during a Bimolecular reaction," J. Am. Chem. Soc., vol. 130, pp. 6479-6487 (2008).
Krause, G. et al., "Mimicking the active site of protein disulfide-isomerase by substitution of proline 34 in *Escherichia coli* thioredoxin," J. Biol. Chem., vol. 266, No. 15, pp. 9494-9500 (May 25, 1991).
Kraut, D. A. et al., "Challenges in enzyme mechanism and energetics," Annu. Rev. Biochem., vol. 72, pp. 517-571 (2003).
Kufer, S. K. et al., "Covalent immobilization of recombinant fusion proteins with hAGT for single molecule force spectroscopy," Eur. Biophys. J., vol. 35,, pp. 72-78 (2005).
Kumar, J. K. et al., "Proteomic analysis of thioredoxin-targeted proteins in *Escherichia coli*," Proc. Natl. Acad. Sci. USA, vol. 101, No. 11, pp. 3759-3764 (Mar. 16, 2004).
Kuo, T. L. et al., "Probing static disorder in Arrhenius kinetics by single-molecule force spectroscopy," Proc. Natl. Acad. Sci. USA, vol. 107, No. 25, pp. 11336-11340 (Jun. 22, 2010).

Kuwajima, K. et al., "Kinetics of Disulfide Bond Reduction in α-Lactalbumin by Dithiothreitol and Molecular Basis of Super-reactivity of the Cys6-Cys120 Disulfide Bond," Biochemistry, vol. 29, pp. 8240-8249 (1990).
La Duc, M. T. et al., "Isolation and characterization of bacteria capable of tolerating the extreme conditions of clean room environments," Appl. Environ. Microbiol., vol. 73, No. 8, pp. 2600-2611 (Apr. 2007).
Labit, H. et al., "A simple and optimized method of producing silanized surfaces for FISH and replication mapping on combed DNA fibers," Biotechniques, vol. 45, pp. 649-658, 8 pgs. (Dec. 2008).
LaMantia, M. L. et al., "The essential function of yeast protein disulfide isomerase does not reside in its isomerase activity," Cell, vol. 74, No. 5, pp. 899-908 (Sep. 10, 1993).
Lancelin, J. M. et al., "NMR structures of thioredoxin m from the green alga Chlamydomonas reinhardtii," Proteins: Structure, Function, and Genetics, vol. 41, pp. 334-349 (2000).
Land, A. et al., "Folding of the human immunodeficiency virus type 1 envelope glycoprotein in the endoplasmic reticulum," Biochimie, vol. 83, pp. 783-790 (2001).
Lemaire, S.D. et al., "New thioredoxin targets in the unicellular photosynthetic eukaryote Chlamydomonas reinhardtii," Proc. Natl. Acad. Sci. USA, vol. 101, No. 19, pp. 7475-7480 (May 11, 2004).
Lennon, B. W. et al., "Twists in catalysis: alternating conformations of *Escherichia coli* thioredoxin reductase," Science, vol. 289, pp. 1190-1194 (Aug. 18, 2000).
Li, H. et al., "Mechanical Design of the First Proximal Ig Domain of Human Cardiac Titin Revealed by Single Molecule Force Spectroscopy," J. Mol. Biol., vol. 334, pp. 75-86 (2003).
Li, H. et al., "Reverse engineering of the giant muscle protein titin," Nature, vol. 418, pp. 998-1002 (Aug. 29, 2002).
Li, W. J. et al., "Atomistic Evidence of How Force Dynamically Regulates Thiol/Disulfide Exchange," Journal of the American Chemical Society, vol. 132, pp. 16790-16795 (2010).
Li, Y. et al., "Conformational fluctuations coupled to the thiol-disulfide transfer between thioredoxin and arsenate reductase in Bacillus subtilis," J. Biol. Chem., vol. 282, pp. 11078-11083 (2007).
Liang, J. et al., "Kinetic Measurements on Single-Molecule Disulfide Bond Cleavage," Journal of the American Chemical Society, vol. 133, pp. 3528-3534 (2011).
Liang, J. et al., "Mechanochemistry: One Bond at a Time," ACS Nano, vol. 3, No. 7, pp. 1628-1645 (Jul. 28, 2009).
Liberles, David A., "Ancestral sequence reconstruction," Oxford University Press, 252 pages (2007).
Lide, David R., "CRC Handbook of Chemistry and Physics," 75th Edition, CRC Press, Boca Raton, Ann Arbor, London, Tokyo, 9 pages (1994-1995).
Lide, David R., "CRC Handbook of Chemistry and Physics: A Ready-Reference Book of Chemical and Physical Data," 76th Edition, CRC Press, Boca Raton, New York, London, Tokyo, 9 pages (1995-1996).
Light, A. et al., "Enterokinase (enteropeptidase): comparative aspects," Trends Biochemical Sciences, vol. 14, No. 3, pp. 110-112 (Mar. 1989).
Lillig, C. H. et al., "Thioredoxin and related molecules-from biology to health and disease," Antioxidants & Redox Signaling, vol. 9, No. 1, pp. 25-47 (2007).
Liu, R. C. et al., "Mechanical Characterization of Protein L in the Low-Force Regime by Electromagnetic Tweezers/Evanescent Nanometry," Biophysical Journal, vol. 96, No. 9, pp. 3810-3821 (May 2009).
Lopez-Otin, C. et al., "Proteases: multifunctional enzymes in life and disease," J. Bioi. Chem., vol. 283, No. 45, pp. 30433-30437 (Nov. 7, 2008).
Lu, D. et al., "Crystal structure of enteropeptidase light chain complexed with an analog of the trypsinogen activation peptide," J. Mol. Biol., vol. 292, No. 2, pp. 361-373 (1999).
Lundstrom, J. et al., "A Pro to His mutation in active site of thioredoxin increases its disulfide-isomerase activity 10-fold: New refolding systems for reduced or randomly oxidized ribonuclease," J. Biol. Chem., vol. 267, No. 13, pp. 9047-9052 (May 5, 1992).

(56) References Cited

OTHER PUBLICATIONS

Lundstrom, J. et al., "Protein disulfide-isomerase is a substrate for thioredoxin reductase and has thioredoxin-like activity," J. Biol. Chem., vol. 265, No. 16, pp. 9114-9120 (Jun. 5, 1990).
Maeda, K. et al., "Structural basis for target protein recognition by the protein disulfide reductase thioredoxin," Structure, vol. 14, pp. 1701-1710 (Nov. 2006).
Maier, B. et al., "A force-dependent switch reverses type IV pilus retraction," PNAS, vol. 101, No. 30, pp. 10961-10966 (Jul. 27, 2004).
Malone, A. S. et al., "Genes of *Escherichia coli* O157:H7 that are involved in high-pressure resistance," Appl. Environ. Microbiol., vol. 72, No. 4, pp. 2661-2671 (Apr. 2006).
Mamathambika, B. S. et al., "Disulfide-linked protein folding pathways," Annu. Rev. Cell. Dev. Biol., vol. 24, pp. 211-235 (2008).
Marcus, R. A. et al., "Electron transfers in chemistry and biology," Biochimica et Biophysica Acta, vol. 811, pp. 265-322 (1985).
Marszalek, P. E. et al., "Atomic force microscopy captures quantized plastic deformation in gold nanowires," PNAS, vol. 97, No. 12, pp. 6282-6286 (Jun. 6, 2000).
Marszalek, P. E. et al., "Mechanical unfolding intermediates in titin modules," Nature, vol. 402, pp. 100-103 (Nov. 4, 1999).
Marszalek, P. E., "Polysaccharide elasticity governed by chair-boat transitions of the glucopyranose ring," Nature, vol. 396, pp. 661-664 (Dec. 17, 1998).
Martin, Jennifer L., "Thioredoxin—a fold for all reasons," Structure, vol. 3, No. 3, pp. 245-250 (1995).
Matthias, L. J. et al., "Disulfide exchange in domain 2 of CD4 is required for entry of HIV-I," Nat. Immunol., vol. 3, No. 8, pp. 727-732 (Aug. 2002).
Matthias, L. J. et al., "Redox control on the cell surface: implications for HIV-1 entry," Antioxidants & Redox Signaling, vol. 5, No. 1, pp. 133-138 (Feb. 2003).
Mayans, O. et al., "Structural Evidence for a Possible Role of Reversible Disulphide Bridge Formation in the Elasticity of the Muscle Protein Titin," Structure, vol. 9, pp. 331-340 (Apr. 2001).
McLendon, G. et al., "Applying Marcus's theory to electron transfer in vivo," Electron Transfer: From Isolated Molecules to Biomolecules, Part Two, vol. 107, pp. 591-600 (1999).
Menzel, U. et al., "The internal pH of Acetobaceterium wieringae and Acetobacter aceti during growth and production of acetic acid," Archives of Microbiology, vol. 143, pp. 47-51 (1985).
Mesecar, A. D. et al., "Orbital Steering in the Catalytic Power of Enzymes: Small Structure Changes with Large Catalytic Consequences," Science, vol. 277, pp. 202-206 (Jul. 11, 1997).
Meyer, Y. et al., "Evolution of redoxin genes in the green lineage," Photosynth. Res., vol. 89, pp. 179-192 (2006).
Milanesi, L. et al., "A method for the reversible trapping of proteins in non-native conformations," Biochemistry, vol. 47, No. 51, pp. 13620-13634 (2008).
Ming, H. et al., "Crystal structure of thioredoxin domain of ST2123 from thermophilic archaea Sulfolobus tokodaii strain7," Proteins, vol. 69, pp. 204-208 (2007).
Miranda-Vizuete, A. et al., "Cloning, expression, and characterization of a novel *Escherichia coli* thioredoxin," J. Biol. Chem., vol. 272, No. 49, pp. 30841-30847 (Dec. 5, 1997).
Mori, T. et al., "How kinesin waits between steps," Nature, vol. 450, pp. 750-754 (Nov. 2007).
Mustacich, D. et al., "Thioredoxin reductase," Biochem. J., vol. 346, Part 1, pp. 1-8. (2000).
Nelder, J. A. et al., "A Simplex-Method for Function Minimization," Computer Journal, vol. 7, pp. 308-313 (1965).
Nisbet, E. G. et al., "The habitat and nature of early life," Nature, vol. 409, pp. 1083-1091 (Feb. 22, 2001).
Oberhauser, A. F. et al., "Stepwise unfolding of titin under force-clamp atomic force microscopy," PNAS, vol. 98, No. 2, pp. 468-472 (Jan. 16, 2001).
Oberhauser, A. F. et al., "The Mechanical Hierarchies of Fibronectin Observed with Single-molecule AFM." J. Mol. Biol., vol. 319, pp. 433-447 (2002).
Olsson, M. H. et al., "Dynamical Contributions to Enzyme Catalysis: Critical Tests of a Popular Hypothesis," Chem. Rev., vol. 106, pp. 1737-1756 (2006).
Palmer, Arthur G., 3rd., "NMR Characterization of the Dynamics of Biomacromolecules," Chem. Rev., vol. 104, pp. 3623-3640 (2004).
Pappas, Jan A., "Theoretical studies of reactions of sulfur-sulfur bond. 1. General heterolytic mechanisms," J. Am. Chem. Soc., vol. 99, No. 9, pp. 2926-2930 (Apr. 27, 1977).
Paravicini, T. M. et al., "Redox signaling in hypertension," Cardiovascular Research, vol. 71, pp. 247-258 (2006).
Peregrin-Alvarez, J. M. et al., "The phylogenetic extent of metabolic enzymes and pathways," Genome Research, vol. 13, pp. 422-427 (2003).
Perez-Jimenez, R. et al., "Diversity of chemical mechanisms in thioredoxin catalysis revealed by single-molecule force spectroscopy," Nature structural & molecular biology, vol. 16, No. 8, pp. 890-896 (Aug. 2009).
Perez-Jimenez, R. et al., "Force-clamp spectroscopy detects residue co-evolution in enzyme catalysis," J. Biol. Chem., vol. 283, No. 40, pp. 27121-27129 (Oct. 3, 2008).
Perez-Jimenez, R. et al., "Single-molecule paleoenzymology probes the chemistry of resurrected enzymes," Nat. Struct. Mol. Biol., vol. 18, No. 5, pp. 592-596 (May 2011).
Peterson, F. C. et al., "Solution structure of thioredoxin h1 from Arabidopsis thaliana," Protein Sci., vol. 14, pp. 2195-2200 (2005).
Pollock, D. D. et al., "Dealing with uncertainty in Ancestral sequence reconstruction: sampling from the posterior distribution," Chapter 8, Ancestral Sequence Reconstruction, Oxford University Press, pp. 85-94, 12 pages (2007).
Popa, I. et al., "Direct Quantification of the Attempt Frequency Determining the Mechanical Unfolding of Ubiquitin Protein," Journal of Biological Chemistry, vol. 286, No. 36, pp. 31072-31079 (Sep. 9, 2011).
Powis, G. et al., "Properties and biological activities of thioredoxins," Annu. Rev. Biophys. Biomol. Struct., vol. 30, pp. 421-455 (2001).
Qin, J. et al., "Solution structure of human thioredoxin in a mixed disulfide intermediate complex with its target peptide from the transcription factor NFκB," Structure, vol. 3, pp. 289-297 (Mar. 15, 1995).
Qin, J. et al., "The high-resolution three-dimensional solution structures of the oxidized and reduced states of human thioredoxin," Structure, vol. 2, pp. 503-522 (Jun. 15, 1994).
Qin, J. et al., "The solution structure of human thioredoxin complexed with its target from Ref-1 reveals peptide chain reversal," Structure, vol. 4, pp. 613-620 (May 15, 1996).
Raymond, J. et al., "The effect of oxygen on biochemical networks and the evolution of complex life," Science, vol. 311, pp. 1764-1767 (Mar. 24, 2006).
Ren, G. et al., "Properties of the thioredoxin fold superfamily are modulated by a single amino acid residue," J. Biol. Chem., vol. 284, No. 15, pp. 10150-10159 (Apr. 10, 2009).
Ren, X. et al., "Mutagenesis of structural half-cystine residues in human thioredoxin and effects on the regulation of activity by selenodiglutathione," Biochemistry, vol. 32, pp. 9701-9708 (1993).
Rief, M., "Reversible Unfolding of Individual Titin Immunoglobulin Domains by AFM," Science, vol. 276, pp. 1109-1112 (May 16, 1997).
Rief, M., "Single Molecule Force Spectroscopy on Polysaccharides by Atomic Force Microscopy," Science, vol. 275, pp. 1295-1297 (Feb. 28, 1997).
Riggs, A. D. et al., "Lac Repressor-Operator Interaction .3. Kinetic Studies," Journal of Molecular Biology, vol. 53, No. 3, pp. 401-417, 22 pages (1970).
Rosenfield, R. E. et al., "Directional preferences of nonbonded atomic contacts with divalent sulfur. 1. Electrophiles and nucleophiles," J. Am. Chem. Soc., vol. 99, No. 14, pp. 4860-4862 (Jul. 6, 1977).
Rubio-Bollinger, G. et al., "Mechanical Properties and Formation Mechanisms of a Wire of Single Gold Atoms," Physical Review Letters, vol. 87, No. 2, pp. 026101-1-026101-4 (Jul. 9, 2001).

(56) References Cited

OTHER PUBLICATIONS

Russell, M. J. et al., "The emergence of life from iron monosulphide bubbles at a submarine hydrothermal redox and pH front," J. Geol. Soc. Lond., vol. 154, Part 3, pp. 377-402, 29 pages (May 1997).
Ryser, H. J. et al., "Keynote review: Progress in targeting HIV-1 entry," Drug Discov. Today, vol. 10, No. 16, pp. 1085-1094 (Aug. 2005).
Sarkar, A. et al., "Simultaneous atomic force microscope and fluorescence measurements of protein unfolding using a calibrated evanescent wave," Proc. Natl. Acad. Sci. USA, vol. 101, No. 35, pp. 12882-12886 (Aug. 31, 2004).
Schlierf, M. et al., "The unfolding kinetics of ubiquitin captured with single-molecule force-clamp techniques," Proc. Natl Acad. Sci. USA, vol. 101, No. 19, pp. 7299-7304 (May 11, 2004).
Schramm, Vern L., "Enzymatic transition states and transition state analogues," Curr. Opin. Struct. Biol., vol. 15, 604-613 (2005).
Schrijver, I. et al., "Cysteine Substitutions in Epidermal Growth Factor-Like Domains of Fibrillin-1: Distinct Effects on Biochemical and Clinical Phenotypes," Am. J. Hum. Genet., vol. 65, pp. 1007-1020 (1999).
Schulte, Mitchell, "The Emergence of Life on Earth," Oceanography, vol. 20, No. 1, pp. 42-49 (Mar. 2007).
Senn, H. M., et al., "QM/MM studies of enzymes," Current Opinion in Chemical Biology, vol. 11, pp. 182-187 (2007).
Sevier, C. S. et al., "Formation and transfer of disulphide bonds in living cells," Nat. Rev. Mol. Cell Biol., vol. 3, pp. 836-847 (Nov. 2002).
Sharma, A. et al., "Microbial activity at gigapascal pressures," Science, vol. 295, pp. 1514-1516 (Feb. 22, 2002).
Singh, R. et al., "Degenerate Intermolecular Thiolate-Disulfide Interchange Involving Cyclic Five-Membered Disulfides is Faster by ~103 Than That Involving Six- or Seven-Membered Disulfides," J. Am. Chem. Soc., vol. 112, pp. 6304-6309 (1990).
Smeets, A. et al., "Crystal structures of oxidized and reduced forms of human mitochondrial thioredoxin 2," Protein Sci., vol. 14, pp. 2610-2621 (2005).
Smith, S. B. et al., "Overstretching B-DNA: The Elastic Response of Individual Double-Stranded and Single-Stranded DNA Molecules," Science, vol. 271, No. 5250, pp. 795-799, 6 pages (Feb. 9, 1996).
Snyder, G. H. et al., "Electrostatic Influence of Local Cysteine Environments on Disulfide Exchange Kinetics," Biochemistry, vol. 20, No. 23, pp. 6509-6519 (Nov. 10, 1981).
Spyrou, G. et al., "Cloning and expression of a novel mammalian thioredoxin," J. Biol. Chem., vol. 272, No. 5, pp. 2936-2941 (Jan. 31, 1997).
Stanford, N .P . et al., "One- and three-dimensional pathways for proteins to reach specific DNA sites," The Embo Journal, vol. 19, No. 23, pp. 6546-6557 (2000).
Starks, C. M. et al., "Atomic-resolution crystal structure of thioredoxin from the acidophilic bacterium Acetobacter aceti," Protein Sci., vol. 16, pp. 92-98 (2007).
Stewart, E. J. et al., "Disulfide bond formation in the *Escherichia coli* cytoplasm: an in vivo role reversal for the thioredoxins," The EMBO Journal, vol. 17, No. 19, pp. 5543-5550 (1998).
Stirnemann, G. et al., "Elasticity, structure, and relaxation of extended proteins under force," Proc. Natl. Acad. Sci. USA, vol. 110, No. 10, pp. 3847-3852 (Mar. 5, 2013).
Suarez, M. et al., "Using multi-objective computational design to extend protein promiscuity," Biophys. Chem., vol. 147, Issues 1-2, pp. 13-19, 9 pages (Mar. 2010).
Szoszkiewicz, R. et al., "Dwell Time Analysis of a Single-Molecule Mechanochemical Reaction," Langmuir, vol. 24, pp. 1356-1364 (2008).
Tachibana, C. et al., "The yeast EUG 1 gene encodes an endoplasmic reticulum protein that is functionally related to protein disulfide isomerase," Mol. Cell Biol., vol. 12, No. 10, pp. 4601-4611 (Oct. 1992).
Taniguchi, Y. et al., "Application of HaloTag Protein to Covalent Immobilization of Recombinant Proteins for Single Molecule Force Spectroscopy," Langmuir Letter, vol. 26, No. 13, pp. 10433-10436 (2010).
Tao, L. et al., "Cardioprotective effects of thioredoxin in myocardial ischemia and reperfusion: role of S-nitrosation," Proc. Natl Acad. Sci. USA, vol. 101, No. 31, pp. 11471-11476, 7 pages (Aug. 3, 2004).
Thomson, J. M. et al., "Resurrecting ancestral alcohol dehydrogenases from yeast," Nat. Genet., vol. 37, pp. 630-635, 13 pages (Jun. 2005).
Thornton, Joseph W., "Resurrecting ancient genes: experimental analysis of extinct molecules," Nat. Rev. Genet., vol. 5, No. 5, pp. 366-375, 12 pages (May 2004).
Turk, Boris, "Targeting proteases: successes, failures and future prospects," Nat. Rev. Drug Discov., vol. 5, No. 9, pp. 785-799 (Sep. 2006).
Uehara, T. et al., S-Nitrosylated protein-disulphide isomerase links protein misfolding to neurodegeneration, Nature, vol. 441, pp. 513-517 (May 2006).
von Hippel, P. H. et al., "Facilitated target location in biological systems," The Journal of Biological Chemistry, vol. 264, No. 2, pp. 675-678 (Jan. 15, 1989).
Wagner, G. et al., "Dynamic model of globular protein conformations based on NMR studies in solution," Nature, vol. 275, pp. 247-248 (Sep. 21, 1978).
Walker, B. et al., "Strategies for the inhibition of serine proteases," Cellular and Molecular Life Sciences, vol. 58, No. 4, pp. 596-624 (2001).
Walker, James C. G., "Possible Limits on the Composition of the Archean Ocean," Nature, vol. 302, pp. 518-520, 5 pages (Apr. 1983).
Walther, K. A. et al., "Signatures of hydophobic collapse in extended proteins captured with force spectroscopy," Proc. Natl. Acad. Sci. USA, vol. 104, No. 19, pp. 7916-7921 (May 8, 2007).
Wang, L. et al., "Coordinated effects of distal mutations on environmentally coupled tunneling in dihydrofolate," PNAS, vol. 103, No. 43, pp. 15753-15758 (Oct. 24, 2006).
Wang, T. et al., "Force Measurement and Inhibitor Binding Assay of Monomer and Engineered Dimer of Bovine Carbonic Anhydrase B," Biochemical and Biophysical Research Communications, vol. 285, pp. 9-14 (2001).
Wickner, W. et al., "Protein translocation across biological membranes," Science, vol. 310, pp. 1452-1456, 6 pages (2005).
Wierzbicka-Patynowski, I. et al., "The ins and outs of fibronectin matrix assembly," Journal of Cell Science, vol. 116, pp. 3269-3276 (2003).
Wiita, A. P. et al., "Force-dependent chemical kinetics of disulfide bond reduction observed with single-molecule techniques," Proc. Natl Acad. Sci. USA, vol. 103, No. 19, pp. 7222-7227 (May 9, 2006).
Wiita, A. P. et al., "Probing the chemistry of thioredoxin catalysis with force," Nature, vol. 450, pp. 124-127 (Nov. 1, 2007).
Williams, C. H. et al., "Thioredoxin reductase two modes of catalysis have evolved," Eur. J. Biochem., vol. 267, No. 20, pp. 6110-6117 (2000).
Windle, H. J. et al., "The thioredoxin system of Helicobacter pylori," J. Biol. Chem., vol. 275, pp. 5081-5089 (Feb. 18, 2000).
World, C. J. et al., "Thioredoxin in the cardiovascular system," J. Mol. Med., vol. 84, pp. 997-1003 (2006).
Wouters, M. A. et al., "Cross-strand disulphides in cell entry proteins: poised to act," BioEssays, vol. 26, pp. 73-79 (2004).
Wynn, R. et al., "Chemical modification of protein thiols: formation of mixed disulfides," Methods in Enzymology, vol. 251, pp. 351-356, 8 pages (1995).
Xiao, R. et al., "Catalysis of thiol/disulfide exchange: Glutaredoxin 1 and protein-disulfide isomerase use different mechanisms to enhance oxidase and reductase activities," J. Biol. Chem., vol. 280, No. 22, pp. 21099-21106 (Jun. 3, 2005).
Xie, L. et al., "Control of von Willebrand Factor Multimer Size by Thrombospondin," J. Exp. Med., vol. 193, No. 12, pp. 1341-1349 (Jun. 18, 2001).

(56) References Cited

OTHER PUBLICATIONS

Xu, S. Z. et al., "TRPC channel activation by extracellular thioredoxin," Nature, vol. 451, No. 7174, pp. 69-72, 13 pages (Jan. 3, 2008).

Yan, B. et al., "Mechanism of Integrin Activation by Disulfide Bond Reduction," Biochemistry, vol. 40, pp. 8861-8867 (2001).

Yang, L. W. et al., "Coupling between Catalytic Site and Collective Dynamics: A Requirement for Mechanochemical Activity of Enzymes," Structure, vol. 13, pp. 893-904 (Jun. 2005).

Yang, Z. et al., "A new method of inference of ancestral nucleotide and amino acid sequences," Genetics, vol. 141, pp. 1641-1650 (Dec. 1995).

Yang, Ziheng, "PAML: a program package for phylogenetic analysis by maximum likelihood," Comput. Appl. Biosci., vol. 13, No. 5, pp. 555-556, 7 pages (1997).

Yasui, S. et al., "Irreversibility of single electron transfer occurring from trivalent phosphorus compounds to Iron(III) complexes in the presence of ethanol," Bull. Chem. Soc. Jpn., vol. 75, pp. 1311-1318 (2002).

Ye, J. et al., "Crystal structure of an unusual thioredoxin protein with a zinc finger domain," J. Biol. Chem., vol. 282, No. 48, pp. 34945-34951 (Nov. 30, 2007).

Zakeri, B. et al., "Peptide tag forming a rapid covalent bond to a protein, through engineering a bacterial adhesin," PNAS, vol. 109, No. 12, pp. E690-E697 (Mar. 20, 2012).

Zalatan, J. G. et al., "The far reaches of enzymology," Nat. Chem. Bioi., vol. 5, No. 8, pp. 516-520, 8 pages (Aug. 2009).

Zhong, Dongping, "Ultrafast catalytic processes in enzymes," Current Opinion in Chemical Biology, vol. 11, pp. 174-181 (2007).

Zimmermann, J. L. et al., "Thiol-based, site-specific and covalent immobilization of biomolecules for single-molecule experiments," Nature Protocols, vol. 5, No. 6, pp. 975-985 (2010).

Extended European Search Report for European Patent Application No. 11807541.5 dated Aug. 24, 2016 (9 pages).

Hugel and Seitz, "The Study of Molecular Interactions by AFM Force Spectroscopy," Macromolecular Rapid Communications, vol . 22, No. 13, pp. 989-1016 (2001).

lkai, "Nanomechanics of Protein-Based Biostructures," Japanese Journal of Applied Physics, Japan Society of Applied Physics, JP, vol. 43. No. 11A, p. 7365-7375 (2004).

International Search Report and Written Opinion dated Nov. 21, 2011 corresponding to International Patent Application No. PCT/US2011/044084; 8 pages.

* cited by examiner

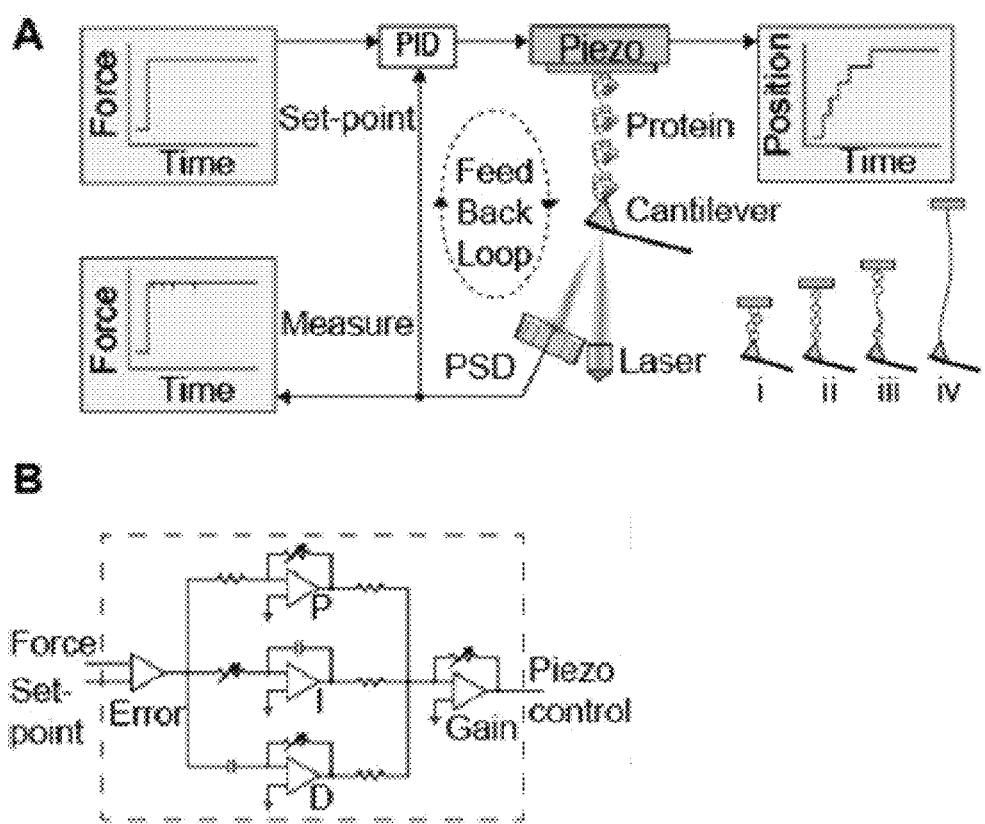
FIGURE 31 A-B

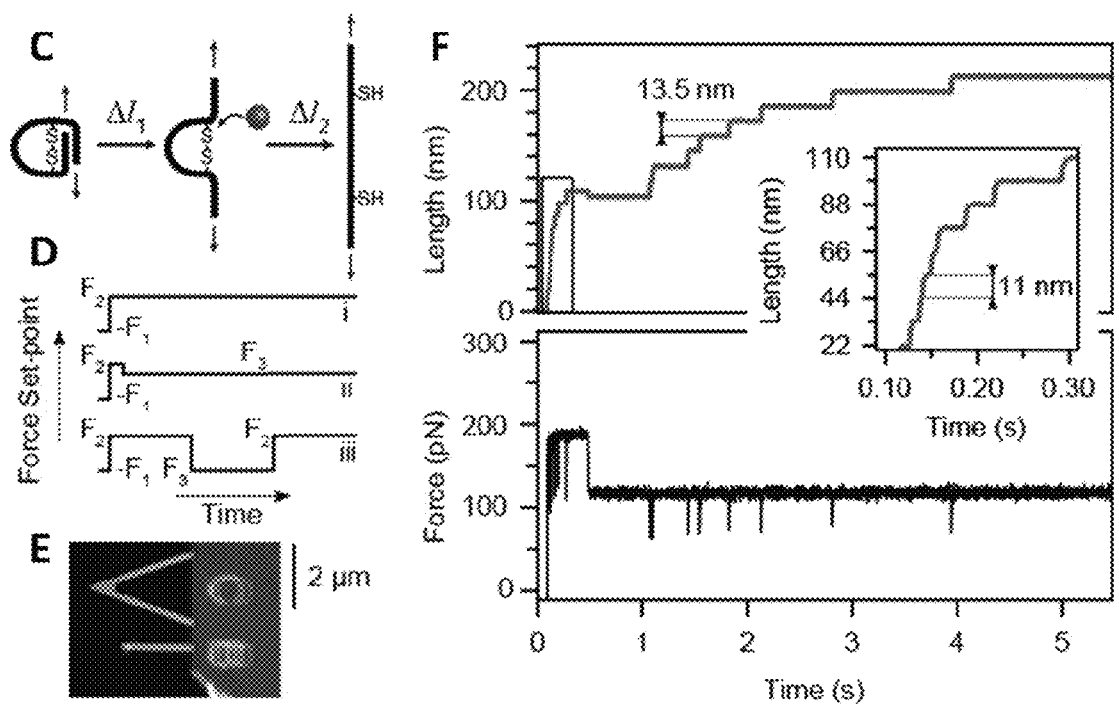
FIGURE 31 C-F

FORCE-CLAMP SPECTROMETER WITH FUNCTIONALIZED CANTILEVER TIP

This application is a continuation-in-part of International Application No. PCT/US2011/044084, filed Jul. 14, 2011, which claims priority to U.S. Provisional Application No. 61/364,208, filed on Jul. 14, 2010, and U.S. Provisional Application No. 61/364,640 filed on Jul. 15, 2010, the contents of each of which are hereby incorporated by reference in their entireties This invention was made with government support under HL66030 and HL61228 awarded by NIH. The government has certain rights in the invention.

All patents, patent applications, published patent applications, granted patents and publications cited herein are hereby incorporated by reference in their entirety. The disclosures of these publications in their entireties are hereby incorporated by reference into this application in order to more fully describe the state of the art as known to those skilled therein as of the date of the invention described herein.

Alegre-Cebollada et al., "Single-molecule Force Spectroscopy Approach to Enzyme Catalysis," Journal of Biological Chemistry, Vol 285, pp. 18961-18966 (2010); Perez-Jimenez et al., "Diversity of Chemical Mechanisms in Thioredoxin Catalysis Revealed by Single-Molecule Force Spectroscopy", Nat. Struct. Mol. Biol., Vol 16(8), pp. 890-896 (2009); Wiita et al., "Probing the Chemistry of Thioredoxin Catalysis With Force", Nature 450, 124-127 (2007); and Wiita et al., "Force-Dependent Chemical Kinetics of Disulfide Bond Reduction Observed With Single-Molecule Techniques. PNAS 103:19, 7222-7227 (2006). For the purposes of the U.S., the contents of Alegre-Cebollada et al., "Single-molecule Force Spectroscopy Approach to Enzyme Catalysis," Journal of Biological Chemistry, Vol 285, pp. 18961-18966 (2010); Perez-Jimenez et al., "Diversity of Chemical Mechanisms in Thioredoxin Catalysis Revealed by Single-Molecule Force Spectroscopy," Nat. Struct. Mol. Biol. Vol 16(8), pp. 890-896 (2009); Wiita et al., "Probing the Chemistry of Thioredoxin Catalysis With Force," Nature 450, 124-127 (2007); and Wiita et al., Force-Dependent Chemical Kinetics of Disulfide Bond Reduction Observed With Single-Molecule Techniques. PNAS 103:19, 7222-7227 (2006)," are herein incorporated by reference.

BACKGROUND

This disclosure relates to force-clamp spectrometers and force-clamp spectroscopy techniques.

The intersection of force and chemistry has been studied for over a century, yet not much is known about this phenomenon compared with more common methods of chemical catalysis. There are a number of reasons for this discrepancy, but one of the most important factors remains that it is quite difficult to directly measure the effect of force on a bulk reaction. This difficulty arises because an applied force is not a scalar property of a system; it is associated with a vector. As a result, it is often not possible to directly probe the effect of force on a particular reaction because of heterogeneous application of force and a distribution of reaction orientations (Beyer, M. K. & Clausen-Schaumann, H. (2005) Chem. Rev. 105, 2921-2948). To fully quantify the effect of an applied force on a chemical reaction, it is necessary to generate an experimental system where the reaction of interest is consistently oriented with respect to the applied force.

The direct manipulation of single molecules allows for the application of force in a vector aligned with the reaction coordinate (Evans, E. & Ritchie, K. (1997) Biophys. J. 72, 1541-1555), avoiding the heterogeneity of bulk studies. Earlier works using single molecule techniques have described the rupture forces necessary to cleave single covalent bonds, including Si—C bonds in polysaccharide attachment (Grandbois, M., Beyer, M., Rief, M., Clausen-Schaumann, H. & Gaub, H. E. (1999) Science 283, 1727-1730), Au—Au bonds in nanowires (Marszalek, P. E., Greenleaf, W. J., Li, H., Oberhauser, A. F.&Fernandez, J. M. (2000) Proc. Natl. Acad. Sci. USA 97, 6282-6286; Rubio-Bollinger, G., Bahn, S. R., Agrait, N., Jacobsen, K. W. & Vieira, S. (2001) Phys. Rev. Lett. 87, 026101), and Ni2+-NTA attachments (Conti, M., Falini, G. & Samori, B. (2000) Angew. Chem. Int. Ed. 39, 215-218).

However, these studies have not been able to describe the effect of force on the dynamics and kinetics of these reactions, nor have they examined more complex chemical reactions beyond simple bond rupture.

Accordingly, there is a need in the art for devices and methods to describe the effect of force on the dynamics and kinetics of these reactions, and to examine more complex chemical reactions beyond simple bond rupture.

SUMMARY

The disclosed subject matter relates to a force-clamp spectrometer that enables operation in constant force mode and allows for automated data acquisition and analysis, using feedback electronics and software. The force-clamp spectrometer may be used in methods for the measurement of the dynamics of chemical reactions, including, but not limited to, the dynamics of the measurement of substrate folding and unfolding, as well as bond cleavage and bond formation.

In some embodiments, the force-clamp spectrometer is used to manipulate substrates, including, but not limited to, single proteins, to study substrate folding and unfolding. For example, the method may directly measure the dynamics of folding and unfolding events in real-time. In one embodiment, the dynamics of folding and unfolding are identified through a fingerprint signal, thus removing the risk of false positives and the need for control experiments. In another embodiment, the dynamics are measured as a function of a force applied. The force may be applied to a bond, allowing for force spectroscopy reactions involving the bond. In other embodiments, the force-clamp spectrometer is used for the measurement of the dynamics of the cleavage of a bond. For example, the method may directly resolve bond cleavage events in real-time. In one embodiment, the dynamics are identified through a fingerprint signal, removing the risk of false positives and the need for control experiments. In another embodiment, the dynamics are measured as a function of a force applied. The force may be applied to a bond, allowing for force spectroscopy reactions involving the bond. In yet other embodiments, the force-clamp spectrometer is used for the measurement of the formation of a bond. For example, the method may measure the dynamics of bond formation in real-time. In one embodiment, the dynamics are identified through a fingerprint signal, removing the risk of false positives and the need for control experiments. In another embodiment, the dynamics are measured as a function of a force applied. The force may be applied to a bond, allowing for force spectroscopy reactions involving the bond.

In some embodiments, a single molecule is suspended between the tip of the cantilever and the coverslip. The extension of this molecule is controlled through a piezo, while the force generated is measured through the bending of the cantilever. The bending angle of the cantilever is constantly monitored by reflecting a laser beam off its backside, and detecting the reflected beam on a split photodetector. The force on the cantilever is thus directly proportional to the difference signal from the photodetector, i.e. the difference in voltage between its two sensors.

The cantilever chip is mounted in the fluid cell, which includes an inclined cantilever mount adjacent to a transparent surface where the laser beam can pass through. The laser can be focused on the cantilever by monitoring the beam spot through the camera. When the alignment is done, the camera and objective are swiveled out of the way. The coverslip is mounted on the piezo, (liquid) sample is added to the coverslip, and the piezo can then be swiveled into place, facing the cantilever.

During force-clamp operation, the feedback system adjusts the extension of a suspended molecule until a set-point force is reached. This is achieved through a negative feedback circuit that takes the difference between the measured force and the setpoint force as error signal, processes it, and then feeds this signal back to the piezo.

In one aspect, the instant disclosure relates to a force-clamp spectrometer. The force-clamp spectrometer may include, for example, a cantilever chip; a piezo-electric positioner; a laser and focusing optics; a split photodetector; a data acquisition card; a computer; feed-back electronics; a cantilever holder or a fluid cell, at least one movable stage; a sample disc or a sample coverslip; a CCD camera; a microscope objective; a prism; at least one mount; an optical bread board; a vibration insulation table; and control and analysis software.

In some embodiments, a force-clamp spectrometer is provided that includes a cantilever, a force applicator mounted on a hinged stage; a coverslip positioned over the force applicator, wherein the coverslip is configured to suspend a single molecule between the tip of the cantilever and the coverslip; and a detector to measure bending of the cantilever. In one embodiment, the force applicator is a piezo-electric positioner. In another embodiment, the detector comprises a laser and optics. In yet another embodiment, the detector comprises a split photodetector.

In some embodiments, the cantilever chip is, for example, a MLCT chip from Veeco; the piezo-electric positioner is a PicoCube™ positioner from Physic Instrumente; the laser & focusing optics is 51 nanoFCM, from Schafter+Kirchhoff; the split photodetector is a QP50 photodetector from Pacific Silicon Sensor; the data acquisition card is USB-6289, from National Instruments. In other embodiments, the cantilever holder or the fluid cell is a MMTMEC holder/cell from Veeco and the movable stages are Agilis™ mounts from Newport®.

The feedback settings, force protocol and data acquisition are all controlled from the computer, for example, through a custom made software package developed in IGOR (Wavemetrics). The software allows for automated operation for several days without manual intervention. Also included in the software are analysis features developed for several specific assays, including the study of bond cleavage, bond formation, and folding and unfolding.

In another aspect, the instant disclosure relates to a method for the measurement of the dynamics of chemical reactions. Dynamics may include, but are not limited to, kinetic rates and shifts in equilibrium. In one embodiment, the kinetic rates are measured. In another embodiment, shifts in equilibrium are measured.

In another embodiment, the instant disclosure relates to a method of measuring the cleavage of a bond. In some embodiments, the bond is a covalent bond. In other embodiments, the bond is a non-covalent bond. The method may include, for example, providing a sample and analyzing the sample using the force-clamp spectrometer of the instant disclosure. In one embodiment, the sample comprises a substrate. In another embodiment, the sample comprises one or more enzymes. In another embodiment, the sample comprises a substrate and an enzyme. In some embodiments, the enzyme is an oxidoreductase enzyme. In other embodiments, the enzyme is a thioredoxin. In still other embodiments, the enzyme is a protein disulfide isomerase. In another embodiment, the enzyme is protease, esterase, phosphodiesterase, or glycosidase. In another embodiment, the enzyme is a hydrolase. In some embodiments, the sample comprises a compound that reacts with a bond. The compound may be, but is not limited to, a reducing agent, an oxidizing agent, a nanoparticle, or a small molecule. In another embodiment, the sample comprises an ion. In some embodiments, the sample comprises an inhibitor. In other embodiments, the sample comprises an activator. Inhibitors and activators may be, but are not limited to, small molecules. In one embodiment, the inhibitor is an enzyme inhibitor. In another embodiment, the activator is an enzyme activator.

In another embodiment, the instant disclosure relates to a method of measuring the formation of a bond. In some embodiments, the bond is a covalent bond. In other embodiments, the bond is a non-covalent bond. The method may include, for example, providing a sample and analyzing the sample using the force-clamp spectrometer of the instant disclosure. In one embodiment, the sample comprises a substrate. In another embodiment, the sample comprises one or more enzymes. In another embodiment, the sample comprises a substrate and an enzyme. In some embodiments, the enzyme is an oxidoreductase enzyme. In other embodiments, the enzyme is a thioredoxin. In still other embodiments, the enzyme is a protein disulfide isomerase. In another embodiment, the enzyme is protease, esterase, phosphodiesterase, or glycosidase. In another embodiment, the enzyme is a hydrolase. In some embodiments, the sample comprises a compound that reacts with a bond. The compound may be, but is not limited to, a reducing agent, an oxidizing agent, a nanoparticle, or a small molecule. In another embodiment, the sample comprises an ion. In some embodiments, the sample comprises an inhibitor. In other embodiments, the sample comprises an activator. Inhibitors and activators may be, but are not limited to, small molecules. In one embodiment, the inhibitor is an enzyme inhibitor. In another embodiment, the activator is an enzyme activator.

In another embodiment, the instant disclosure relates to a method of measuring the folding and/or the unfolding of a substrate. The method may include, for example, providing a sample and analyzing the sample using the force-clamp spectrometer of the instant disclosure. In one embodiment, the sample comprises a substrate. In another embodiment, the sample comprises one or more enzymes. In another embodiment, the sample comprises a substrate and an enzyme. In some embodiments, the enzyme is an oxidoreductase enzyme. In other embodiments, the enzyme is a thioredoxin. In still other embodiments, the enzyme is a protein disulfide isomerase. In some embodiments, the sample comprises a compound that reacts with a bond. The compound may be, but is not limited to, a reducing agent, an oxidizing agent, a nanoparticle, or a small molecule. In another embodiment, the sample comprises an ion. In some embodiments, the sample comprises an inhibitor. In other embodiments, the sample comprises an activator Inhibitors and activators may be, but are not limited to, small molecules. In one embodiment, the inhibitor is an enzyme inhibitor. In another embodiment, the activator is an enzyme activator.

In another aspect, the instant disclosure relates to a substrate used for measuring the dynamics of chemical reactions. In one embodiment, the substrate is used for measuring the cleavage of a bond. In another embodiment, the substrate is used for measuring the formation of a bond. In yet another embodiment, the substrate is used for measuring folding and/or unfolding. In one embodiment, the substrate is a polymer. In one embodiment, the substrate is a protein or a polypeptide. In another embodiment, the substrate is a nucleic acid. In another embodiment, the substrate is a polysaccharide. In another embodiment, the substrate is an engineered polymer.

In one embodiment, the commercial opportunity for the disclosed subject matter lies in the precision of measurement of the reactivity of a reagent (such as an enzyme or a chemical compound) towards a specific bond. Coupled with force spectroscopy, the reaction kinetics measurements can reveal details about the reagent, for example, the direct detection of bond cleavage and/or bond formation events, as well as folding and/or unfolding events, as opposed to the measurement of coupled reactions that might introduce bias in the data.

BRIEF DESCRIPTION OF THE DRAWINGS

The following figures are provided for the purpose of illustration only and are not intended to be limiting. The patent or application file contains at least one drawing executed in color. Copies of this patent or patent application publication with color drawing(s) will be provided by the Office upon request and payment of the necessary fee.

FIG. 2 is a series of views showing an illustrative flip platform of an illustrative force clamp spectrometer according to some embodiments of the disclosed subject matter.

FIG. 7A shows three recordings are shown of single (I27G32C-A75C)8 polyproteins that were extended with the same double-pulse protocol shown in FIG. 6B. FIG. 7B upper shows a four-trace average (red trace) of the double-pulse experiments shown in FIG. 7A and FIG. 6B. FIG. 7B lower shows the average force traces.

FIG. 15A is a graphic representation of the force clamp experiment. FIG. 15B is a trace showing the unfolding and consequent disulfide reductions of a (I27G32C-A75C)8 polyprotein. FIGS. 15C and 15D are plots showing the probability of reduction (Pred(t)) obtained by summing and normalizing traces of disulfide bond reductions at different forces (second pulse) for pea Trxm (10 mM) (FIG. 15C) and for poplar Trxh1 (10 mM) (FIG. 15D).

FIG. 21A-21B, Protein disulfide isomerase (PDI) catalyzes disulfide formation in a polypeptide (blue) undergoing ER translocation. FIG. 21C-21D, With the use of an atomic force microscope, we could reproduce the in vivo cysteine separation (a) and initiate folding from this state. Disulfides and folded structures were subsequently identified through their mechanical fingerprints.

FIG. 22A, Mechanical unfolding and refolding of an individual Ig domain in the presence of reduced PDI a. Applied force enables stochastic unfolding that is hindered by the presence of an intramolecular disulfide, yielding a stepwise extension of 11 nm and exposing the disulfide. This bond can now be cleaved by reduced PDI a, yielding an additional 14 nm extension step and establishing an intermediate complex. Switching off the force triggers collapse and folding. FIG. 22B, Representative trace using a polyprotein substrate consisting of sequential Ig domains. A [denature-$\Delta$t-probe] protocol was used, as described in the text. Arrowheads indicate disulfide cleavage events (14 nm steps). In this trace, six Ig domains were completely unfolded and reduced. Four of these subsequently underwent complete oxidative folding. Other traces revealed refolding without disulfide formation (25 nm step, inset). FIG. 22C, Step size histograms confirm that PDI a catalyzes oxidative folding in some domains and reduce other domains.

FIG. 23A, The Ig polyprotein was unfolded and refolded in the presence of reduced human TRX. Arrowheads indicate disulfide cleavage events (14 nm steps). In this trace, seven domains were completely denatured. Four of these subsequently refolded, albeit without disulfide formation. FIG. 23B, Step size histograms confirm that TRX did not catalyze oxidative folding, as seen from the absence of 14 nm steps in the probe pulse. FIG. 23C, Representative trace showing that TRX C35S can cleave disulfides and also catalyze oxidative folding. In the probe pulse, 14 nm steps were occasionally seen without preceding 11 nm steps, indicating that disulfide formation had taken place whereas folding of these domains had not completed. FIG. 23D, Step size histograms show that disulfides were formed in all refolded domains.

FIG. 24A, Substrate refolding after $\Delta$t=5 s. All three enzymes allowed refolding to take place. FIG. 24B, Percent of refolded domains displaying intramolecular disulfides. FIG. 24C, Percent of substrate domains having successfully completed oxidative folding. PDI and TRX C35S displayed no significant difference in the catalysis of oxidative folding, whereas TRX showed no detectable activity. FIG. 24D, Substrate refolding kinetics, as percentage of initial number of folded substrate domains. FIG. 24E, Disulfide formation kinetics, as percentage of initial number of disulfides in substrate. Solid lines show exponential fits to the data. N=84 traces (TRX), N=344 traces (TRX C35S) FIG. 24F, In TRX, rapid nucleophilic attack by Cys35 S$\gamma$ leaves the substrate reduced before folding can take place. FIG. 24G, Substitution of a single atom (S$\rightarrow$O) eliminates the escape pathway of TRX, and the enzyme lingers on the extended substrate. Switching off the applied force (or continued translocation in vivo) triggers collapse and enables folding, while retention of the intermediate enzyme complex enables catalyzed oxidation of the substrate disulfide. Error bars indicate the s.e.m. as determined from bootstrap analysis.

FIG. 25A, Thiol-disulfide oxidoreductases in the thioredoxin superfamily catalyze disulfide exchange by forming a mixed disulfide intermediate complex with the substrate. FIG. 25B, TRX catalyzes only reduction in vivo. FIG. 25C, PDI exhibits two reaction paths. The results show that the pathway preference results from a kinetic competition between the escape pathway and substrate folding.

FIG. 27A, Representative trace. FIG. 27B, Step size histograms.

FIG. 31. Force-clamp Atomic Force Microscope (AFM). FIG. 31A, Schematics of the setup. The applied force is measured through the reflection of a laser beam from a tip cantilever onto a quadrant photodiode (PSD). At any time, the value of the measured force can be compared with the value of the set-point force and the PID feedback drives the piezo actuator to reduce the error between these values. Under force-clamp conditions, protein unfolding events can be detected as stair-case like steps in the measured length. Each step reports on the unfolding of an individual domain of the tethered polyprotein. An unfolding event triggers a drop in force, which can be corrected by the feedback through the movement of the piezo to a new position. The diagram shows four stages of the experiment: (i) the cantilever being pushed into the protein layer, (ii) pulling of the polyprotein construct, (iii) unfolding of one domain, and (iv) unfolding of all tethered domains. FIG. 31B, Schematics of the analog PID controller used to maintain the force at a given set-point. The error between the measured force and the set-point can be constantly measured and minimized through displacement of the piezo. FIG. 31C, Schematics of the experiment measuring rates of chemical reactions under force. An initial force pulse unfolds the composing protein domains in short time with a step size $\Delta l_1$. A small nucleophile molecule such as DTT, TCEP, hydroxyl or an enzyme like thioredoxin, PDI reduces the exposed disulfide bond, displaying a different step increase, $\Delta l_2$. FIG. 31D, Different force protocols used in force-clamp AFM. (i) A pushing short force is followed by a constant pulling force. This pulse is best suited for studies of mechanical protein unfolding. The negative sign shows a push force and the positive sign a pull force. (ii) Two pulling forces are used, one at which proteins unfold and one at which the chemical reaction occurs. (iii) The force is quenched between two pulling pulses. This combination of force pulses is best suited to follow protein collapse and refolding at a low force (Fernandez, J. M. & Li, H. Science 303, 1674-1678 (2004); Kosuri, P. et al., Cell 151, 794-806 (2012)). Refolding can be quantified from the number of domains that regain mechanical stability during the quench, as probed during the second pulling pulse or probe pulse. FIG. 31E, Picture of an AFM probe (MLCT, Bruker), showing a rectangular and a V-shaped cantilever. The laser has been focus on the end of the rectangular cantilever. FIG. 31F, Length (top) and force (bottom) traces of the unfolding and reduction of an $(I27)_8$ polyprotein mutated to have a buried disulfide bond. A first 190 pN short pulse unfolds the eight component domains with a step size of 11 nm (marked with blue). The force is then decreased to 110 pN where disulfide bonds are cleaved by the enzyme thioredoxin, showing extension steps of 13.5 nm.

FIG. 32A, Spectra showing thermal oscillations of three cantilever models: Bruker MLCT-B (red trace), Olympus BL-RC150VB-A (orange trace), and Olympus BL-AC40TS (blue trace). Smaller cantilevers have higher resonance frequencies and enable better response times under force-clamp. The circles mark the limits of the main resonance peak. The grey area represents the signal area effectively used in the calibration of the Bruker MLCT-B. FIG. 32B, Deflection-extension curves measured on approach and retraction of the piezo relative to the cantilever. The slope calculated from the contact region (dotted line) yields the bending distance of the cantilever as a function of the measured photodiode output.

FIG. 33A, Schematics of the experiment. Glass surfaces are functionalized with a chloroalkane ligand which forms an ester bond with the HaloTag protein (red), placed at one end of the construct. The opposite end has a cysteine amino acid that reacts with the gold functionalized cantilever. FIG. 33B, Force-clamp traces showing the unfolding of the HaloTag, followed by eight unfolding steps of I27 and the detachment at a force of ~1 nN.

FIG. 34A, HaloTag-$(I27^{C47/63A})_8$-Cys polyprotein construct exposed to a pulling force of 160 pN shows a staircase increase in length corresponding to the unfolding of the nine proteins composing the construct. FIG. 34B, $(I27^{32/75C})_8$-Cys$_2$ in the presence of 10 µM human thioredoxin is exposed to a force of 190 pN to unfold eight protein domains (11 nm steps) and to a 120 pN force to reduce the disulfide bond and unravel the remaining amino acids. The arrows show where the traces are cut in order to extract the unfolding and reduction kinetics respectively.

FIG. 35A, Several traces, such as the one on FIG. 34A, showing unfolding steps of $I27^{C47/63A}$, measured at a force of 160 pN. Insert: schematics of the unfolding process. FIG. 35B, Several traces, such as the one on FIG. 34B, showing reduction of $I27^{32/75C}$, measure in the presence of 10 µM thioredoxin at a force of 75 pN. Insert: Schematics of the reduction process after unfolding. FIG. 35C, Summed curves obtained by averaging unfolding traces of $I27^{C47/63A}$ at different forces. The dashed lines represent single exponential fits used to extract the unfolding rates. FIG. 35D, Histogram showing the measured rate from randomly chosen populations of 49 traces, using the boot-strapping method and finding for $I27^{C47/63A}$ at 160 pN a value for the unfolding rate of 2.0±0.2 $s^{-1}$.

FIG. 36A, Force-extension curves showing interference (top) and no visible interference (bottom). Red traces are measured while approaching to the surface and blue ones while redrawing from the surface. FIG. 36B, Thermal fluctuations (power) spectrum of a MLCT-B cantilever in HEPES buffer away from the surface (red curve), close to the surface (blue curve), and away from the surface in a HEPES buffer containing 30% glycerol (green curve). The arrows mark the limits of the main resonance peak (see also FIG. 32B). FIG. 36C, Deflection-extension traces obtained on a properly dosed surface and on an overdosed surface (obtained by doping a gold surface with albumin). Small cantilevers capable of bending linearly only a few nm are prone to curvature errors in this part of the calibration. The lines show fitted slopes far and close to the surface, with little change in slope for the correctly dosed surface. Insert: Zoom-in of the area close to the surface. FIG. 36D, Unfolding trace of $I27^{C47/63A}$ showing unfolding kinetics too fast to be captured with the used cantilevers and PID settings. Insert: Drop in force due to unfolding of a protein domain and its exponential fit, having a time decay of 1.6 ms. The blue and red arrows in FIG. 36A and FIG. 36C indicate the change direction of travel of the surface relative to the cantilever.

DETAILED DESCRIPTION

In one aspect, the instant disclosure relates to a device that comprises a flip force spectrometer, a USB electronic controller box, and a computer for data acquisition and analysis.

In a typical experiment, a single molecule is suspended between the tip of the cantilever and the coverslip. The extension of this molecule is controlled through the piezo, while the force generated is measured through the bending of the cantilever. The bending angle of the cantilever is constantly monitored by reflecting a laser beam off its backside, and detecting the reflected beam on a split photodetector. The force on the cantilever is thus directly proportional to the difference signal from the photodetector, i.e. the difference in voltage between its two sensors.

The cantilever chip is mounted in the fluid cell, which in its simplest version consists of an inclined cantilever mount adjacent to a transparent surface where the laser beam can pass through. The laser can easily be focused on the cantilever by monitoring the beam spot through the camera. When the alignment is done, the camera and objective are swiveled out of the way. The coverslip is mounted on the piezo, (liquid) sample is added to the coverslip, and the piezo can then be swiveled into place, facing the cantilever.

During force-clamp operation, the feedback system adjusts the extension of a suspended molecule until a set-point force is reached. This is achieved through a negative feedback circuit that takes the difference between the measured force and the setpoint force as error signal, processes it, and then feeds this signal back to the piezo.

The feedback settings, force protocol and data acquisition can be all controlled from the computer, for example, through a custom made software package developed in IGOR (Wavemetrics). The software allows for automated operation for several days without manual intervention. Also included in the software are analysis features developed for several specific assays, including the study of bond cleavage and formation and protein folding and unfolding.

Figure 1:
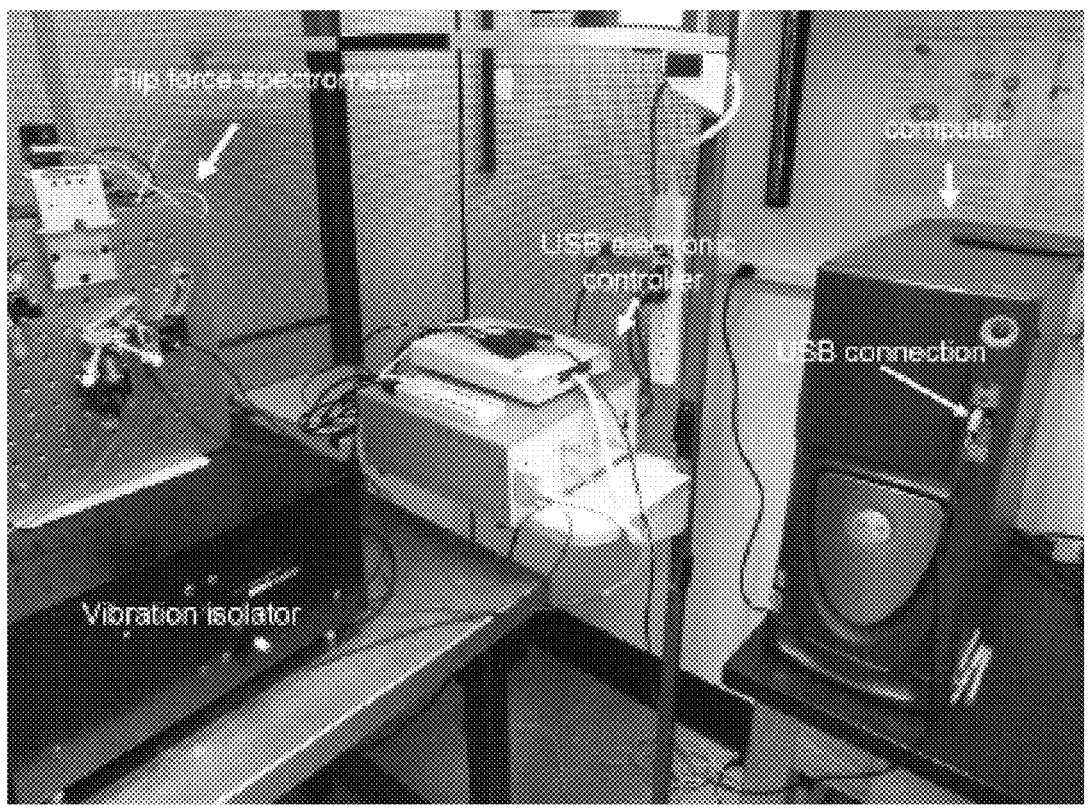
FIG. 1 is a view of an illustrative force clamp spectrometer according to some embodiments of the disclosed subject matter.

This device is uniquely designed for doing force-clamp spectroscopy of single proteins. As shown in FIG. 1, the device includes a PID controller for the force-clamp function together with a high voltage power supply for piezo actuator displacement (gray box). The device includes a USB controller for the piezo motors (smaller elongated controller with buttons) and a USB data acquisition and control unit (white box with cable). The device is mounted on a small perforated optical table and placed on top of a vibration isolation table (black box underneath the spectrometer). The entire instrument may be connected to a computer via, for example, a single USB cable.

The combined effect of these components is the ability, with this device, to mechanically manipulate single proteins to study protein unfolding/folding and chemical reactions. The instrument is easy to use. An operator without any experience, for example, can learn to use it effectively in a few hours of training High quality single protein data can be rapidly obtained, on demand.

Figure 2A:
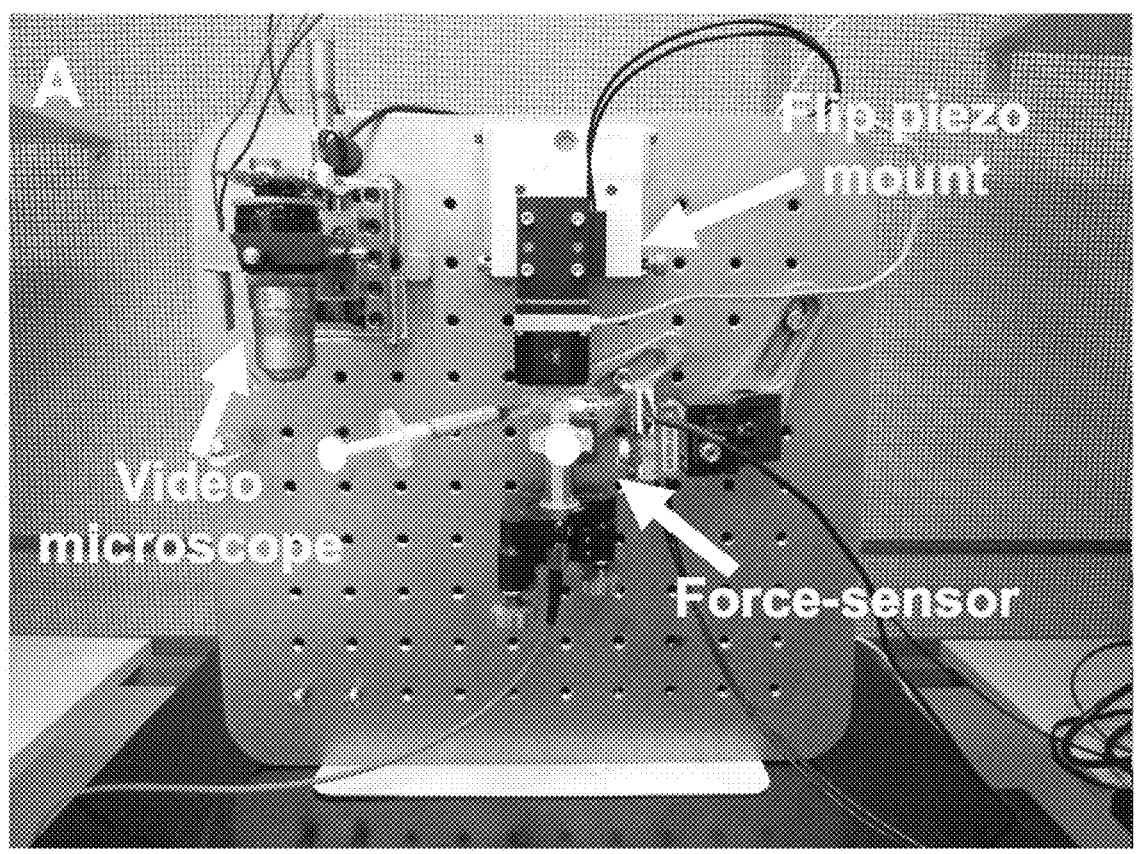
FIG. 2A shows the illustrative flip platform in the measuring position.
Figure 2B:
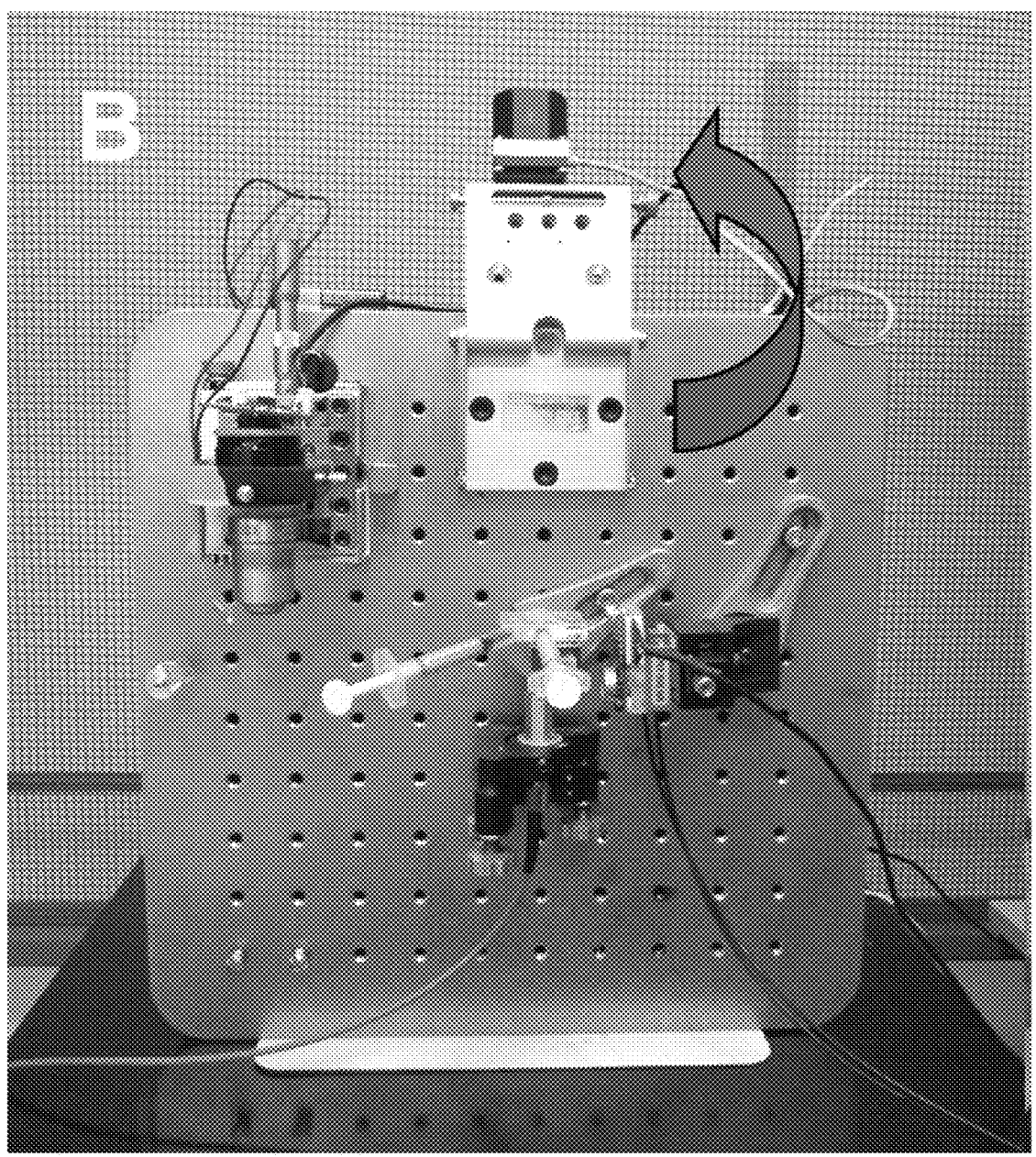
FIG. 2B shows the illustrative flip platform in the sample mounting position.
Figure 2C:
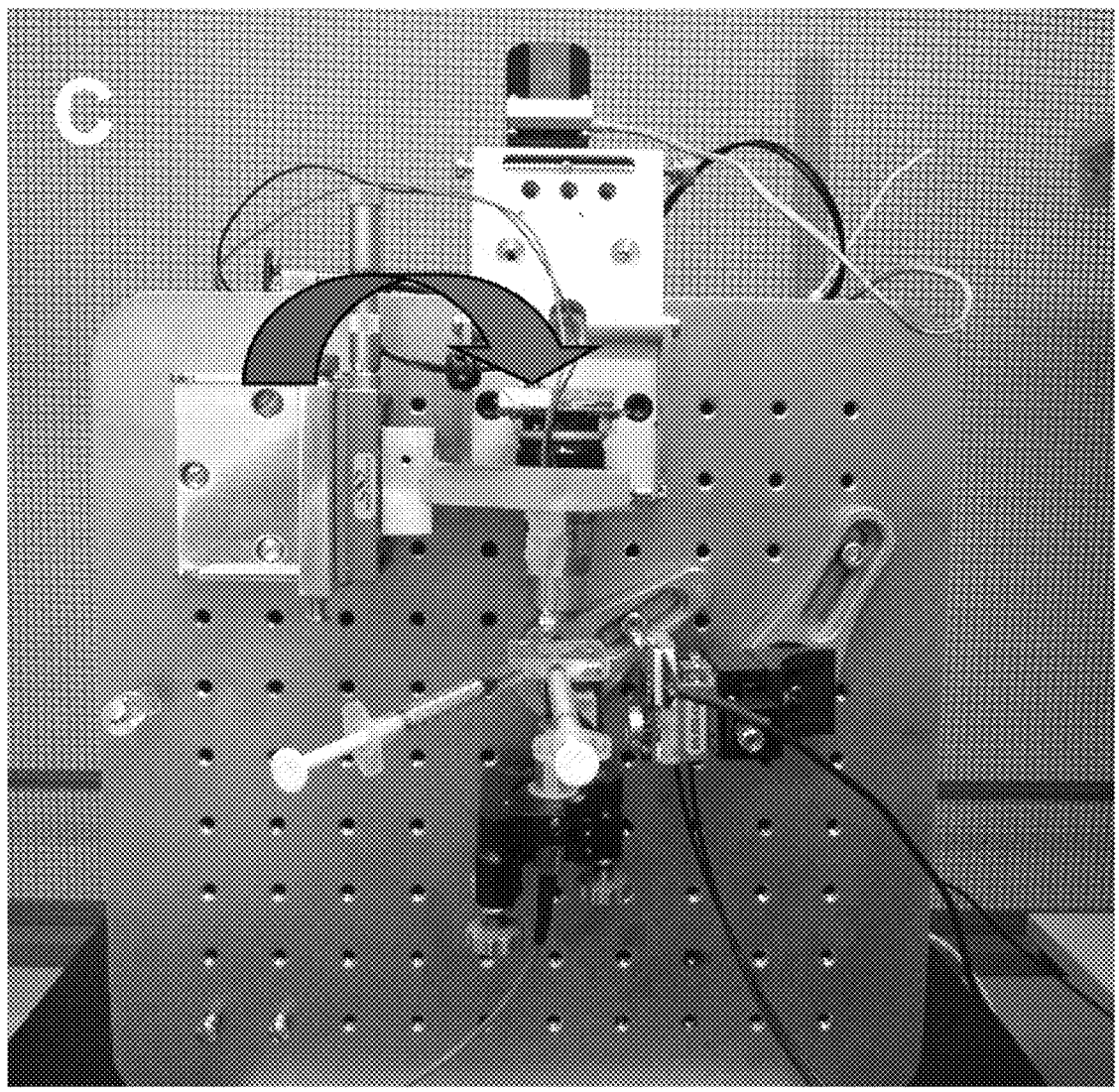
FIG. 2C shows the illustrative flip platform in the laser focusing position.
Figure 3:
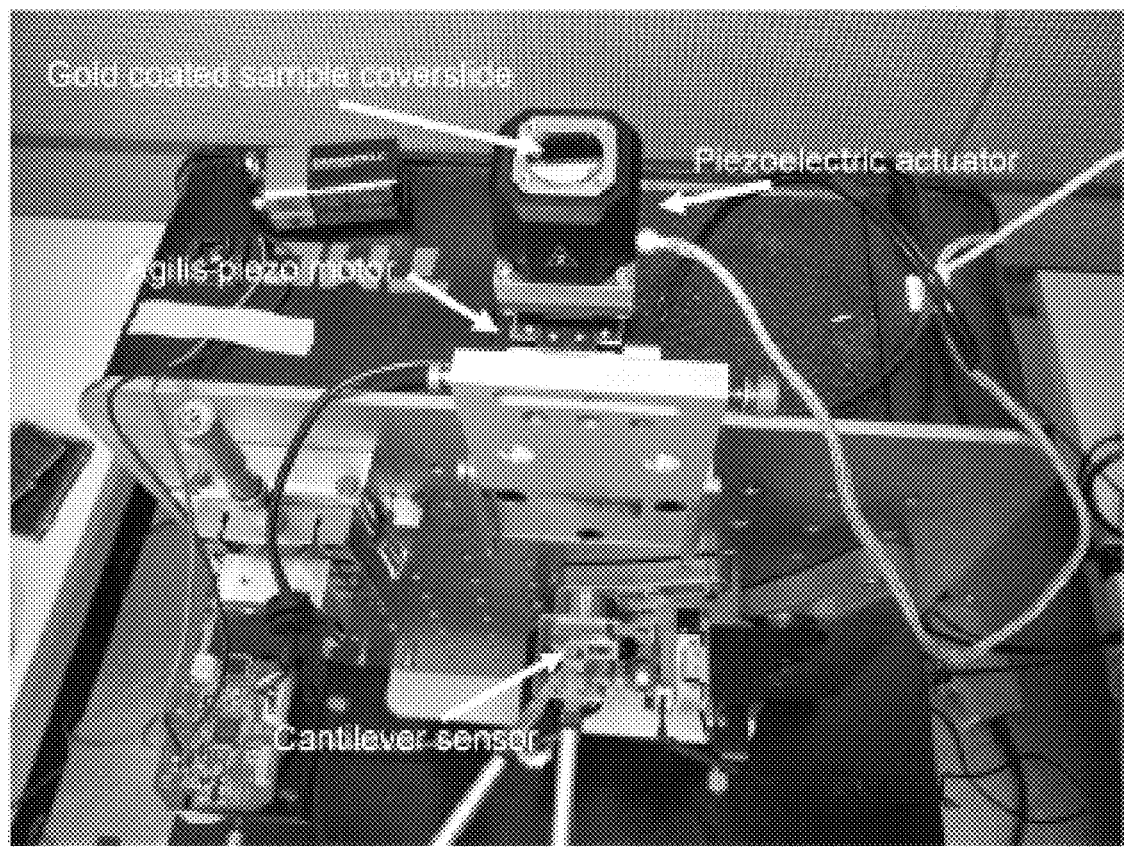
FIG. 3 is a top view of an illustrative flip piezo mount in the up position showing the sample coverslide, the piezo electric actuator and the piezo motor according to some embodiments of the disclosed subject matter.

As shown in FIG. 2 and FIG. 3, the device includes force spectrometer components that have a flip design. The flip design minimizes the number of moving parts of the spectrometer, thereby greatly reducing drift and difficulty of operation. In some embodiments, the flip design includes a flip platform onto which a remotely operated piezo-motor controls the positioning of the main piezoelectric actuator that actually pulls the molecules under feedback. In its measuring position (FIG. 2A), the flip platform is down and presents the sample to a cantilever mounted on the force sensor. In the set up configuration (FIG. 2B and FIG. 3), the piezo mount is flipped up allowing access to the cantilever holder for cantilever placement, and allowing the protein sample to be placed on the surface of the piezo. Once a cantilever is mounted in the force sensor, the video microscope is flipped-in to observe the cantilever at high magnification (FIG. 2C), allowing the operator to precisely focus the laser beam on the cantilever. Once this is done, the video microscope is flipped back, and the piezoelectric actuator with the new sample is flipped down into its measuring position (FIG. 2A). This arrangement and sequence of events is a feature of this device. In some embodiments, the flip-force spectrometer includes at least one flip mount for rapidly and reversibly switching positions of the camera and of the piezo-electric positioner.

Figure 4:
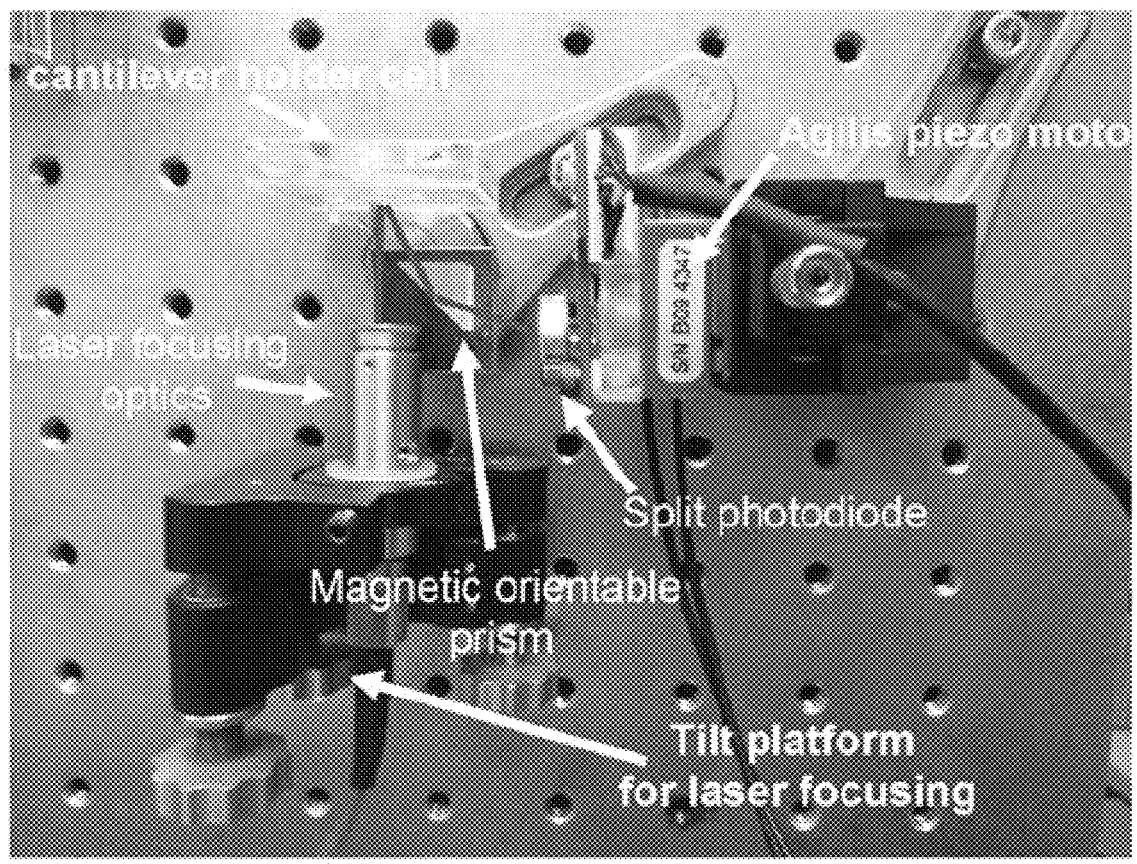
FIG. 4 is a detail front view of an illustrative force sensor according to some embodiments of the disclosed subject matter.

The force sensor may be a modification of AFM instrumentation altered to suit the requirements of a single protein force spectrometer, which include but are not limited to reduce drift, improve ease of operation, and minimize the number of moving parts. As shown in FIG. 4, the device includes a fixed cantilever holder cell mounted with the cantilever facing up to enable the flip design and facilitate cantilever removal and laser focusing. As shown in FIG. 3, the laser is focused on the cantilever using a tilt platform while observing the operation with the video microscope. As shown in FIG. 4, the reflected beam is steered towards the split photodiode using a magnetic orientable prism mounted on magnets to eliminate drift. As shown in FIG. 4, the split photodiode is placed on top of an Agilis piezo motor to precisely position it remotely and automatically by the controlling computer. The device may include, for example, upwards placement of the cantilever, a magnetic mount for the deflecting prism, and an Agilis mounted photodiode which permits a fully hands-off remote operation.

The instrument as it stands is fully automatic and may operate for hours or days without intervention of the operator.

In another aspect, the instant disclosure relates to the use of the force-clamp spectrometer in a method for the measurement of the dynamics of chemical reactions. Dynamics may include, but are not limited to, kinetic rates and/or shifts in equilibrium.

In some embodiments, the force-clamp spectrometer is used in a method for the measurement of the folding of a substrate. In other embodiments, the force-clamp spectrometer is used in a method for the measurement of the unfolding of a substrate. In some embodiments, the dynamics of folding and/or unfolding are measured in real-time. In other embodiments, the dynamics of folding and/or unfolding are identified through a fingerprint signal, thus removing the risk of false positives and the need for control experiments. A fingerprint may include knowledge of the number of bonds within the substrate and/or the location of these bonds. The fingerprint can thereby be verified as the number of steps and/or the amplitude of these steps when monitoring the substrate extension during the reaction, for example. In other embodiments, the dynamics are measured as a function of a force applied. This force may be applied to a bond, allowing for force spectroscopy of the reactions involving the bond. In some embodiments, the folding or unfolding of a substrate is catalyzed by an enzyme.

In other embodiments, the force-clamp spectrometer is used in a method for the measurement of the cleavage of a bond in a substrate. In some embodiments, the dynamics of bond cleavage are measured in real-time. In other embodiments, the dynamics of bond cleavage are identified through a fingerprint signal, thus removing the risk of false positives and the need for control experiments. A fingerprint may include knowledge of the number of bonds within the substrate and/or the location of these bonds. The fingerprint can thereby be verified as the number of steps and/or the amplitude of these steps when monitoring the substrate extension during the reaction, for example. In other embodiments, the dynamics of bond cleavage are measured as a function of a force applied. In some embodiments, the bond is cleaved by a compound that reacts with the bond. In other embodiments, bond cleavage is catalyzed by an enzyme.

In yet other embodiments, the force-clamp spectrometer is used in a method for the measurement of the formation of a bond in a substrate. In some embodiments, the dynamics of bond formation are measured in real-time. In other embodiment, the dynamics of bond formation are identified through a fingerprint signal, thus removing the risk of false positives and the need for control experiments. A fingerprint may include knowledge of the number of bonds within the substrate and/or the location of these bonds. The fingerprint can thereby be verified as the number of steps and/or the amplitude of these steps when monitoring the substrate extension during the reaction, for example. In other embodiments, the dynamics of bond formation are measured as a function of a force. In some embodiments, bond formation is catalyzed by an enzyme.

In one aspect, the instant disclosure relates to a method of measuring the dynamics of bond cleavage in a substrate by single-molecule force spectroscopy, the method comprising a) placing a sample comprising a substrate in the force-clamp spectrometer described herein; b) applying a force to the sample, wherein the force extends the substrate and; c) detecting the absence of a bond(s), wherein the absence is indicative of bond cleavage. Dynamics may include, but are not limited to, kinetic rates and/or shifts in equilibrium. In one embodiment, the dynamics include kinetic rates. The absence of a bond may be detected, for example, by the total length of the substrate, and/or the length increase upon cleavage of a bond. In one embodiment, steps b) and c) of the method described are repeated over time. In another embodiment, the method further comprises measuring the dynamics of one or more additional substrates.

In another aspect, the instant disclosure relates to a method of measuring the dynamics of bond formation in a substrate by single-molecule force spectroscopy, the method comprising a) placing a sample comprising a substrate in the force-clamp spectrometer described herein; b) applying a force to the sample, wherein the force extends the substrate; and; c) detecting the presence of bond(s), wherein the presence is indicative of bond formation. In one embodiment, the method further comprises measuring the dynamics of substrate folding, wherein the presence of a second bond is indicative of substrate folding. The presence of a bond may be detected, for example, by the total length of the substrate, and/or the length increase upon formation of a bond. In one embodiment, the dynamics of substrate folding and bond formation are measured independently. Dynamics may include, but are not limited to, kinetic rates and/or shifts in equilibrium. In one embodiment, the dynamics include kinetic rates. In another embodiment, steps b) and c) of the method described are repeated over time. In another embodiment, the method further comprises measuring the dynamics of one or more additional substrates.

In one aspect, the instant disclosure relates to a method of measuring substrate folding by single-molecule force spectroscopy, the method comprising a) placing a sample comprising a substrate in the force-clamp spectrometer described herein; b) applying a force to the sample, wherein the force extends the substrate; and; c) detecting the presence of bond(s), wherein the presence is indicative of substrate folding. The presence of a bond may be detected, for example, by the total length of the substrate, and/or the length increase upon formation of a bond. Dynamics may include, but are not limited to, kinetic rates and/or shifts in equilibrium. In one embodiment, the dynamics include kinetic rates. In one embodiment, steps b) and c) of the method described are repeated over time. In another embodiment, the method further comprises measuring the dynamics of one or more additional substrates.

In another aspect, the instant disclosure relates to a method of measuring substrate unfolding by single-molecule force spectroscopy, the method comprising a) placing a sample comprising a substrate in the force-clamp spectrometer described herein; b) applying a force to the sample, wherein the force extends the substrate; and; c) detecting the absence of bond(s), wherein the absence is indicative of substrate unfolding. The absence of a bond may be detected, for example, by the total length of the substrate, and/or the length increase upon cleavage of a bond. Dynamics may include, but are not limited to, kinetic rates and/or shifts in equilibrium. In one embodiment, the dynamics include kinetic rates. In one embodiment, steps b) and c) of the method described are repeated over time. In another embodiment, the method further comprises measuring the dynamics of one or more additional substrates.

In one aspect, the instant disclosure relates to a method of measuring the dynamics of folding and bond formation in a substrate by single-molecule force spectroscopy, the method comprising a) placing a sample comprising a substrate in the force-clamp spectrometer described herein; b) applying a force to the sample, wherein the force extends the substrate; and; c) detecting the presence of a first bond(s) and a second bond(s), wherein the presence of a first bond(s) is indicative of substrate folding and the presence of a second bond(s) is indicative of bond formation. In one embodiment, the dynamics of substrate folding and bond formation are measured independently. The presence of a bond may be detected, for example, by the total length of the substrate, and/or the length increase upon formation of a bond. Dynamics may include, but are not limited to, kinetic rates and/or shifts in equilibrium. In one embodiment, the first bond is a non-covalent bond. In another embodiment, the first bond is a covalent bond. In one embodiment, the second bond is a non-covalent bond. In another embodiment, the second bond is a covalent bond. In another embodiment, the first bond is a non-covalent bond and the second bond is a covalent bond. In another embodiment, the first bond is a covalent bond and the second bond is a non-covalent bond. In one embodiment, the dynamics include kinetic rates. In one embodiment, steps b) and c) of the method described are repeated over time. In another embodiment, the method further comprises measuring the dynamics of one or more additional substrates.

In another aspect, the instant disclosure relates to a method of measuring the dynamics of unfolding and bond cleavage of a substrate by single-molecule force spectroscopy, the method comprising a) placing a sample comprising a substrate in the force-clamp spectrometer described herein; b) applying a force to the sample, wherein the force extends the substrate; and c) detecting the absence of a first bond(s) and a second bond(s), wherein the absence of a first bond is indicative of substrate unfolding and the absence of a second bond is indicative of bond cleavage. The absence of a bond may be detected, for example, by the total length of the substrate, and/or the length increase upon cleavage of a bond. In one embodiment, the first bond is a non-covalent bond. In another embodiment, the first bond is a covalent bond. In one embodiment, the second bond is a non-covalent bond. In another embodiment, the second bond is a covalent bond. In another embodiment, the first bond is a non-covalent bond and the second bond is a covalent bond. In another embodiment, the first bond is a covalent bond and the second bond is a non-covalent bond. In one embodiment, the dynamics of substrate unfolding and bond cleavage are measured independently. Dynamics may include, but are not limited to, kinetic rates and/or shifts in equilibrium. In one embodiment, the dynamics include kinetic rates. In another embodiment, steps b) and c) of the method described are repeated over time. In another embodiment, the method further comprises measuring the dynamics of one or more additional substrates.

In some embodiments, the sample comprises a compound that reacts with one or more bond(s). The compound may be, but is not limited to, a reducing agent (for example, dithiothreitol or DTT), an oxidizing agent, a nanoparticle, or a small molecule. In another embodiment, the sample may comprise an ion.

In some embodiments, the sample comprises an inhibitor. In other embodiments, the sample comprises an activator. Inhibitors and activators may be, but are not limited to, small molecules. In one embodiment, the inhibitor is an enzyme inhibitor. In another embodiment, the activator is an enzyme activator.

In one embodiment, the sample comprises one or more enzyme(s). In one embodiment, the enzyme is an oxidoreductase enzyme. In another embodiment, the enzyme is an oxidase enzyme. In one embodiment, the enzyme is thioredoxin. In another embodiment, the oxidase enzyme is protein disulfide isomerase. In another embodiment, the enzyme is a protease, esterase, phosphodiesterase, or glycosidase. In another embodiment, the enzyme comprises one or more mutations. Mutations may include, but are not limited to, substitutions, deletions and/or point mutations.

In another aspect, the instant disclosure relates to a substrate used for measuring the dynamics of chemical reactions. In one embodiment, the substrate is a polymer. In another embodiment, the substrate has a folded structure. In one embodiment, the substrate is a protein or a polypeptide. In one embodiment, the substrate is a natural protein or natural polypeptide. In one embodiment, the substrate is cadherin, selectin, IgCAM, fibronectin, fibrilin or titin. In another embodiment, the substrate is an engineered polymer. In one embodiment, the polymer contains domain repeats. In one embodiment, the substrate is a nucleic acid. A nucleic acid may include, but is not limited to, a deoxyribonucleic acid, a ribonucleic acid or an oligonucleotide. In another embodiment, the substrate is a polysaccharide. In another embodiment, the substrate contains domain repeats. In one embodiment, the substrate comprises one or more bonds. In one embodiment, the bond is a single bond. In another embodiment, the bond is a double bond. In one embodiment, the bond is a covalent bond. In another embodiment, the bond is a non-covalent bond. In another embodiment, the bond is a disulfide bond. In another embodiment, the substrate comprises one or more mutations. Mutations may include, but are not limited to, substitutions, deletions and/or point mutations. Such mutations can be made using any suitable mutagenesis method known in the art.

In one embodiment, the substrate is used for measuring the dynamics of folding. In another embodiment, the substrate is used for measuring the dynamics of unfolding. In one embodiment, the substrate is used for measuring the dynamics of cleavage of a bond. In another embodiment, the substrate is used for measuring the dynamics of formation of a bond. Dynamics may include, but are not limited to, kinetic rates and/or shifts in equilibrium. In one embodiment, the dynamics include kinetic rates.

Although several substrates are described herein, one of skill in the art will recognize that other substrates can also be used in the methods described herein. Substrates can be also generated using the methods described herein, including, but not limited to therapeutic proteins and proteins susceptible to industrial use.

Substrates produced according to the methods described herein can be from any source or origin and can include a substrate found in prokaryotes, viruses, and eukaryotes, including fungi, plants, yeasts, insects, and animals, including mammals (e.g. humans). Substrates that can be produced according to the methods described herein include, but are not limited to any polypeptide sequences, known or hypothetical or unknown, which can be identified using common sequence repositories. Example of such sequence repositories include, but are not limited to GenBank EMBL, DDBJ and the NCBI. Other repositories can easily be identified by searching on the internet. Substrates that can be produced using the methods described herein also include polypeptides have at least about 60%, 70%, 75%, 80%, 90%, 95%, or at least about 99% or more identity to any known or available polypeptide (e.g., a therapeutic polypeptide, a diagnostic polypeptide, an industrial enzyme, or portion thereof, and the like). Substrates that can be produced using the methods described herein also include nucleic acids that have at least about 60%, 70%, 75%, 80%, 90%, 95%, or at least about 99% or more identity to any known or available nucleic acid.

Protein and polypeptide substrates that can be produced according to the methods described herein also include polypeptides comprising one or more non-natural amino acids. As used herein, a non-natural amino acid can be, but is not limited to, an amino acid comprising a moiety where a chemical moiety is attached, such as an aldehyde- or keto-derivatized amino acid, or a non-natural amino acid that includes a chemical moiety. A non-natural amino acid can also be an amino acid comprising a moiety where a saccharide moiety can be attached, or an amino acid that includes a saccharide moiety.

Protein and polypeptide substrates can also comprise peptide derivatives (for example, that contain one or more non-naturally occurring amino acids). In specific embodiments, the library members contain one or more non-natural or non-classical amino acids or cyclic peptides. Non-classical amino acids include but are not limited to the D-isomers of the common amino acids, -amino isobutyric acid, 4-aminobutyric acid, Abu, 2-amino butyric acid; -Abu, -Ahx, 6-amino hexanoic acid; Aib, 2-amino isobutyric acid; 3-amino propionic acid; ornithine; norleucine; norvaline, hydroxyproline, sarcosine, citrulline, cysteic acid, t-butylglycine, t-butylalanine, phenylglycine, cyclohexylalanine, .beta.-alanine, designer amino acids such as .beta.-methyl amino acids, C-methyl amino acids, N-methyl amino acids, fluoro-amino acids and amino acid analogs in general. Furthermore, the amino acid can be D (dextrorotary) or L (levorotary).

A substrate may comprise substrates that are well known to those of skill in the art and have been described in detail in the scientific literature. Several common modifications, such as glycosylation, lipid attachment, sulfation, gamma-carboxylation of glutamic acid residues, hydroxylation and ADP-ribosylation, for instance, are described in most basic texts, such as, for instance Creighton, Protein Structure and Molecular Properties, 2nd ed., W. H. Freeman and Company (1993). Many detailed reviews are available on this subject, such as, for example, those provided by Wold, in Johnson (ed.), Posttranslational Covalent Modification of Proteins, pgs. 1-12, Academic Press (1983); Seifter et al., Meth. Enzymol. 182: 626-646 (1990) and Rattan et al., Ann. N.Y. Acad. Sci. 663: 48-62 (1992).

One can prepare a protein or polypeptide substrate that has post-translational modifications. Examples of types of post-translational modifications include, but are not limited to: (Z)-dehydrobutyrine; 1-chondroitin sulfate-L-aspartic acid ester; 1'-glycosyl-L-tryptophan; 1'-phospho-L-histidine; 1-thioglycine; 2'-(S-L-cysteinyl)-L-histidine; 2'-[3-carboxamido(trimethylammonio)propyl]-L-histidine; 2'-alpha-mannosyl-L-tryptophan; 2-methyl-L-glutamine; 2-oxobutanoic acid; 2-pyrrolidone carboxylic acid; 3'-(1'-L-histidyl)-L-tyrosine; 3'-(8alpha-FAD)-L-histidine; 3'-(S-L-cysteinyl)-L-tyrosine; 3',3",5'-triiodo-L-thyronine; 3'-4'-phospho-L-tyrosine; 3-hydroxy-L-proline; 3'-methyl-L-histidine; 3-methyl-L-lanthionine; 3'-phospho-L-histidine; 4'-(L-tryptophan)-L-tryptophyl quinone; 42 N-cysteinyl-glycosylphosphatidylinositolethanolamine; 43-(T-L-histidyl)-L-tyrosine; 4-hydroxy-L-arginine; 4-hydroxy-L-lysine; 4-hydroxy-L-proline; 5'-(N6-L-lysine)-L-topaquinone;

5-hydroxy-L-lysine; 5-methyl-L-arginine; alpha-1-microglobulin-Ig alpha complex chromophore; bis-L-cysteinyl bis-L-histidino diiron disulfide; bis-L-cysteinyl-L-N3'-histidino-L-serinyl tetrairon' tetrasulfide; chondroitin sulfate D-glucuronyl-D-galactosyl-D-galactosyl-D-xylosyl-L-serine; D-alanine; D-allo-isoleucine; D-asparagine; dehydroalanine; dehydrotyrosine; dermatan 4-sulfate D-glucuronyl-D-galactosyl-D-galactosyl-D-xylosyl-L-serine; D-glucuronyl-N-glycine; dipyrrolylmethanemethyl-L-cysteine; D-leucine; D-methionine; D-phenylalanine; D-serine; D-tryptophan; glycine amide; glycine oxazolecarboxylic acid; glycine thiazolecarboxylic acid; heme P450-bis-L-cysteine-L-tyrosine; heme-bis-L-cysteine; hemediol-L-aspartyl ester-L-glutamyl ester; hemediol-L-aspartyl ester-L-glutamyl ester-L-methionine sulfonium; heme-L-cysteine; heme-L-histidine; heparan sulfate D-glucuronyl-D-galactosyl-D-galactosyl-D-xylosyl-L-serine; heme P450-bis-L-cysteine-L-lysine; hexakis-L-cysteinyl hexairon hexasulfide; keratan sulfate D-glucuronyl-D-galactosyl-D-galactosyl-D-xylosyl-L-threonine; L oxoalanine-lactic acid; L phenyllactic acid; 1'-(8alpha-FAD)-L-histidine; L-2',4',5'-topaquinone; L-3',4'-dihydroxyphenylalanine; L-3',4',5'-trihydroxyphenylalanine; L-4'-bromophenylalanine; L-6'-bromotryptophan; L-alanine amide; L-alanyl imidazolinone glycine; L-allysine; L-arginine amide; L-asparagine amide; L-aspartic 4-phosphoric anhydride; L-aspartic acid 1-amide; L-beta-methylthioaspartic acid; L-bromohistidine; L-citrulline; L-cysteine amide; L-cysteine glutathione disulfide; L-cysteine methyl disulfide; L-cysteine methyl ester; L-cysteine oxazolecarboxylic acid; L-cysteine oxazolinecarboxylic acid; L-cysteine persulfide; L-cysteine sulfenic acid; L-cysteine sulfinic acid; L-cysteine thiazolecarboxylic acid; L-cysteinyl homocitryl molybdenum-heptairon-nonasulfide; L-cysteinyl imidazolinone glycine; L-cysteinyl molybdopterin; L-cysteinyl molybdopterin guanine dinucleotide; L-cystine; L-erythro-beta-hydroxyasparagine; L-erythro-beta-hydroxyaspartic acid; L-gamma-carboxyglutarnic acid; L-glutamic acid 1-amide; L-glutamic acid 5-methyl ester; L-glutamine amide; L-glutamyl 5-glycerylphosphorylethanolamine; L-histidine amide; L-isoglutamyl-polyglutamic acid; L-isoglutamyl-polyglycine; L-isoleucine amide; L-lanthionine; L-leucine amide; L-lysine amide; L-lysine thiazolecarboxylic acid; L-lysinoalanine; L-methionine amide; L-methionine sulfone; L-phenyalanine thiazolecarboxylic acid; L-phenylalanine amide; L-proline amide; L-selenocysteine; L-selenocysteinyl molybdopterin guanine dinucleotide; L-serine amide; L-serine thiazolecarboxylic acid; L-seryl imidazolinone glycine; L-T-bromophenylalanine; L-T-bromophenylalanine; L-threonine amide; L-thyroxine; L-tryptophan amide; L-tryptophyl quinone; L-tyrosine amide; L-valine amide; meso-lanthionine; N-(L-glutamyl)-L-tyrosine; N-(L-isoaspartyl)-glycine; N-(L-isoaspartyl)-L-cysteine; N,N,N-trimethyl-L-alanine; N,N-dimethyl-L-proline; N2-acetyl-L-lysine; N2-succinyl-L-tryptophan; N4-(ADP-ribosyl)-L-asparagine; N4-glycosyl-L-asparagine; N4-hydroxymethyl-L-asparagine; N4-methyl-L-asparagine; N5-methyl-L-glutamine; N6-1-carboxyethyl-L-lysine; N6-(4-amino hydroxybutyl)-L-lysine; N6-(L-isoglutamyl)-L-lysine; N6-(phospho-5'-adenosine)-L-lysine; N6-(phospho-5'-guanosine)-L-lysine; N6,N6,N6-trimethyl-L-lysine; N6,N6-dimethyl-L-lysine; N6-acetyl-L-lysine; N6-biotinyl-L-lysine; N6-carboxy-L-lysine; N6-formyl-L-lysine; N6-glycyl-L-lysine; N6-lipoyl-L-lysine; N6-methyl-L-lysine; N6-methyl-N-6-poly(N-methyl-propylamine)-L-lysine; N6-mureinyl-L-lysine; N6-myristoyl-L-lysine; N6-palmitoyl-L-lysine; N6-pyridoxal phosphate-L-lysine; N6-pyruvic acid 2-iminyl-L-lysine; N6-retinal-L-lysine; N-acetylglycine; N-acetyl-L-glutamine; N-acetyl-L-alanine; N-acetyl-L-aspartic acid; N-acetyl-L-cysteine; N-acetyl-L-glutamic acid; N-acetyl-L-isoleucine; N-acetyl-L-methionine; N-acetyl-L-proline; N-acetyl-L-serine; N-acetyl-L-threonine; N-acetyl-L-tyrosine; N-acetyl-L-valine; N-alanyl-glycosylphosphatidylinositolethanolamine; N-asparaginyl-glycosylphosphatidylinositolethanolamine; N-aspartyl-glycosylphosphatidylinositolethanolamine; N-formylglycine; N-formyl-L-methionine; N-glycyl-glycosylphosphatidylinositolethanolamine; N-L-glutamyl-poly-L-glutamic acid; N-methylglycine; N-methyl-L-alanine; N-methyl-L-methionine; N-methyl-L-phenylalanine; N-myristoyl-glycine; N-palmitoyl-L-cysteine; N-pyruvic acid 2-iminyl-L-cysteine; N-pyruvic acid 2-iminyl-L-valine; N-seryl-glycosylphosphatidylinositolethanolamine; N-seryl-glycosyOSPhingolipidinositolethanolamine; O-(ADP-ribosyl)-L-serine; O-(phospho-5'-adenosine)-L-threonine; O-(phospho-5'-DNA)-L-serine; O-(phospho-5'-DNA)-L-threonine; O-(phospho-5'rRNA)-L-serine; 0-(phosphoribosyl dephospho-coenzyme A)-L-serine; O-(sn-1-glycerophosphoryl)-L-serine; O4'-(8alpha-FAD)-L-tyrosine; O4'-(phospho-5'-adenosine)-L-tyrosine; O4'-(phospho-5'-DNA)-L-tyrosine; O4'-(phospho-5'-RNA)-L-tyrosine; O4'-(phospho-5'-uridine)-L-tyrosine; O4-glycosyl-L-hydroxyproline; O4'-glycosyl-L-tyrosine; O4'-sulfo-L-tyrosine; O5-glycosyl-L-hydroxylysine; O-glycosyl-L-serine; O-glycosyl-L-threonine; omega-N-(ADP-ribosyl)-L-arginine; omega-N-omega-N'-dimethyl-L-arginine; omega-N-methyl-L-arginine; omega-N-omega-N-dimethyl-L-arginine; omega-N-phospho-L-arginine; O' octanoyl-L-serine; O-palmitoyl-L-serine; O-palmitoyl-L-threonine; O-phospho-L-serine; O-phospho-L-threonine; O-phospho-pantetheine-L-serine; phycoerythrobilin-bis-L-cysteine; phycourobilin-bis-L-cysteine; pyrroloquinoline quinone; pyruvic acid; S hydroxycinnamyl-L-cysteine; S-(2-aminovinyl)methyl-D-cysteine; S-(2-aminovinyl)-D-cysteine; S-(6-FW-L-cysteine; S-(8alpha-FAD)-L-cysteine; S-(ADP-ribosyl)-L-cysteine; S-(L-isoglutamyl)-L-cysteine; S-12-hydroxyfarnesyl-L-cysteine; S-acetyl-L-cysteine; S-diacylglycerol-L-cysteine; S-diphytanylglycerot diether-L-cysteine; S-farnesyl-L-cysteine; S-geranylgeranyl-L-cysteine; S-glycosyl-L-cysteine; S-glycyl-L-cysteine; S-methyl-L-cysteine; S-nitrosyl-L-cysteine; S-palmitoyl-L-cysteine; S-phospho-L-cysteine; S-phycobiliviolin-L-cysteine; S-phycocyanobilin-L-cysteine; S-phycoerythrobilin-L-cysteine; S-phytochromobilin-L-cysteine; S-selenyl-L-cysteine; S-sulfo-L-cysteine; tetrakis-L-cysteinyl diiron disulfide; tetrakis-L-cysteinyl iron; tetrakis-L-cysteinyl tetrairon tetrasulfide; trans-2,3-cis 4-dihydroxy-L-proline; tris-L-cysteinyl triiron tetrasulfide; tris-L-cysteinyl triiron trisulfide; tris-L-cysteinyl-L-aspartato tetrairon tetrasulfide; tris-L-cysteinyl-L-cysteine persulfido-bis-L-glutamato-L-histidino tetrairon disulfide trioxide; tris-L-cysteinyl-L-N3'-histidino tetrairon tetrasulfide; tris-L-cysteinyl-L-NM'-histidino tetrairon tetrasulfide; and tris-L-cysteinyl-L-serinyl tetrairon tetrasulfide.

Additional examples of post translational modifications can be found in web sites such as the Delta Mass database based on Krishna, R. G. and F. Wold (1998). Posttranslational Modifications. Proteins—Analysis and Design. R. H. Angeletti. San Diego, Academic Press. 1: 121-206; Methods in Enzymology, 193, J. A. McClosky (ed) (1990), pages 647-660; Methods in Protein Sequence Analysis edited by Kazutomo Imahori and Fumio Sakiyama, Plenum Press, (1993) "Post-translational modifications of proteins" R. G. Krishna and F. Wold pages 167-172; "GlycoSuiteDB: a new curated relational database of glycoprotein glycan structures and their biological sources" Cooper et al., Nucleic Acids Res. 29; 332-335 (2001) "O-GLYCBASE version 4.0: a revised database of O-glycosylated proteins" Gupta et al., Nucleic Acids Research, 27: 370-372 (1999); and "PhosphoBase, a database of phosphorylation sites: release 2.0.", Kreegipuu et al., Nucleic Acids Res 27(1):237-239 (1999) see also, WO 02/211 39A2, the disclosure of which is incorporated herein by reference in its entirety.

Exemplary substrates that can be produced according to the methods described herein include but are not limited to, cytokines, inflammatory molecules, growth factors, their receptors, and oncogene products or portions thereof. Examples of cytokines, inflammatory molecules, growth factors, their receptors, and oncogene products include, but are not limited to e.g., alpha-1 antitrypsin, Angiostatin, Antihemolytic factor, antibodies (including an antibody or a functional fragment or derivative thereof selected from: Fab, Fab', F(ab)2, Fd, Fv, ScFv, diabody, tribody, tetrabody, dimer, trimer or minibody), angiogenic molecules, angiostatic molecules, Apolipopolypeptide, Apopolypeptide, Asparaginase, Adenosine deaminase, Atrial natriuretic factor, Atrial natriuretic polypeptide, Atrial peptides, Angiotensin family members, Bone Morphogenic Polypeptide (BMP-1, BMP-2, BMP-3, BMP-4, BMP-5, BMP-6, BMP-7, BMP-8a, BMP-8b, BMP-10, BMP-15, etc.); C—X—C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant polypeptide-1, Monocyte chemoattractant polypeptide-2, Monocyte chemoattractant polypeptide-3, Monocyte inflammatory polypeptide-1 alpha, Monocyte inflammatory polypeptide-1 beta, RANTES, 1309, R83915, R91733, HCC1, T58847, D31065, T64262), CD40 ligand, C-kit Ligand, Ciliary Neurotrophic Factor, Collagen, Colony stimulating factor (CSF), Complement factor 5a, Complement inhibitor, Complement receptor 1, cytokines, (e.g., epithelial Neutrophil Activating Peptide-78, GRO alpha/MGSA, GRO beta, GRO gamma, MIP-1 alpha, MIP-1 delta, MCP-1), deoxyribonucleic acids, Epidermal Growth Factor (EGF), Erythropoietin ("EPO", representing a preferred target for modification by the incorporation of one or more non-natural amino acid), Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog polypeptides (e.g., Sonic, Indian, Desert), Hemoglobin, Hepatocyte Growth Factor (HGF), Hepatitis viruses, Hirudin, Human serum albumin, Hyalurin-CD44, Insulin, Insulin-like Growth Factor (IGF-I, IGF-II), interferons (e.g., interferon-alpha, interferon-beta, interferon-gamma, interferon-epsilon, interferon-zeta, interferon-eta, interferon-kappa, interferon-lambda, interferon-T, interferon-zeta, interferon-omega), glucagon-like peptide (GLP-1), GLP-2, GLP receptors, glucagon, other agonists of the GLP-1R, natriuretic peptides (ANP, BNP, and CNP), Fuzeon and other inhibitors of HIV fusion, Hurudin and related anticoagulant peptides, Prokineticins and related agonists including analogs of black mamba snake venom, TRAIL, RANK ligand and its antagonists, calcitonin, amylin and other glucoregulatory peptide hormones, and Fc fragments, exendins (including exendin-4), exendin receptors, interleukins (e.g., IL-1, IL-2, IL-3, IL-4, IL-5, IL-6, IL-7, IL-8, IL-9, IL-10, IL-11, IL-12, etc.), I-CAM-1/LFA-1, Keratinocyte Growth Factor (KGF), Lactoferrin, leukemia inhibitory factor, Luciferase, Neurturin, Neutrophil inhibitory factor (NIF), oncostatin M, Osteogenic polypeptide, Parathyroid hormone, PD-ECSF, PDGF, peptide hormones (e.g., Human Growth Hormone), Oncogene products (Mos, Rel, Ras, Raf, Met, etc.), Pleiotropin, Polypeptide A, Polypeptide G, Pyrogenic exotoxins A, B, and C, Relaxin, Renin, ribonucleic acids, SCF/c-kit, Signal transcriptional activators and suppressors (p53, Tat, Fos, Myc, Jun, Myb, etc.), Soluble complement receptor 1, Soluble I-CAM 1, Soluble interleukin receptors (IL-1, 2, 3, 4, 5, 6, 7, 9, 10, 11, 12, 13, 14, 15), soluble adhesion molecules, Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), Steroid hormone receptors (such as those for estrogen, progesterone, testosterone, aldosterone, LDL receptor ligand and corticosterone), Superoxide dismutase (SOD), Toll-like receptors (such as Flagellin), Toxic shock syndrome toxin (TSST-1), Thymosin a 1, Tissue plasminogen activator, transforming growth factor (TGF-alpha, TGF-beta), Tumor necrosis factor beta (TNF beta), Tumor necrosis factor receptor (TNFR), Tumor necrosis factor-alpha (TNF alpha), transcriptional modulators (for example, genes and transcriptional modular polypeptides that regulate cell growth, differentiation and/or cell regulation), Vascular Endothelial Growth Factor (VEGF), virus-like particle, VLA-4/VCAM-1, Urokinase, signal transduction molecules, estrogen, progesterone, testosterone, aldosterone, LDL, corticosterone.

Other substrates that can be produced according to the methods described herein include, but are not limited to, agriculturally related polypeptides such as insect resistance polypeptides (e.g., Cry polypeptides), starch and lipid production enzymes, plant and insect toxins, toxin-resistance polypeptides, Mycotoxin detoxification polypeptides, plant growth enzymes (e.g., Ribulose 1,5-Bisphosphate Carboxylase/Oxygenase), lipoxygenase, and Phosphoenolpyruvate carboxylase.

Other substrates that can be produced according to the methods described herein include, but are not limited to, antibodies, immunoglobulin domains of antibodies and their fragments. Examples of antibodies include, but are not limited to antibodies, antibody fragments, antibody derivatives, Fab fragments, Fab' fragments, F(ab)2 fragments, Fd fragments, Fv fragments, single-chain Fv fragments (scFv), diabodies, tribodies, tetrabodies, dimers, trimers, and minibodies.

In another embodiment, the disclosed subject matter is directed to a composition comprising a substrate for use in the methods described herein and produced according to the methods described herein, and an additional component selected from the group consisting of pharmaceutically acceptable diluents, carriers, excipients and adjuvants.

Substrates that can be produced according to the methods described herein can also further comprise a chemical moiety selected from the group consisting of: cytotoxins, pharmaceutical drugs, dyes or fluorescent labels, a nucleophilic or electrophilic group, a ketone or aldehyde, azide or alkyne compounds, photocaged groups, tags, a peptide, a polypeptide, a polypeptide, an oligosaccharide, polyethylene glycol with any molecular weight and in any geometry, polyvinyl alcohol, metals, metal complexes, polyamines, imidizoles, carbohydrates, lipids, biopolymers, particles, solid supports, a polymer, a targeting agent, an affinity group, any agent to which a complementary reactive chemical group can be attached, biophysical or biochemical probes, isotypically-labeled probes, spin-label amino acids, fluorophores, aryl iodides and bromides.

In some embodiments, the disclosed subject matter involves mutating nucleotide sequences of substrates to add/create or remove/disrupt sequences. Such mutations can be made using any suitable mutagenesis method known in the art, including, but not limited to, site-directed mutagenesis, oligonucleotide-directed mutagenesis, positive antibiotic selection methods, unique restriction site elimination (USE), deoxyuridine incorporation, phosphorothioate incorporation, and PCR-based mutagenesis methods. Details of such methods can be found in, for example, Lewis et al., (1990) Nucl. Acids Res. 18, p 3439; Bohnsack et al., (1996) Meth. Mol. Biol. 57, p 1; Vavra et al., (1996) Promega Notes 58, 30; Altered SitesII in vitro Mutagenesis Systems Technical Manual #TM001, Promega Corporation; Deng et al. (1992) Anal. Biochem. 200, p 81; Kunkel et al., (1985) Proc. Natl. Acad. Sci. USA 82, p 488; Kunke et al., (1987) Meth. Enzymol. 154, p 367; Taylor et al., (1985) Nucl. Acids Res. 13, p 8764; Nakamaye et al., (1986) Nucl. Acids Res. 14, p 9679; Higuchi et al., (1988) Nucl. Acids Res. 16, p 7351; Shimada et al., (1996) Meth. Mol. Biol. 57, p 157; Ho et al., (1989) Gene 77, p 51; Horton et al., (1989) Gene 77, p 61; and Sarkar et al., (1990) BioTechniques 8, p 404. Numerous kits for performing site-directed mutagenesis are commercially available, such as the QuikChange II Site-Directed Mutagenesis Kit and the Altered Sites II in vitro mutagenesis system. Such commercially available kits may also be used to optimize sequences. Other techniques that can be used to generate modified nucleic acid sequences are well known to those of skill in the art. See for example Sambrook et al., (2001) Molecular Cloning: A Laboratory Manual, 3rd Ed., Cold Spring Harbor Laboratory, Cold Spring Harbor, N.Y.

In another aspect, the instant disclosure relates to an enzyme used in the methods described herein. Examples of enzymes include, but are not limited to amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases. In one embodiment, the enzyme is an oxidoreductase enzyme. In another embodiment, the enzyme is thioredoxin. In one embodiment, the enzyme is an oxidase enzyme. In another embodiment, the enzyme is protein disulfide isomerase. In another embodiment, the enzyme is a protease, esterase, phosphodiesterase, or glycosidase. In another embodiment, the enzyme is a hydrolase. In one embodiment, the enzyme comprises one or more mutations. Mutations may include, but are not limited to, substitutions, deletions and/or point mutations. Such mutations can me made using any suitable mutagenesis method known in the art.

Although there are different ways to carry out the methods described herein, in one embodiment, the method is carried out as follows: a force-clamp spectrometer is used to stretch a specifically engineered polymer substrate containing a bond of interest, in an environment containing a bond-cleaving or a bond-forming reagent of interest. The force-clamp spectrometer applies a constant force to the substrate while measuring its extension. The force applied is high enough to break non-covalent bonds and elongate the substrate, but not high enough to break covalent bonds. The substrate is a polymer crosslinked with linker molecules containing the bond of interest. Each time one of the bonds of interest breaks, a concomitant substrate extension is detected. This stepwise extension corresponds to elongation of the substrate region that was previously sequestered behind the crosslink. The extension step has a precise length and thus constitutes a fingerprint for the bond cleavage reaction.

Although different types of substrates can be used, in one embodiment, a substrate is constructed by chemically ligating a polymer scaffold molecule with a customized linker molecule. In one embodiment, a protein polymer consisting of repeats of the I27 domain from human cardiac titin, expressed in *E. coli* and purified using affinity and size exclusion chromatography, is used as a scaffold. This protein is designed to contain in each domain two exposed cysteine residues, which are then crosslinked using a commercially available linker derivatized at both ends with maleimide. In another embodiment, the linker is designed to contain any bond not present in the scaffold molecule.

Disulfide Bond Reduction Studied by Single-Molecule Force Spectroscopy

Figure 19:
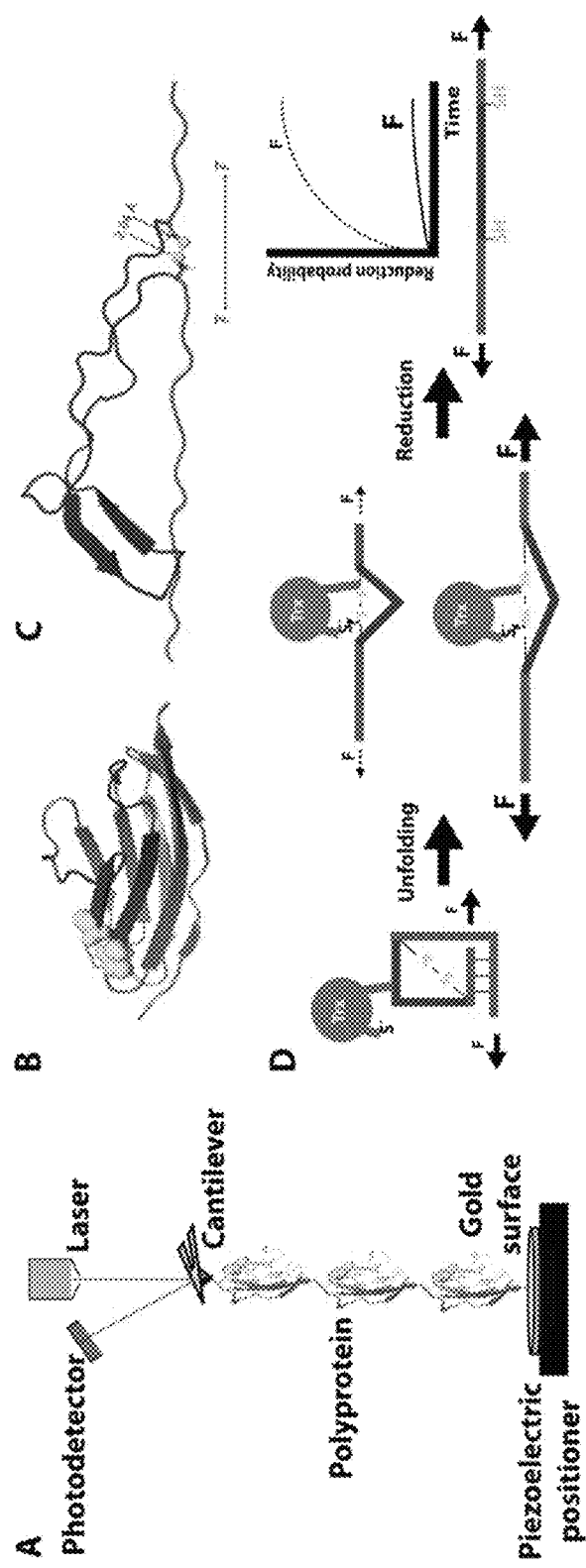
FIG. 19 is a schematic diagram of an illustrative single-molecule force spectroscopy assay for the detection of single reduction events by the enzyme thioredoxin.

Single-molecule force spectroscopy by Atomic Force Microscope (AFM) may be used to study the force dependency of the reduction of disulfide bonds both by chemicals and different Trxs. Although different types of substrates can be used in this approach, in one embodiment, the substrate is a polyprotein composed of several copies of an immunoglobulin domain from human cardiac titin (I27) is held between the tip of an AFM cantilever and a gold surface on top of a piezoelectric positioner (FIG. 19A). Polyproteins composed of eight I27 modules are usually employed. Each one of the I27 modules includes an engineered disulfide bond between residues 32 and 75, (I27G32C-A75C)8 (FIG. 19B). In the force-clamp mode of the AFM, it is possible to set the force exerted to the polyprotein up to several hundreds of pico Newtons. In this mode of operation, the deflection of the cantilever is held constant by an electronic feedback system that controls the extension of the polyprotein via the piezoelectric positioner. Response times around 5 ms can be easily achieved with the current instrumentation.

Figure 20:
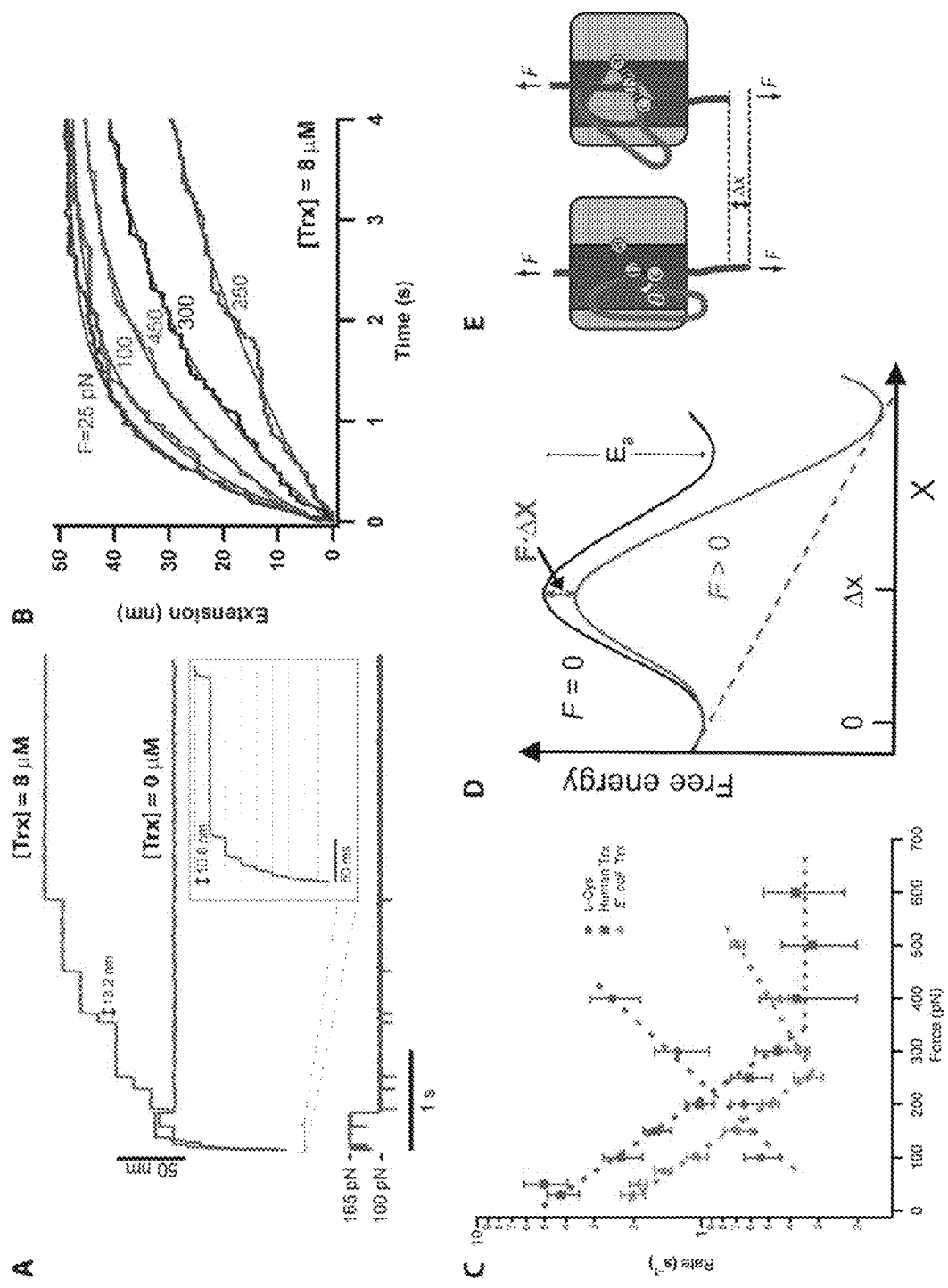
FIG. 20 presents data and a schematic diagram illustrating the use of an illustrative single-molecule force spectroscopy method as a probe to study chemical reactions and enzymatic catalysis.

The behavior of both I27 and I27G32C-A75C upon application of mechanical loads has been thoroughly examined by AFM. The unfolding rate of I27G32C-A75C around 200 pN is high (30 s−1). Thus, a double pulse protocol is employed to detect the reduction of disulfide bonds. A first pulse of force (160-190 pN during 0.3-1.0 s) unfolds the domains of the polyprotein. In these experiments, the disulfide bonds act as force transducers; therefore, the I27G32C-A75C modules extend only up to the disulfide bonds (FIGS. 19C and 19D), as forces higher than 1 nN are required to cleave covalent bonds. The individual unfolding events can be detected as step increases of ~10.8 nm in the length of the polyprotein, which give rise to a well-defined staircase in a length vs. time plot (FIG. 20A). Each step in size is accompanied by a sudden decrease in the force, which is rapidly compensated by the feedback (FIG. 20A). Therefore, this series of unfolding steps serves as a well-defined fingerprint that distinguishes the polyprotein of interest from any other spurious interactions. In addition, the unfolding events promote a steric switch which now allows the disulfide bonds that were buried in the protein to be reduced by reducing agents contained in the solution (FIG. 19D). After the unfolding of the domains, a second pulse of force is applied for up to minutes to monitor single disulfide reductions. When a disulfide bond is reduced, the region of the protein whose unfolding was hampered by the disulfide bond now extends. These extensions are recorded as a second series of steps of ~13.2 nm per disulfide bond reduction (FIG. 20A). As in the unfolding steps, a sudden decrease in the force accompanies the reduction events (FIG. 20A). Generally, 15-50 traces as that shown in FIG. 20A are accumulated per force. In the more straightforward analysis, the traces are averaged and fitted with a single exponential with time constant τ (FIG. 20B). From this fit, it is possible to obtain the reduction rate at a given force (r=1/τ). It has been observed that, as a consequence of the detachment kinetics of the polyprotein from the surface or the cantilever, the results can be biased to faster rates. In order to avoid this artifact, only traces with long detachment times should be included in the analysis. As an alternative to exponential fits, a dwell time analysis technique has been recently implemented for the study of single-molecule mechanochemical reactions. This procedure overcomes the limitations of exponential fits when multiple reaction pathways occur simultaneously; however, a large pool of events (over one thousand) needs to be collected.

Chemical Reactions Under Force at the Single-Molecule Level

In order to better understand the effects of force on a reaction catalyzed by an enzyme, first consider the case of more simple uncatalyzed chemical reactions was considered. It has been shown that the rate of reduction of the disulfide bonds in (I27G32CA75C)8 by small reducing agents such as DTT or LCys is exponentially dependent on the applied force (FIG. 20C). The exponential dependency is given by a Bell-like relationship: $r(F)=A \exp((F \cdot \Delta x - Ea)/k_B \cdot T)$. In this expression, A is the attempt frequency, $\Delta x$ is the distance to the transition state of the reaction, Ea is the activation energy barrier for the reaction, $k_B$ is the Boltzmann's constant, and T is the absolute temperature. Fitting the experimental results for the reduction by DTT to the equation above yields $\Delta x=0.34$ Å. Interestingly, theoretical calculations have suggested that the length of the disulfide bond at the transition state of a simple Sn2 thiol/disulfide exchange reaction increases by approximately 0.37 Å. Then, these results indicate that the changes in distance between the sulfur atoms at the transition state are responsible for the force dependency of the reaction. Indeed, when different reducing agents are used, the measured distances to the transition states of the corresponding reactions are in agreement with the physicochemical characteristics of the reactants. For thiol-initiated disulfide bond reductions, such as DTT, β-mercaptoethanol, or glutathione, $\Delta x=0.31 \pm 0.05$ Å. When phosphine-based reducing agents (TCEP and THP) are employed, $\Delta x$ is significantly higher, $0.44 \pm 0.03$ Å. Such an increase in the distance to the transition state for the latter compounds is again in agreement with quantum chemical calculations, which show that the distance between sulfur atoms in the transition states of phosphine-based reactions is longer than in thiol-initiated reductions. In addition, it has been demonstrated for phosphine-initiated reductions that $\Delta x$ decreases when glycerol is incorporated into the aqueous solution. This result provides a direct test of theoretical calculations of the role of solvent molecules in the transition state of a bimolecular Sn2 reaction. In summary, the force-clamp experiments using small reducing agents show that the mechanical force imposes a 1-D reaction coordinate for the reaction (FIG. 20D). In this context, $\Delta x$ reports on the progression along that reaction coordinate with sub-Ångström resolution, providing valuable information about the geometry of the transition state. In addition, the information gained about the transition state from force-clamp determinations is probably independent of its lifetime. The rational behind this is that no matter how short- or long-lived a transition state is, it will always be subjected to force. Thus, in theory, the force-spectroscopy methodology applied to chemical reactions might be able to inspect the geometric properties of transitions states independently of their life times.

Force as a New Probe of Enzyme Catalysis

From the experiments using small reducing agents, it is clear that chemical reactions resulting in changes in bond distance will be force dependent and that single-molecule force spectroscopy is able to provide sub-Ångström information about the transition state of the reaction. The same approach has also been employed to investigate the mechanism of disulfide bond reduction by members of the Trx family of enzymes. Trxs show a highly conserved active site (CXXC) that catalyzes the reduction of target disulfide bonds involved in a multitude of cellular processes. Several methods based on bulk spectrophotometry have been widely used to determine the activity of Trxs. These methods are based on the oxidation of NADPH in the presence of thioredoxin reductase (TrxR) or ribonucleotide reductase; the increase in turbidity of insulin solutions concomitant to the reduction of the disulfide bonds in that peptide; or the use of Ellman's reagent (DTNB), which generates colored products upon reduction by thiol groups. The change in the intrinsic fluorescence of Trx has also been used to measure rates of enzyme oxidation and reduction. While highly effective in monitoring the overall activity of Trx enzymes, these methods do not probe the chemical mechanisms underlying their catalysis. The main reason is that many factors influence the measurements, such as the kinetics of reduction of Trx by TrxR, or the kinetics of insulin aggregation after disulfide bond reduction. In addition, they have the limitations inherent to bulk assays, as they only provide average measurements of activity. In the case of the single-molecule force spectroscopy assays, the enzyme is kept in the reduced form due to the presence of TrxR and NADPH (the so-called Trx system). Therefore, the amount of oxidized Trx is negligible and the measured activity only reflects the reduction of the disulfide bond in (I27G32C-A75C)8 at a given Trx concentration.

In contrast to DTT and other small reducing agents, human Trx-mediated disulfide reduction is strongly inhibited by force, with $\Delta x=-0.79$ Å (FIG. 20C). A molecular interpretation of this result has been obtained from the crystal structure of human Trx in complex with a substrate peptide (PDB code 1MDI). A peptide-binding groove is identified on the surface of the protein close to the catalytic cysteine. It is known that the reduction of a disulfide bond proceeds via an Sn2 mechanism, in which the three participating sulfur atoms form a ~180° angle. Given the fact that the disulfide bond in 1MDI forms an angle of ~70° with respect to the axis of the groove, it is evident that the target disulfide bond must rotate with respect to the pulling axis to acquire the correct geometry for reaction (FIG. 20E). Taking into account the orientation of the disulfide bond with respect to the pulling force, it can be estimated that a 0.77 Å shortening of the substrate polypeptide is needed in order to align the participating sulfur atoms, in extraordinary agreement with the experimental $\Delta x$ (−0.79 Å). This interpretation is supported by molecular dynamics simulations and a theoretical model that treats the substrate backbone as a freely jointed chain. Therefore, it appears that, differently to what is observed for the reductions by small reducing agents, the change in bond distance at the transition state is not the main determinant of the force dependency for enzyme-catalyzed reactions. On the contrary, the dynamics of enzyme and substrate during catalysis are the main contributors to the measured $\Delta x$.

When Trx from *E. coli* was assayed, a similar force-dependency up to 200 pN was observed. However, this enzyme shows a second chemical pathway that becomes apparent only at higher forces. The two pathways seem to be independent of each other, since the mutants P34H and G47S selectively inhibit only the first pathway. The second pathway of E. coli Trx is force accelerated with Δx=0.22 Å (FIG. 20C). This catalytic mode might be explained by the reduction happening without the peptide binding the groove; in this regard, the second pathway would be similar to the reduction by agents such as DTT or L-Cys (FIG. 20C).

In summary, the application of single molecule force spectroscopy to the study of catalysis by Trxs, in combination with molecular dynamics simulations, provides detailed information about the dynamics of enzyme and substrate during catalysis. This information has been used to detect residue co-evolution in enzymatic activity, which would have gone unnoticed to standard bulk assays.

Single-Molecule Force Spectroscopy Assays for Other Enzymatic Activities

The results obtained with Trx suggest that it will be highly informative to apply the single molecule force spectroscopy methodology to other enzymes. In principle, the single-molecule assay for the reduction of disulfide bonds by thioredoxin might be adapted to any other enzyme that catalyzes the cleavage of covalent bonds. This would allow a deeper understanding of different mechanisms of catalysis. Proteases, esterases, phosphodiesterases, glycosidases, and glycosyltransferases are enzymes with the ability to cleave covalent bonds. From what has been learned from the single-molecule assay for disulfide bond reduction, it is clear that any new experimental setup aimed to study single-molecule bond cleavage under force should fulfill the following requirements: i) the substrate should be incorporated into a macromolecule providing an unambiguous fingerprint after mechanical unfolding; ii) the rate of substrate cleavage by the enzyme should be low when put together in solution, so that no significant cleavage occur in the timescale needed to conduct AFM experiments; iii) the unfolding of the macromolecule should promote a steric switch in the substrate, rendering it sensitive to cleavage; iv) cleavage should be translated into a new increment in length of the macromolecule.

Single-molecule force spectroscopy may be used to probe the catalytic mechanisms of enzymes. In the examples below, this approach has been used to study the reduction of disulfide bonds by thioredoxin. From the force dependency of the reaction rate, new light has been shed on the dynamics of enzyme and substrate during catalysis. In particular, the Δx parameter, which is derived from exponential fits to the measured force dependency, reports on the spatial rearrangements of the participating atoms at the transition state of the reaction. These rearrangements can be dissected at the sub-Ångström scale, in a manner unachievable by any other current experimental technique.

The following examples illustrate the disclosed subject matter, and are set forth to aid in the understanding of the invention, and should not be construed to limit in any way the scope of the invention as defined in the claims which follow thereafter.

EXAMPLES

Example 1

To test the hypothesis that mechanical force can directly influence the kinetics of a chemical reaction, thiol/disulfide exchange was studied, the reduction of disulfide bonds in a protein. The disulfide bond itself is a covalent bond formed between the thiol groups of two vicinal cysteine residues. In the first step of thiol_disulfide exchange, a new disulfide bond is formed between a thiolate anion of the reducing molecule (in this case DTT) and one cysteine on a protein, whereas the sulfur of the other cysteine reverts to the free thiolate state. This reaction has been extensively studied and is known to be important in the function and folding processes of proteins. This reaction is also of particular interest because it is known that many proteins that are exposed to mechanical stress in vivo contain disulfide bonds. Thus, the effect of force on this reaction could be of significance in biological systems.

Disulfide bonds have been studied in previous atomic force microscopy (AFM) experiments where a protein molecule is stretched at a constant velocity whereas the applied force varies (force-extension AFM). Most of these experiments could identify the presence or absence of a disulfide bond but could not determine when the disulfide reduction reaction occurred. Engineered disulfide bonds were used to precisely correlate disulfide reduction events with increases in protein contour length, developing a molecular fingerprint for identifying individual chemical reactions. In the present work, this fingerprint is used to investigate the kinetics of thiol/disulfide exchange as a function of pulling force using force-clamp AFM. This method provides the only direct means by which to observe the exponential chemical kinetics of thiol/disulfide exchange under a calibrated pulling force. This technique has been used to study the unfolding kinetics as well as refolding of single protein molecules as a function of force, offering insight into the link between protein dynamics and force. By using force-clamp AFM, it was demonstrated that thiol/disulfide exchange, a bimolecular chemical reaction, is catalyzed by mechanical force. The force-dependency of the reaction rate is determined by the structure of the transition state, a result that may be generalized to other chemical reactions. These findings demonstrate that force-clamp AFM is a powerful tool with which to study chemistry at the single molecule level.

Results and Discussion

In the studies herein, the 27th immunoglobulin-like domain of cardiac titin (I27), an 89-residue, β-sandwich protein with well characterized mechanical properties is used. Through cysteine mutagenesis, a disulfide bond in the I27 domain between the 32nd and 75th residues, which are closely positioned in space as determined by the NMR structure of wild-type I27 (Protein Data Bank ID code 1TIT) is engineered. An eight-repeat polyprotein of this modified domain was constructed and expressed, (I27G32C-A75C)8, and used single-molecule force-clamp spectroscopy to manipulate and stretch single polyproteins. Under force-clamp conditions, stretching a polyprotein results in a well defined series of step increases in length, marking the unfolding and extension of the individual modules in the chain. Previous work has demonstrated that there is a close correlation between the size of the observed steps and the number of amino acids released by each unfolding event. Upon stretching a single (I27G32C-A75C)8 polyprotein in an oxidizing environment (FIG. 5B), a series of steps of approximately 10.6 nm were observed, which are significantly shorter than those expected for native I27 unfolding (23.6 nm). This shortening indicates the formation of the engineered disulfide bond within the protein module. The unfolding of 46 "unsequestered" residues (1-31 and 76-89) has a predicted step size of 10.4 nm at 130 pN, very similar to the observed value. At this stage of unfolding, the disulfide bond in each module is directly exposed to the applied stretching force (FIG. 5A), forming a covalent barrier "trapping" residues 33-74 and preventing complete module unfolding. If the bond were to be ruptured by force alone, a second step corresponding to the extension of the trapped polypeptide is expected to be observed. Yet any such steps under these oxidizing conditions (FIG. 5B) were not observed. This outcome was predicted by previous experimental and theoretical studies, where forces <1 nN cannot break a covalent bond. After unsequestered unfolding, the disulfide bond is exposed to the solvent, and thiol_disulfide exchange can occur if DTT is present in solution. In FIG. 1C, a single (I27G32C-A75C)8 molecule in the presence of 50 mM DTT was pulled. During the first second, a series of steps of approximately 10.8 nm as unsequestered unfolding occurs in individual domains is observed. The one step of 24.0 nm denotes a domain with its disulfide reduced before mechanical unfolding, giving a full-length step approximately equal to that for wild-type I27. Such full-length unfolding was rare, however; previous studies have indicated that the disulfide bond in I27G32C-A75C is particularly solvent-inaccessible in the folded protein. After this first series of steps relating to protein unfolding, which occur over approximately 1 s, a second series of steps of approximately 13.8 nm over approximately 4 s was then observed. The predicted step size for trapped residue extension as determined from force-extension experiments is 13.5 nm at 130 pN. In addition, these steps were observed only after unsequestered protein unfolding and only in the presence of DTT. Hence, it is concluded that at a pulling force of 130 pN, the 13.8-nm steps monitor the thiol/disulfide exchange reaction as single disulfide bonds are reduced in each protein module, allowing for the extension of the trapped residues.

Figure 6:
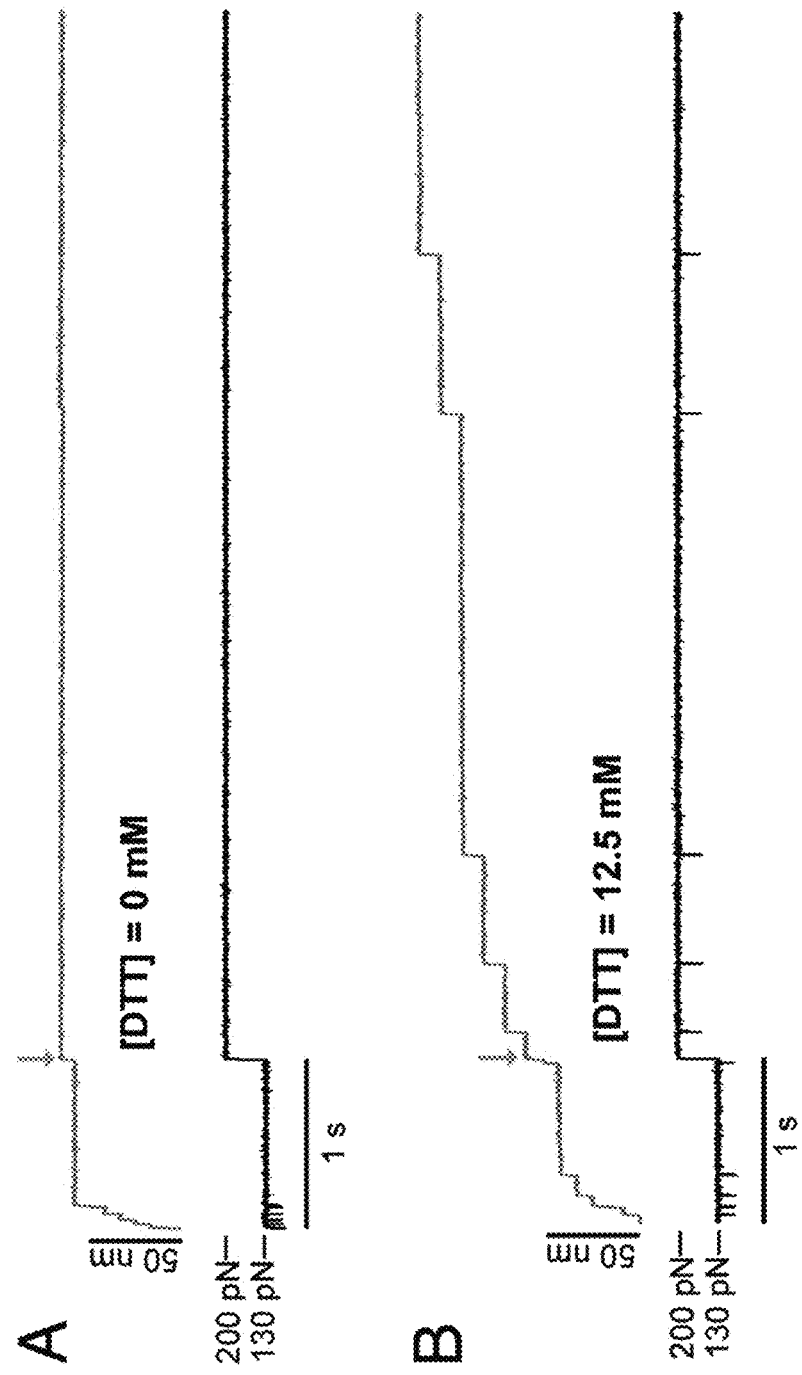
FIG. 6A shows a typical double-pulse force-clamp experiment pulling the (I27G32C-A75C)8 protein first at 130 pN for 1 s and then stepping to a force of 200 pN for 7 s (black trace).
FIG. 6B shows the same experiment in the presence of 12.5 mM DTT.

To study the kinetics of disulfide bond reduction as a function of the pulling force, a double pulse protocol in force-clamp was designed. The first pulse to 130 pN allows the monitoring of the unfolding of the unsequestered region of the I27G32C-A75C modules in the polyprotein, exposing the disulfide bonds to the solution. With the second pulse, the rate of reduction of the exposed disulfides at various pulling forces was tracked. FIG. 6 demonstrates the use of the double-pulse protocol in the absence (FIG. 6A) and in the presence of DTT (FIG. 6B). In both cases, the first pulse elicits a rapid series of steps of approximately 10.6 nm marking the unfolding and extension of the 46 unsequestered residues. The second pulse in FIG. 6 increases the stretching force up to 200 pN. Upon application of the second pulse, an elastic extension of the polyprotein by approximately 10 nm was observed. In the presence of DTT (12.5 mM), this elastic extension is followed by a series of five additional approximately 14.2-nm steps that mark single thiol/disulfide exchange reactions (expected steps of 14.2 nm at 200 pN, whereas no further steps were observed in the absence of DTT (FIG. 6A).

Figure 7:
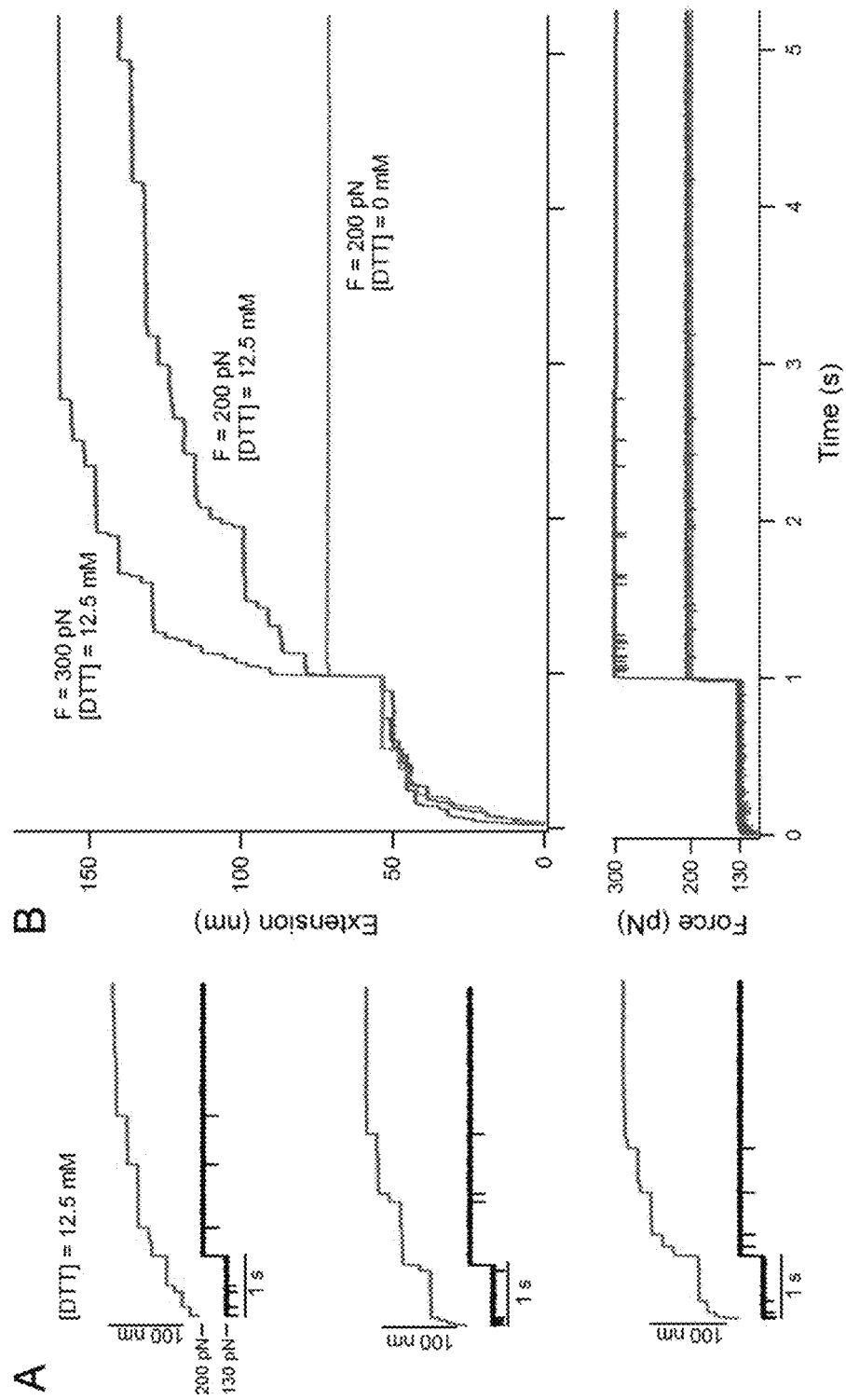
FIG. 7 shows ensemble measurements of the kinetics of thiol/disulfide exchange.

To measure the rate of reduction at 200 pN and at a DTT concentration of 12.5 mM, the pulse pattern shown in FIG. 6B was repeated many times, obtaining an ensemble of single-molecule recordings. FIG. 7A shows three additional recordings demonstrating the stochastical nature of both the unsequestered unfolding and of the thiol/disulfide exchange events. The red trace in FIG. 3B was obtained by simple averaging of these four recordings. The green trace in FIG. 7B was obtained following similar procedures with the second force pulse to 300 pN. By comparison, the blue trace in FIG. 7B corresponds to the averaging of four traces obtained with the second force pulse set to 200 pN and in the absence of DTT. It is apparent from FIG. 7B that protein unfolding during the first pulse to 130 pN is independent of DTT, following a similar exponential time course in all cases at this force. However, thiol/disulfide exchange during the second pulse appears both DTT- and force-dependent. The double-pulse protocol as shown here effectively separates protein unfolding from the disulfide-bond reduction events. Hence, in the subsequent analysis the unsequestered unfolding observed during the first pulse and only analyze thiol/disulfide exchange events in the second pulse was ignored.

Figure 8:
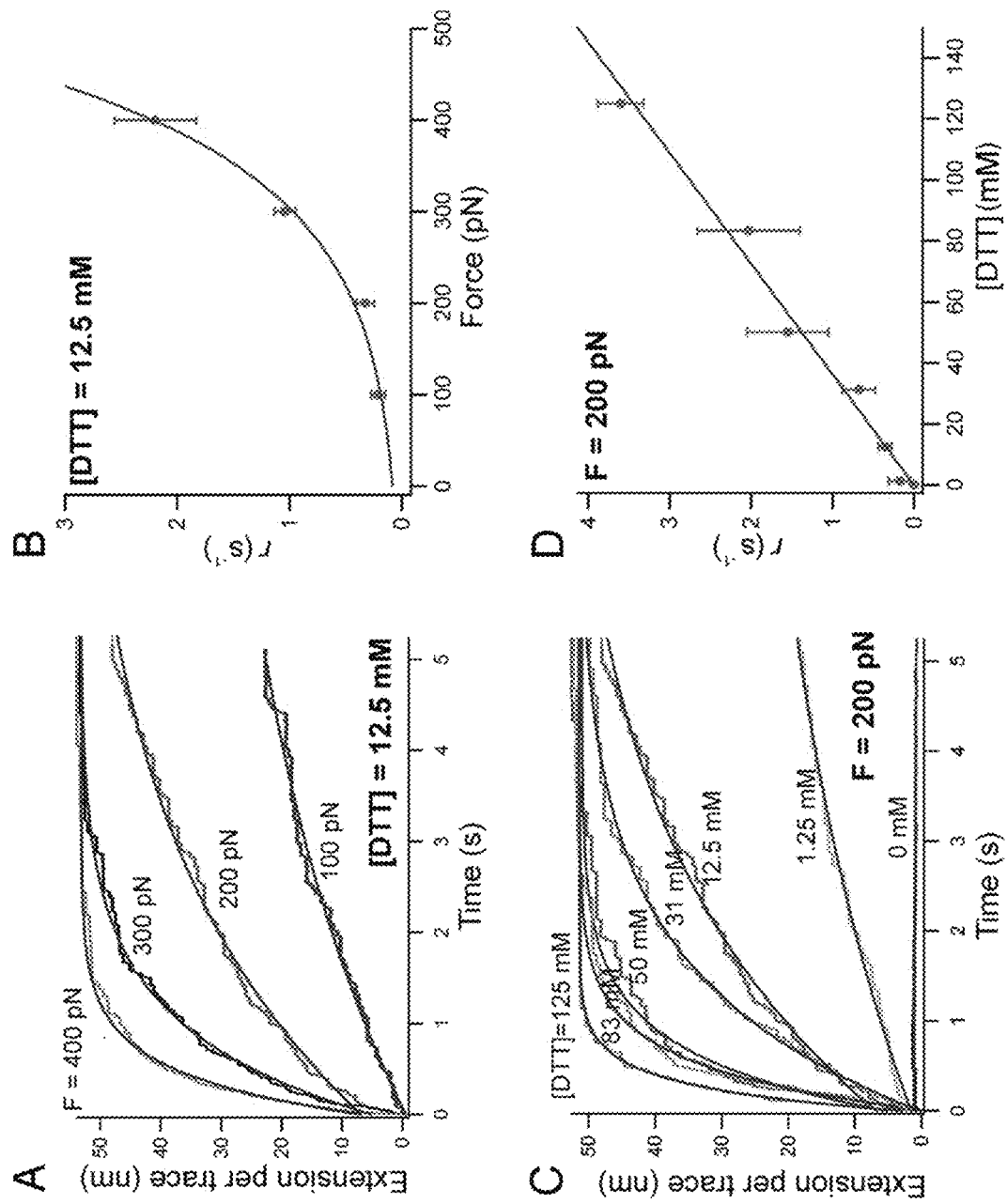
FIG. 8 shows graphs of thiol/disulfide exchange events measured by using the double-pulse protocol as a function of force and DTT concentration.

Multiple double-pulse experiments were conducted, all with an identical first force pulse to 130 pN lasting 1 s. FIG. 8A shows multiple (>25) trace averages of only the second pulse at four different forces (100, 200, 300, and 400 pN) and at a constant DTT concentration of 12.5 mM. Only traces that included a clear unsequestered unfolding fingerprint in the first pulse and that contained only disulfide reduction events in the second pulse were included in this analysis. By fitting a single exponential to the traces shown in FIG. 8A, the observed rate of thiol/disulfide exchange as $r=1/\tau r$, where $\tau r$ is defined as the time constant measured from the exponential fits. FIG. 8B, shows that r is exponentially dependent on the applied force (12.5 mM DTT) ranging from 0.211 s−1 (100 pN) up to 2.20 s−1 (400 pN). FIG. 8C shows the second-pulse averages (>20) of experiments conducted at 200 pN, at different concentrations of DTT (0, 1.25, 12.5, 31, 50, 83, and 125 mM). FIG. 8D, shows that r has a first-order dependence on the concentration of DTT, demonstrating that the thiol/disulfide exchange reaction in this system is bimolecular.

Given these observations, an empirical relationship $r=k(F)[DTT]$ is derived, where $k(F)$ depends exponentially on the applied force and is given by a Bell-like (25) relationship: $k(F)=A \exp((F\Delta xr-Ea)/kBT)$. In this equation, A is a constant with units of M−1·s−1, $\Delta xr$ is the distance to the transition state for the reaction, and Ea is the activation energy barrier for the thiol/disulfide exchange at zero force. Fitting this equation to the data presented in FIG. 4B, a value of $\Delta xr=0.34$ Å and a value of $k(0)=6.54$ M−1·s−1 are obtained, which is similar to the second-order rate constant for DTT reduction of disulfide bonds in insulin at neutral pH [k=5 M−1·s−1]. Other studies have found that under certain solution conditions, thiol_disulfide exchange can occur with a second-order rate constant as high as 132,000 M−1·s−1 but also can be up to 6 orders of magnitude slower, in accord with other observations. From the linear fit in FIG. 8D, an applied force is seen that alters the second-order rate constant in the system; k(200 pN)_27.6 M−1·s−1, a 4-fold increase from zero force. Assuming that A ranges from 105 to 1012 M−1·s−1, Ea is estimated to be in the range of 30-65 kJ/mol. The upper values in this range overlap with the calculated energy barriers for a number of thiol_disulfide exchange reactions in solution [60-66 kJ/mol], and each 100 pN of force lowers the energy barrier by approximately 2 kJ/mol.

Figure 9:
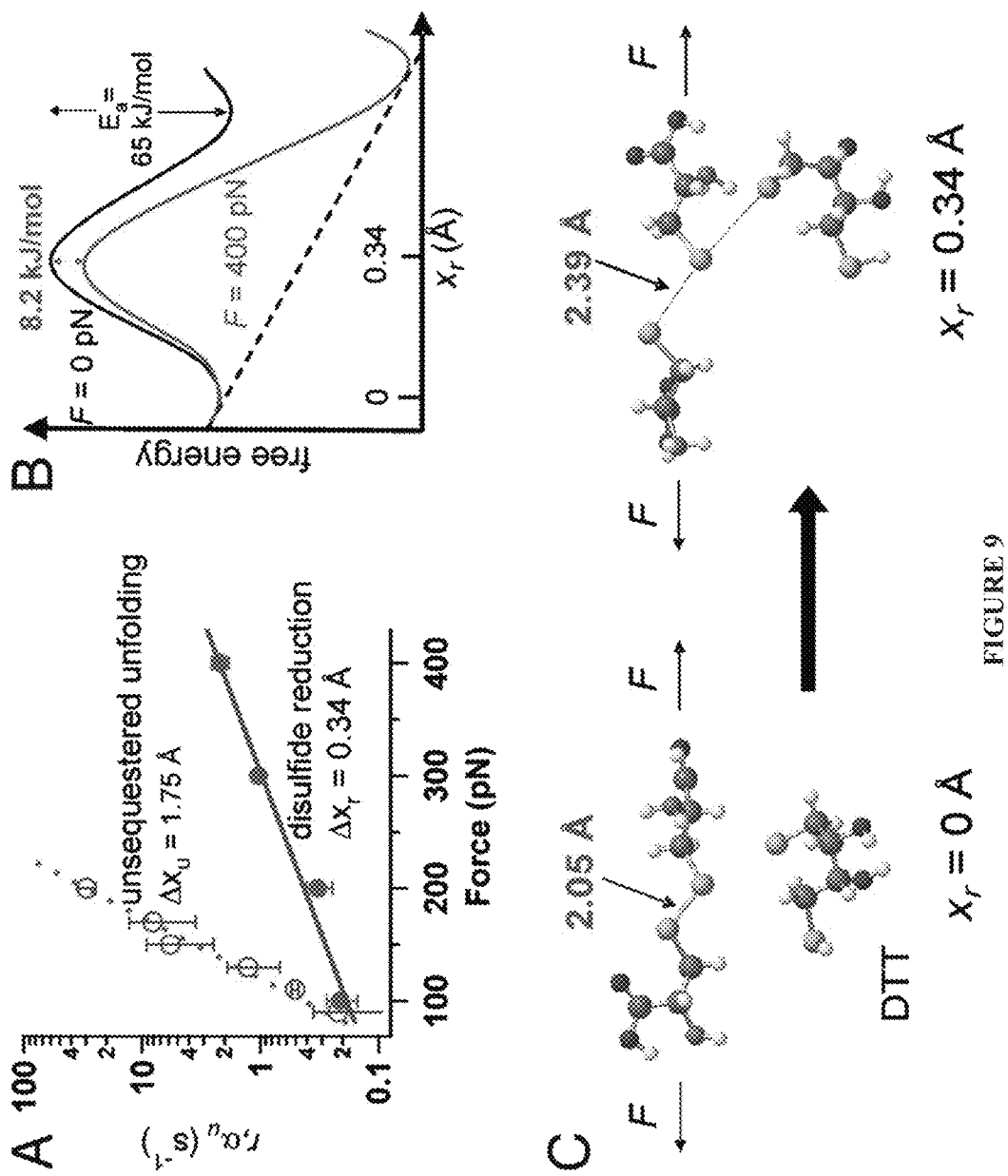
FIG. 9A is a plot of the rate of the thiol/disulfide exchange.
FIG. 9B is a plot of the energy landscape of the thiol_disulfide exchange reaction under force.
FIG. 9C is an illustration of the thiol/disulfide exchange reaction between a DTT molecule and a disulfide bond under a stretching force

Although the empirical Bell-like model is a useful first approximation to examine the data, it may not hold over all combinations of DTT and force. It also cannot completely describe the effect of a force on the thiol/disulfide exchange reaction. The force constant for an S—S bond, found by vibrational spectrum in the gas phase, is 4.96 N/cm. As a result, an applied force of 400 pN will stretch this bond by only 0.008 Å, which is a negligible effect on the geometry of the S—S bond. However, as pointed out by Beyer, the reactivity of a stretched molecule is likely to depend on the pulling force despite only minor changes in bond geometry. Furthermore, a reorganization of the energy landscape of the bond is likely to occur during bond lengthening. These effects are not accounted for by this model. Hence, further theoretical developments on the effect of a mechanical force on the thiol/disulfide exchange reaction will be required to fully understand these experiments. These limitations notwithstanding, useful parameters can be extracted from this analysis. For example, the sensitivity of the rate of reduction to a pulling force is well represented by the measured value of $\Delta xr$, which can be contrasted to that of unfolding the unsequestered region of the protein. By fitting a single exponential to an average of traces containing solely unsequestered unfolding events of the type shown in FIG. 1B (no DTT), the rate of unfolding is measured, $\alpha u=1/\tau u$, at different pulling forces. FIG. 9A shows a semilogarithmic plot of both $\alpha u$ and r as a function of the pulling force. The dashed line corresponds to a fit of $\alpha u$ (F)=$\alpha u(0)$ exp(F$\Delta xu$/kBT) (19), obtaining $\Delta xu$=1.75 Å for the unsequestered unfolding. The solid line is a fit of the Bell-like model described earlier, where $\Delta xr$=0.34 Å for the thiol/disulfide exchange reaction. FIG. 9A confirms the difference in force sensitivity between the unsequestered unfolding and the thiol/disulfide exchange reaction, which are two distinct processes occurring within the same protein.

From the measurements above a preliminary description of the energy landscape for the thiol/disulfide exchange chemical reaction was obtained under a stretching force (FIG. 9B). Recent theoretical calculations have proposed that the length of an S—S bond at the transition state of a simple SN2 thiol/disulfide exchange reaction in solution increases by 0.36 Å or 0.37 Å. These values suggest that the value of $\Delta xr$ that has been measured experimentally corresponds to the lengthening of the S—S bond during an SN2 reaction with a DTT molecule (FIG. 9C). Furthermore, in these theoretical studies, varying the reaction mechanism could result in S—S lengthening at the transition state as small as 0.24 Å or as large as 0.78 Å (28). Different values of $\Delta xr$ would result in very different sensitivities of the reaction to a pulling force. Hence, it is proposed that by experimentally measuring the value of $\Delta xr$, as demonstrated here for a single disulfide bond, different types of reaction mechanisms can be distinguished. Conversely, this work also suggests that other bimolecular reactions that result in bond lengthening may be force dependent.

Although force-dependent thiol/disulfide exchange in an engineered protein has been demonstrated, there are many native proteins that contain disulfide bonds and that are exposed to mechanical forces in vivo. Some examples include cellular adhesion proteins such as cadherins, selectins, and IgCAMs. Others are important in maintaining the extracellular matrix, such as fibronectin, or in tissue elasticity, such as fibrillin and titin. It has been shown that thiol/disulfide exchange in integrin $\alpha IIb\beta III$ as well as disulfide reduction in von Willebrand factor multimers is necessary for hemostasis and regulating clot formation under high shear forces generated by blood flow. Even the mechanical process of HIV virus fusion and entry into helper T cells has been shown to require disulfide bond reduction in both gp120 of HIV and the CD4 cell surface receptor.

Forces >100 pN are necessary to achieve a measurable increase in the rate of thiol/disulfide exchange. Such forces are thought to be toward the high end of the range experienced in biology: single protein complexes may produce forces >100 pN, and single selectin-ligand bonds can withstand forces >200 pN. Although it is not yet known how often a single disulfide bond in vivo will be exposed to the force levels explored in this study, it does seem likely that the sensitivity of any particular thiol/disulfide exchange reaction to a pulling force will depend very specifically on the environment surrounding the bond as well as the type of chemical reaction involved. For example, $\Delta xr$ is likely to depend on a number of factors that also affect the rate of the thiol/disulfide exchange reaction, including the temperature, type of reducing agent, pH, electrostatics the reaction mechanism, and the torsional strain present in the protein structure. Any combination of these effects that cause $\Delta xr$ to be >1 Å would lead to a near 2-fold increase in reduction rate over just 20 pN of applied force, suggesting that force-catalyzed disulfide reduction may play an important role in vivo.

Materials and Methods

Protein Engineering and Purification. The QuikChange site-directed mutagenesis kit (Stratagene) was used to mutate residues Gly-32 and Ala-75 in the 27th Ig-like domain of human cardiac titin to Cys residues. Native Cys-47 and Cys-62, which do not form a disulfide bond, were mutated to alanines. An eight-domain N—C linked polyprotein of this I27G32C-A75C domain was constructed through rounds of successive cloning in modified pT7Blue vectors and then expressed the gene using vector pQE30 in *Escherichia coli* strain BL21(DE3) as described. Pelleted cells were lysed by sonication and the His-6-tagged soluble protein was purified first by immobilized metal ion affinity chromatography (IMAC) and then by gel filtration. The protein was stored at 4° C. in 50 mM sodium phosphate/150 mM sodium chloride buffer (pH 7.2).

Single-Molecule Force-Clamp Spectroscopy.

A custom-built atomic force microscope equipped with a PicoCube P363.3-CD piezoelectric translator (Physik Instruments, Karlsruhe, Germany) controlled by an analog proportional-integral-differential feedback system is described elsewhere (Schlierf et al., *PNAS USA*, 101:7299-7304). All data were obtained and analyzed by using custom software written for use in IGOR 5.0 (WaveMetrics, Lake Oswego, Oreg.). There was $\approx$0.5 nm of peak-to-peak noise and a feedback response time of $\approx$5 ms in all experiments. The spring constant of silicon-nitride cantilevers (Veeco, Santa Barbara, Calif.) was calibrated; the average spring constant was $\approx$15 pN/nm. All experiments were conducted in PBS buffer with the indicated amount of DTT (Sigma). Buffers were all controlled to pH 7.2. All experiments were conducted over $\approx$8 h at room temperature (298 K) in an atmosphere open to air. Small changes in active DTT concentration due to evaporation and air-oxidation of DTT did not appear to greatly affect the results, because traces compiled over the course of 1 day's experiment at the same force demonstrated similar single-exponential kinetics. Approximately 5 µL of protein sample ($\approx$0.1 mg/mL) in phosphate buffer was added to $\approx$70 µL of DTT-containing buffer in each experiment. Single protein molecules were stretched by first pressing the cantilever on the gold-coated coverslide for 3 s at 350-500 pN, then retracting at a constant force. The success rate at picking up a single molecule was $\approx$1% of trials. Gold-coated coverslides were used because they resulted in a better success rate than glass coverslides even in the absence of thio-gold bonds. In all force-dependent experiments (FIG. 8A), the molecule was stretched for 1 s at 130 pN and then 5-7 s at the second pulse force. In the concentration-dependent experiments (FIG. 8C), the molecule was pulled at 130 pN for 1 s (0-31 mMDTT) or 140-145 pN for 0.2-0.5 s (50-125 mM DTT; the shorter first pulse times are to reduce thiol/disulfide events during the first pulse), then the force increased to 200 pN for 5-7 s. The interaction between protein and cantilever/coverslide is nonspecific. Thus, in most cases fewer than eight domains were unfolded when a molecule was stretched.

Data Analysis.

The fingerprint of a single $(I27_{G32C-A75C})_8$ was considered to be two well resolved steps of $\approx$10.5 nm during the first pulse. No traces that included unsequestered unfolding events during the second pulse were included in the analysis.

Such mixed spectra were very rarely observed (<1%) at forces of 200 pN or greater because of the very rapid kinetics of unsequestered unfolding at these forces. At a second pulse force of 100 pN, such mixed spectra were observed ≈15% of the time; such traces were not included in the averaging analysis because the unsequestered unfolding steps would corrupt the time course of disulfide reduction. It is assumed that disulfide reduction in this protein is Markovian (i.e., each reduction event is independent of all others); thus, averaging traces with different numbers of reduction steps will result in invariant exponential kinetics. Error bars in FIG. 8B and FIG. 8D and FIG. 9A were obtained by partitioning the entire set of traces into random subsets (for example, if 20 total single-molecule traces were used, then two subsets of 10 traces each were constructed). These traces in these subsets then were averaged and fit with a single exponential. The rate of thiol_disulfide exchange (FIG. 8A and FIG. 8B) or rate of unsequestered unfolding (FIG. 9A) was determined as described from the exponential fit. The standard deviation of the rate was then calculated with n=the number of subsets (in the case of the example, n=2). This value then was used as the magnitude of the error bar shown in the figures.

One of the principal challenges of understanding enzyme catalysis, a central problem in biology, is resolving the dynamics of enzyme-substrate interactions with sub-ångström resolution—the length scale at which chemistry occurs. Although nuclear magnetic resonance (NMR) and X-ray crystallography determinations of protein structures can reach down to the sub-ångström level, they cannot yet provide dynamic information about enzyme catalysis at this length scale. This demonstrates the ability of single-molecule techniques in probing the dynamics of enzyme catalysis at the sub-ångström scale.

Figure 10:
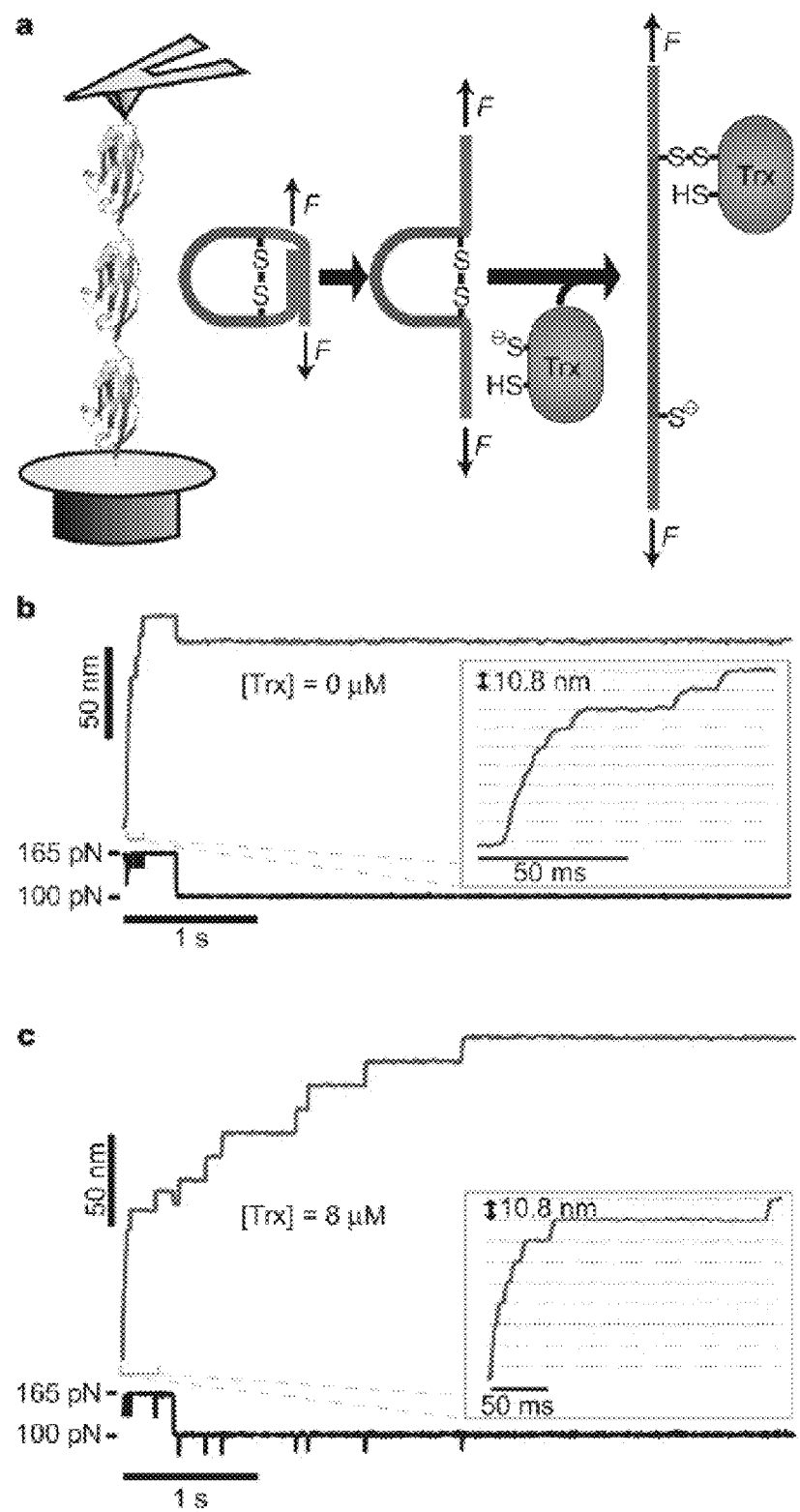
FIG. 10A is a schematic illustrating molecular stretching.
FIG. 10B shows the results of stretching a single (I27SS)8 molecule is stretched in the absence of Trx.
FIG. 10C shows the results of stretching a single (I27SS)8 molecule is stretched in the presence of 8 μM Trx.

A polyprotein made of eight repeats of the I27 domain of human cardiac titin with engineered cysteines, (I27SS)8, was used as a substrate protein to monitor the Trx-catalysed reduction of individual disulphide bonds (SS) placed under a stretching force. In these experiments, an atomic force microscopy in force-clamp mode to extend single (I27SS)8 polyproteins was used (FIG. 10A, far left). The constant applied force caused individual domains to unfold, resulting in a stepwise increase in the length of the molecule after each unfolding event. This is illustrated in FIG. 10b, in which a single (I27SS)8 polyprotein was first mechanically unfolded at 165 pN for 400 ms. A series of 10.8-nm steps was rapidly observed (FIG. 10B, inset); each step corresponds to the partial unfolding of a single I27SS domain up to the disulphide bond (red, FIG. 10A). The disulphide bond is buried in the folded protein and is exposed to the bathing solution only after partial unfolding. The unfolding force pulse was followed by a test pulse (100 pN in this case). No further steps were observed during the test pulse because the disulphide bond could not be broken by the applied force alone in the absence of Trx. After unfolding, the stretching force was applied directly to the disulphide bond and, if Trx is present in solution, the bond can be chemically reduced by the enzyme. Such a result is shown in FIG. 10C, with a similar experiment in the presence of 8 μM Trx. Now, during the test pulse, seven steps of ~13.2 nm were observed as individual disulphide bonds were reduced by single Trx enzymes, allowing for the immediate extension of the residues previously trapped behind the disulphide bond (blue, FIG. 10A). The size of the increases in step length observed during these force-clamp experiments corresponds to the number of amino acids released, serving as a precise fingerprint to identify the reduction events.

Figure 11:
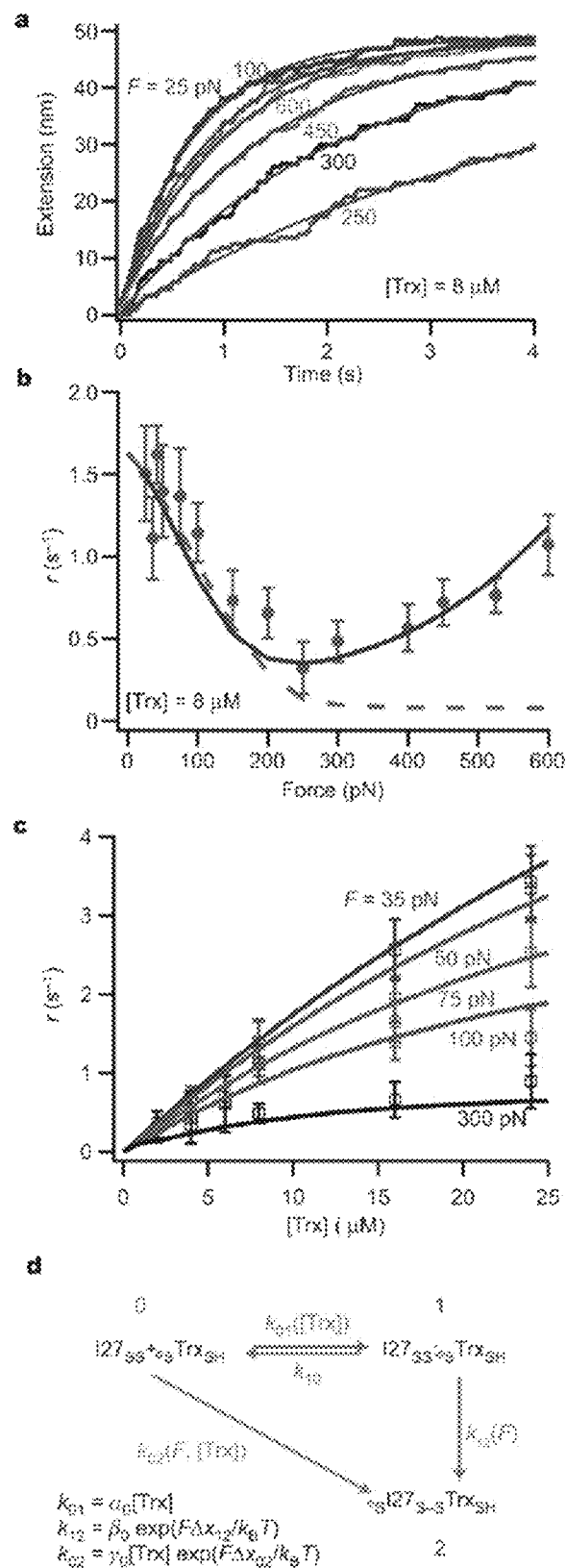
FIG. 11A shows results of an experiment where multiple single-molecule recordings of the test pulse only (n=10-30) were averaged to monitor the kinetics of disulphide bond reduction under force F. A single exponential is fitted to each averaged trace (smooth line), and the rate constant of reduction r=1/τ.
FIG. 11B shows r as a function of force at [Trx]=8 μM.
FIG. 11C shows r as a function of [Trx] at various forces. Error bars in 11B and 11C represent the s.e.m. obtained from bootstrapping. Solid lines in FIGS. 11B and 11C are fits using the kinetic model shown in FIG. 11D.

An ensemble of single-molecule recordings to measure the kinetics of disulphide bond reduction by Trx was used. At each force and Trx concentration, 10-30 test-pulse recordings of the type shown in FIG. 10C were averaged. Averaged traces at various forces are shown in FIG. 11A. The averaged traces were fitted by a single exponential with a time constant t (see Supplementary FIG. 11 and FIG. 12). The observed rate constant of disulphide reduction is defined as $r=1/\tau$.

FIG. 11B shows a plot of r as a function of the applied (test pulse) force. The figure shows that the rate of reduction decreases fourfold between 25 and 250 pN, and then increases approximately threefold when the force is increased up to 600 pN, demonstrating a biphasic force dependency. This result is in contrast with the uniform acceleration of dithiothreitol (DTT) reduction rate with increasing force4, underlining a much more complex chemical reaction catalysed by Trx. Furthermore, the rate of reduction becomes saturated as the concentration of Trx is increased (FIG. 11C).

To explain the data, different kinetic models of force-dependent Trx catalysis were tested. It was found that the model that could best describe the data incorporates an intermediate state as well as two different force-dependent rate constants (FIG. 11D). Path I (red, FIG. 11D) is similar to a Michaelis-Menten mechanism, with a catalytic step inhibited by force. Path II (blue, FIG. 11D) is governed solely by the rate constant κ02 (where subscripts refer to steps in FIG. 11D), which is accelerated by force. The model can be globally fitted to the data of FIGS. 11D and 11C (solid lines), obtaining values for the model parameters. The goodness of fit for this model was measured using statistical methods (see Methods and Supplementary Table 3; $\chi 2v=0.835$, and $v=26$, six free parameters; $P(\chi 2v=0.705)$). An extrapolation to zero force predicts a second-order rate constant for Trx reduction of $2.2 \times 10^5$ M−1 s−1. This is 30,000 times faster than that found for I27SS disulphide reduction by DTT (6.5 M−1 s−1). This result is consistent with bulk biochemical experiments, in which Trx has been found to reduce insulin disulphide bonds 20,000 times faster than DTT ($1 \times 10^5$ M−1 s-1 for Trx versus 5M−1 s−1 for DTT at pH7.

Figure 12:
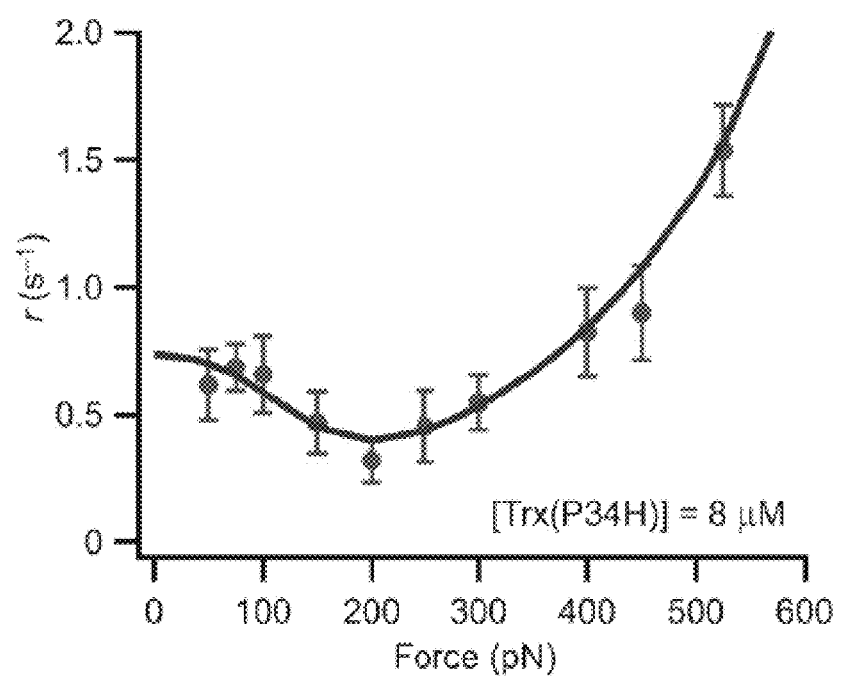
FIG. 12 is a plot of r as a function of force at [Trx(P34H)]=8 μM.

The experimental data shown in FIG. 11B suggest that there are two separate pathways for disulphide bond reduction by Trx. Further support for this hypothesis was gained by probing the force-dependent reduction kinetics of an active site mutant, Trx(P34H) (FIG. 12). In the single-molecule experiments, the extrapolated zero-force rate of reduction for Trx(P34H) is less than one-half of that for the wild-type enzyme ($8.8 \times 10^4$ M−1 s−1 versus $2.2 \times 10^5$ M−1 s−1, showing a similar relationship to bulk biochemical experiments ($3 \times 10^3$ M−1 s−1 for Trx(P34H) versus $2 \times 10^4$ M−1 s−1 for wild-type Trx at pH8 and 15° C.). In Trx (P34H), the rate of Trx binding to the substrate (κ01) decreased significantly, whereas the other kinetic parameters remain mostly unchanged. By fitting this data with two alternate kinetic models, it was found that the Trx(P34H) mutant supports the view that Trx has two distinct forms of catalysis, without a common intermediate.

In the kinetic model shown in FIG. 11D, the catalytic rate constants are described by a straightforward Arrhenius term. For example, $\kappa 12=\beta 0 \exp(F\Delta x12/\kappa BT)$, where $\beta 0$ is the rate constant at zero force, $\kappa B$ is Boltzmann's constant, T is the temperature and $\Delta x12$ is the distance to the transition state along the length coordinate. Fits of the kinetic model (FIG. 11D) to the data of FIGS. 11B and 11C gave values of $\Delta x12=-0.79\pm0.09$ Å for the catalytic step of path I and Δx12=0.17±0.02 Å for the catalytic step of path II (±s.e.m. obtained by downhill simplex procedure for model fitting). Similar parameters were also found for the Trx(P34H) mutant. Thus, the two catalytic pathways are very different: the transition state of reduction by way of path I requires a shortening of the substrate polypeptide by ~0.8 Å, whereas path II requires an elongation by ~0.2 Å.

Figure 13:
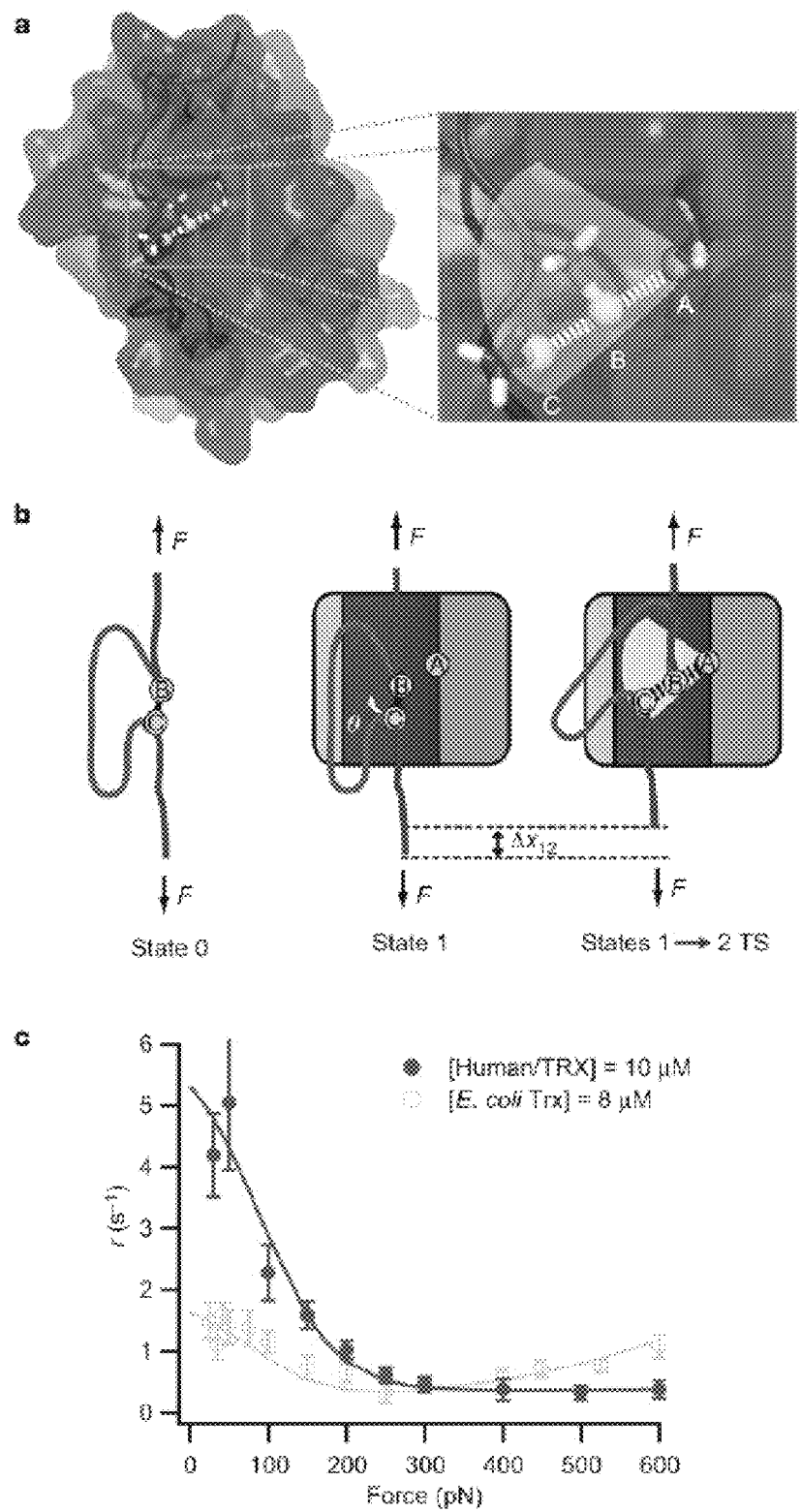
FIG. 13A is a diagram of TRX (peptide-binding groove in dark green) bound to an NF-κB peptide. The inset (yellow spheres are sulphur atoms A, B and C) shows the relative position of the disulphide bond between TRX Cys 32 (sulphur atom A) and the NF-κB cysteine (sulphur atom B).
FIG. 13B is a cartoon representation of the reduction by Trx of a disulphide bond in a stretched polypeptide.
FIG. 13C shows force-dependent reduction by human TRX compared to E. coli Trx.

The experiments show that sub-angstrom-level distortions of the substrate disulphide bond take place dynamically during Trx catalysis. A glimpse of the transition state for Trx catalysis can be obtained from the NMR structure of human TRX (also known as TXN) a homologue of the E. coli enzyme, in a complex with a substrate peptide from the signalling protein NF-κB (FIG. 13A, PDB accession number 1MDI). In this structure, as well as in the structure of human TRX bound to REF-1 (also known as APEX1), a peptide-binding groove is identified on the surface of TRX in the vicinity of the catalytic Cys 32. The sulphur atom in Cys 32 (sulphur atom A) of the active site of TRX forms a disulphide bond with the sulphur atom of the NF-κB peptide (sulphur atom B).

The orientation of the disulphide bond within the Trx active site was used in an attempt to predict the structure of the catalytic transition state in the experiments. It is known that disulphide bond reduction proceeds by means of an SN2 mechanism. This reaction is highly directional, proceeding via a transition state in which the three involved sulphur atoms form an ~180° angle. Thus, the relative positions of these sulphur atoms must be important for efficient Trx catalysis. It was found that the disulphide bond in 1MDI forms an angle of ~70° with respect to the axis of the peptide-binding groove. Assuming that this orientation applies to the SN2 reaction that reduces the I27SS bond of the experiments, and that the stretched polypeptide is bound to the groove, it is apparent that the target disulphide bond must rotate with respect to the pulling axis to acquire the correct SN2 geometry (FIG. 13B). Given that the disulphide bond in the stretched polypeptide is aligned within ~20° of the pulling force, a further rotation by an angle θ=50° would be required for catalysis (FIG. 13B), causing a contraction of the target polypeptide by ~1.2 Å, close to the measured value of Δx12≈−0.8 Å. However, molecular dynamics simulations have previously identified multiple conformations of the catalytic thiol in glutaredoxin, a member of the thioredoxin superfamily.

Similarly, molecular dynamics simulations of the 1MDI structure was performed to examine the conformational diversity of the NF-κB to Cys 32 disulphide bond. The simulations show that the disulphide bond samples a range of conformations with θ=50°-80° in either the clockwise or the counterclockwise direction (shaded area in the inset of FIG. 13A). The results of these molecular dynamics simulations were combined with a theoretical model that treats the substrate backbone as a freely jointed chain. This model predicts the likelihood of the substrate disulphide achieving the correct geometry for the reaction transition state under a pulling force. It was found that, in the cases of NF-κB, REF-1 and the apo TRX, an average bond rotation on the sub-ångström scale (resulting in Δx12 values of −0.77, −0.45 and −0.19 Å, respectively) must take place to allow SN2 chemistry in the TRX active site.

To probe this model of catalysis, which is based on the structure of human TRX complexes, the force-dependent mechanism of disulphide bond reduction by human TRX (FIG. 13C) was also tested. At low forces, it is clear that human TRX catalyses disulphide bond reduction in I27SS much more rapidly than Trx from E. coli. However, at high forces it appears that path II is quite diminished in the human TRX variant. Thus, the data for human TRX resemble a simple Michaelis-Menten model (dashed green line in FIG. 11B), indicating that the two thioredoxin variants differ in their catalytic mechanisms at high force. The three-state kinetic model also describes the human TRX data well with a fixed Δx12=−0.79 Å (FIG. 13C). Thus, it is clear that the mechanism that governs the force-dependence of path I is conserved between these homologues, and the results for human TRX at low forces can also be explained by the structural model.

The origin of the Δx12=−0.79 Å elongation at the transition state of catalysis for E. coli Trx, measured from the force-dependency of path II, is less clear. However, as demonstrated in the theoretical calculations of thiol/disulphide exchange, other reaction geometries are possible, even if they are typically unfavourable energetically. Thus, Δx02 may correspond to the lengthening of the I27SS disulphide bond at a transition state other than the standard SN2 form.

The results show that a mechanical force can alter the chemistry of the catalytic site in thioredoxin significantly. This is a novel concept in biology, that mechanical stresses applied to tissues may completely change the enzymatic chemistry from that observed in solution biochemistry. These effects may be particularly significant in tissues exposed to pathological force levels such as those that occur during mechanical injury. For example, it is well known that the increased mechanical stress during hypertension triggers an oxidative stress response in vascular endothelium and smooth muscle that is compensated by an increase in the activity of thioredoxin. In this context, it is predicted that the increased mechanical forces applied to target disulphide bonds would inhibit the activity of thioredoxin, diminishing the effectiveness of the antioxidant properties of the enzyme. The capability of single-molecule atomic force microscopy techniques directly to probe the dynamic sub-angstrom molecular rearrangements during catalysis may prove to be an important tool in understanding the fundamental mechanisms underlying enzymatic chemistry.

Methods Summary

The buffer used in the experiments contained 10 mM HEPES, 150 mM NaCl, 1 mMEDTA, 2 mM NADPH, 50 nM thioredoxin reductase (from E. coli for Trx and from rat liver for TRX) and the indicated concentration of Trx or TRX, and was controlled to pH 7.2. Single (I27SS)8 protein molecules were stretched by first pressing the cantilever on the coverslide at a constant force of 800 pN for 3 s, then retracting to a constant force of 165 pN for 400 ms during the unfolding pulse. The indicated test-pulse force was applied for ~5 s. All data were obtained and analysed using custom software written for use in Igor 5.0 (Wavemetrics). The test-pulse portions of numerous (n=10-30) recordings that contained only disulphide reduction events and no unsequestered unfolding events were summed and normalized to obtain the experimental value r. The differential rate equations were solved using matrix analysis methods, and error analysis was performed using the nonparametric bootstrap method in combination with the downhill simplex method. All error bars shown represent standard error.

Methods

Protein Engineering, Expression and Purification.

In brief, the QuikChange site-directed mutagenesis method (Stratagene) was used to introduce Gly 32 Cys and Ala 75 Cys mutations into the I27 module from human cardiac titin. Multiple rounds of successive cloning were used to create an amino-carboxy linked, eight-domain polyprotein gene, (I27G32C-A75C)8. In this work, this construct is called (I27SS)8. This gene was encoded in vector pQE30 and expressed in *E. coli* strain BL21(DE3). Pelleted cells were lysed by sonication, and the His 6-tagged protein was first purified using an immobilized Talon-Co2+ column (Clontech) and then further purified by gel filtration on a Superdex 200 column (GE Healthcare). The purified protein was verified by SDS-PAGE and stored at 4° C. in a buffer of 10 mM HEPES, 150 mM NaCl, 1 mM EDTA and 0.02% NaN3 (w/v), pH 7.2.

Both wild-type Trx and Trx(P34H) were expressed and purified by the same method described previously 26. Briefly, the *E. coli* Trx gene encoded in plasmid pTK100, was expressed in *E. coli* strain JF521. Cell pellets were lysed using a French press and stirred with streptomycin sulphate (10% w/v) at 4° C. for 16 h. The filtered supernatant was then loaded onto a 2-1 Sephacryl S-100 High Resolution (GE Healthcare) gel filtration column. Trx fractions were pooled and applied to a 250-ml Fractogel EMD DEAE(M) (Merck) ion exchange column equilibrated in a buffer containing 1 mM EDTA and 30 mM TRIZMA, pH 8.3. The protein was eluted by a linear gradient between 0 and 0.5M NaCl. The proteins were pure, as measured by SDS-PAGE gel densitometry. The molecular weight of pure proteins was confirmed by mass spectrometry. Trx fractions were dialysed into a buffer of 10 mM HEPES, 150 mM NaCl and 1 mM EDTA, pH7.2. Trx concentration was determined spectrophotometrically at 280 nm using a molar absorption coefficient $\Sigma 280$ of 13,700 M−1 cm−1. The bulk activity of Trx and Trx(P34H) was confirmed by monitoring spectrophotometrically at 412 nm the reduction of 5,5'-dithiobis(2-nitrobenzoic acid) (DTNB, Sigma) as described (Perez-Jimenez et al., *Biophys. Chem.*, 115:105-107 (2005)).

TRX was purified as previously described. Briefly, the pACA/TRX plasmid was expressed in BL21(DE3) cells. Cell pellets were lysed using a French press and stirred with 7% w/v streptomycin sulphate. Protein was then precipitated by adding ammonium sulphate to 85% saturation. The crude extracts were applied to a DEAE 52 column equilibrated with 50 mM Tris-HCl, pH 7.5, 1 mMEDTA and 0.1 mM DTT. Protein was eluted with an NaCl gradient, pooled and concentrated, and then applied to a Sephadex G-50 column equilibrated with 50 mM Tris-HCl, pH 7.5, 1 mM EDTA and 0.1 mM DTT. Fractions were pooled, concentrated and further purified using *E. coli* Trx antibody affinity chromatography. Protein concentration was determined spectrophotometrically at 280 nm using an $\Sigma 280$ of 8,050 M−1 cm−1.

Single-Molecule Force-Clamp Spectroscopy.

Typical resolution in extension was ~0.5 nm and typical analogue feedback lag in the force-clamp following unfolding was ~5 ms. The spring constant of silicon nitride cantilevers (Veeco), typically ~20 pN nm-1, was calibrated as described previously. The buffer used for all experiments contained 10 mM HEPES, 150 mM NaCl, 1 mM EDTA and 2 mM NADPH, and was controlled to pH 7.2. Before beginning the experiment, thioredoxin reductase (Sigma; from *E. coli* for *E. coli* Trx experiments, or from rat liver for human TRX experiments) was added to the experimental buffer to a final concentration of 50 nM. Thioredoxin was then added to the experimental buffer to the indicated concentration. An excess of NADPH and a catalytic amount of thioredoxin reductase are both necessary to maintain, 98% of Trx in the active, reduced form during the experiment. In the Trx system, reducing equivalents are donated from NADPH to the FAD domain of thioredoxin reductase, and these electrons subsequently reduce a catalytic disulphide bond in thioredoxin reductase. Reduced *E. coli* thioredoxin reductase is very specific for reducing the disulphide bond in oxidized Trx1 and does not non-specifically reduce other disulphides. When Trx was not included in the solution, no disulphide reduction in I27SS was observed even in the presence of thioredoxin reductase and NADPH.

In the experiment, ~5 µl (I27SS)8 solution was added to a ~100 µl droplet of Trx-containing experimental buffer deposited on a substrate coverslide. Single (I27SS)8 protein molecules were stretched by first pressing the cantilever on the coverslide at a constant force of 800 pN for 3 s, then retracting to a constant force of 165 pN for 400 ms during the unfolding pulse. The indicated test-pulse force was applied for ~5 s. In these experiments, the precise point of attachment between the (I27SS)8 molecule and the cantilever was not controlled; thus, varying numbers of disulphide reduction events may be observed in a given single-molecule recording.

Data Analysis.

All data were recorded and analysed using custom software written in Igor Pro 5.0 (Wavemetrics). Only recordings that exhibited disulphide reduction events of the expected step size in the test pulse were analyzed. (For a discussion of expected disulphide reduction step size as a function of force, see Wiita et al., *PNAS USA*, 103: 7222-7227 (2006)). The test-pulse portions of numerous (n=10-30) recordings that contained only disulphide reduction events and no unsequestered unfolding events were summated and normalized. These averaged traces were fitted with a single exponential to obtain the observed rate constant of reduction, r. This type of summation procedure is standard in the ion channel literature and has been used in many contexts to obtain macroscopic kinetics from single-molecule recordings. It is assumed that disulphide reduction in (I27SS)8 is markovian (that is, that each reduction event is independent of all others); thus, averaging traces with different numbers of reduction steps will result in invariant exponential kinetics4. To estimate the error on the experimentally obtained rate constant, the nonparametric bootstrap method was carried out. At a given value of force and [Trx], n staircases were randomly drawn with replacement from the original data set. These were summed and fitted to obtain a rate constant. This procedure was repeated 1,000 times for each data set, resulting in a distribution that provided the standard error of the mean for the reduction rate constant, shown as the error bars in FIGS. 11B and 11B, FIG. 12 and FIG. 13B.

Kinetic Model.

In the kinetic model shown in FIG. 11D, three states are used to describe the experimental system. The rate equations for the concentrations of states 0, 1 and 2 as a function of time τ are:

$$d[0]/d\tau = -\kappa_{01}[0] - k_{02}[0] + k_{10}[1] \quad (1)$$

$$d[1]/d\tau = \kappa_{01}[0] - k_{10}[1] - k_{12}[1] \quad (2)$$

$$d[2]/d\tau = \kappa_{02}[0] + k_{12}[1] \quad (3)$$

Where each rate constant is defined by the following parameters ($\alpha 0$, $\beta 0$, $\gamma 0$ and $\delta 0$ are coefficients used to calculate each rate constant as a function of force and [Trx]):

$$\kappa_{01} = \alpha_0[Trx] \quad (4)$$

$$\kappa_{12} = \beta_0 \exp(F\Delta x_{12}/k_B T) \quad (5)$$

$$\kappa_{02} = \gamma_0[Trx]\exp(F\Delta x_{02}/k_B T) \quad (6)$$

$$\kappa_{10} = \delta 0 \quad (7)$$

As shown in FIG. 11D, rate constants κ01 and κ02 are linearly dependent on the concentration of Trx and have units of μM−1 s−1. κ10 is a constant with units of s−1. κ12 is in units of s−1 and is modelled to be exponentially dependent on the applied force, following the Bell equation. κ02 also demonstrates an exponential dependence on the applied force. There are no reverse rate constants for the 0→2 and 1→2 transitions (that is, κ20=0 and κ21=0). Immediately after disulphide bond reduction in an I27SS module by Trx, the two thiol groups in I27SS are pulled more than 10 nm apart by the applied force. This prevents any reoxidation of the disulphide bond in I27SS, so the formation of state 2 is irreversible in the experiment. It is assumed that the concentration of Trx remains constant throughout the experiment because the rare oxidation of single enzymes will not significantly affect the overall solution concentration of active Trx. The [Trx] term is input as a constant from the experimental conditions. The I27SS concentration is not a factor in the rate equations because only single molecules are monitored at any given time and all results are unaffected by the bulk concentration of I27SS.

To describe the obtained experimental data, this kinetic model using matrix analysis was solved. By determining the eigenvalues and eigenvectors of the kinetic matrix (see equation (8)) it is possible to calculate the probability of a single I27SS module being in a given state as a function of time.

$$A = \begin{pmatrix} -(\kappa_{01} + \kappa_{02}) & \kappa_{10} & 0 \\ \kappa_{01} & -(\kappa_{10} + \kappa_{12}) & 0 \\ \kappa_{02} & \kappa_{12} & 0 \end{pmatrix} \quad (8)$$

If values are inputted for the parameters $\alpha_0$, $\beta_0$, $\gamma_0$, $\delta_0$, $\Delta x_{12}$ and $\Delta x_{02}$ as well as the experimental [Trx], the matrix for a discrete set of forces in the range of 0-600 pN can be solved. The output of the analysis shows the probability of a single disulphide bond existing in state 0, state 1 or state 2 as a function of time. It is noted that the model is solved with the initial condition of P(0)=1 at time=0, State 2, where disulphide reduction by Trx has occurred, is the only state that can be directly monitored using the experimental technique. Thus, the calculated probability of being in state 2 as a function of time directly corresponds to the observed single-molecule recordings shown in FIG. 11A. By fitting these calculated probabilities with a single exponential, the observed rate constant of reduction (r=1/τ from the exponential fit to the model plot) can be obtained in the same manner that r was determined for the experimental data.

To find the optimal kinetic parameters to describe the experimental data, the kinetic model for several, widely ranging values for each parameter (typically over three orders of magnitude) was solved first. Then the model r values were compared to those obtained experimentally (see FIGS. 2C, D for wild-type Trx, and FIG. 3B for Trx(P34H)) and calculated the goodness of the fit χ2, where $$\chi^2 = \sum_1^N \left(\frac{y_i - f(x_i)}{\sigma}\right)^2;$$

here, N is the number of data points, $y_i$ is the experimentally observed rate, f ($x_i$) is the calculated rate from the kinetic model, and σ is the magnitude of the error of the observed rate. The combination of parameter values with the lowest χ2 then served as the starting point for the downhill simplex method to optimize further the global fit of the model to the data.

Errors for each parameter were again obtained with the bootstrap method in combination with the downhill simplex method. At each given value of force and [Trx], a value for the rate constant from the distribution obtained with the bootstrap method (see the 'Data Analysis' section above) was picked at random. By using different values for the rate at each force, extracted from the bootstrap analysis, the experimental error in each rate constant is accounted for when performing fits to the model. The downhill simplex method was then applied to these rate constants, giving the best fitting values for each parameter for that particular combination of rates. The downhill simplex simultaneously varied all six fitting parameters to globally fit the 32 data points for wild-type Trx (14 at 8 μM Trx; 18 at other concentrations). This procedure was repeated 200 times, resulting in distributions, and thereby standard errors, for each model parameter.

To determine the goodness of fit of the various kinetic models, the above methods were first used to globally fit each model to the force-dependent and concentration-dependent data for wild-type Trx. An overall χ2 value was measured for the best fit to each model (best-fitting parameters shown in Table 1).

TABLE 1

Figure 5:
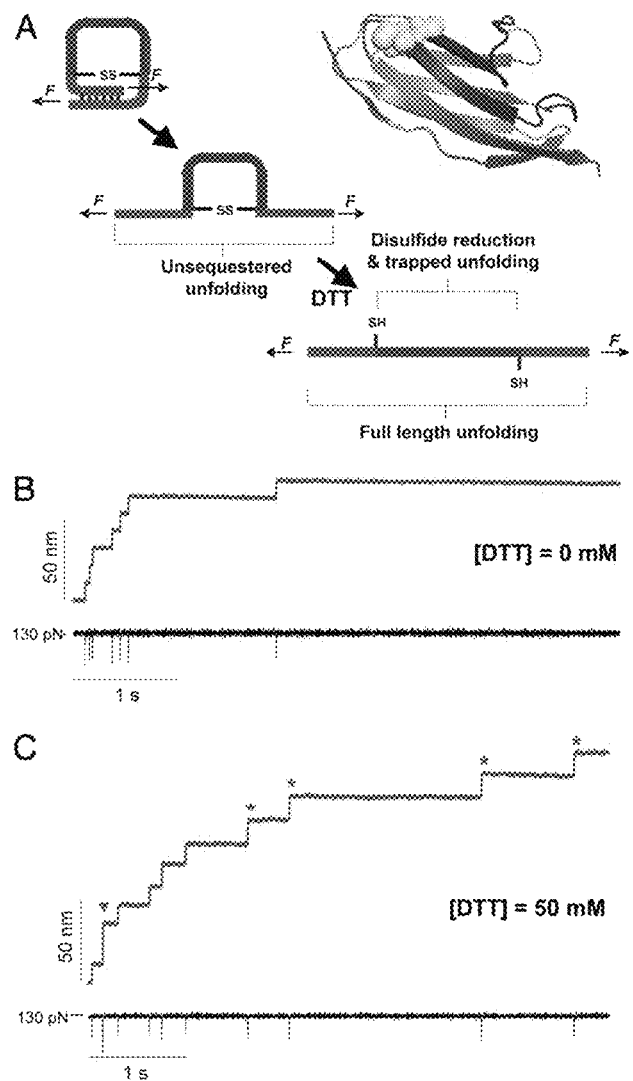
FIG. 5A is a schematic showing the unfolding of I27G32C-A75C.
FIG. 5B shows the stepwise elongation (red trace) of an (I27G32C-A75C)8 polyprotein pulled at a constant force of 130 pN (black trace) in the absence of DTT.
FIG. 5C shows the stepwise elongation (red trace) of an (I27G32C-A75C)8 polyprotein pulled at a constant force of 130 pN (black trace) in the presence of 50 mM DTT.

Parameters obtained from global fits to alternate kinetic models (see Supplementary FIGS. 5 and 6). Error bars are given by the standard error for each parameter obtained from the downhill simplex filling procedure (see "Kinetic Model" in Methods).

| WT Trx | $\alpha_0$ (μM$^{-1}$s$^{-1}$) | $\beta_0$ (s$^{-1}$ or μM$^{-1}$s$^{-1}$) | $\gamma_0$ (s$^{-1}$) | $\delta_0$ (s$^{-1}$) | $\Delta x_{12(A)}$ (Å) | $\Delta x_{12, B}$ (Å) | $\Delta x_{02(A)}$ (Å) | $\Delta x_{12(B)}$ (Å) |
|---|---|---|---|---|---|---|---|---|
| Model 1 | 0.24 ± 0.07 | 0.060 ± 0.009 | — | — | — | — | −0.9 ± 0.2 | — |
| Model 2 | 0.25 ± 0.04 | 0.020 ± 0.007 | — | — | — | — | −0.6 ± 0.1 | 0.13 ± 0.03 |
| Michaelis-Menten | 0.22 ± 0.02 | 25 ± 4 | — | 3.5 ± 0.9 | −0.67 ± 0.07 | — | — | — |
| Model 3 | 0.24 ± 0.02 | 28 ± 4 | 2.7 ± 0.3 | 4.1 ± 0.6 | −1.2 ± 0.2 | — | — | — |
| Model 4 | 0.24 ± 0.03 | 33 ± 4 | 0.4 ± 0.1 | 4.4 ± 0.5 | −0.9 ± 0.1 | 0.20 ± 0.02 | — | — |
| Trx P34H Model 4 | 0.14 ± 0.02 | 30 ± 2 | 0.37 ± 0.08 | 3.3 ± 0.6 | −0.9 ± 0.2 | 0.36 ± 0.03 | — | — |

A reduced chi-squared value, χ2v=χ2/v, where v is the number of degrees of freedom in the fit (v=N−c, where N is the number of data points and c is the number of free fitting parameters) was then obtained. To determine the statistical goodness of fit, P(χ2v) was calculated, the likelihood of obtaining the observed χ2v n if the experimental data are truly represented by the proposed kinetic model. This method has been used previously to determine the goodness of fits of various kinetic models to single-molecule data. $P(\chi2v)$ was calculated using the web-based program available at http://www.fourmilab.ch/rpkp/experiments/analysis/chiCalc.html. Parameters relating to the analysis of various kinetic models are shown in Table 2.

TABLE 2

Statistical Analysis of kinetic model fitting (see Supplementary FIGS. 5 and 6). For WT Trx, number of data points N = 32; for Trx P34H, N = 10; for hTrx, N = 10 and $\Delta\chi_{12}$ = 0.079 (fixed)

| | Reduced chi-squared $(\chi^2_v)$ | Degrees of Freedom (v) | Free parameters | $p(\chi^2_v)$ |
|---|---|---|---|---|
| WT Trx | | | | |
| Final Model | 0.835 | 26 | 6 | 0.705 |
| Model 1 | 1.96 | 29 | 3 | 0.0015 |
| Model 2 | 1.39 | 28 | 4 | 0.110 |
| Michaelis-Menten | 5.06 | 28 | 4 | $<1 \cdot 10^{-10}$ |
| Model 3 | 1.21 | 27 | 5 | 0.211 |
| Model 4 | 0.973 | 26 | 6 | 0.503 |
| Trx P34H | | | | |
| Final Model | 0.580 | 4 | 6 | 0.677 |
| Model 4 | 3.09 | 4 | 6 | 0.015 |
| hTrx | | | | |
| Final Model | 0.750 | 5 | 5 | 0.586 |

Force-Probe Molecular Dynamics and Structural Modeling.

Simulations were carried out with the Gromacs 3.3.1 simulation suite (http://www.gromacs.org). The simulations were started from the NMR structure of human TRX in an intermediate complex with a disulphide bond to a substrate, the NF-κB peptide (PDB accession number 1MDI). Protonation states of the standard amino acids were adopted from the solution structure.

The OPLS (optimized potentials in liquid simulations) force field was applied. The protein was solvated in a 7.3×7.3×7.4 nm3 box of TIP4P water molecules. Twenty-two sodium and 18 chloride ions were added to the simulation system to compensate for the overall positive charge of the protein and to mimic physiological conditions. This yielded a total system size of 49,220 atoms. Simulations were carried out with periodic boundary conditions. Application of the Lincs and Settle methods allowed for an integration time step of 2 fs. Electrostatic and Lennard-Jones interactions were calculated within a cut-off of 1 nm, and the neighbour list was updated every ten steps. For the long-range electrostatic interactions, the Particle-Mesh-Ewald (PME) method41 with a grid spacing of 0.12 nm was used. An N, p, T ensemble, where N is the number of atoms, p is the pressure and T is the temperature, was simulated, with separate coupling of the protein, solvent and ions to a 300K heat bath (τ=0.1). The system was isotropically coupled to a 1 bar pressure bath (τ=1.0). Initially, the system was energy-minimized (steepest descent, 1,000 steps), before equilibrating the solvent for 700 ps with positional restraints on protein heavy atoms. Then, the whole system was equilibrated (300 K).

To model an approximate transition state geometry for the SN2 reaction in the active site of Trx, in a subsequent simulation the Trx-NF-κB disulphide bond was elongated from 2.05 Å to 2.60 Å (the length of the extended bond found for the transition state in an SN2 reaction) within 160 ps using the free-energy perturbation code in Gromacs and starting from the equilibrated system. Next, the third sulphur atom taking part in the SN2 reaction was placed along the resulting vector of the extended disulphide bond between Trx and the NF-κB peptide in a distance of 2.40 Å, as found for the SN2 transition state. The cysteine residue to which the third sulphur atom is bound was placed into the location defined by the sulphur atom, and was oriented such that it did not clash with Trx or peptide residues. Using 20 different starting structures of equilibrated Trx for the modelling of the reduction transition state resulted in somewhat different active-site geometries. The angle between the peptide-binding groove and the axis of the sulphur atoms varies and exists in the range between 50° and 130°. The average conformation of the disulphide bond was observed to fall into two populations. The resulting structures were plotted with Pymol.

In another set of simulations, titin I27 with residues 32 and 75 mutated to cysteines was unfolded to monitor the disulphide bond orientation in the unfolded state with respect to the pulling direction. The OPLS force field was applied for I27. The wild-type protein (PDB accession number 1TIT) was solvated in TIP4P water in a 6.8×5.7×5.0 nm3 box. Sixteen sodium and ten chloride atoms were added to neutralize the protein charges and to give physiological ion strength. The resulting system size was 23,524 atoms. I27 was minimized, the solvent initially equilibrated with restraints on the protein heavy atoms (500 ps), and then the entire system subsequently equilibrated for a further 8 ns. The simulation software and parameters as described above were applied. Residues 32 and 75 of the equilibrated structure were mutated to cysteine residues using the program WHATIF. The mutant I27SS was re-solvated in a larger box (19.2×5.5×5.0 nm3), allowing sufficient space to completely unfold the protein, yielding a system size of 112,156 atoms. The system was minimized, resulting in a shortening of the S—S bond to the value typical for an S—S bond (2.05 Å). The solvent was equilibrated with restraints on the protein heavy atoms (2 ns), followed by the equilibration of side chains with restraints on the protein backbone atoms (2 ns), and finally by the equilibration of the whole system (11 ns). No distortion of the structure adjacent to the point mutations was observed. Force-probe molecular dynamics simulations of the equilibrated I27SS mutant were performed. The Cα-atoms of the terminal residues were subjected to harmonic pulling potentials with a spring constant of 500 kJ mol-1 nm-2, and were moved away from each other with a constant velocity of 0.4 nm ns-1. As expected, the unfolded structure, obtained after ~14 ns of the force-probe molecular dynamics simulation time, showed alignment of the disulphide bond within ~20° of the pulling direction, with a projection of the S—S bond length on the pulling axis of ~1.9 Å.

For comparison of the active-site geometry, additional standard equilibrium molecular dynamics simulations have been performed for the reduced state of Trx in the absence of a peptide, and for the other available Trx intermediate, the Trx-Ref-1 complex. For the simulation of the reduced state, the NF-κB peptide in the 1MDI structure was deleted. The apo structure with an unprotonated Cys 32 was solvated in water. After addition of ions to yield physiological ion strength, the system comprised 33,606 atoms. The Trx-Ref-1 complex (PDB accession number 1CQH) was solvated in water with physiological ion strength, resulting in a system size of 38,760 atoms.

Example 3

Selection of Trxs from Different Species

To investigate the various catalytic mechanisms developed by Trx, a set of Trxs belonging to a representative group of species from different kingdoms were selected: Animalia, Eubacteria, Protista and Plantae (covering two domains of life: bacteria and eukaryotes). Trx is widely distributed in all living organisms from bacteria to mammals. In addition, the existence of a second paralogous Trx gene (Txn2) seems to be common in animals, protists and Gram-negative bacteria. In protists and animals, Trx1 is located in the cytoplasm, whereas Trx2 is present in mitochondria. Notably, mitochondrial Trx2 from mammals has been shown to have higher similarity with *E. coli* Trx1 than with cytosolic Trx1 from mammals. In the case of plants, a rich variety of Trx genes can be found encoding more than 20 different types of Trxs that are classified into six isoforms: Trxf, h, m, x, y and o. The f, m, x and y forms are plastidic Trxs, h forms are mainly cytosolic and o forms are found in mitochondria. In this study, both human cytosolic and mitochondrial Trxs from animals were included, poplar Trxh1 (featuring a CPPC active site instead of the canonical CGPC), poplar Trxh3 and pea chloroplastic Trxm from plants, *E. coli* Trx1 and Trx2 from bacteria and, finally, *Plasmodium falciparum* (malaria parasite) Trx1 from protists.

Figure 14:
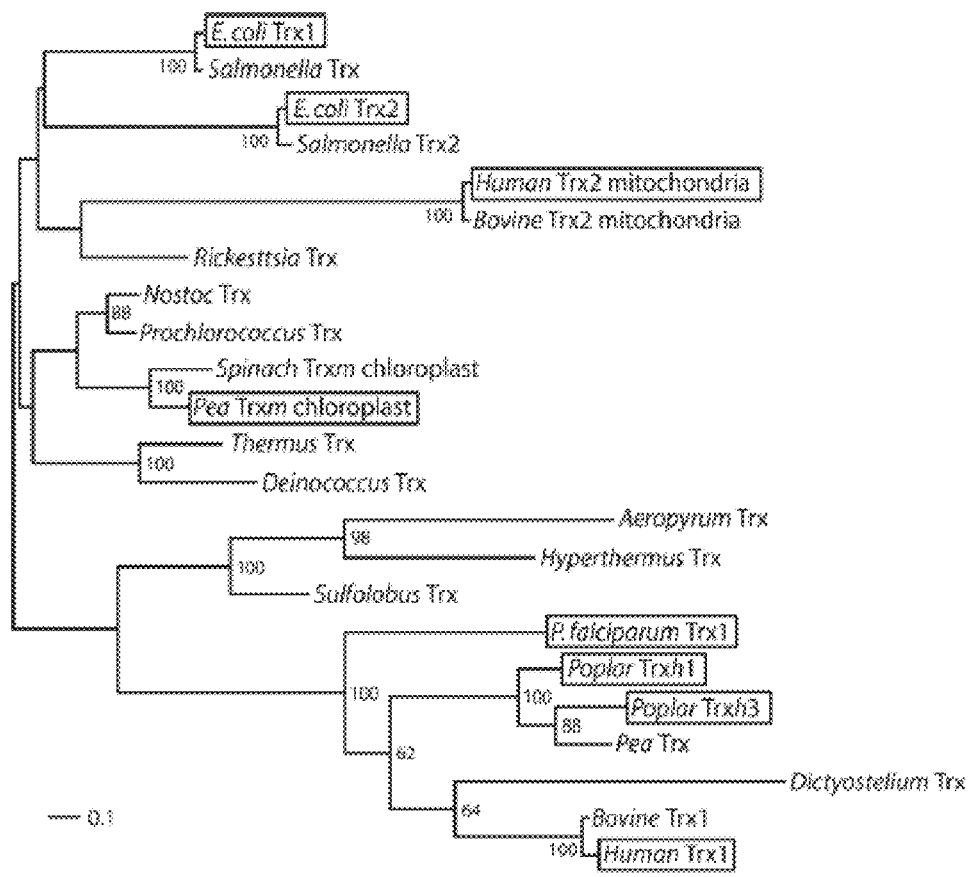
FIG. 14 shows the phylogeny of Trx homologs from representative species of the three domains of life.

A sequence alignment of the Trxs of interest shows that the residues around the active site are highly conserved. The construction of a phylogenetic tree (FIG. 14), incorporating additional Trxs from the three domains of life, classifies *E. coli* Trx1 and Trx2, human TRX2 and pea Trxm as 'bacterial-type' Trxs (upper branches in FIG. 14) and human TRX1, poplar Trxh1 and Trxh3 and *P. falciparum* Trx1 as 'eukaryotic-like' Trxs (lower branches in FIG. 14). The construction of a larger tree incorporating more than 200 Trx sequences corroborates the suggestion that the sequences used are widely distributed and that they are representative for the entire Trx family.

Force-Dependent Chemical Kinetics of Disulfide Reduction

Figure 15:
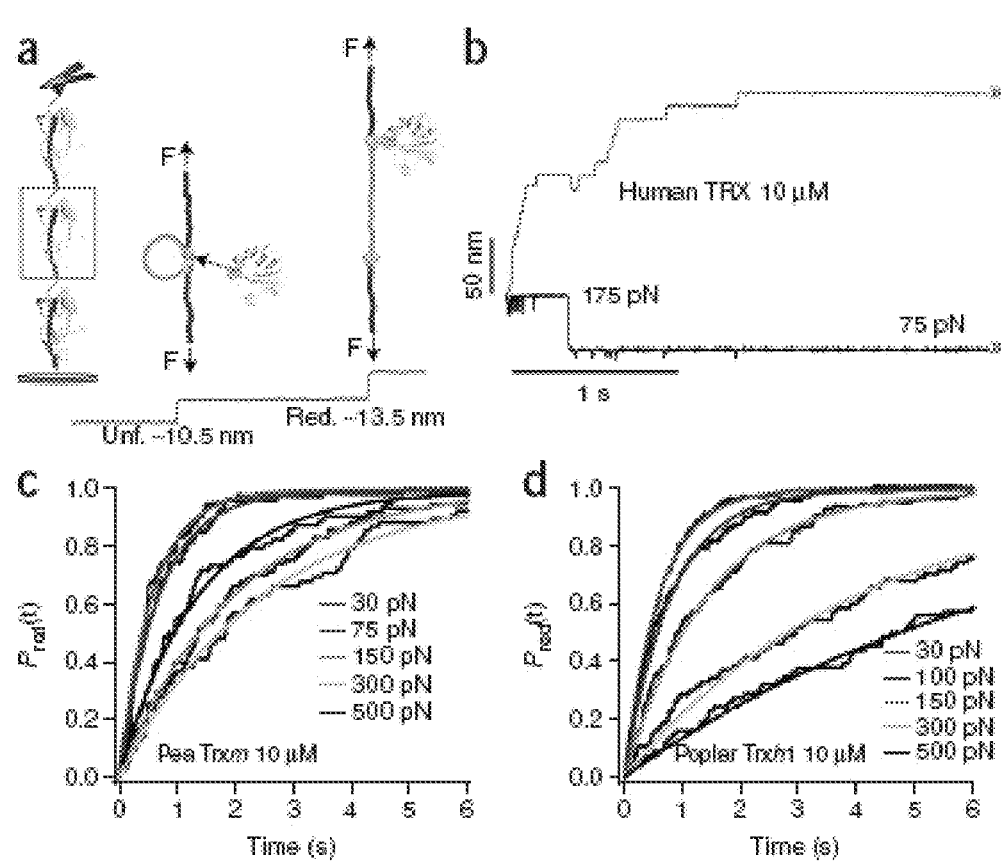
FIG. 15 shows results from single-molecule force-clamp detection of disulfide bond-reduction events catalyzed by Trx enzymes.

An atomic force microscope was used in its force-clamp mode to study the chemistry of disulfide reduction by Trx. Briefly, a polyprotein composed of eight domains of the 27th module of human cardiac titin was chosen for a substrate, in which each module contains an engineered disulfide bond between the 32nd and 75th positions (I27G32C-A75C)8. The first pulse of force (175 pN, 0.3 s) applied to the polyprotein allows the rapid unfolding of the I27G32C-A75C modules up to the disulfide bond. The individual unfolding events can be registered as steps of B10.5 nm per module. After the first pulse, the disulfide bonds become exposed to the solvent, where the Trx molecules are present in the reduced form owing to the presence of Trx reductase and NADPH (Trx system)6. A second pulse of force is applied to monitor single disulfide reductions by Trx enzymes, recorded as a second series of steps of B13.5 nm per domain (FIG. 15A, 15B). Several traces per force (15-50) have been accumulated, which have been averaged and fit with a single exponential with a time constant t (FIG. 15C, 15D). Thus, the reduction rate at a given force (r=1/t) is obtained.

Figure 16:
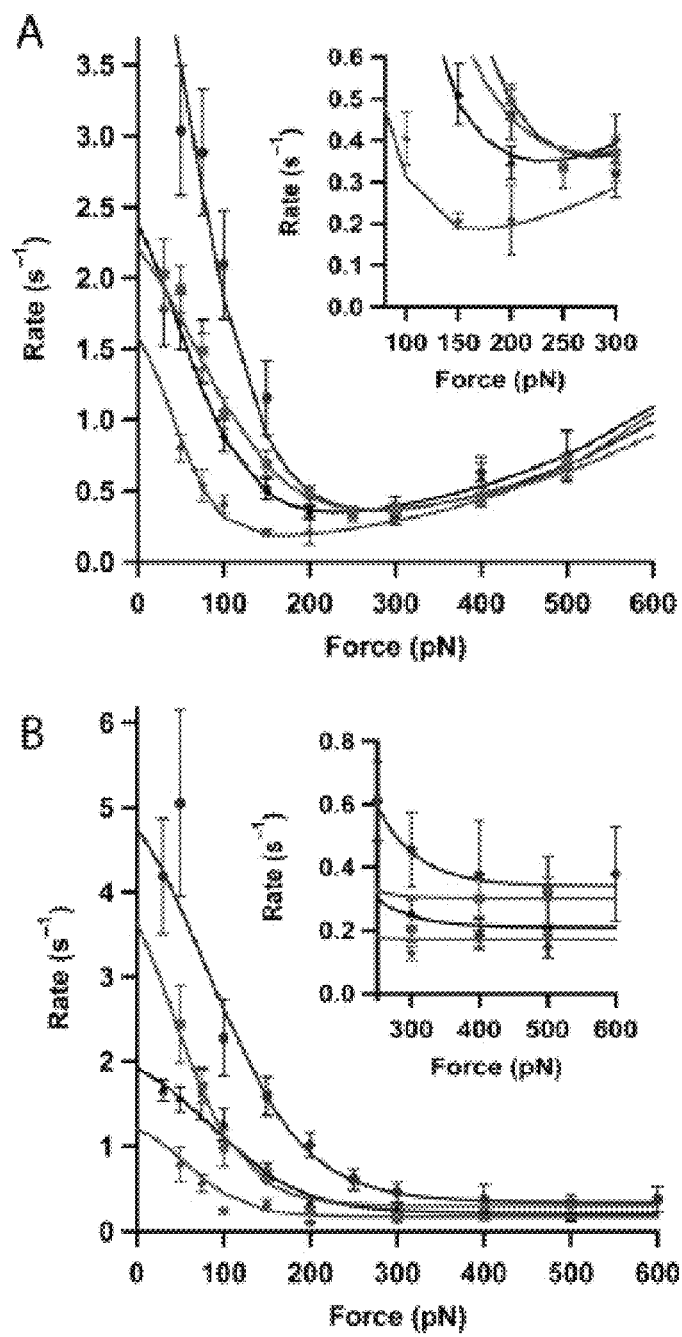
FIG. 16 shows graphs depicting the force-dependency of the rate of disulfide reduction by Trx enzymes from different species.

The single-molecule assay was applied to obtain the force-dependency of the rate of reduction by the selected Trxs (FIG. 16). From these data three different types of force-dependencies can be readily distinguished. First, all tested Trx enzymes showed a negative force-dependency in the range 30-200 pN. Second, all Trx enzymes from bacterial origin show that, after reaching a minimum rate at around 200 pN, the rate of reduction increases exponentially at greater forces. Third, at forces greater than 200 pN, enzymes from eukaryotic origin show a rate of reduction that becomes force-independent. Therefore, the previous observations in *E. coli* and human TRXs can now be generalized to bacterial-origin and eukaryotic-origin Trxs.

As previously proposed, the reduction mechanism observed when the substrate is stretched at low forces (30-200 pN) is similar to a Michaelis-Menten (MM-SN2) reaction in which the formation of an enzyme-substrate complex is determinant. Upon binding, the substrate disulfide bond needs to rotate to achieve the correct geometry necessary for an SN2 reaction to occur, that is, the three involved sulfur atoms form an ~180° angle. This rotation causes the shortening of the substrate polypeptide along the stretching force axis, as determined by the negative value of $\Delta x_{12}$ in the kinetic model (Table 3, FIG. 17). This mechanism is rapidly inhibited as the force increases, generating the negative dependence of the reduction rate with the pulling force in all Trx enzymes (FIG. 16). Here it is demonstrated that, whereas the absolute rate of reduction varies from enzyme to enzyme, the general characteristics of this mechanism of reduction are apparent in all of them.

TABLE 3

Kinetic parameters for Trx enzymes from different species

| | $\alpha_0$ ($\mu M^{-1} s^{-1}$) | $\beta_0$ ($s^{-1}$) | $\gamma_0$ ($\mu M^{-1} s^{-1}$) | $k_{10}$ ($s^{-1}$) | $\Delta\chi_{12}$ (Å) | $\Delta\chi_{02}$ (Å) | $\lambda_0$ ($s^{-1}$) |
|---|---|---|---|---|---|---|---|
| *E. coli* Trx1 | 0.25 ± 0.02 | 24 ± 2 | 0.012 ± 0.002 | 4.7 ± 0.5 | −0.75 ± 0.05 | 0.16 ± 0.01 | 0.08 ± 0.02 |
| *E. coli* Trx2 | 0.18 ± 0.04 | 23 ± 3 | 0.009 ± 0.002 | 4.5 ± 0.5 | −1.41 ± 0.03 | 0.19 ± 0.01 | 0.07 ± 0.03 |
| Human TRX2 | 0.65 ± 0.15 | 25 ± 2 | 0.019 ± 0.004 | 3.8 ± 0.6 | −0.84 ± 0.05 | 0.19 ± 0.02 | 0.06 ± 0.04 |
| Pea Trx m | 0.28 ± 0.03 | 22 ± 2 | 0.012 ± 0.002 | 5.0 ± 0.6 | −0.93 ± 0.08 | 0.17 ± 0.02 | 0.09 ± 0.04 |
| *P. falciparum* Trx1 | 0.43 ± 0.05 | 25 ± 2 | — | 4.8 ± 0.5 | −1.01 ± 0.05 | — | 0.34 ± 0.02 |
| Human TRX1 | 0.52 ± 0.05 | 33 ± 2 | — | 3.1 ± 0.9 | −0.71 ± 0.05 | — | 0.35 ± 0.02 |
| Poplar Trxh3 | 0.12 ± 0.03 | 30 ± 3 | — | 4.4 ± 0.4 | −1.16 ± 0.08 | — | 0.17 ± 0.02 |
| Poplar Trxh1 | 0.22 ± 0.02 | 28 ± 3 | — | 5.5 ± 0.6 | −0.68 ± 0.07 | — | 0.17 ± 0.03 |

According to the parameters obtained from the fit of the data to a simple MM-SN2-type kinetic model (Table 3), it was found that an extrapolation to zero force predicts rate constants ranging from $1.2 \times 10^5$ M−1 s−1 for poplar Trxh3 to 6.5×105 M−1 s−1 for human TRX2. These values are markedly similar to those obtained previously using insulin disulfides as substrates and *E. coli* Trx8. The value of $\Delta x12$ remained below 1 Å, except for *E. coli* Trx2 and poplar Trxh3, which gave values of more than 1 Å (Table 3). These high values of $\Delta x12$ represent a higher rotation angle of the substrate disulfide bond for the SN2 reaction. This mechanism is unique to Trx enzymes, and it seems to be the result of evolutionary pressure toward developing an efficient mechanism of disulfide reduction that is not possible with simple chemical reagents.

When forces of more than 200 pN were applied to the substrate, the MM-SN2 mechanism was blocked, and a second force-dependent mechanism of reduction became dominant. This was true for all types of Trx enzymes that were tested. In enzymes of bacterial origin, this high-force mechanism (FIG. 16A) seems to be analogous to that of simple chemical compounds such as cysteine, glutathione or DTT, which reduce disulfide bonds through a force-dependent SN2 thioldisulfide exchange reaction with bond elongation at the transition state. This reaction was incorporated into the kinetic model (k02), obtaining a value for the elongation of the disulfide bond at the transition state of ~0.18 Å ($\Delta x02$ in Table 3), a value that is similar to those obtained when using cysteine as a nucleophile (~0.2 Å). Absence of the SN2-like mechanism seems to be common to all eukaryotic-origin Trx, where the rate of the reaction became force-independent at greater forces (FIG. 16B). This force-independent mechanism was measured as a constant rate of reduction that ranged from 0.2 s−1 to 0.4 s−1 (FIG. 16B, inset). It is speculated that in enzymes of bacterial origin the minimum value of the reduction rate is also limited by this force-independent 'floor' in the rate of reduction, which varies in the range 0.2-0.4 s−1 (FIG. 16A, inset). This mechanism was incorporated into the kinetic model in the form of a constant parameter, 1, which contributes equally to the reduction rate throughout the entire range of forces (Table 3).

A possibility that may explain this force-independent chemical mechanism is a SET reaction via tunneling, a process that has been observed in enzymes containing metallic complexes In addition, it has been suggested that SET reactions are highly favored when steric hindrance occurs. To test whether an electron transfer mode of reduction would be force-independent, the kinetics of disulfide reduction under force by a metal was investigated. Some metals participate in oxidation-reduction processes in proteins via electron-transfer reactions that are governed by the reduction potential. The reduction of disulfide bonds by zinc nanoparticles (diameter <50 nm) was experimentally studied. In sharp contrast to all other reducing agents that were studied, the rate of reduction of disulfide bonds by zinc was force-independent (FIG. 17A). Owing to the experimental difficulty of working at low forces with zinc nanoparticles, only experiments done using forces of more than 200 pN were included. The results support the idea that the force-independent mechanism is a barrier-free electron-tunneling reaction that does not require the precise orientation for the SN2 reaction.

Another piece of evidence in support of the SET mechanism can be obtained from the analysis of the concentration-dependencies of the MM-SN2 and SET reduction mechanisms. Reduction kinetics by human TRX1 were measured at different forces and concentrations (50-600 pN and 2-15 µM of TRX1) and found that the low-force MM-SN2 mechanism (50-200 pN) is clearly dependent on the concentration of the enzyme, whereas the high-force SET mechanism (>300 pN) is essentially concentration-independent. As expected for a first-order MM-SN2 mechanism, where substrate binding to the groove is determinant, the rate of reduction showed linear concentration-dependence when working below saturating concentrations of TRX1 enzyme (<15 µM). However, given that the TRX1 and NADPH system was in equilibrium owing to the presence of TrxR, the redox potential of TRX1 would be expected to remain constant (from the Nernst equation). Therefore, the potential difference between TRX1 and substrate, and thus the rate of electron transfer, would also be constant in this TRX1 concentration range. Hence, the SET mechanism should be essentially independent of the enzyme concentration.

Figure 17:
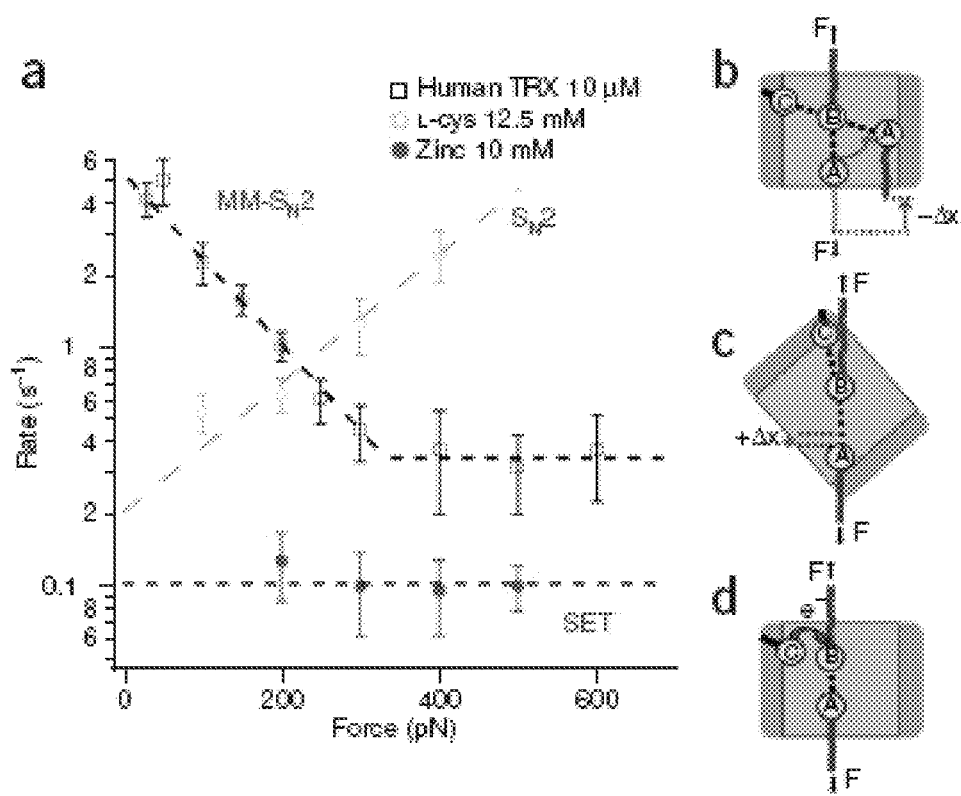
FIG. 17 shows three chemical mechanisms of disulfide reduction detected by force-clamp spectroscopy.

The results suggest that there are three distinct mechanisms of reduction that operate simultaneously in a Trx enzyme. These mechanisms are identified by their force-dependency, as shown in FIG. 17. The most complex mechanism is characterized by a negative force-dependency and is unique to enzymatic catalysis by Trx (FIG. 17A, 17B). This enzymatic mechanism of reduction is characterized by a MM-SN2 reaction between the substrate polypeptide and the binding groove of the enzyme, followed by a rotation of the substrate disulfide bond to gain position for the SN2 reduction mechanism (FIG. 17A, 17B). A much simpler mechanism is that of a regular SN2 reaction, characterized by a rate of reduction that increases exponentially with the applied force. This mechanism is well represented by nucleophiles such as L-cysteine (FIG. 17A), glutathione and DTT. By this mechanism, the substrate disulfide bond and the catalytic cysteine of the enzyme orient themselves with the pulling force, without needing a rotation of the substrate disulfide bond (FIG. 17C). It was suspected that this mechanism would be possible only if the Trx enzyme had a shallow binding grove that allowed many other orientations of the substrate-enzyme complex. Finally, the third mechanism is the force-independent, barrier-free electron-tunneling transfer mechanism, revealed by the action of metallic zinc (FIG. 17D). It is inevitable that, if the disulfide bond gets close enough to the thiolate anion of the catalytic cysteine, the electron tunneling will occur, albeit at a low rate.

Figure 18:
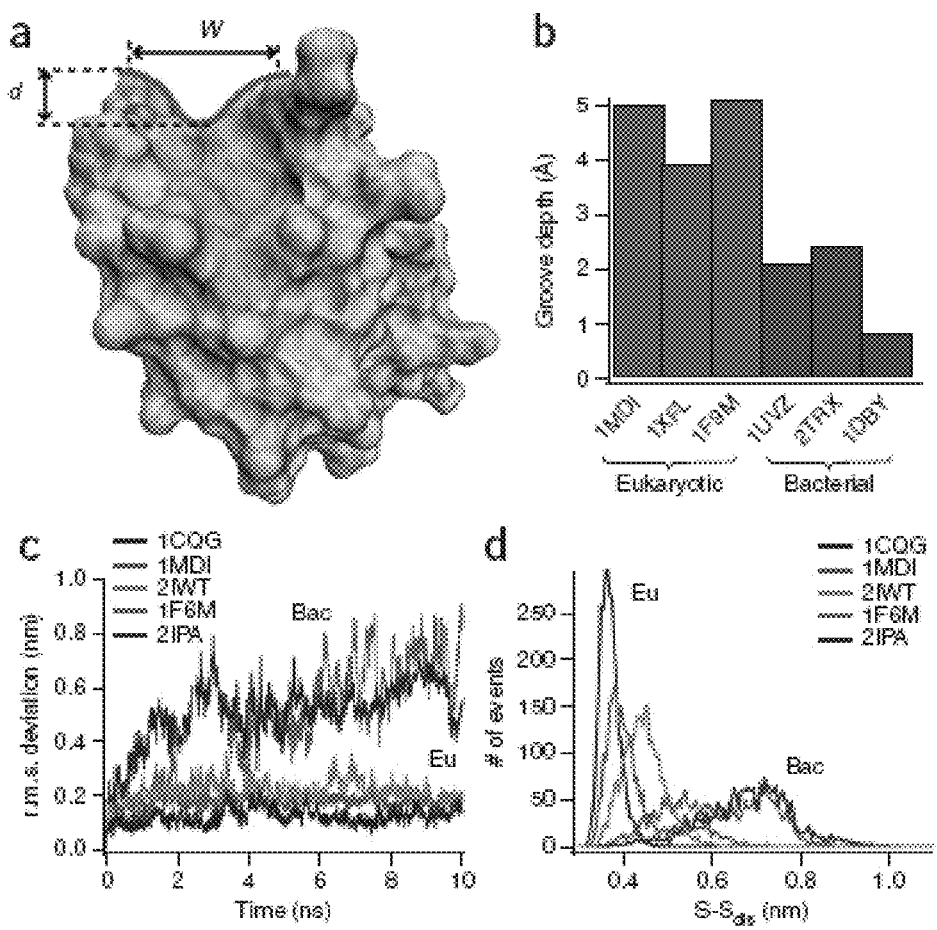
FIG. 18 depicts structural analysis and molecular dynamics simulations of the binding groove in Trx enzymes.

Thus, comparing the data in FIG. 16 and FIG. 11, it is clear that the main difference between enzymes of bacterial and eukaryotic origin is the elimination of the high-force, simple SN2-like mechanism of reduction. This drastic change in the catalytic chemistry may be caused by changes in the structure of the enzyme as it evolved. The most salient feature in the structure of Trx enzymes is the binding groove into which the target polypeptide first binds, to be subsequently reduced by the exposed thiol of the catalytic cysteine (FIG. 18A).

Structural Analysis and Molecular Dynamics Simulations

To study the role of the structure in the chemical behavior of Trxs, the structure of the binding groove of a set of bacterial-origin and eukaryotic-origin Trxs were analyzed. Three eukaryotic-origin enzymes—human TRX1, *Arabidopsis thaliana* Trxh1 and spinach Trxf—and three bacterial-origin enzymes—human mitochondrial TRX2, *E. coli* Trx1 and *Chlamydomonas reinhardtii* Trxm were studied. From the X-ray or NMR structures, structural axes were defined that allowed the calculation of the depth and width of the binding groove in the region surrounding the catalytic cysteine (FIG. 18A). It was found that eukaryotic Trx enzymes have binding grooves that are several angstroms deeper than those of bacterial origin (FIG. 18B). By contrast, the width of the binding groove remained the same.

The consequences of a deepening binding groove using molecular dynamics simulations to probe the mobility of a bound polypeptide were explored. For these simulations, a set of enzyme structures obtained with mixed disulfide intermediates between the catalytic cysteine and a cysteine in the bound substrate were considered. Such structures capture the general disposition of the substrate in the catalytic site of the Trx enzyme. Three eukaryotic complexes— human TRX1 with the substrate REF-1, human TRX1 with NF-κB and barley Trxh2 with protein BASI—and two bacterial complexes—E. coli Trx1 with Trx reductase and B. subtilis Trx with ArsC complex were used. To compare these structures, 13 residues of the substrates, with the binding cysteine always set as the seventh residue were taken into account. For the molecular dynamics simulations, the substrate-enzyme disulfide bond was removed to allow substrate mobility. The shallow binding groove of bacterial Trxs allows the substrate to be mobile (FIG. 18C). By contrast, the deeper groove found in Trx enzymes of eukaryotic origin tends to freeze the substrate into a much smaller range of conformations. Similarly, the measured distribution of the distances between the reacting sulfur atoms is smaller and more narrowly distributed in the deeper binding groove of Trx enzymes of eukaryotic origin than in those with the shallower grooves found in enzymes of bacterial origin (FIG. 18D).

As an additional test, molecular dynamics simulations were carried out in which the substrate was removed from the Protein Data Bank structures for two Trx complexes: one from eukaryotic origin, barley Trxh2 with protein BASI (PDB 2IWT), and the other from bacterial origin, B. subtilis Trx with ArsC complex (PDB 2IPA). No appreciable difference in the dynamics of the groove between the bacterial and the eukaryotic Trxs was found. In fact, the averaged value of the r.m.s. deviation difference is 0.035±0.028 for PDB 2IWT and 0.023±0.031 for PDB 2IPA (the error indicates s.d.). These results support the idea that the large differences in the mobility of the substrate that is being reported (FIG. 18C, 18D) are due to the different binding constraints of the groove.

Finally, the B-factor distribution of the substrate from the PDB structures were compared. The B-factors of protein crystal structures reflect the fluctuation of atoms around their average positions and provide information about protein dynamics. In particular, the B-factors of eukaryotic barley Trxh2 bound to protein BASI (PBD 2IWT) were compared with that of E. coli Trx bound to Trx reductase (PDB 1F6M), both from X-ray crystallographic experiments. Consistent with the simulation results (FIG. 18C), the substrate in 1F6M (bacterial-origin Trx) has larger B-factors than does eukaryotic Trx 2IWT.

These structural observations suggest that a major feature in the evolution of Trx enzymes has been an increase in the depth of the binding groove, increasing the efficiency of the MM-SN2 mechanism and eliminating the simple SN2 mechanism of catalysis.

Over the past 4 billion years, the chemistry of living organisms has changed continuously in response to changes in atmospheric conditions and biological phenomena. For example, the large increase in the level of atmospheric oxygen that occurred about ~2.5 billion years ago is thought to have triggered a chemical expansion that had a large impact on the chemistry of enzymatic reactions, especially those involving redox transformations. However, understanding how enzymes have adapted their chemical mechanisms to evolutionary pressures remains a challenge in molecular biology.

Here it is shown that single-molecule force-clamp spectroscopy can be a valuable tool to examine the evolution of Trx catalysis by studying the chemistry of eight Trx enzymes from four different kingdoms. It is shown that three different chemical mechanisms for disulfide reduction can be distinguished in Trx enzymes by their sensitivity to a mechanical force applied to their substrate. Common to all Trx enzymes is a highly efficient Michaelis-Menten-type mechanism of disulfide bond reduction, characterized by a negative force-dependency (FIG. 17A, 17B). Also common to all enzymes is a low-rate, force-independent mechanism of reduction that, owing to its similarity to metallic zinc, may be due to a barrier-free electron-tunneling mechanism (FIG. 17A, 17D). Finally, enzymes of bacterial origin show an additional mechanism of reduction, comparable to that of a simple SN2 reaction and showing a force-dependency similar to that of glutathione or cysteine (FIG. 17A, 17C). This simple SN2 mechanism seems to have been eliminated from Trx enzymes of eukaryotic origin, suggesting that the mechanism of disulfide bond reduction by Trx enzymes was altered at an early stage of eukaryotic evolution.

The physical characteristics of the binding groove are identified as important factors in the evolution of Trx catalysis. The appearance of the hydrophobic binding groove allowed Trxs to bind the substrate in a specific fashion, generating a stabilizing interaction that allows the enzyme to regulate the geometry and orientation of the substrate disulfide bond in the catalytic site of the enzyme. This binding mechanism results in the Michaelis-Menten-type kinetics of reduction observed in all Trx. It is noteworthy that, as the binding groove deepens in enzymes of eukaryotic origin, the SN2-like mechanism of in the evolution of Trx catalysis. The appearance of the hydrophobic binding groove allowed Trxs to bind the substrate in a specific fashion, generating a stabilizing interaction that allows the enzyme to regulate the geometry and orientation of the substrate disulfide bond in the catalytic site of the enzyme. This binding mechanism results in the Michaelis-Menten-type kinetics of reduction observed in all Trx. It is noteworthy that, as the binding groove deepens in enzymes of eukaryotic origin, the SN2-like mechanism of reduction disappears. These observations are in agreement with the view that the SN2-like mechanism of reduction observed in bacterial Trx enzymes results from less specific enzyme-substrate interactions (FIG. 17C). The emergence of eukaryotes gave rise to vastly more complex biological systems, resulting in a myriad of new functions and targets. It is tempting to speculate that the deepening of the binding groove in eukaryotic Trx (FIG. 18) may have been an important structural adaptation that improved the specificity of substrate-enzyme interactions.

However, evolutionary optimization of Trx activity is clearly a much more complex multiparameter function involving other structural features and cofactors. Most importantly, Trxs work together with TrxRs, which convert oxidized Trx to its active dithiol form. There are major differences in the structure and mechanism of TrxR across the evolutionary tree, and it is reasonable to consider that the evolution of the chemical mechanisms found in Trx has been tightly associated with the evolution of TrxR. In the experiments, generic bacterial and eukaryotic TrxR have been used to keep the Trx enzymes in the reduced state. It is anticipated that this assay can be expanded by contrasting the effect of different TrxR enzymes in the observed chemistry of Trx.

From a biological point of view, an interesting hypothesis is that the simple SN2-like mechanism present in bacterial Trxs might be related to their ability to live in extreme environments, where elevated mechanical forces might result as a consequence of the high pressures or extreme salinity that cause cells to swell or shrink. Under such conditions the enzymatic Michaelis-Menten-type mechanism of reduction would become inoperative. In support of this view, Trx has been shown to promote high-pressure resistance in *E. coli*.

This work generally demonstrates the usefulness of combining single-molecule force spectroscopy together with molecular dynamics simulations in probing enzymatic chemistry. Substantial differences in the chemical mechanisms of extant Trx enzymes are observed. It would be interesting to track the evolution of these chemical mechanisms using resurrected ancient Trx enzymes. Owing to an extensive sequence database and the development of sophisticated maximum-likelihood algorithms for the reconstruction of ancient DNA sequences, reconstructing the evolution of chemical mechanisms in this class of important enzymes now seems entirely plausible. It is anticipated that the enzymatic studies carried out on Trx at the single-molecule level can serve as a starting point to investigate the chemistry of other enzymes, such as C—S lyases or proteases, for which the catalyzed rupture of covalent bonds is the fundamental process.

Protein expression and purification. Preparation of (I27G32S-A75C)8 polyprotein has been described extensively. The expression and purification of the different Trxs used have also been described: *P. falciparum*, *Drosophila melanogaster* Trx1, poplar Trxh1 and Trxh3, pea Trxm60, *E. coli* Trx1, *E. coli* Trx2 and human TRX2.

Sequence Analysis.

Sequence alignment was carried out using ClustalW and modified by hand. Tree topology and branch lengths of the tree were estimated using Mr. Bayes (v. 3.5) (http://mrbayes.csit.fsu.edu/), with rate variation modeled according to a gamma distribution. The following GI numbers were accessed from GenBank. Bacteria: *E. coli* Trx1 (67005950), *Salmonella* Trx1 (16767191), *E. coli* Trx2 (16130507), *Salmonella* Trx2 (16765969), human TRX2 mitochondria (21361403), bovine Trx2 mitochondria (108935910), *Rickettsia* Trx (15603883), *Nostoc* Trx (17227548), *Prochlorococcus* Trx (126696505), spinach Trxm chloroplast (2507458), pea Trxm chloroplast (1351239), *Thermus* Trx (46199687), *Deinococcus* Trx (15805968), *Archaea Aeropyrum* Trx (118431868), *Hyperthermus* Trx (124027987), *Sulfolobus* Trx (15897303). Eukaryote: *P. falciparum* Trx (75024181), poplar Trxh1 (19851972), poplar Trxh3 (2398305), pea Trx (27466894), *Dictyostelium* Trx (165988451), bovine Trx (27806783), human TRX1 (135773).

Single-Molecule Force-Clamp Experiments.

Silicon nitride cantilever (Veeco) was used with a typical spring constant of 20 pN nm-1, calibrated using the equipartition theorem. The force-clamp mode provides an extension resolution of ~0.5 nm and a piezoelectric actuator feedback of ~5 ms. The buffer used in all the experiments was 10 mM HEPES, 150 Mm NaCl, 1 mM EDTA, 2 mM NADPH at pH 7.2. Before the beginning of the experiment, TrxR, bacterial or eukaryotic depending on the case, was added to a final concentration of 50 nM. The different Trxs were added to the desired concentration. The reaction mixture and the substrate were added and allowed to absorb onto a freshly evaporated gold coverslip before the experiments. The force-clamp experiment consisted of a double-pulse force protocol. The first pulse was set at 175 pN during 0.3-0.4 s. The second pulse can be set at different forces and was held long enough to capture all the possible reduction events. The experiments using metallic zinc in 100 mM citrate buffer at pH 6 were carried out. After adding zinc nanoparticles (Sigma) to a concentration of 10 mM, the solution was sonicated to allow resuspension. The pH of the buffer was verified during the time of the experiment, and no appreciable changes were observed. In addition, to verify the behavior of the substrate in citrate buffer, several control experiments in the absence of zinc nanoparticles were carried out, and detected no reduction events. Data using custom-written software in IGOR Pro 6.03 (Wavemetrics) was collected and analyzed. The collected traces (15-50 per force) containing the reduction events were summated and averaged. The resulting averaged traces were fit with a single exponential from which the rate constant was obtained.

As will be apparent to one of ordinary skill in the art from a reading of this disclosure, the present disclosed subject matter can be embodied in forms other than those specifically disclosed above. The particular embodiments described above are, therefore, to be considered as illustrative and not restrictive. Those skilled in the art will recognize, or be able to ascertain, using no more than routine experimentation, numerous equivalents to the specific embodiments described herein. The scope of the disclosed subject matter is as set forth in the appended claims and equivalents thereof, rather than being limited to the examples contained in the foregoing description.

Example 4

Disulfide bonds are formed as essential posttranslational modifications in a third of human proteins (Hatahet, F. et al., *Antioxid Redox Signal* 11, 2807-2850 (2009)). Formation of disulfides also plays a critical role in numerous pathologies including bacterial infection (Heras, B. et al., *Nat Rev Microbiol* 7, 215-225 (2009)), virus replication (Land, A. & Braakman, I. *Biochimie* 83, 783-790 (2001)) and protein misfolding disease (Uehara, T. et al., *Nature* 441, 513-517 (2006)); Culotta, V. C., Yang, M. & O'Halloran, T. V. *Biochim Biophys Acta* 1763, 747-758 (2006)). In the cytosol of eukaryotic cells, thioredoxin (TRX) maintains cysteines reduced (Holmgren, A. Thioredoxin. *Annu Rev Biochem* 54, 237-271 (1985)). Disulfides are formed in the endoplasmic reticulum where the thioredoxin-like protein disulfide isomerase (PDI) catalyzes co-translocational oxidative folding (Hatahet, F. et al., *Antioxid Redox Signal* 11, 2807-2850 (2009); Mamathambika, B. S. & Bardwell, J. C. Disulfide-linked protein folding pathways. *Annu Rev Cell Dev Biol* 24, 211-235 (2008); Di Jeso, B. et al., *Mol Cell Biol* 25, 9793-9805 (2005)). However, the precise involvement of PDI during protein folding has remained elusive. A kinetic model for PDI activity during catalyzed oxidative folding is presented, including a method enabling, for the first time, independent kinetic measurements of folding and disulfide formation in a single protein substrate. The data indicate that catalyzed disulfide formation is rate limited by structural folding. Enzyme-substrate intermediate complexes do not impede folding and are necessary for disulfide formation. It is proposed that the spontaneous rate of enzyme release modulates oxidative catalysis during co-translocational folding. Replacement of a single atom in TRX was shown to inhibit spontaneous release and enable efficient catalysis of disulfide formation. These findings show that contrary to the prevailing view, oxidative folding is best described as a non-equilibrium process governed by enzyme kinetics.

Figure 21:
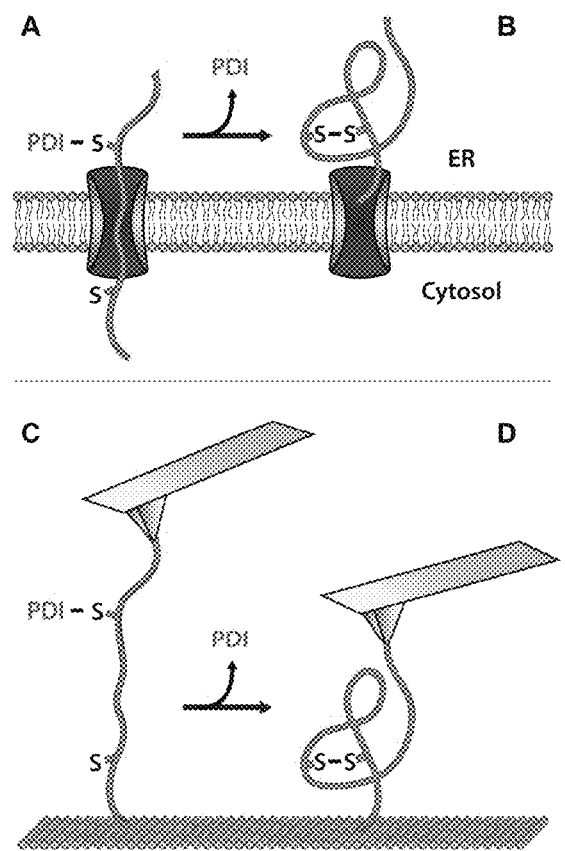
FIG. 21. A single-molecule approach to the study of oxidative folding.

In both pro- and eukaryotes, the Sec translocase machinery mediates transport of unfolded polypeptides from the cytosol to compartments where disulfide formation takes place (Sevier, C. S. & Kaiser, C. A. Formation and transfer of disulphide bonds in living cells. *Nat Rev Mol Cell Biol* 3, 836-847 (2002); Wickner, W. & Schekman, R. Protein translocation across biological membranes. *Science* 310, 1452-1456 (2005); Bechtluft, P. et al., Direct observation of chaperone-induced changes in a protein folding pathway. *Science* 318, 1458-1461 (2007)). Oxidase enzymes in these compartments engage with exposed cysteines in translocating substrates by forming covalently linked complexes (FIG. 21A). Identification of such complexes (Di Jeso, B. et al., *Mol Cell Biol* 25, 9793-9805 (2005); Kadokura, H., Tian, H., Zander, T., Bardwell, J. C. & Beckwith, J. *Science* 303, 534-537 (2004); Kadokura, H. & Beckwith, J. *Cell* 138, 1164-1173 (2009)) has established their role as obligatory intermediates during oxidative folding. An intermediate complex can be resolved upon emergence of a second substrate cysteine from the translocase channel, whereby the enzyme is released and an intramolecular disulfide is formed in the substrate (FIG. 21B). Oxidative folding in vivo is thus governed by the kinetic interplay between disulfide oxidation and polypeptide collapse from an extended state. However, conventional experimental approaches are unable to measure these processes independently.

A force-clamp atomic force microscope was used to extend individual polypeptides to an initial unfolded state wherein the two substrate cysteines were spatially separated and an intermediate complex was formed (FIG. 21C), in analogy to ongoing translocation. Allowing the polypeptide to collapse, the progress of oxidative folding could be directly probed (FIG. 21D). This technique allows to separately monitor the two concurrent processes of folding and disulfide formation within the same molecule.

Figure 22:
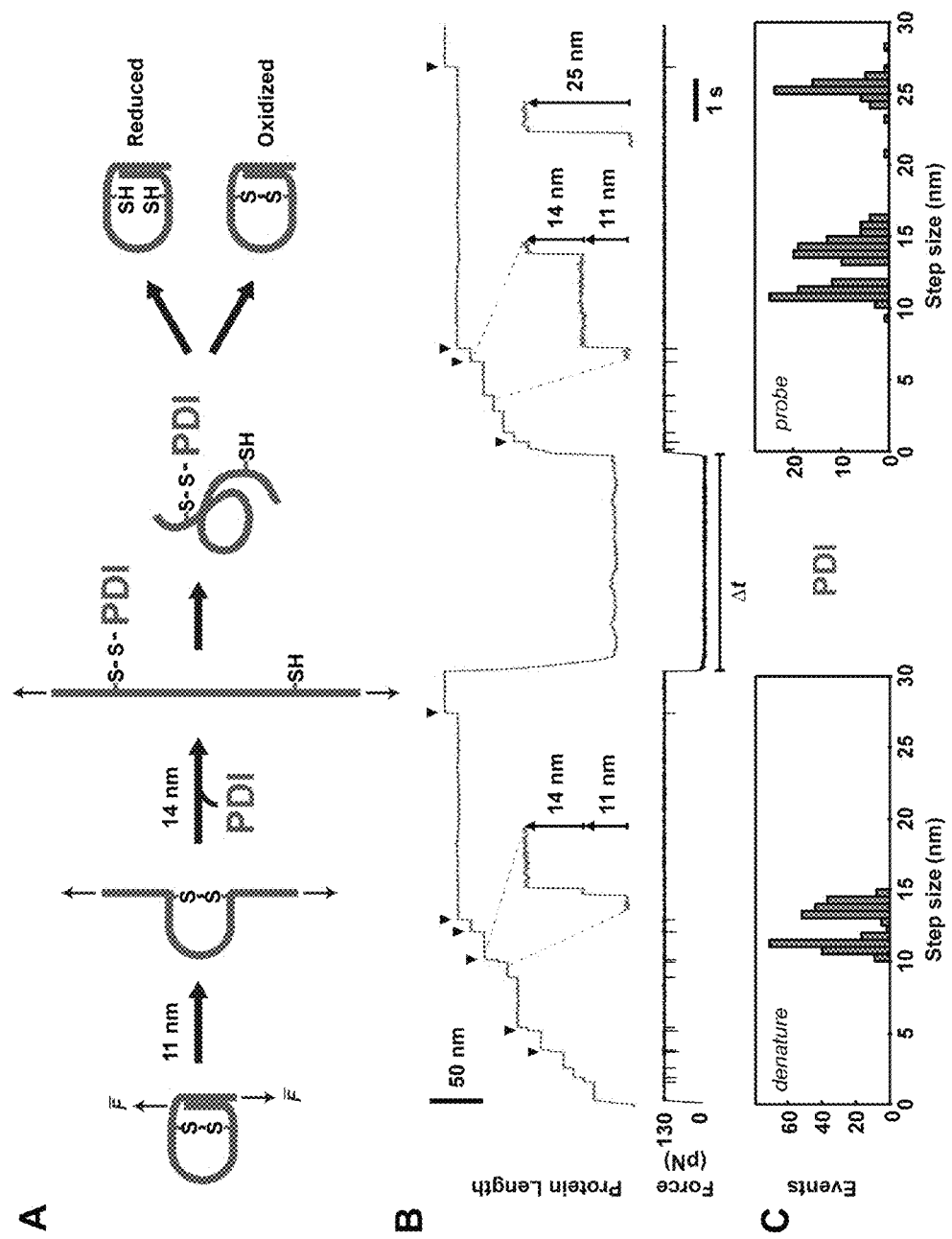
FIG. 22. PDI-catalyzed oxidative folding of Ig domains.

PDI consists of two catalytically active a domains and two redox-inactive b domains (Hatahet, F. et al., *Antioxid Redox Signal* 11, 2807-2850 (2009)). Each a domain exhibits the same oxidase activity in isolation as in full-length PDI (Darby, N. J., Kemmink, J. & Creighton, T. E. *Biochemistry* 35, 10517-10528 (1996)). The interaction of PDI a with immunoglobulin (Ig) proteins undergoing oxidative folding was studied. The model substrate consisted of sequential repeats of the $27^{th}$ Ig domain from human cardiac titin, each with a buried disulfide between residues 32 and 75 (Wiita, A. P. et al., *Nature* 450, 124-127 (2007)). A calibrated stretching force was applied to a single substrate protein while measuring its extension (Alegre-Cebollada, J., Perez-Jimenez, R., Kosuri, P. & Fernandez, J. M. Single-molecule Force Spectroscopy Approach to Enzyme Catalysis. *Journal of Biological Chemistry* 285, 18961-18966 (2010)). During mechanical denaturation of the substrate, folded structures and disulfide bonds were identified as obstructions in the unfolding pattern (Wiita, A. P., Ainavarapu, S. R., Huang, H. H. & Fernandez, J. M. *Proc Natl Acad Sci USA* 103, 7222-7227 (2006)). Reduced PDI a was used to cleave substrate disulfides, thereby attaining mixed disulfide complexes of the sort identified in vivo (Di Jeso, B. et al., *Mol Cell Biol* 25, 9793-9805 (2005)) (FIG. 22A). Folding by switching off the force was initiated, and after a time delay the substrate was probed by again applying force, resulting in a [denature-$\Delta$t-probe] protocol.

Figure 28:
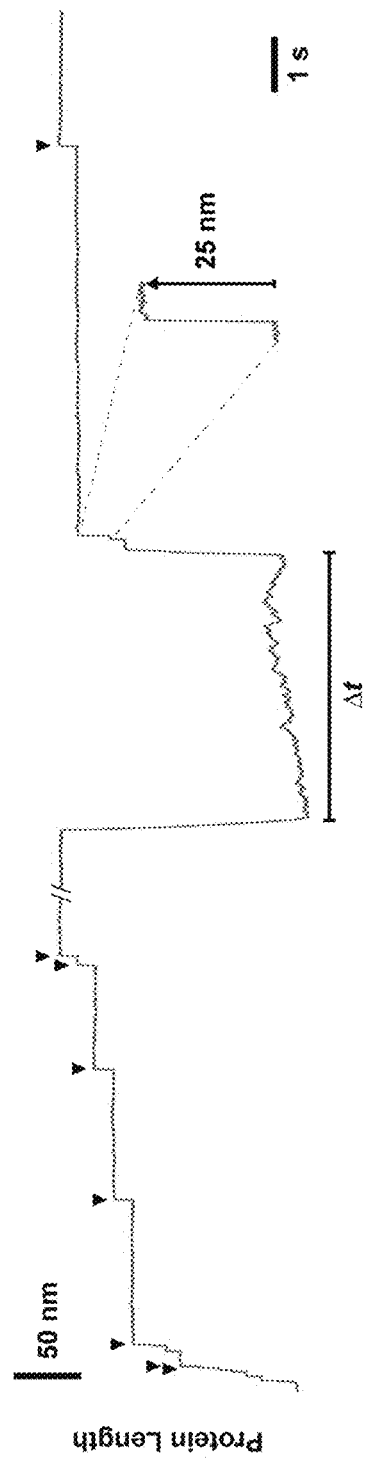
FIG. 28. Oxidative folding with PDI a shows 25 nm steps in the probe pulse, evidence of incomplete oxidative folding.

A representative trace is displayed in FIG. 22B. During the denature pulse, stepwise extensions of 11 and 14 nm were seen. As previously shown (Wiita, A. P., Ainavarapu, S. R., Huang, H. H. & Fernandez, J. M. *Proc Natl Acad Sci USA* 103, 7222-7227 (2006)), an 11 nm step corresponds to an unfolding event wherein a single Ig domain extends up to the disulfide bond. This exposes the disulfide and enables enzymatic cleavage. Upon cleavage of the disulfide bond, an additional 14 nm of the polypeptide chain is released and a mixed disulfide complex is generated. After a few seconds, the force was switched off and the substrate was allowed to refold ($\Delta t=5$ s). Folding and disulfide formation was then probed by again applying a stretching force (probe pulse). The reappearance of 11 and 14 nm steps in the probe pulse indicate that oxidative folding had taken place. In other traces, the probe pulse revealed 25 nm steps (FIG. 28 & FIG. 22B, inset), identified as the sum of unfolding (11 nm) and reduction (14 nm) steps. A 25 nm step thus indicates the presence of a folded domain in which the disulfide bond is not formed, suggesting that in these cases, PDI had failed to induce disulfide formation and instead acted as a reductase. Step size histograms generated from multiple experiments underline this finding (FIG. 22C), revealing an apparent dichotomy in the activity of PDI.

Figure 25:
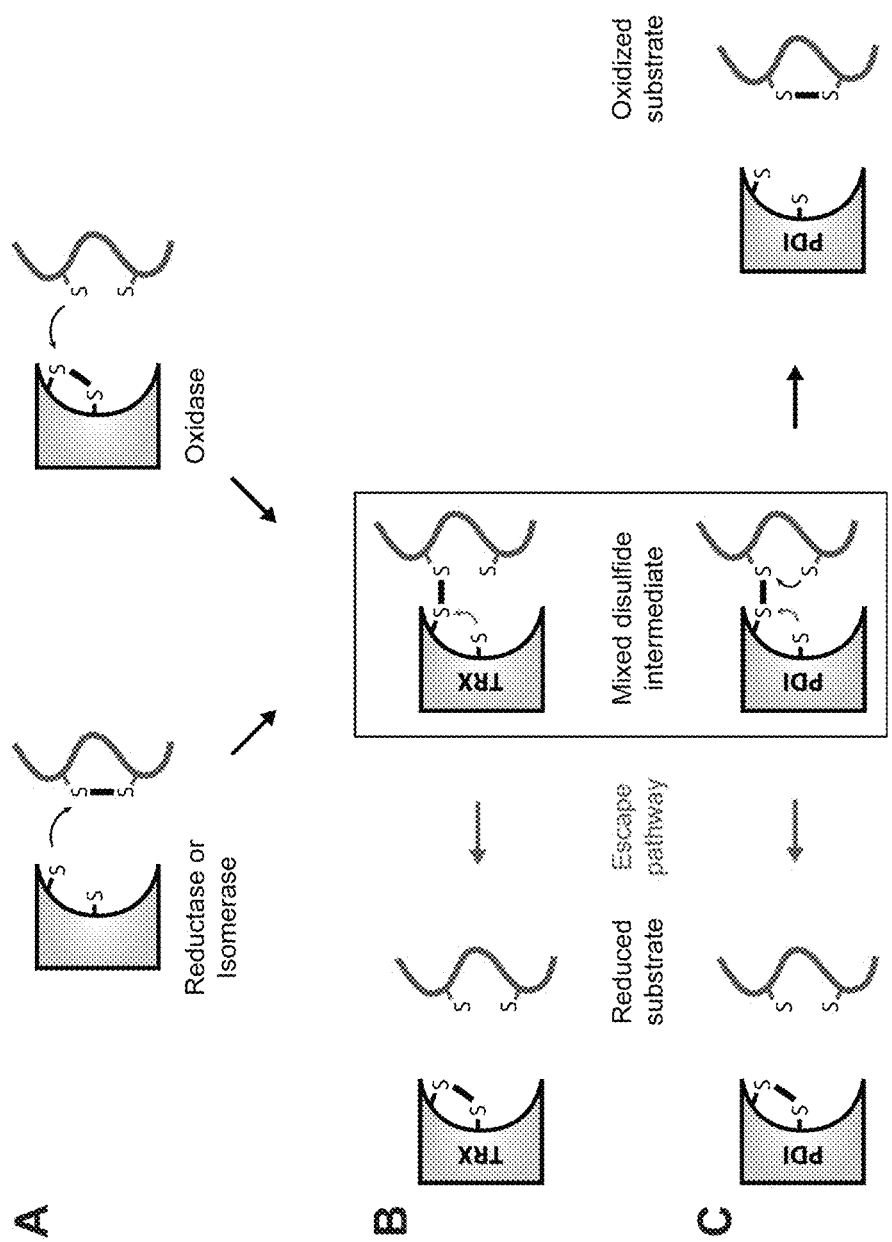
FIG. 25. Conceptual summary.

This dichotomy may be explained through the similarity of PDI to TRX, a cytosolic reductase. Both enzymes feature the thioredoxin fold and a CXXC active site motif (Sevier, C. S. & Kaiser, C. A. *Nat Rev Mol Cell Biol* 3, 836-847 (2002); Martin, J. L. *Structure* 3, 245-250 (1995)). The reaction path of both PDI and TRX involves formation of a mixed disulfide intermediate between the substrate and the N-terminal active site cysteine of the enzyme (FIG. 25A). The symmetry is then broken as the enzymes generally resolve this intermediate in different ways (Lundstrom, J., Krause, G. & Holmgren, A. *J Biol Chem* 267, 9047-9052 (1992); Xiao, R., Lundstrom-Ljung, J., Holmgren, A. & Gilbert, H. F. *J Biol Chem* 280, 21099-21106 (2005)). During substrate reduction, TRX resolves the intermediate through the "escape" pathway, whereby nucleophilic attack by the C-terminal cysteine in the enzyme active site yields a reduced substrate (Holmgren, A. *Annu Rev Biochem* 54, 237-271 (1985)) (FIG. 25B). During oxidative folding, PDI resolves the intermediate through attack by a substrate cysteine, leaving the substrate oxidized (Hatahet, F. et al., *Antioxid Redox Signal* 11, 2807-2850 (2009); Mamathambika, B. S. & Bardwell, J. C. *Annu Rev Cell Dev Biol* 24, 211-235 (2008)) (FIG. 25C). Experiments with PDI suggest flexibility in the pathway by which PDI resolves the intermediate. Similar observations have been made, including activity reversal for both PDI and TRX (Stewart, E. J., Aslund, F. & Beckwith, J. *EMBO J* 17, 5543-5550 (1998); Lundstrom, J. & Holmgren, A. *J Biol Chem* 265, 9114-9120 (1990)). These findings raise the questions of how the apparent flexibility affects oxidative folding, and what determines the pathway preference.

The effects of human TRX on the oxidative folding of the Ig substrate were studied. The experimental procedure outlined in FIG. 22 was repeated using reduced TRX instead of PDI to cleave the substrate disulfides. The trace in FIG. 23A reveals that despite successful refolding of the substrate, none of the disulfides were reformed. Histograms in FIG. 23B further strengthen the conclusion that TRX is a poor catalyst of oxidative folding. The reaction mechanism of TRX has been well characterized (Holmgren, A. *Annu Rev Biochem* 54, 237-271 (1985)), allowing the conclusion that a mixed disulfide intermediate was formed upon each 14 nm step in the denature pulse. However, the successful folding of the substrate without formation of intramolecular disulfides suggests the TRX enzymes had dissociated through the escape pathway prior to substrate refolding. A simple explanation for the different propensities of PDI and TRX in catalyzing oxidative folding could thus be a difference in the escape pathway kinetics for the two enzymes; TRX escapes from the intermediate rapidly, leaving behind an unreactive substrate thiol; PDI lingers as part of the intermediate complex for a longer time, allowing a second substrate cysteine to attack the mixed disulfide upon substrate collapse.

To test if this hypothesis was sufficient to explain the catalytic difference between PDI and TRX, the escape pathway in TRX was disabled and its influence on a folding protein was studied. Through site-directed mutagenesis the TRX C-terminal cysteine was replaced with a serine (TRX C35S), thereby switching the identity of only one atom, from sulfur to oxygen. The vastly higher $pK_a$ of a hydroxyl renders it much less reactive than a thiol at physiological pH. TRX C35S is thus still able to initially cleave a substrate disulfide but cannot resolve a mixed disulfide intermediate through the escape pathway.

Figure 23:
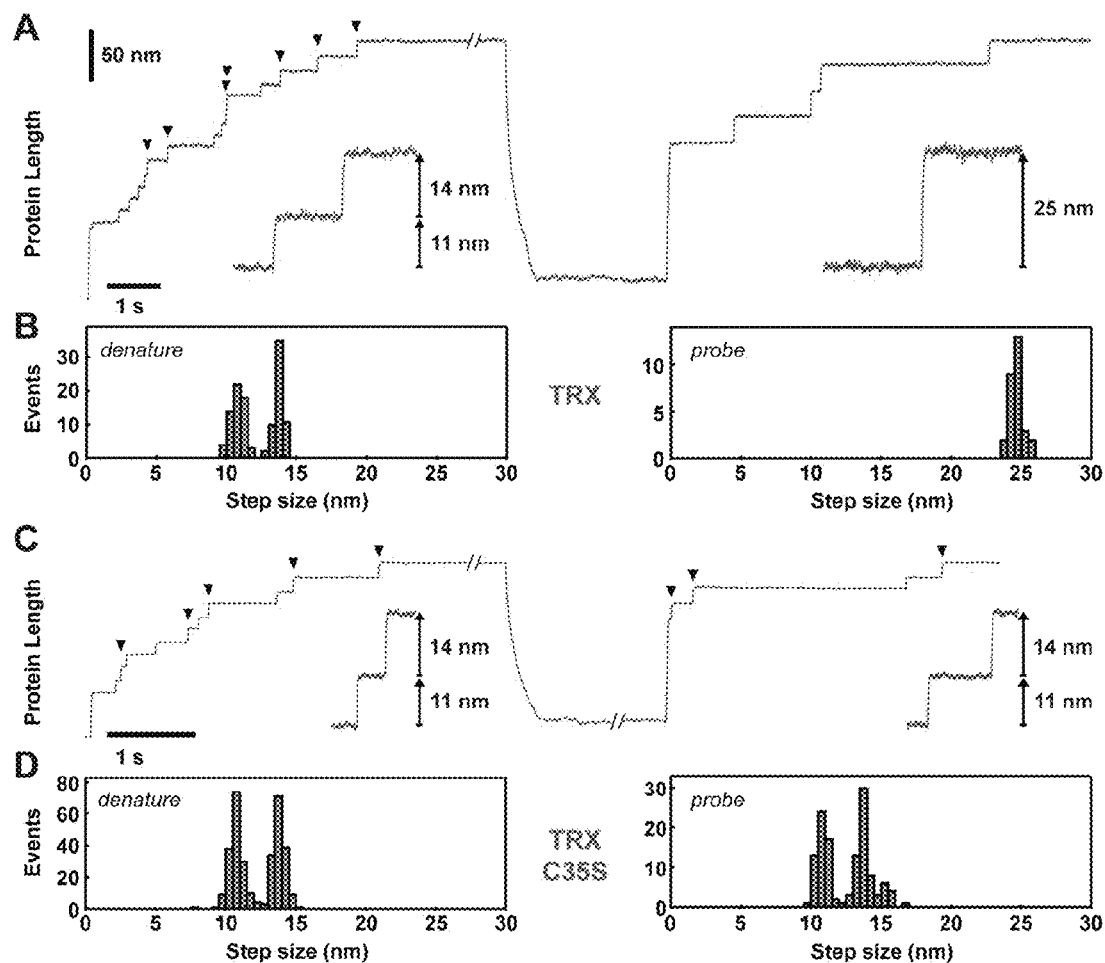
FIG. 23. Replacement of a single atom in TRX enables PDI-like catalysis of oxidative folding.

The collapse of Ig-TRX C35S intermediate complexes was studied, and a representative trace can be seen in FIG. 23C. The trace shows the reappearance of both 11 and 14 nm steps in the probe pulse, indicating that the substrate had undergone oxidative folding involving both structural folding and formation of the intramolecular disulfide. As seen from the absence of a 25 nm peak in the probe pulse histogram (FIG. 23D), every folded domain had undergone disulfide oxidation. The stark contrast between the histograms in FIGS. 23B and 23D strongly suggests the role of the Sγ atom in TRX Cys35 as an enzyme functionality switch.

Figure 24:
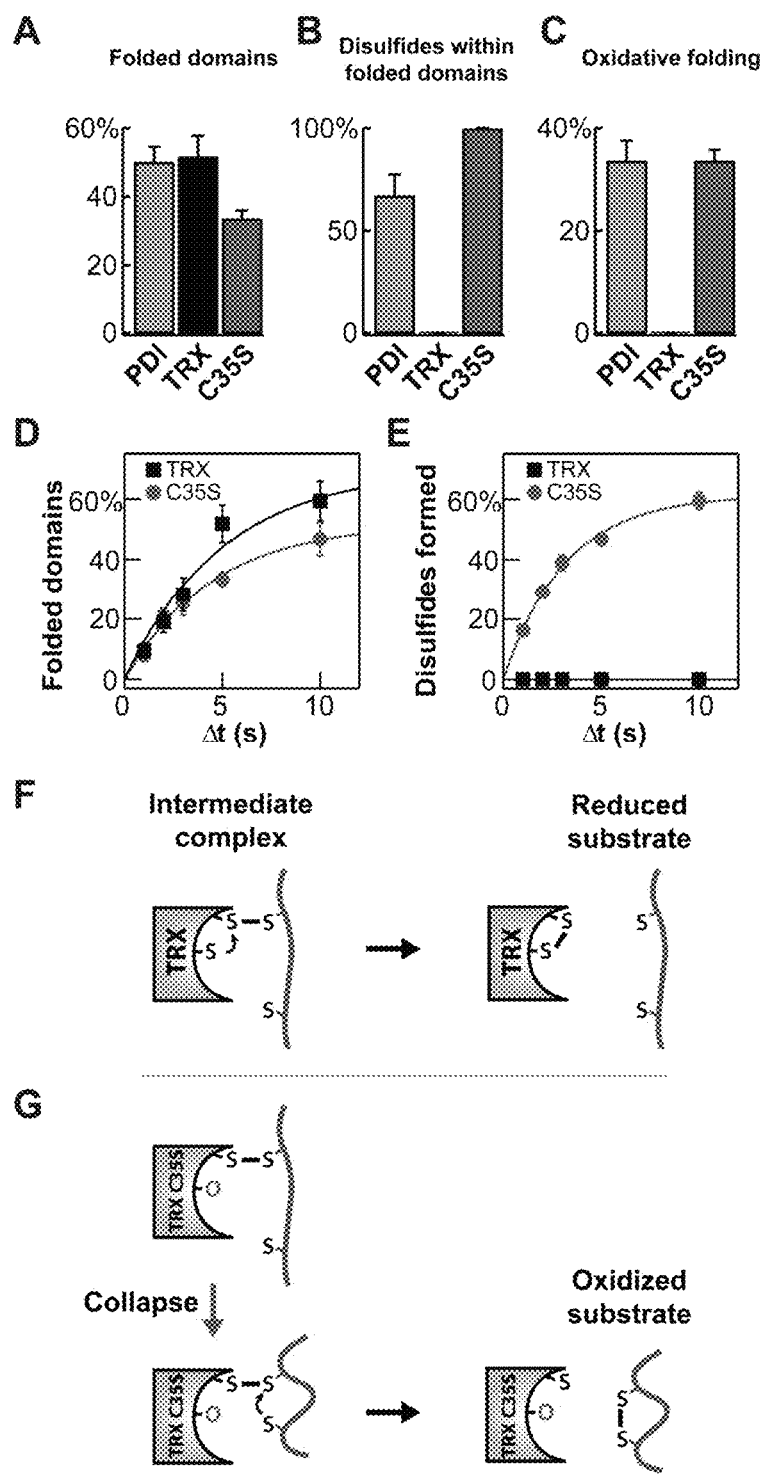
FIG. 24. Quantitative comparison of enzyme catalyzed oxidative folding.

A quantitative comparison of substrate folding at Δt=5 s revealed no significant difference between PDI and TRX (FIG. 24A); however TRX C35S seemed to impede folding slightly. PDI had introduced disulfides in 60% of the refolded Ig domains (FIG. 24B). TRX had not introduced any disulfides, whereas TRX C35S had introduced a disulfide in every refolded domain. Overall, there was no significant difference in the number of domains that had undergone complete oxidative folding with PDI and with TRX C35S (FIG. 24C). It seems unlikely that the introduced hydroxyl in TRX C35S generated this gain of function. Rather, the results suggest TRX being intrinsically adept at catalyzing oxidative folding. This is not a natural activity of TRX, but can be explained if the requirements for catalysis of substrate disulfide cleavage and formation are identical. Cys35 acts as a release trigger, breaking the symmetry between oxidases and reductases. If the time constant of the escape pathway determines whether or not a disulfide is formed in a folding substrate, then FIG. 24B reflects this time constant for the different enzymes. TRX shows rapid escape whereas TRX C35S lingers indefinitely. PDI escape kinetics appear to fall somewhere between these two extremes. Tuning the kinetics of the escape pathway can thus modulate the oxidase activity of a TRX-like enzyme, and can explain the ability of PDI to catalyze oxidative folding in a subset of folded domains. Mutational studies may hold the key to understanding which residues play a role in this tuning (Lundstrom, J., Krause, G. & Holmgren, A. *J Biol Chem* 267, 9047-9052 (1992); Karala, A. R., Lappi, A. K. & Ruddock, L. W. *J Mol Biol* 396, 883-892 (2010); Ren, G. et al., *J Biol Chem* 284, 10150-10159 (2009)).

The folding and disulfide formation kinetics for TRX and TRX C35S were compared by varying Δt in the pulse protocol (FIG. 24D, E). Folding appeared to be an exponential process with a rate of $k_{fold}$=0.2±0.1 s$^{-1}$ for both TRX and TRX C35S, consistent with earlier measurements (Ainavarapu, S. R. et al., *Biophys J* 92, 225-233 (2007)). Even though kinetics were not altered with the mutant, the total fraction of folded domains was slightly lower, possibly reflecting a subpopulation of complexes unable to fold. FIG. 24D reveals no substrate disulfides at any of the time points with TRX, whereas TRX C35S disulfide formation kinetics followed a single exponential with $k_{ox}$=0.32±0.04 s$^{-1}$, indicating a single rate limiting step in the process. The similarity of the rates of disulfide formation and unhindered folding suggests that structural rearrangement of the substrate is this rate limiting step during catalyzed disulfide formation.

The properties of thiol-disulfide oxidoreductases are often described in terms of their reduction potential $E_R$, a measure of how likely they are to oxidize or reduce substrate disulfides under equilibrium conditions (Sevier, C. S. & Kaiser, C. A. *Nat Rev Mol Cell Biol* 3, 836-847 (2002)). However, oxidative folding is not well characterized as an equilibrium process, as the reactivity of cysteines can be vastly different in the unfolded and folded state of a protein (Hatahet, F. et al., *Antioxid Redox Signal* 11, 2807-2850 (2009); Mamathambika, B. S. & Bardwell, J. C. *Annu Rev Cell Dev Biol* 24, 211-235 (2008)). In vivo, proteins undergo oxidative folding during ongoing translocation. In these cases, disulfide formation is determined not by equilibrium energetics but by the presence of a mixed disulfide complex upon folding. In the case of TRX, escape is fast and the complex is likely to dissociate prior to or during folding (FIG. 24F), failing to oxidize the substrate. If this escape is slowed down or prevented altogether, as in the case of TRX C35S, the complex is stable upon folding and allows catalysis of native disulfide formation (FIG. 24G). The reactivity of the C-terminal cysteine in the enzyme active site can thus function as a switch, enabling or disabling catalysis of oxidative folding depending on its reactivity. In support of this conclusion, recent in vivo experiments have suggested excessively slow kinetics of the escape pathway in the prokaryotic disulfide oxidase DsbA (Kadokura, H., Tian, H., Zander, T., Bardwell, J. C. & Beckwith, J. *Science* 303, 534-537 (2004); Kadokura, H. & Beckwith, J. *Cell* 138, 1164-1173 (2009)).

Methods

The polyprotein substrate, TRX and TRX C35S were expressed and purified as described elsewhere (Wiita, A. P. et al., *Nature* 450, 124-127 (2007); Ren, X., Bjornstedt, M., Shen, B., Ericson, M. L. & Holmgren, A. *Biochemistry* 32, 9701-9708 (1993); Perez-Jimenez, R. et al., *J Biol Chem* 283, 27121-27129 (2008)). PDI a domain consisted of residues 18-134 in human PDI and was produced as described in the methods section. The custom-made atomic force microscope has been described previously (Fernandez, J. M. & Li, H. *Science* 303, 1674-1678 (2004). Experiments were carried out at pH 7.2 in 10 mM HEPES, 150 mM NaCl, 1 mM EDTA. Before each experiment, reduced DTT was added together with the enzyme. 200 µM DTT was used with TRX (10 µM) and TRX C35S (40 µM). 500 µM DTT was used with PDI a (120 µM). The polyprotein substrate was absorbed onto a gold coverslip. Experiments consisted of repeated trials of pressing the tip against the surface at 1000 pN for 0.5 s and subsequently retracting. The pulse protocol was applied when attachment was achieved. Traces showing in the denature pulse step sizes other than 11 nm or 14 nm or contained less than 4 unfolding events were excluded from analysis. Only traces showing equal extension at the end of the probe and denature pulses were included. Step size histograms included all steps >5 nm after the initial elastic extension in each force pulse.

Protein Expression and Purification

The (I2732S-75C)8 polyprotein substrate was prepared as previously described (Wiita, A. P. et al., *Nature* 450, 124-127 (2007)). Human TRX and TRX C35S were expressed and purified as described (Ren, X., Bjornstedt, M., Shen, B., Ericson, M. L. & Holmgren, A. Biochemistry 32, 9701-9708 (1993); Perez-Jimenez, R. et al., J Biol Chem 283, 27121-27129 (2008)). Human PDI a domain was generated by PCR from Ultimate ORF Clone IOH9865 (Invitrogen) as an Nde I-BamH I fragment. The insert (amino acids 18-134 in the full length PDI sequence) was cloned into Nde I-BamH I sites of pET-15b vector (Novagen) containing the N-terminal His6 tag and expressed in Escherichia coli BL21-Gold (DE3) (Stratagene). Cells with the construct were grown in LB media supplemented with 100 μg/mL ampicillin at 37° C. for 10 h ($OD_{600nm}$~0.6). Protein expression was induced with 0.5 mM isopropyl β-D-thiogalactoside overnight. Cells were lysed by sonication and recombinant PDI a domain was first purified from cell lysate using Ni Sepharose 6 Fast Flow (GE Life Sciences) and then using gel filtration Superdex 300 column. The fractions containing PDI a domain were pooled together and dialyzed into 20 mM sodium phosphate buffer pH 8 and verified by SDS-PAGE. Protein concentration was determined using Bradford assay.

Single-Molecule Force-Clamp Experiments

The details of the custom-made atomic force microscope have been described (Fernandez, J. M. & Li, H. Science 303, 1674-1678 (2004)). Silicon nitride cantilevers (Veeco) with a typical spring constant of 20 pN $nm^{-1}$ was used, calibrated using the equipartition theorem. The force-clamp mode provides a feedback time constant of 5 ms. The buffer used in all the experiments was 10 mM HEPES, 150 mM NaCl, 1 mM EDTA, at pH 7.2. Before the beginning of the experiment, reduced DTT was added together with the enzyme. 200 μM DTT was used with TRX (10 μM) and TRX C35S (40 μM). 500 μM DTT was used with PDI a (120 μM), to ensure that the enzyme was in its reduced form, while minimizing the effects by DTT on the substrate. The polyprotein substrate was added in a droplet and allowed to absorb onto a freshly evaporated gold coverslip before the experiments. Every experiment consisted of repeated trials where the tip was pressed against the surface for 0.5 s and subsequently retracted. If attachment was achieved, a pulse protocol was applied until detachment occurred. The oxidative folding force-clamp experiments used a triple-pulse force protocol. The first pulse was maintained at 110-130 pN for a time long enough to ensure complete denaturation of the substrate (>5 s). The second pulse was set at 0 pN and maintained for the desired amount of refolding time. The third pulse was set at a force identical to the first and maintained until complete denaturation could be ensured (>5 s). Data using custom-written software in IGOR Pro (Wavemetrics) were collected and analyzed. Traces were selected based on the fingerprint consisting of at least 4 unfolding events in the denature pulse. Traces exhibiting step sizes other than 11 nm or 14 nm in the denature pulse were excluded from the analysis to ensure homogeneity. Only traces showing equal extension at the end of the probe pulse and the end of the denature pulse were included, to ensure that the same protein was stretched in the two pulses. Step size histograms were generated using all steps >5 nm detected after the initial elastic extension in each force pulse.

Figure 26:
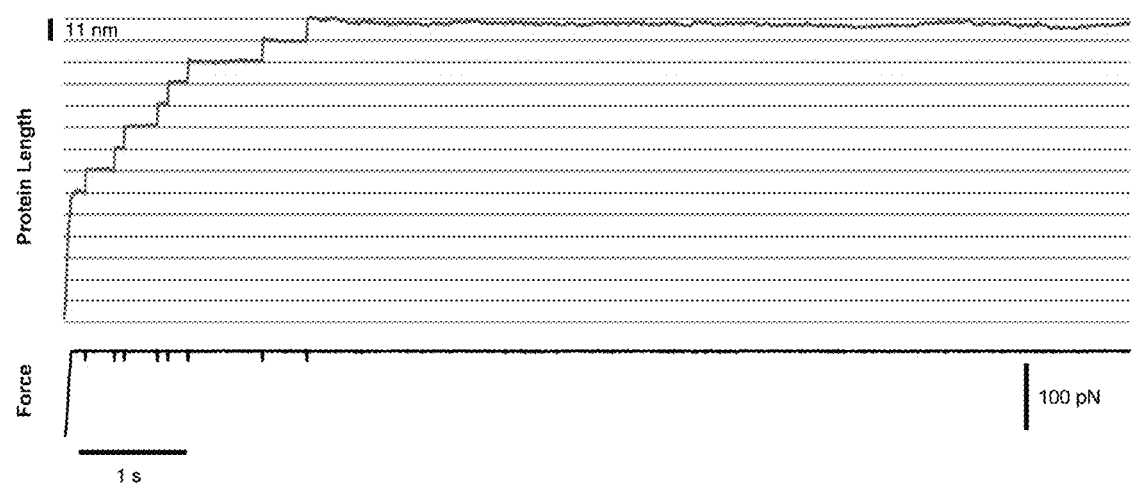
FIG. 26. The Ig polyprotein unfolded in the presence of only 500 µM DTT displayed 11 nm partial unfolding steps but did not show any 14 nm reduction steps.
Figure 27:
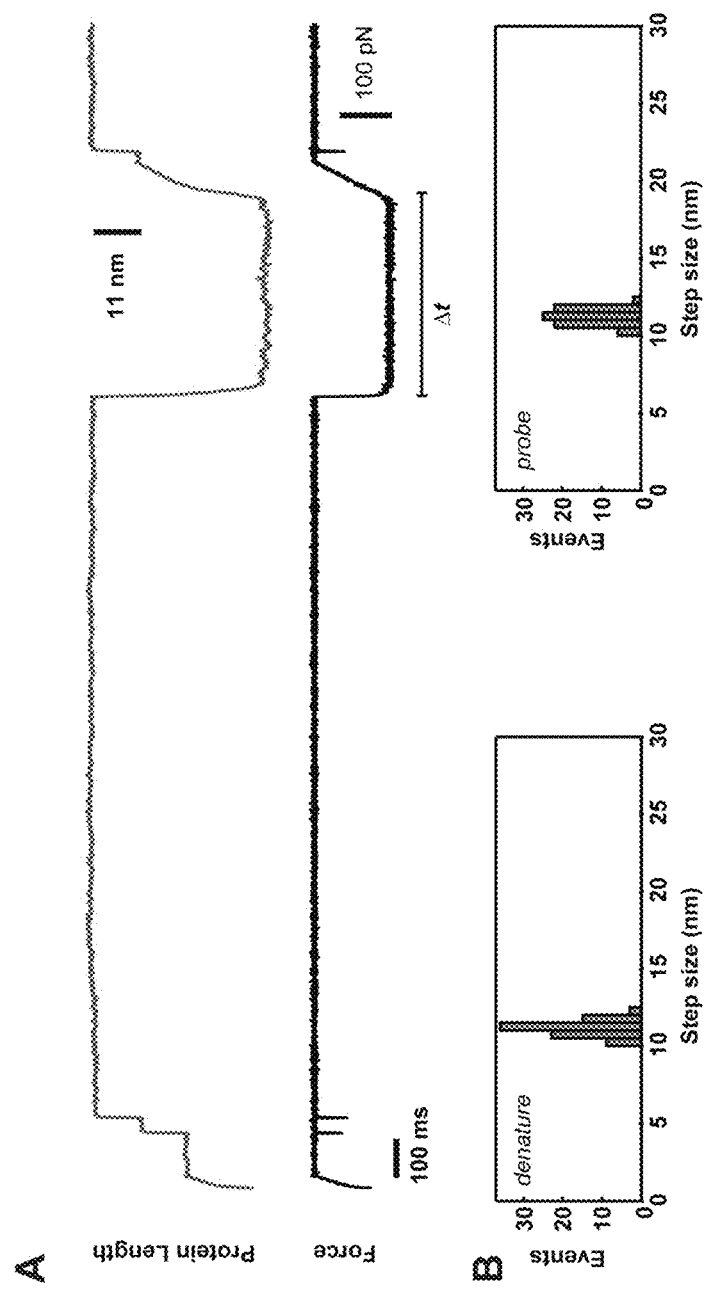
FIG. 27. Experiments on the Ig polyprotein in the presence of 500 µM DTT showed only unfolding and refolding of the unsequestered part of the substrate.

As DTT was used to keep the enzyme reduced in all experiments, control experiments were performed to verify that the reduction events observed were not caused by DTT. The Ig polyprotein was therefore unfolded in a buffer containing 500 μM DTT, without adding any enzyme. In these experiments, only 11 nm steps were observed during the first 10 seconds of the pulse. A representative trace is shown in FIG. 26. At longer times, occasional reduction steps were observed, but at a frequency too low for rate estimation. Refolding experiments were also conducted under these conditions, and revealed only 11 nm steps in both denature and probe pulses (FIG. 27).

Example 5

Figure 29:
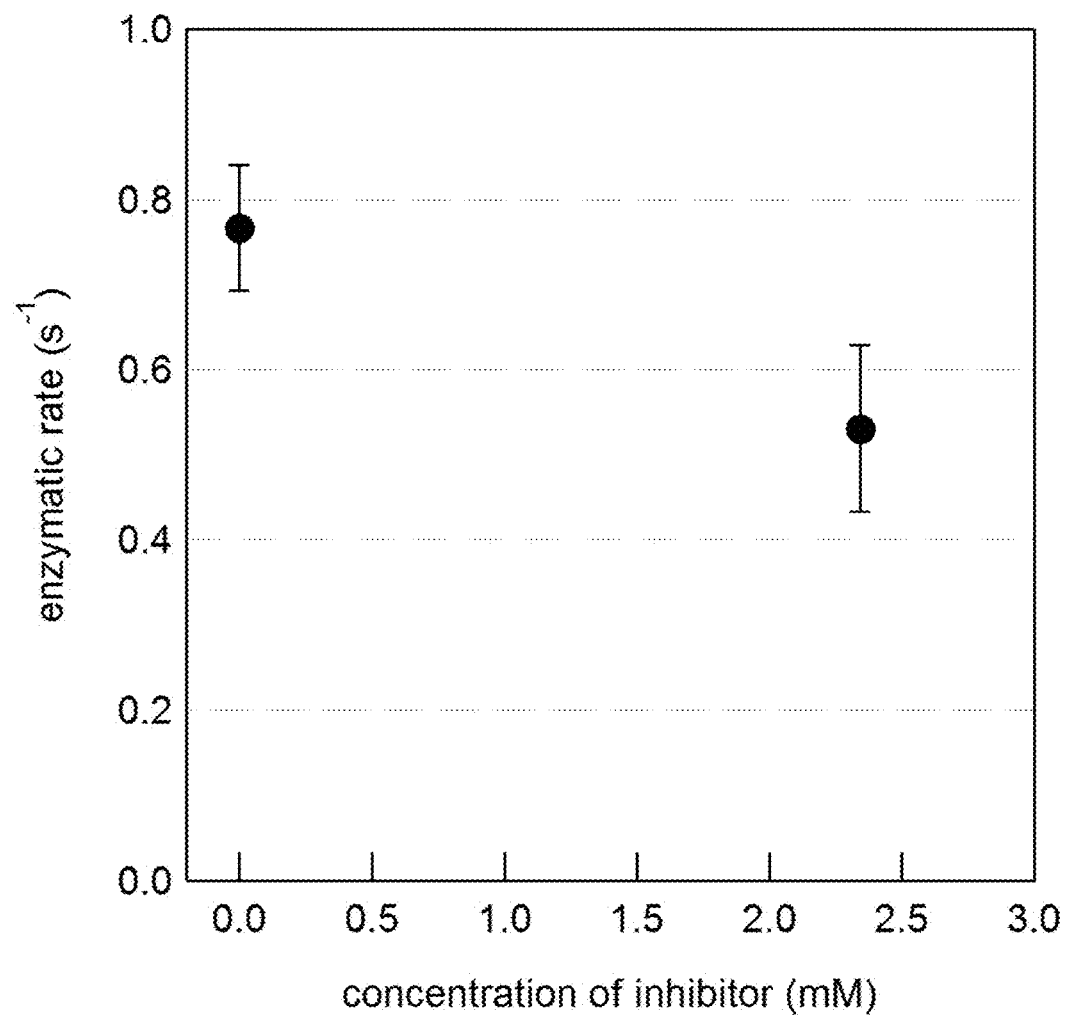
FIG. 29. Functional assay to measure effect of inhibitor molecule on enzymatic activity. Using a force-clamp spectrometer, the enzymatic activity of 200 µM PDI was measured by detecting the cleavage of a disulfide in a substrate I27 protein. Accumulation of hundreds of such events yielded a kinetic rate given as events per second. By adding the inhibitor to the reaction volume, the measured rate decreased in a concentration-dependent manner.

FIG. 29 shows the results of a functional assay to measure the effect of an inhibitor molecule on enzymatic activity. Using a force-clamp spectrometer, the enzymatic activity of 200 μM PDI was measured by detecting the cleavage of a disulfide in a substrate I27 protein. Accumulation of hundreds of such events yielded a kinetic rate given as events per second. By adding the inhibitor to the reaction volume, the measured rate decreased in a concentration-dependent manner.

Methods

A substrate polyprotein composed of eight domains of the 27th domain of human cardiac titin, in which each domain contained an engineered disulfide bond between the 32nd and 75th residues (I27G32C-A75C)8, was used. In the force-clamp experiments, the first pulse of force (175 pN, 0.3 s) applied to the polyprotein lead to the rapid unfolding of the I27G32C-A75C domains up to the disulfide bond. The individual unfolding events could be registered as steps of 11 nm per domain. After the first pulse, the disulfide bonds become exposed to the solvent, where active PDI enzyme is present. A second pulse of force was then applied to monitor single disulfide cleavage reactions by PDI enzymes, recorded as a second series of steps of 14 nm per domain. Several traces (~20) were accumulated, which were then averaged and fit with a single exponential with a time constant t. The reduction rate at a given force (r=1/t) was thus obtained. Repeating the experiment in the presence of an increasing concentration of an inhibitor molecule allowed for measurement of enzymatic activity as a function of inhibitor concentration. In this manner, the functional efficiency (as opposed to merely binding) of a specific inhibitor could readily be assessed.

Example 6

Figure 30:
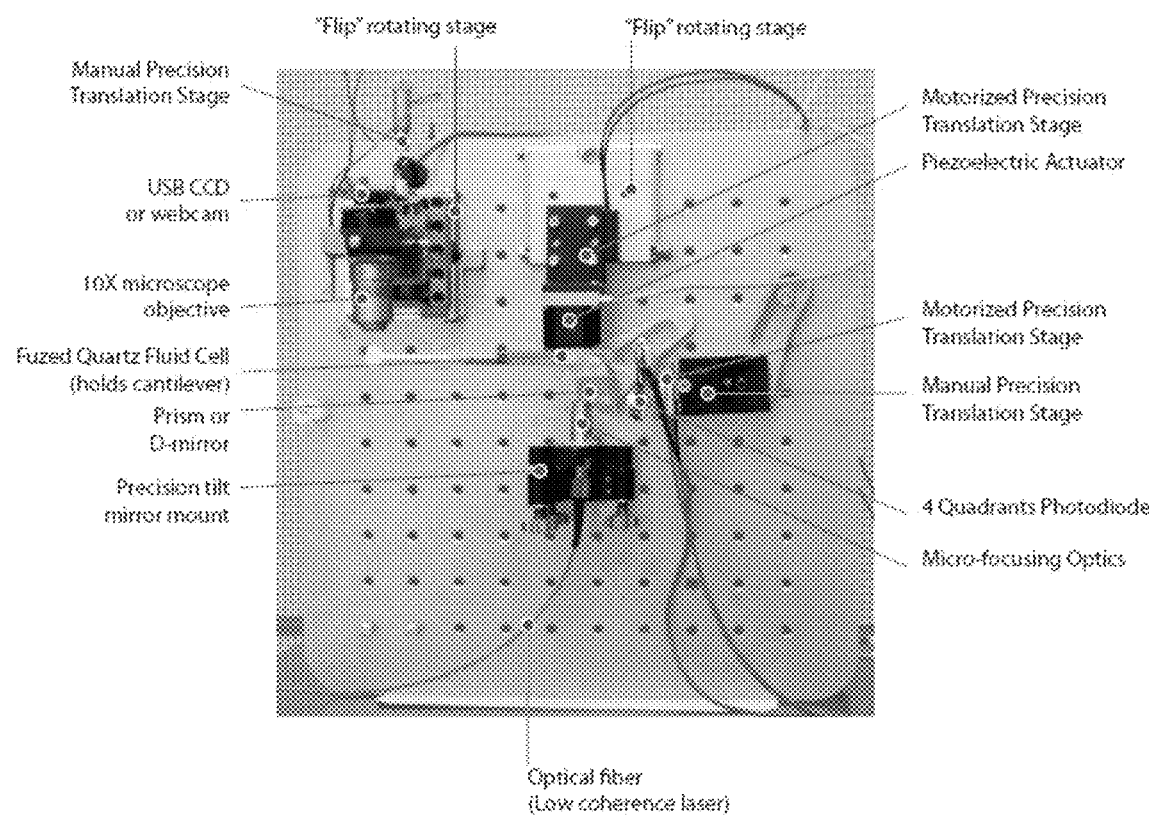
FIG. 30. is a view of an illustrative force clamp spectrometer according to some embodiments of the disclosed subject matter.

FIG. 30 presents an illustrative force clamp spectrometer according to some embodiments of the disclosed subject matter. Specifically, the spectrometer includes, for example, one or more "flip" rotating stages, one or more motorized precision translation stages, a piezoelectric actuator, one or more manual precision translation stages, a 4 quadrants photodiode, microfocusing optics, a precision tilt mirror mount, a prism or a D-mirror, a fuzed quartz fluid cell (that holds the cantilever), a 10× microscope objective and a USB CCD or webcam.

Example 7

Force-clamp spectroscopy is described herein as a precise method to quantify the effects of force on the modulation of biochemical reactions. A calibrated force can be used to control the exposure of reactive sites in a single protein substrate. Biochemical reactions can then be measured directly by detecting length changes of the substrate held at a constant force. Certain embodiments of the layout of a force-clamp spectrometer are described herein, along with protocols to design and conduct experiments. These results described herein show measurement of reaction kinetics as a function of applied force. The methods and compositions described herein can also be used to measure data of the force dependency of different reactions, including, but not limited to, protein unfolding and disulfide reduction. These data, which can be acquired in a few days, reveal mechanistic details of the reactions that currently cannot be resolved by any other technique.

Force-clamp atomic force microscopy (AFM) can be used to monitor many processes leading to a change in separation between cantilever and surface at a constant force. Force-clamp AFM has been used to study the force dependence of chemical reactions (Wiita, A. P., et al., Proc Natl Acad Sci USA 103, 7222-7227 (2006); Wiita, A. P. et al., Nature 450, 124-127 (2007)) and mechanical unfolding of proteins (Oberhauser, A. F., et al., P Natl Acad Sci USA 98, 468-472 (2001); Schlierf, M., et al., P Natl Acad Sci USA 101, 7299-7304 (2004)). Successful trajectories can be fingerprinted by the appearance of staircases composed of identical step changes in the length of the protein, where each step marks a single unfolding event or a single chemical reaction. Owing to the probabilistic nature of processes taking place at single molecule level, no two traces are identical. Nevertheless, the averaged summed extensions of enough number of individual traces (typically n>20, see FIG. 35C) can render reproducible results.

The proportion of successful recordings showing clean staircases can vary among proteins. Some proteins adsorbed on gold, such as I27, protein L or ubiquitin, can provide over a thousand pickups per day, with an estimated 5-10% of traces showing clean fingerprints that can be used for further analysis. Covalent attachment chemistry can yield high pick-up yield as well, but has the advantage of an increase probability of tethering the polyprotein to its ends. Experiments using this chemistry show even 40-50% pick-up efficiency, out of which about 25% are full length unfolding traces. Therefore, a force dependency composed of four data points can be obtained in just one or a few days of experiments. However, not all proteins behave the same way and some may aggregate or become inactive in a matter of days after their purification. Presence of reducing species in the measuring buffer can also affect the pick-up yield by disrupting the attachment to the gold surface. For proteins that are more challenging to measure, investing time in optimizing the experimental conditions (buffer, concentration of protein, incubation time, etc.) so that at least 5-10 good traces are obtained per day is recommended.

Force clamp AFM can be used to measure different force dependences for different processes including but not limited to: mechanical protein unfolding, chemical reduction of disulfides and enzyme-catalyzed reduction of disulfides. The different force dependences report on the different nature of the energy landscape of the reactions. Chemical reactions using small nucleophiles such as short thiols, phosphines or hydroxyl ions exhibit a small distance to transition state, spanning between 0.3-0.5 Å (Wiita, A. P., et al., Proc Natl Acad Sci USA 103, 7222-7227 (2006); Garcia-Manyes, S., et al., Nature chemistry 1, 236-242 (2009); Ainavarapu, S. R. K., et al., Journal of the American Chemical Society 130, 6479-6487 (2008)) and depending on the chemistry of the attacking nucleophile. Notably, thiol based reducing agents such as DTT exhibit a smaller distance to the transition state ($\Delta x=0.31$ Å) than phosphine-based reducing agents ($\Delta x=0.44$ Å) (Ainavarapu, S. R. K., et al., Journal of the American Chemical Society 130, 6479-6487 (2008)). Interestingly, ab-initio simulations showed that during the reaction with an S-based nucleophile, the disulfide bond extends at the transition state with approximately the same length as the measured distance to the transition state $\Delta x$ (Wiita, A. P., et al., Proc Natl Acad Sci USA 103, 7222-7227 (2006)). This trend was further confirmed by studying the atomistic mechanisms underlying the reduction of nucleophiles with different central atoms (P, O) (Ainavarapu, S. R. K., et al., Journal of the American Chemical Society 130, 6479-6487 (2008)). Hence, these observations suggest a direct relation between the slope of the force dependency of a chemical reaction experimentally measured with sub-Angstrom resolution by force-clamp AFM and the conformation of the transition state of the process along the pulling coordinate.

In contrast to the simple exponential force-dependency of disulfide reduction by small chemical nucleophiles (Garcia-Manyes, S., et al., Nature chemistry 1, 236-242 (2009)), reduction by thioredoxin enzyme exhibits a complex force-dependency lay-out, composed of different independent regimes (Wiita, A. P. et al., Nature 450, 124-127 (2007)). These regimes highlight different chemical mechanisms and conformational rearrangements employed by the enzyme during its catalytic activity (Perez-Jimenez, R. et al., Nature structural & molecular biology 16, 890-896 (2009)). In the low force regime, the negative force dependency of thioredoxin-catalyzed reactions underlies a shortening of the substrate while the transition state acquires the geometry required for the $S_N2$ mechanism (Wiita, A. P. et al., Nature 450, 124-127 (2007). Alternative reaction mechanisms become prominent at high forces over 200 pN, making thioredoxin enzymes active over the whole range of experimental forces (Perez-Jimenez, R. et al., Nature structural & molecular biology 16, 890-896 (2009)). The extrapolated rate at zero force also contains important information, which can be used to estimate to the free energy of the process using specific attempt frequencies (Popa, I., et al., Journal of Biological Chemistry 286, 31072-31079 (2011); Liang, J. & Fernandez, J. M. Journal of the American Chemical Society 133, 3528-3534 (2011)).

The AFM setup described herein uses a linear piezo based without hysteresis. While this piezo is currently limited to relatively small travel distances of 800 nm, future models can increase this range. Smaller and softer cantilevers are expected to emerge alongside with better laser focusing optics. These cantilevers will have a fast response time and a small thermal noise. A change of the laser detection system with fluorescence or electromagnetic methods can allow to further reduce the cantilever size and to increase the bandwidth of the AFM.

Results obtained in different setups and/or by different experimenters are also consistent. Altogether, single molecule force-clamp spectroscopy reveals itself as a robust technique able to provide insights into the molecular mechanisms governing biological reactions at the single molecule level, such as, but not limited to, protein folding or chemical reactions under mechanical force. These experiments have prompted a new field of computational analysis (Wiita, A. P. et al., Nature 450, 124-127 (2007); Li, W. J. & Grater, F. Journal of the American Chemical Society 132, 16790-16795 (2010); Iozzi, M. F., et al., J Phys Chem A 115, 2308-2315 (2011)), which will complement single molecule experiments to provide an integrated framework to understand force-induced processes occurring within the core of an individual molecule.

Single molecule force-spectroscopy is a field of research studying molecules under mechanical force. (Smith, S. B., et al., Science 271, 795-799 (1996); Marszalek, P. E., et al., Nature 396, 661-664 (1998); Rief, M., et al., Science 275, 1295-1297 (1997); Rief, M., et al., Science 276, 1109-1112 (1997)). AFM can be used to study the mechanical properties of recombinant polyproteins, which are typically less than 50 nm in length. Single molecule AFM can be performed to stretch single polyprotein molecules tethered between a gold substrate and the tip of an AFM cantilever probe (Rief, M., et al., Science 276, 1109-1112 (1997); Carrion-Vazquez, M. et al., Prog Biophys Mol Biol 74, 63-91 (2000); Carrion-Vazquez, M. et al., Prog Biophys Mol Biol 74, 63-91 (2000)). Single molecule AFM can be used to examine fundamental properties of proteins exposed to mechanical perturbations, in a way that cannot be captured using classical bulk biochemistry techniques. For example, the unfolding pattern of fibronectin and titin revealed that modular proteins unfold under force following a mechanical hierarchy (Oberhauser, A. F., et al., Journal of molecular biology 319, 433-447 (2002); Li, H. et al., Nature 418, 998-1002 (2002)) and that the mechanical stability of a protein changes depending on where the force is being applied (Carrion-Vazquez, M. et al., Nature Structural Biology 10, 738-743 (2003); Brockwell, D. J. et al., Nature Structural Biology 10, 731-737 (2003); Dietz, H. & Rief, M. P Natl Acad Sci USA 101, 16192-16197 (2004)).

Force-extension experiments are of limited use when studying chemical reactions. For example, studies of the oxidation and reduction of buried (cryptic) disulfide bonds proved difficult using force-extension experiments. In the absence of DTT, sawtooth patterns showed unfolding of a polyprotein, with each domain extending right up to the disulfide bond; whereas in the presence of DTT a second regime was observed at higher forces corresponding to the rupture of the disulfides bonds (Ainavarapu, S. R. et al., Biophys J 92, 225-233 (2007)). From such data the incorrect conclusion that the rupture forces measured the mechanical stability of a disulfide bond can be reached. In reality, mechanical unfolding of a domain exposed the cryptic disulfide and started the clock for the $S_N2$ chemical reaction between the disulfide and DTT (Wiita, A. P., et al., Proc Natl Acad Sci USA 103, 7222-7227 (2006)). At the same time the protein continued to be extended reaching increasingly higher forces until the disulfide bond was cleaved. Hence, the observed rupture force, far from measuring mechanical stability of a disulfide bond, represents a complex convolution of chemical kinetics, force, length and time, which is impossible to unravel. Due to these limitations the force-sensitivity of a chemical reaction cannot be studied using force-extension techniques. By contrast, force-clamp techniques readily separate force, length and time allowing for the accurate measurement of reaction rates and their sensitivity to force.

Developing suitable instrumentation and methods of analysis for examining mechanical biochemistry under force-clamp conditions has been a challenge over the years. (Oberhauser, A. F., et al., P Natl Acad Sci USA 98, 468-472 (2001); Wiita, A. P., et al., Proc Natl Acad Sci USA 103, 7222-7227 (2006); Schlierf, M., et al., P Natl Acad Sci USA 101, 7299-7304 (2004); Wiita, A. P. et al., Nature 450, 124-127 (2007); Kuo, T. L. et al., P Natl Acad Sci USA 107, 11336-11340 (2010); Garcia-Manyes, S., et al., P Natl Acad Sci USA 106, 10540-10545 (2009); Popa, I., et al., Journal of Biological Chemistry 286, 31072-31079 (2011); Garcia-Manyes, S., et al., Proc Natl Acad Sci USA 106, 10534-10539 (2009); Berkovich, R. et al., Proc Natl Acad Sci USA 109, 14416-14421 (2012); Garcia-Manyes, S., et al., Biophys J 93, 2436-2446 (2007); Walther, K. A. et al., P Natl Acad Sci USA 104, 7916-7921 (2007); Wiita, A. P., et al., Proc Natl Acad Sci USA 103, 7222-7227 (2006); Wiita, A. P. et al., Nature 450, 124-127 (2007); Garcia-Manyes, S., et al., Nature Chemistry 1, 236-242 (2009); Ainavarapu, S. R. K., et al., Journal of the American Chemical Society 130, 6479-6487 (2008); Liang, J. & Fernandez, J. M. Journal of the American Chemical Society 133, 3528-3534 (2011); Perez-Jimenez, R. et al., Nature Structural & Molecular Biology 18, 592-596 (2011); Perez-Jimenez, R. et al., Nature Structural & Molecular Biology 16, 890-896 (2009)).

The force-clamp technique now makes it possible to tackle key scientific questions that lie at the interface between the physics, biology and chemistry. In certain non limiting examples, the technique can be used to study chemical redox chemistry of disulfide bonds as well as chemical reactions that cleave many other types of covalent bonds in molecules including, but not limited to, polysaccharides, nucleic acids and other molecules. As described herein, the technique can be used for a single molecule analysis.

In one embodiment, the force clamp device described herein can be used to fully automated operation in force-clamp mode (FIG. 31A-B). In an exemplary measurement, the proportional-integral-derivative (PID) feedback loop follows a given set-point force protocol, appropriate for the studied process. Depending on the process under investigation, this protocol can have one or several constant pulling forces (FIG. 31C-D). The cantilever (FIG. 31E) can be initially pushed onto the surface in order to attach to a polyprotein chain. Once a polyprotein is tethered between the cantilever and the surface, the length of the polyprotein can be monitored over time. Each time an unfolding or disulfide reduction event takes place, the unraveling of the trapped amino acids can lead to a sudden increase in extension, which in turn can induce a relaxation of the cantilever (FIG. 31F). In certain embodiments, the PID feedback loop can move the surface in the opposite direction until the measured force matches again the set-point. When using polyproteins, the length versus time plot can show a staircase-like change in length, with each step corresponding to the unfolding of one domain in the polyprotein.

Described in this example of one non-limiting embodiment of the force-clamp AFM of the invention. The piezo-electric actuator (denoted "piezo" in FIG. 31A) is the moving stage that controls the extension of the molecule. This positioning stage is based on the piezoelectric effect, where a ceramics-made device can move with Angstrom resolution under the effect of a voltage. Typical piezo actuators can have travel ranges from hundreds of nanometers to few micrometers. High travel ranges come with the drawback of stronger nonlinearity and hysteresis. Nevertheless, the movement of the piezo can be independently measured using a capacitive or resistive sensor. In certain embodiments, the peizo used in connection with the force-clam AFM of the invention can be a piezo that incorporates a mechanical mechanism to correct for nonlinearity and removes the need of an independent measurement of the position (e.g. P-313 PicoCube). This type of peizo can reduce noise associated with measurement of its position and the position of the piezo can be theoretically determined with unlimited bandwidth.

In certain embodiments, the force experienced by the cantilever can be measured through the reflected position of a laser beam, which can be monitored by a split photodiode. In certain embodiments, the device described herein can use a 670 nm fiber-coupled laser diode with a 12 mm fiber collimator, capable of giving a sharp focused beam on the back of the cantilever. In certain aspects and for certain applications, sharp focusing can lead to less light leakage, limiting the effect of interference when using reflective surfaces, such as gold. The laser diode has good beam stability, important for the decrease in the time-dependent noise of the measured force. The output of the sensor is proportional to the force on the cantilever, assuming all responses are in a linear regime. In certain embodiments, a force-clamp AFM setup as described herein can further comprise a video camera suitable for aligning and focusing the laser on the cantilever (FIG. 31E).

The cantilever can be held in place using a spring based mechanism implemented inside the fluid cell. The laser beam passes through the quartz surface of the fluid cell and bounces back from the cantilever though the same quartz glass. A silicon O-ring provides a tight enclosure between the fluid cell and the surface, slowing the evaporation of the solution.

Instrument control and data acquisition can be performed on a PC using a USB connected National Instruments data acquisition card. Force-clamp operation can be implemented using a PID feedback system that drives the AFM to follow a given force protocol (FIG. 31D). In certain embodiments, the analog PID features two inputs—the force set-point (from the PC) and the measured force (from the AFM)—and one output that controls the piezo displacement (FIG. 31A). In certain embodiments, inside the PID controller (FIG. 31B), the two inputs are first fed into a differential amplifier, generating an error signal. This error signal can be processed in three parallel gain stages (proportional, integral and derivative). The outputs of these three stages can be summed, amplified and sent to the output, thus driving the AFM to attain the required set-point force. The individual gains of the feedback system can be set to minimize the response time while still ensuring stability (meaning that the system converges at the desired set-point). As shown in FIG. 31B, the individual gain parameters can be controlled through appropriately placed variable resistors. To avoid artifacts resulting from rapid transients, the output signal can be passed through a low-pass filter (5 kHz) before being sent to the piezo.

Fully automated operation of the AFM can be enabled by the addition of stages that continuously correct for mechanical drift. The positions of the piezo actuator and the quadrant photodiode can be adjusted using such auxiliary piezo stages. In the absence of sample degradation, experiments can be run continuously for several days, without user intervention.

Vibration isolation can be achieved by placing the AFM setup on top of a passive vibration isolation platform, which in turn can be placed on a pneumatic table.

Example 8

Mechanical fingerprints unambiguously report on the interaction of interest and can be used in any form of force spectroscopy. Mechanical fingerprints make it possible to discard events containing nonspecific interactions. As described herein polyproteins can be engineered to be suitable for force spectroscopy experiments. The use of polyproteins allows the unambiguous identification of successful events and reject traces showing spurious interactions (Carrion-Vazquez, M. et al., Prog Biophys Mol Biol 74, 63-91 (2000); Carrion-Vazquez, M. et al., Proc Natl Acad Sci USA 96, 3694-3699 (1999)). The unfolding of the domains composing the polyproteins is accompanied by identical step increases of the measured end-to-end length, rendering a staircase profile in the length versus time plot. Such a staircase is virtually impossible to obtain from rupture of multiple nonspecific interactions (Rief, M., et al., Science 276, 1109-1112 (1997)).

In one configuration (gold surface-silicon nitride cantilever), the AFM tip can attach to the polyprotein at any point along its length, rendering traces that have a varying number of unfolding domains (Carrion-Vazquez, M. et al., Prog Biophys Mol Biol 74, 63-91 (2000)). In certain embodiments, only recordings with a minimum number of identical steps and lasting longer than the measured process can be included in the analysis. Unfolding traces can have additional steps apart from the expected fingerprint, indicative of attachment to more than one molecule, attachment to a dimer molecule (from the oxidation of the terminal thiol), or aggregation, for instance. Although these recordings can also be excluded from the analysis, they can, in certain embodiments, be used in connection with the steps detected at the beginning of a trace. In this case nonspecific interactions between the cantilever and small surface-adsorbed contaminants can be broken and immediately after, the protein construct can experience the set-point force (Carrion-Vazquez, M. et al., Prog Biophys Mol Biol 74, 63-91 (2000)).

Polyprotein constructs used in the force-clamp measurements can be engineered through molecular biology techniques (Carrion-Vazquez, M. et al., Prog Biophys Mol Biol 74, 63-91 (2000)). Natural polyproteins such as, but not limited to, ubiquitin (Carrion-Vazquez, M. et al., Nature Structural Biology 10, 738-743 (2003)), titin (Rief, M., et al., Science 276, 1109-1112 (1997)) and filamin (Furuike, S., et al., FEBS Lett 498, 72-75 (2001)) can also be used in these experiments with minimal modification. The polyprotein construction can be performed by amplifying DNA encoding the protein of interest using polymerase chain reaction (PCR) and adding the specific restrictions sites. The DNA of this single monomeric protein can then be sequentially digested and ligated using the restriction sites of a cloning vector, resulting in dimers, tetramers, octamers, etc (Carrion-Vazquez, M. et al., Prog Biophys Mol Biol 74, 63-91 (2000)). Upon digestion with the appropriate enzymes, the DNA insert of the multimeric protein can be cloned into a specific expression vector having a $His_6$ tag (Alegre-Cebollada, J., et al., The Journal of biological chemistry 285, 11235-11242 (2010)). This expression vector endows transformed bacteria with antibiotic resistance and offers the possibility of triggering the expression of the protein of interest by the addition of IPTG. After protein expression, the cells can be harvested and lysed using enzymatic and mechanical treatments. The soluble fraction can be passed through two separation columns, a $His_6$ tag affinity column and a size-exclusion column. Depending on the expressed protein, the concentrated fractions are then stored at 4 or −80° C. until further use.

Figure 32:
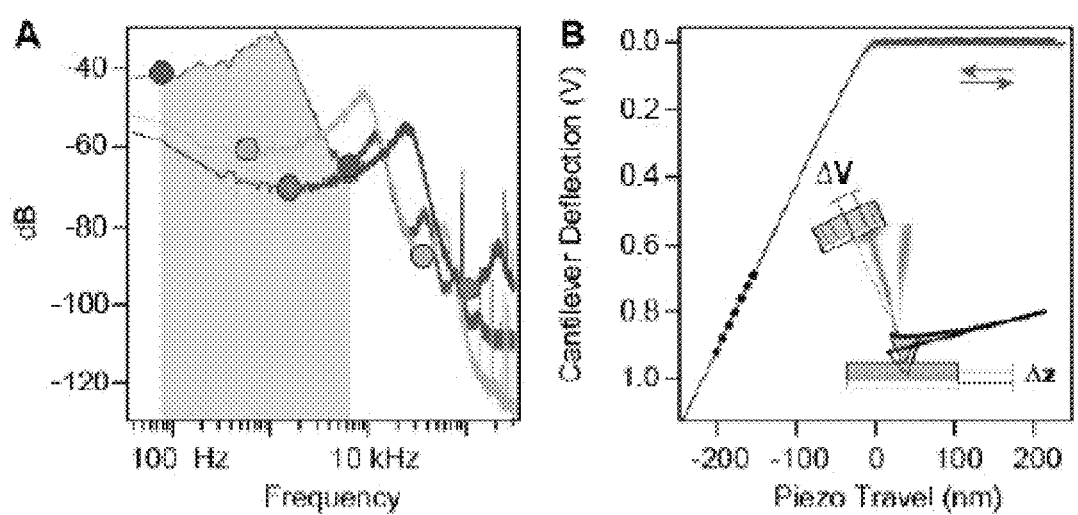
FIG. 32. Calibration of AFM cantilevers.

Cantilevers can be manufactured using microelectromechanical systems (MEMS) from silicon, borosilicate glass or silicon nitride and can have a gold coating layer, in order to improve their reflectivity. The cantilevers have on the surface-facing side a tip with a radius of 10-30 nm, which can increase the probability of attachment to only one molecule. For small bending angles, the cantilever can behave like a Hookean spring, with a spring constant that is determined by its material and dimensions. Each cantilever can be calibrated using the thermal fluctuations method, based on the equipartition theorem (Hutter, J. L. & Bechhoefer, J. Review of Scientific Instruments 64, 1868-1873 (1993)). The equipartition theorem states that the kinetic energy of each degree of freedom (such as a vibrational mode) equals half the thermal energy $k_BT$ (=4.11 pN·nm). The calibration of cantilevers comprises two steps (FIG. 32). In a first step, the thermal fluctuations of the cantilever far from the surface are measured and Fourier transformed, in order to separate the main vibration mode. By integrating the area below the first resonance peak, the mean squared displacement $<x^2>$ is measured in units of $V^2$ (FIG. 32A). In the second step of the calibration procedure, the cantilever is approached close to the surface and a deflection-extension curve is measured (FIG. 32B). When in contact, the piezo and the cantilever travel identical distances. The slope $s=\Delta z/\Delta V$ of this constant compliance region of the curve yields a correlation between the change in voltage ($\Delta V$) measured by the photodiode and the bending distance ($\Delta z$) measured from the movement of the piezo, in units of nm/V. Finally, the spring constant of the cantilever in pN/nm units is obtained according to:

$$k_c = \frac{k_B T}{\langle x^2 \rangle s^2}$$

The choice of cantilevers can be important for the experimental outcome, since cantilevers influence the signal-to-noise, drift and feedback response times. The lateral dimensions of the cantilever have to be large enough to reflect the laser beam. Cantilevers with small spring constants give a better signal-to-noise, since they deflect more for the same change in force. Cantilevers with small dimensions can have higher spring constant, but also higher resonance frequency. The resonance frequency of the cantilever limits the response time of the feedback loop. FIG. 32A shows the power spectrums of three typically used cantilevers; MLCT-B (Bruker), BL-RC150VB-A (Olympus) and BL-AC40TS (Olympus). The MLCT cantilevers yield stable signal, are linear on a high ranges of forces, have a good price/performance ratio and give a response time of down to 1 ms. BL-RC150VB cantilevers have a higher spring constant, but can yield feed-back response times down to 150 µs and are ideal to measure fast processes (Berkovich, R. et al., Proc Natl Acad Sci USA 109, 14416-14421 (2012)).

One surface of choice for adsorbing polyprotein constructs can be gold, which can bind to the thiol group of a terminal cysteine in a protein. The gold surfaces can be prepared by evaporating 40 nm of gold on top of a 20 nm 'gluing' layer of 1:1 Chromium/Nickel mixture deposited on a clean glass surface.

Figure 33:
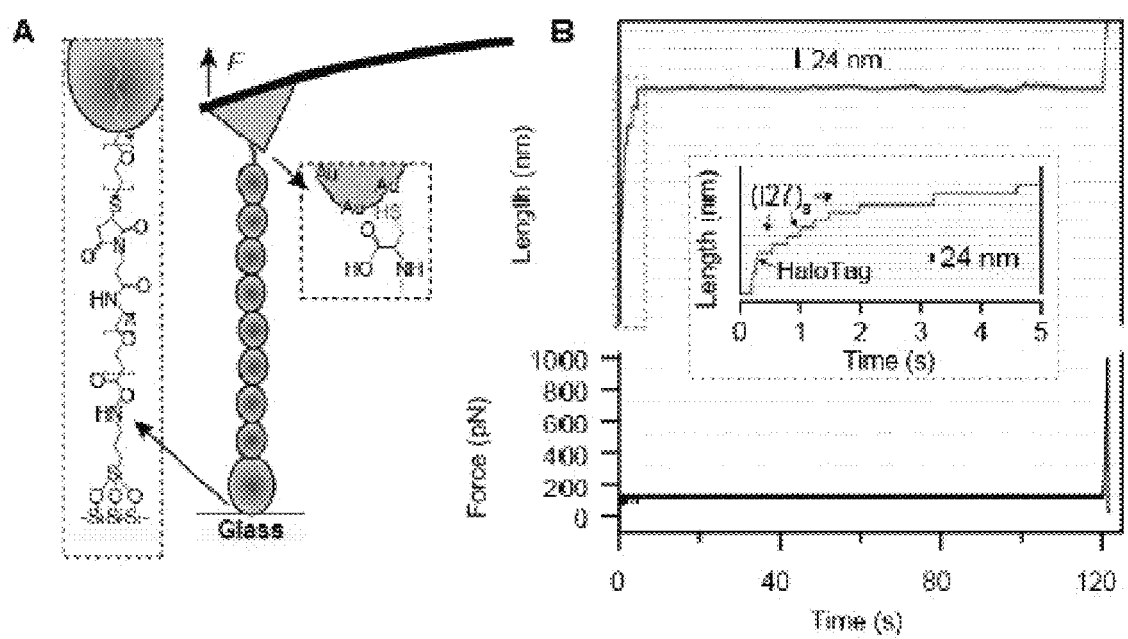
FIG. 33. Covalent attachment chemistry for AFM measurements.

A recently developed method for dual specific covalent attachment can increase the probability of having full-length tethered proteins, and of holding on to a single protein for long times, over several minutes (FIG. 33). This attachment chemistry was first described by Taniguchi and Kawakami (Taniguchi, Y. & Kawakami, M. Langmuir: the ACS journal of surfaces and colloids 26, 10433-10436 (2010)). In this approach, polyprotein constructs were engineered to have a HaloTag protein (a mutant haloalkane dehalogenase) at one terminus and a cysteine at the opposite end. The HaloTag forms an ester bond with a chloroalkane ligand linked covalently to the glass surface. Cantilevers can be similarly functionalized or coated with a gold layer. As opposed to gold surface-silicon nitride cantilever method described herein, the chloroalkane surface-gold cantilever approach is prone to more user manipulation errors and its success varies more from experiment to experiment.

Other covalent attachment approaches for AFM experiments have also been explored in the past. Ikai and colleagues managed to attach a protein to an AFM cantilever, using thiol chemistry to tether carbonic anhydrase to AFM cantilevers and a silicon substrates (Wang, T., Arakawa, H. & Ikai, A. Biochemical and biophysical research communications 285, 9-14 (2001)). Gaub and collaborators engineered a polyprotein containing a SNAP-tag enzyme at its C-terminus, which reacts with benzylguanine forming a covalent bond (Kufer, S. K. et al., Eur. Biophys. J. Biophys. Lett. 35, 72-78 (2005)). Zakeri and colleagues developed an attachment method based on the isopeptide bond using a peptide chain to form an amide bond with its protein partner (Zakeri, B. et al., P Natl Acad Sci USA 109, E690-E697 (2012)).

A minimum duration for each recording can be defined to avoid biasing the measured rates. Weak polyprotein anchoring leads to a high probability of detachment, which can take place before all the events have occurred. Without a strong selection criterion for minimum duration, slow events can be missed and the rate can be overestimated creating an artifactual plateau in the force dependency (Garcia-Manyes, S., et al., Biophys J 93, 2436-2446 (2007)). In certain embodiments, the analysis includes only traces that are long enough for the rate being measured. A simple way to ensure that random detachment times are not introducing an artifact is to show that the measured rate is not affected by increasing the minimum trace duration (Garcia-Manyes, S., et al., Biophys J 93, 2436-2446 (2007)). With covalently tethered polyproteins and more stable cantilevers unambiguous long lasting recordings that easily meet these criteria can be made. When analyzing these recordings it can be important to detect and include fast early events that may be poorly resolved. Overlooking fast events can cause an artifactual underestimation of the measured rate.

Figure 34:
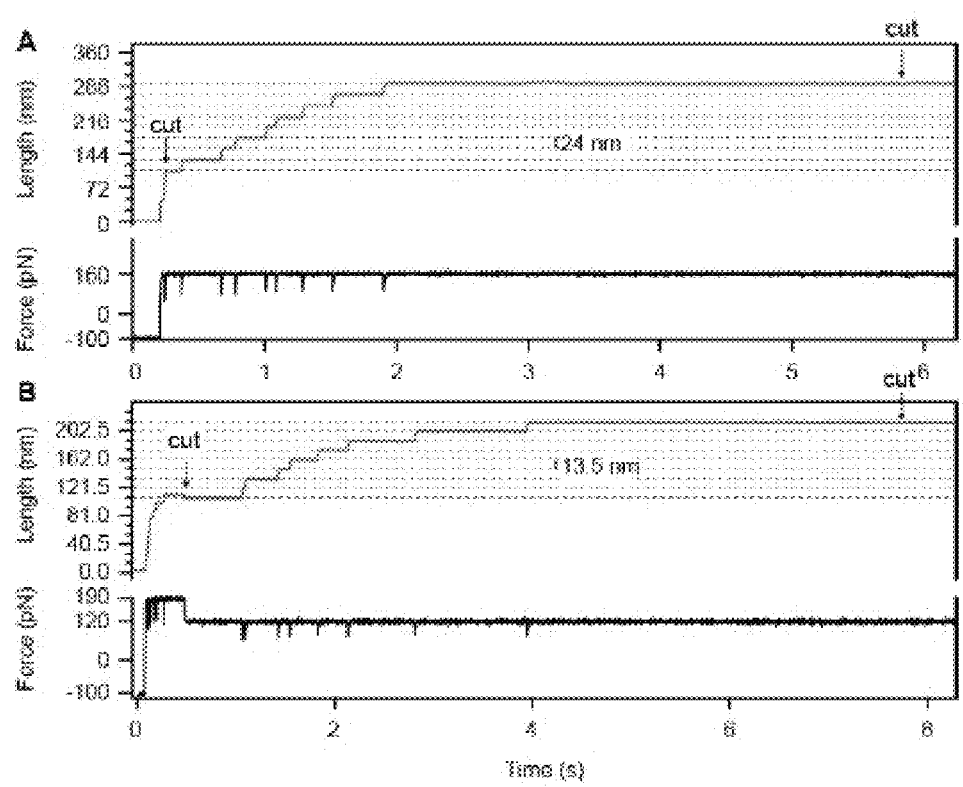
FIG. 34. Force-clamp traces measuring length (red curves) and force (black curves) from two different experiments.
Figure 35:
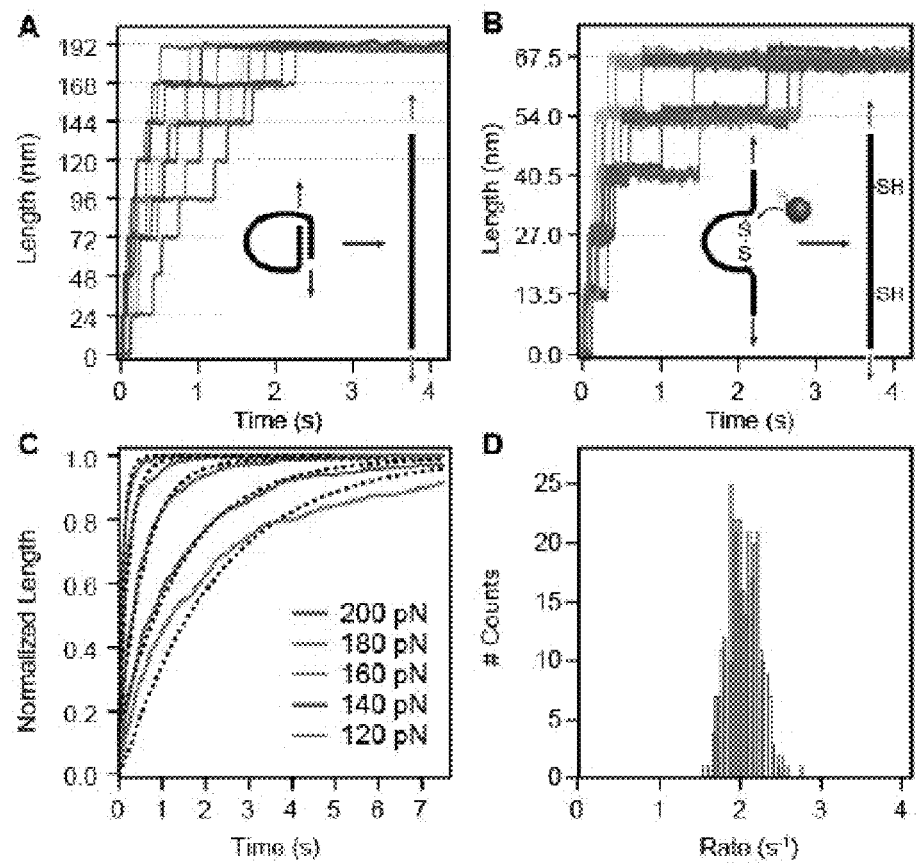
FIG. 35. A walkthrough from cut traces to measured rates.

Recordings that pass all selection criteria can be used to calculate reaction rates. First, each trace can be cropped so that it starts with the onset of the reaction and ends at the previously determined minimum duration requirement (FIG. 34). The cropped trace can consist of flat regions interrupted only by a series of steps corresponding to the studied reaction. For unfolding experiments, the first cut can be made at the beginning of the plateau that precedes the first unfolding event (FIG. 34A). This cropping protocol leaves out the initial elastic extension of the polyprotein and any changes in length caused by nonspecific interactions with the surface, which are unrelated to the unfolding of the polyprotein. In the case of disulfide reduction experiments, the first cut can be made at the start of the reduction pulse (FIG. 34B). From this point onwards, the cropped traces from unfolding and reduction experiments can be analyzed in an identical way. For each force, all of the cropped traces can be summed and normalized (FIG. 35A-C). The time course of the resulting summed trace reflects the progression of the studied process, as every length increment reports on a single reaction.

Dwell time analysis is an alternative to summed traces (Kuo, T. L. et al., P Natl Acad Sci USA 107, 11336-11340 (2010); Brujic, J., et al., Biophys J 92, 2896-2903 (2007); Szoszkiewicz, R. et al., Langmuir: the ACS journal of surfaces and colloids 24, 1356-1364 (2008); Alegre-Cebollada, J., et al., Nature chemistry 3, 882-887 (2011); Garcia-Manyes, S., et al., Journal of the American Chemical Society 133, 3104-3113 (2011)). In this analysis, zero time can be set at the beginning of the plateau preceding the first unfolding or reduction event. A dwell time is the time at which a single event happens, measured from the zero time reference. The result of this method of analysis is a distribution of all dwell times for a given process.

If the process follows simple exponential kinetics, the reaction rate r at a given set force can easily be extracted by fitting the normalized extension l to: $l=1-\exp(-r \cdot t)$ (Schlierf, M., et al., P Natl Acad Sci USA 101, 7299-7304 (2004)). For some reactions, the force dependency can appear as a straight line when displayed in a semilogarithmic plot. In those cases, data can be analyzed assuming simple Arrhenius kinetics, where the reaction rate changes according to $$r = r_0 \cdot \exp\left(\frac{F \cdot \Delta x}{k_B \cdot T}\right),$$

(where $r_0$ is the rate in the absence of force, F is force, $\Delta x$ is the distance to the transition state, $k_B$ is Boltzmann constant and T is the absolute temperature) (Bell, G. I. Science 200, 618-627 (1978); Evans, E. Annu Rev Bioph Biom 30, 105-128 (2001)). Thus in this model, the distance to the transition state is obtained from the slope of the semilogarithmic plot. The height of the energy barrier of the chemical reaction or unfolding process can be obtained from the extrapolated value in the absence of force combined with the pre-exponential factor that was measured to be A ~$10^8$ $M^{-1}$ $s^{-1}$ for chemical reactions (Liang, J. & Fernandez, J. M. Journal of the American Chemical Society 133, 3528-3534 (2011)) and A ~$10^9$ $s^{-1}$ for mechanical unfolding (Popa, I., et al., Journal of Biological Chemistry 286, 31072-31079 (2011)). In some other cases, force dependencies may not be linear and other methods of analysis are needed to interpret the results (Wiita, A. P. et al., Nature 450, 124-127 (2007); Dudko, O. K., et al., Phys Rev Lett 96 (2006)).

Using dwell time analysis it is shown that the time course of mechanical unfolding of the ubiquitin and I27 proteins does not follow simple exponential kinetics (Kuo, T. L. et al., P Natl Acad Sci USA 107, 11336-11340 (2010); Brujic, J., et al., Biophys J 92, 2896-2903 (2007); Garcia-Manyes, S., et al., Journal of the American Chemical Society 133, 3104-3113 (2011); Brujic, J., et al., Nat Phys 2, 282-286 (2006)). For both proteins, the origin of the non-exponential behavior can be explained in terms of a static disorder scenario (Kuo, T. L. et al., P Natl Acad Sci USA 107, 11336-11340 (2010); Garcia-Manyes, S., et al., Journal of the American Chemical Society 133, 3104-3113 (2011)). In this framework, static disorder originates from the existence of an ensemble of conformations that populate the transition state of the unfolding process that cannot interconvert during the timescale of the experiment. Dwell time analysis of the unfolding and reduction processes taking place within the same protein show the presence of static disorder for the unfolding process and the lack of it for the chemical reaction (Garcia-Manyes, S., et al., Journal of the American Chemical Society 133, 3104-3113 (2011)). This finding also excludes the possibility of static disorder being a consequence of instrumental errors.

The force dependency of a reaction can be determined by the underlying free-energy landscape of the molecule (Berkovich, R., et al., Biophys J 98, 2692-2701 (2010)).

The error of a measured rate can be determined through a nonparametric bootstrapping procedure (Wiita, A. P. et al., Nature 450, 124-127 (2007); Efron, B. The Jackknife, the Bootstrap, and Other Resampling Plans (SIAM, 1982)). The bootstrap analysis uses the number of iterations $N_{BS}$ as an input parameter, and carries out the following procedure for each experimental condition (e.g. for each force). In the pool of traces selected for analysis, each trace is considered an independent observation. Based on this original dataset, a chosen number ($N_{BS}$) of artificial datasets are then created, each containing the same number of traces as the original dataset. Individual traces from the original data set are randomly selected to populate the artificial datasets. If simple exponential kinetics are assumed, the traces in each artificial dataset can be summed and fitted to a single exponential to yield a rate. These $N_{BS}$ rates obtained from the chosen number of data sets give the spread of the data, and hence the standard error of the mean (s.e.m., FIG. 35D). The s.e.m. measured by this method converges to a single value as the number of bootstrap iterations $N_{BS}$ increases, and a sufficiently large number of iterations should therefore be used. It has been found empirically that $N_{BS}$=300 iterations are usually sufficient to converge into a reliable result.

Figure 36:
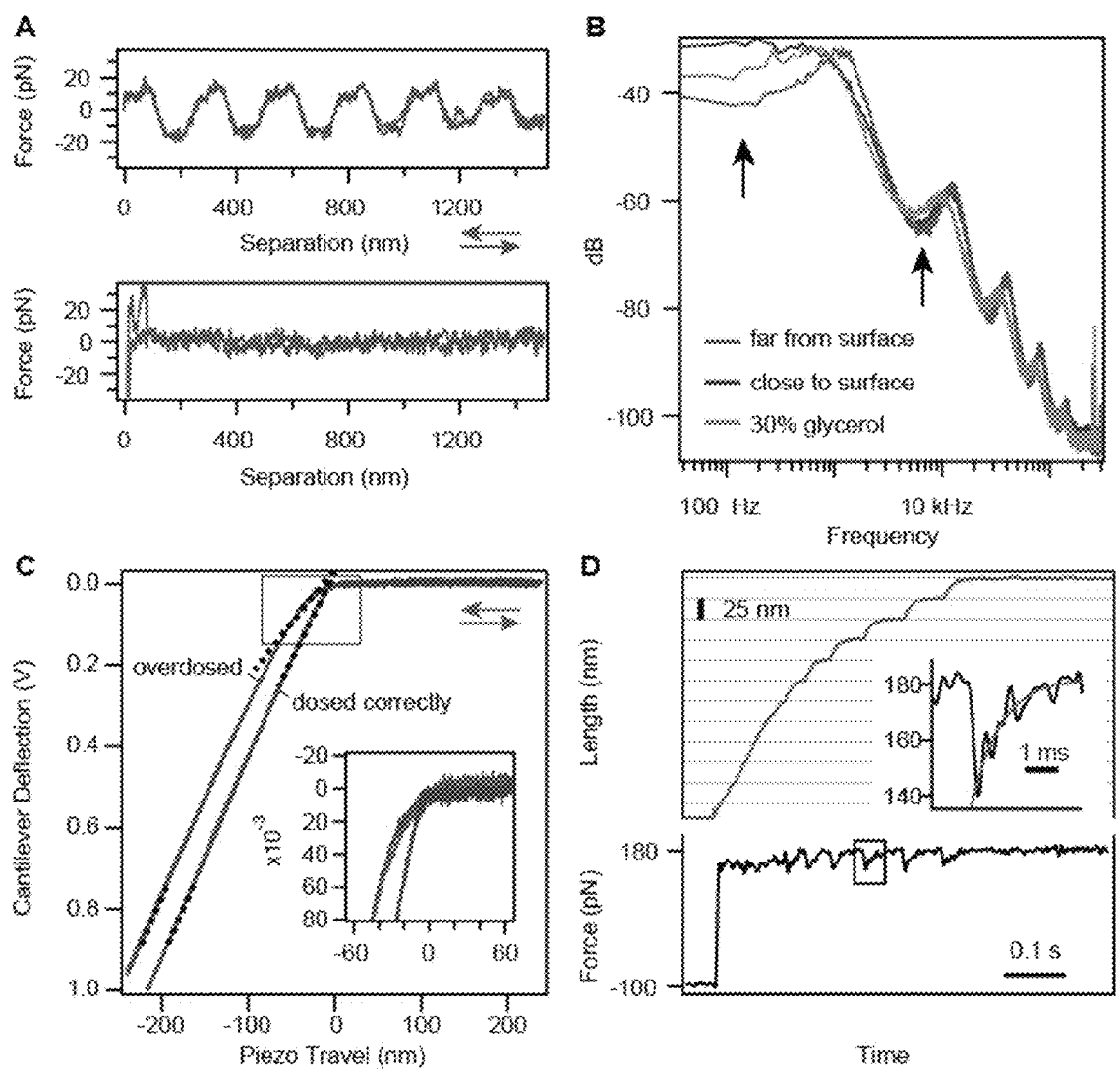
FIG. 36. Illustration of possible problems during an AFM force-clamp experiment.
Figure 37:
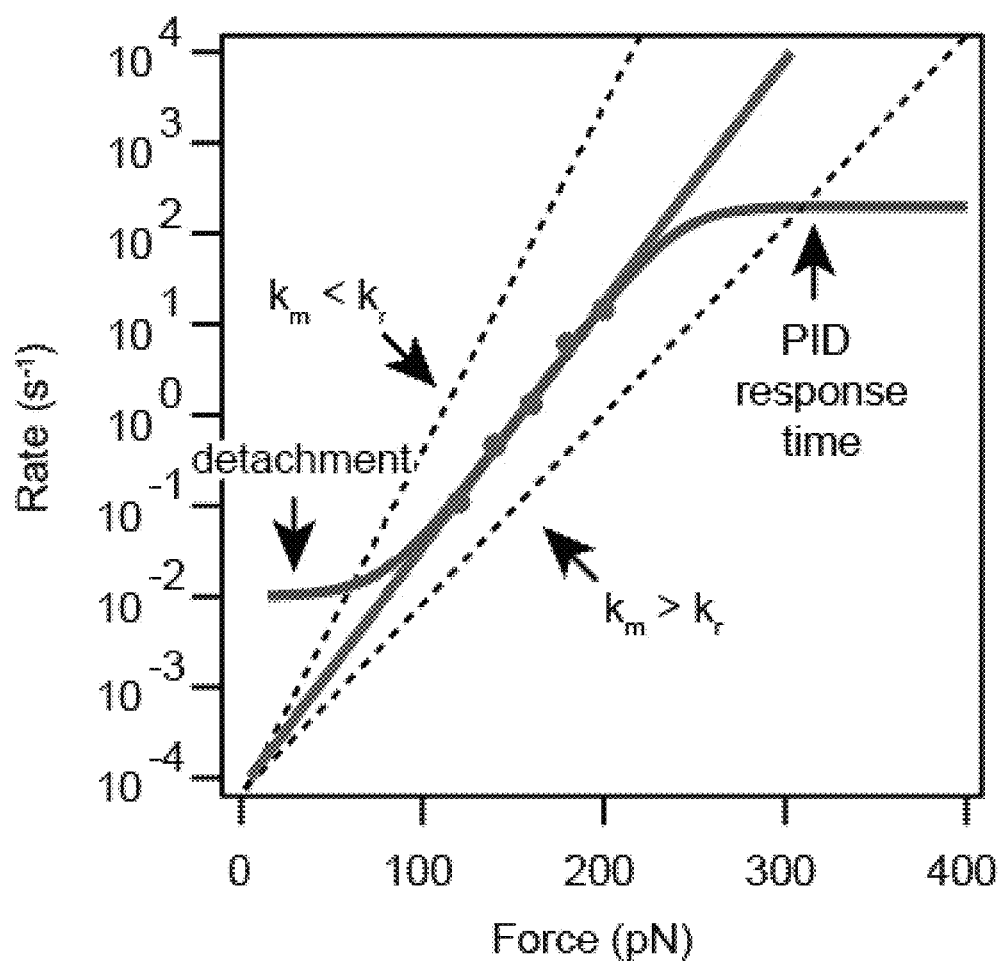
FIG. 37. Summary of possible artifacts in force-clamp AFM. Unfolding rates at different forces (red circles) and the fitted rate (red line). The blue line represents regions where instrumental and analysis errors influence the measured rates. The time response of the PID sets an upper limit to the rates that is possible to measure. Detachment and selection of short traces that do not capture all the events produce an artifactual plateau at lower rates. Cantilever calibrations errors have a direct impact on the measured force sensitivity (dotted lines). Overestimation of the measured spring constant, $k_m$, compared to its real value, $k_r$, leads to smaller experimental slopes, while underestimation has the opposite effect.

The main sources of experimental errors arise from laser interference, errors in the thermal fluctuations spectrum, non-linearity in the contact slope measured during cantilever calibration and feedback response time (FIG. 36 and FIG. 37).

Example 9

Provided in Example 9 is a non-limiting example of a procedure for using certain embodiments of the force-clamp devices described herein:

1. Mount the cantilever in the fluid cell. Turn on the laser and move the camera such that the cantilever is in focus. Align the laser beam at the tip of the cantilever and focus it using the laser positioning screws until the laser spot looks small compared to the size of the cantilever (see also FIG. 31E). Optionally, align the laser focus on the cantilever and compare the total PSD voltage in different focusing positions until the maximum voltage is obtained. The diameter of the laser should not exceed the surface dimensions of the cantilever, in order to minimize light leakage. When using a small cantilever, this requirement might not be possible to fulfill. In this case align and focus the laser as much as possible onto the free end of the cantilever.

2. Centrifuge the polyprotein sample at 20,000 g for 10 min at 4° C. to get rid of possible aggregates and filter and degas the buffer solution before usage. Filter buffer using 0.22 μm filters and degas.

3. Glue the surface to the piezo using vacuum grease. Add a small volume of polyprotein solution (2-10 μL) to the surface and spread it with the pipette tip, without scratching the surface. Wait for 10-20 minutes to allow the protein to adsorb, without letting the solution to dry out completely. When using silicon or silicon nitride cantilevers, the protein can also be added directly to the cantilever, skipping steps 4 and 5. This approach increases the probability of having proteins adsorbed on the surface area close to the cantilever.

4. Gently wash the nonspecifically adsorbed proteins with buffer. Skip this step if the protein is very dilute or not very sticky (for example lacks terminal cysteines, or a reductive environment is used).

5. Add a drop of buffer solution (typically 20-100 μL of HEPES or phosphate buffer) on the cantilever tip and check for air bubbles using the camera on the instrument. Air bubbles can attach to the cantilever in this step. Focus the camera on the cantilever and look for air bubbles. If air bubbles are present, clean and dry the fluid cell and repeat step 5.

6. Close the fluid cell by approaching the piezo towards the cantilever until the O-ring seals the cell.

7. Align the PSD so that the reflected laser beam is aimed at the center of the detector. Verify that the experimental solution is completely free of particulate matter by examining the force signal, since even low concentrations of micron-size particles can have a strong adverse effect on the stability of the measurements by scattering the laser beam used to monitor the position of the cantilever. After closing the fluid cell, wait for 10-60 minutes for the system to thermally equilibrate and for the drift of the cantilever (measured from the PSD output) to settle.

8. Measure the thermal fluctuations (power) spectrum of the oscillations of the cantilever using a fast Fourier transform analyzer. Select the main vibration mode and integrate the resonance peak. The thermal fluctuations spectrum contains information about the quality of the experiment. Mechanical drift will increase the contribution in the low frequency region of the power spectrum, while electronic noise will yield sharp peaks in the high frequency range. A change in the position of the resonance peak within the same class of cantilevers can be indicative of the presence of a bubble or of structural damage to the cantilever. Record power spectrum far from the surface to avoid dampening of the signal 9. Approach the cantilever to the surface by monitoring its reflection. An automatic procedure can be implemented using the piezo motor linear stage to control the distance between cantilever and surface. The AFM is programmed to approach the surface to the cantilever by monitoring the total intensity of the reflected laser beam.

10. Move the piezo actuator such that the cantilever touches the surface and then retracts to break the contact. Do a force-deflection curve. Fit a line in the region where the cantilever is in contact with the piezo-moving surface and has a linear behavior (this region is often referred as "the constant compliance region", FIG. 32B and FIG. 366C). The slope of the variation relates the PSD signal in mV with cantilever tip displacement in nm (see the calibration section above). A good practice to check if the calibration is correct is to run the spectrometer in force-extension mode for a few cycles. The force-extension recordings using a correctly calibrated cantilever will show the expected unfolding force (which depends also on the approach-retract velocity) and increment in the contour length of the protein (when fitted with a phenomenological model for polymer elasticity, such as worm-like chain). Analyze the part of the force curve before the cantilever gets in contact with the surface for laser interference, normally evident as a sinusoidal curve (FIG. 36A). Interference affects the force applied to the protein in force-clamp mode.

11. Input the desired force protocol. Set the AFM to push the cantilever into the protein layer adsorbed on the surface, at −1 nN for 1 s. Use a short 0.2 s pulse with a pushing force of −100 pN to find the position of the surface. The experimental force has to be chosen such that the domains composing the polyprotein construct unfold with a detectable rate. FIG. 34A shows the unfolding of a polyprotein construct composed of a HaloTag and eight I27 domains. Refolding processes can be studied in a similar way by decreasing the pull force (Fernandez, J. M. & Li, H. Science 303, 1674-1678 (2004); Kosuri, P. et al., Cell 151, 794-806 (2012)). Chemical reactions such as the reduction of disulfide bonds are studied by adding a second pulse with a different force set-point than the unfolding part. The unfolding pulse should be at a force high enough to unfold all domains as fast as possible (usually less than 0.3 s), so that all cryptic bonds are exposed approximately at the same time. FIG. 34B shows the unfolding of eight domains of an I27 mutant, having a disulfide bond between the position 32 and 75. Unfolding of the protein domains exposes the disulfide bonds to the solvent environment. Then, reduction of the disulfides by thioredoxin produces a second staircase in the recording (FIG. 34B).

12. After setting the desired pulse protocol, adjust the feedback gain constants. Typically the integral gain is the only parameter that needs adjustment from the standard values. Start with a small gain value and increase in small increments until the system goes close to resonance (high-frequency oscillations in force and length), then reduce the gain with one step.

13. Once started, the experiment can be set up to run fully automatic for extended amounts of time, up to several days. During every attempt to attach a protein, the experimental pulse is automatically stopped if the attachment is unsuccessful. After a complete successful pulse protocol, the pulling force is increased to a high value until the attachment is broken, and the cycle of force pulses is repeated. Data is saved when complying with the requirements set by the user—the number of measured steps and the duration of the trace.

14. Change the value of the force in order to obtain the force dependence of the studied reaction.

15. Select traces having clear equal unfolding steps and crop them between the beginning of the plateau that precedes the first unfolding event and close to their detachment point (see FIG. 34A); for disulfide reduction experiments, the first cut is made at the start of the reduction pulse (see FIG. 34B). Discard traces having mixed unfolding and reduction steps in the second pulse. Cut the traces as shown in FIG. 34A and FIG. 34B.

16. Superimpose all selected traces at a given force and choose a duration limit based on the traces showing slower kinetics. Exclude all traces where detachment occurred before this duration.

17. Average the selected traces and normalize them (FIG. 35C).

18. Calculate the measured rate and error using a bootstrapping analysis procedure which assumes a specific model for the process (such as an exponential constrained through origin, specific for a two-state process—FIG. 35C and FIG. 35D—or a more complex model, taking for example into account static disorder (Kuo, T. L. et al., P Natl Acad Sci USA 107, 11336-11340 (2010).

19. Plot the measured rates in logarithmic scale as a function of force. Use Arrhenius or other kinetic model to extract the rate at zero force and the distance to transition state Example 10

Provided in Example 10 is a non-limiting example of preparation of the surfaces and cantilevers for covalent attachment of proteins.

$SM(PEG)_{24}$: Dissolve $SM(PEG)_{24}$ in DMSO to a concentration of 250 mM, aliquot in small volumes, freeze in liquid nitrogen and exchange the air with argon inside the recipients. Keep the aliquots at −80° C. until use.

HaloTag O4 chloroalkane ligand: Dissolve HaloTag O4 chloroalkane ligand in DMSO to a concentration of 100 mM, aliquot in small volumes, freeze in liquid nitrogen and exchange the air with argon inside the recipients. Keep the aliquots at −80° C. until use.

The functionalization of glass coverslips with a chloroalkane ligand specific for HaloTag involves a three step reaction: 1. amino-functionalization of the glass surface; 2. reaction with a bifunctional crosslinker; 3. final reaction with a thiolated Halotag ligand. In the first step the slides are reacted with an aminosilane (Labit, H. et al., Biotechniques 45, 649-+ (2008)). The amino-functionalized coverslips are reacted in a second step (Zimmermann, J. L., et al., Nat Protoc 5, 975-985 (2010)). In the final step the bifunctional thiol-chloroalkane ligand is covalently attached. Gold coated cantilevers are obtained using standard evaporation techniques in low pressure, of ~5·10$^{-6}$ torr or can be bought already coated with gold. The amount of gold and intermediate chromium/nickel layer affects the radius and spring constant of the cantilever.

Preparation of Functionalized Glass Coverslips for HaloTag Chemistry

1. Clean the glass coverslips using Piranha cleaning procedure (a 3:1 mixture of conc. $H_2SO_4$ and 30% $H_2O_2$ for 30 min at 80° C.). Piranha solution is corrosive and can lead to violent reactions with organic solvents.
2. Wash the surfaces with water, dry them with nitrogen, expose them to oxygen plasma for 1 min on each side and heat them for 5 min in a preheated oven at 150° C.
3. Add the surfaces one by one in a glass beaker containing 0.1% (3-aminopropyl)trimethoxysilane in heptane and leave them overnight in a desiccator.
4. Wash the surface by subsequently sonicating them for 5 min in heptane, water and chloroform.
5. Dry the surfaces in an oven for 1 h at 150° C.
6. Sandwich silanized coverslips with freshly prepared SM(PEG)$_{24}$ 10 mM, dissolved in borax buffer pH 8.5 and incubate in the dark for 1 h.
7. Separate the sandwiches, wash the coverslips with DD water and dry them with nitrogen.
8. Sandwich the coverslips freshly prepared chloroalkane ligand 7.5 mM, dissolved in borax buffer pH 8.5 and incubate in the dark overnight.
9. Separate the sandwiches, wash the coverslips with DD water and dry them with nitrogen.
10. Quench the reaction with 2-mercaptoethanol 50 mM for 5 min.
11. Wash the coverslips with DD water, dry them with nitrogen and store them at −20° C. until use.

Preparation of Functionalized Gold Cantilevers for HaloTag Chemistry

1. Expose cantilevers to oxygen-plasma for 1 min.
2. Mount the cantilevers in the evaporator and apply vacuum.
3. Evaporate 2 nm of Ni/Cr mixture.
4. Evaporate 10-15 nm of Au.
5. Store the Au cantilevers until usage. Gold cantilevers can be washed with 100% ethanol before experiment.

Example 11

In certain embodiments there can be unbiased random noise ("shaky" signal) in the recordings, on a sub-second to second timescale, which can be indicative of particulate diffusion in the solution. Particles present in the measuring buffer can scatter the laser beam and add noise to the force measurement (in force-extension), or length measurement (in force-clamp). Shaky signals can be mitigated or reduced by dismantling the experiment, clean the fluid cell and replace the surface, and start again from step 2.

Example 12

In certain embodiments the shape of the thermal fluctuations spectrum can indicate problems. A broken arm of a V-shape cantilever or an air bubble can change the position of the resonance peak and can be solved by either replacing the cantilever or the buffer. Boxes of individual cantilevers are recommended rather than wafers to avoid damaging the cantilever in the process of carving. A thermal spectrum taken too close to the surface can affect the power spectrum, resulting into an overestimation of $<x^2>$ and a underestimation of the spring constant of the cantilever (FIG. 36B, blue trace). The separation between the surface and the cantilever can be increased in such a case. Presence of viscous compounds in the measuring solvent such as glycerol can lead to a shift in all the fluctuation peaks that has to be taken into account to integrate the full range of the resonant mode (FIG. 36B, green trace).

Example 13

In certain embodiments interference pattern can be measured in the non-contact part of the force-extension traces. Interference can appear when using reflective surfaces such as gold. Such an example is represented in FIG. 36A. The presence of interference can induce a change in the real applied force as a function of separation during the force-clamp experiment. Measurements obtained in the presence of interference can have an error in the force proportional to the magnitude of the measured interference in force-extension curves. Using non-reflective surfaces such as glass and mica can eliminate interference, but attachment of proteins to these surfaces can be poorer than on gold (with the possible exception of attachment to glass using covalent chemistry methods, such as the Halotag method) If working with reflective surfaces (such as gold), interference can be reduced or eliminated by slightly changing the position of the laser on the cantilever without severely affecting the total reflected voltage, or by refocusing the laser so that there is no light leakage. Alternatively, the surface can be slightly tilted so that the reflected light does not hit the PSD, or the cantilever can be replaced altogether.

Example 14

In certain embodiments (FIG. 36C), the constant compliance region may not have a linear domain when too much protein is adsorbed on the surface or when using small cantilevers. If too much protein is adsorbed, restart the experiment decreasing the amount of protein. If small cantilevers are used, a clean uncovered surface can be used to obtain the slope of the variation of the PSD signal with bending cantilever distance. Due to the lack of a protein layer, this surface will have a well-defined inflection point when the cantilever touches the surface. Most probably, due to the absence of protein the deflection-extension curve will also show a high-force detachment peak, but this peak does not interfere with estimation of the slope.

Example 15

In certain embodiments, piezo hysteresis can have a profound effect on cantilever calibration and measured separation. The force-deflection curve used to obtain the constant compliance region can, in this case, show a different slope for the approach and retract part and the measured distance can have errors arising from the linear extrapolation of the applied voltage vs piezo moving distance. Linear piezo actuators or piezo actuators with position feedback can be used. The presence of different slopes on the approach and redraw part of the constant compliance region can be indicative of a loosely attached surface (solution: glue again the surface to the piezo), a thick protein layer (solution: set up a new experiment with less protein), a bubble (solution: replace the buffer), or even a broken piezo (solution: send the piezo to repair or replace the piezo with a better one; if an instrument with a piezo having large hysteresis is used and cannot be replace, a way to reduce the calibration error can be to measure the slope on both approach and retract curves and average them).

Example 16

In certain embodiments, the calibration of the capacitive sensor of the piezo as a function of applied voltage can be reported by the manufacturer, and can have a significant error coming from the limitations of the used calibration method. The linear piezo actuator described herein is less prone to this kind of errors. Whenever using a new piezo, verify and adjust the calibration of the positioning sensor from the unfolding steps of a known protein (for example unfolding of Ubiquitin at 100 pN shows step increases of 20 nm).

Example 17

In certain embodiments, there can be large variations of the measured spring constant compared to other cantilevers within the same family or with the value reported by the manufacturer. Most cantilevers are reproducibly manufactured to have the same spring constant and little variation can be expected from cantilevers within the same box. Table 4 shows measured values for the spring constant of Bruker MLCT-B cantilevers on the same instrument.

TABLE 4

Calibration parameters obtained on the same setup using different cantilevers from different boxes.

| Box Number | s (nm/V) | $<x^2>$ ($V^2$) | $k_c$ (pN/nm) |
|---|---|---|---|
| 1 | 146.7 | 1.30E-05 | 15.2 |
|   | 128.8 | 1.80E-05 | 14.1 |
|   | 134.9 | 1.50E-05 | 15.4 |
|   | 129.3 | 1.50E-05 | 15.8 |
|   | 135.7 | 1.60E-05 | 14.0 |
|   | 127.1 | 1.70E-05 | 14.9 |
| 2 | 133.7 | 1.60E-05 | 14.7 |
|   | 140.0 | 1.60E-05 | 13.9 |
|   | 120.4 | 2.00E-05 | 14.0 |
|   | 117.2 | 1.90E-05 | 15.4 |
| 3 | 140.8 | 1.40E-05 | 14.9 |
|   | 157.9 | 1.20E-05 | 13.3 |
|   | 163.8 | 1.10E-05 | 13.3 |
|   | 149.0 | 1.30E-05 | 13.9 |
|   | 153.9 | 1.00E-05 | 16.9 |
|   | 141.5 | 1.50E-05 | 13.9 |
|   | 132.2 | 1.60E-05 | 14.6 |
|   | 142.1 | 1.50E-05 | 13.9 |
|   | 137.3 | 1.60E-05 | 14.6 |
|   | 146.3 | 1.40E-05 | 13.5 |
| 4 | 146.8 | 1.30E-05 | 14.5 |
|   | 136.7 | 1.60E-05 | 13.6 |
|   | 115.8 | 1.80E-05 | 16.8 |
|   | 113.4 | 2.20E-05 | 14.6 |
|   | 130.5 | 1.80E-05 | 13.7 |
|   | 116.4 | 2.30E-05 | 13.4 |
|   | 116.2 | 2.30E-05 | 13.4 |
| 5 | 117.0 | 2.00E-05 | 15.0 |
|   | 120.3 | 2.00E-05 | 14.1 |
|   | 128.0 | 1.70E-05 | 14.5 |
|   | 121.3 | 1.90E-05 | 14.4 |
|   | 115.6 | 2.20E-05 | 14.2 |
|   | 103.8 | 2.70E-05 | 14.3 |
| 6 | 148.9 | 1.40E-05 | 13.3 |
|   | 138.3 | 1.50E-05 | 14.0 |
|   | 126.8 | 2.00E-05 | 12.6 |

In certain embodiments, a significant deviation from the average spring constant of the cantilever can be a consequence of a broken arm or the presence of a bubble close to the laser reflection point. Try changing the buffer. If the anomalous value maintains, change the cantilever. Other reasons for errors in the calibration of cantilevers can arise from a wrongly calibrated piezo and other instrumental and user errors. Data obtained using different AFM setups can have an error related to the measuring instrument. To quantify this variability, measure the spring constant of the same cantilever on all the available instruments and recalibrate the positioning sensor for the outliners. Data obtained for the same cantilever on three different instruments is shown in Table 5, which shows that very similar values can be obtained for the same cantilever in different setups.

TABLE 5

Spring constants measured for the same cantilever on three different instruments.
$k_s$ (pN/nm)

| 14.34 |
| 14.27 |
| 15.50 |

Example 18

In certain embodiments (FIG. 36D), the feedback response time can be too slow to capture the unfolding of the fast events. In these conditions, the set-point force is reached in a comparable time to the rate of the measured process or is not reached at all for the fast occurring events. The response time it takes the feedback loop to recover to the set-point force after an extension event can depend on the size and sensitivity of the cantilever, and the settings of the PID loop. The integral gain can be increased until close to the resonance of the system or a faster cantilever can be used. For longer than normal response time of a given cantilever model, replace the cantilever. A plateau at high rates in the force dependence (FIG. 37) can be indicative that PID response time is limiting the rates that can be measured.

Example 19

In certain embodiments, the feedback can create oscillations, visible as high-frequency periodic noise in the recordings or as an audible high-pitch noise from the piezo. The gain factors in the feedback circuit can be decreased. Prolonged high-frequency oscillations can be avoided since they have a direct impact on the lifetime of the piezo actuator. This issue can also appear after prolonged usage during the same experiment. Evaporation of the buffer can induce a change in the optimal feedback parameters.

Example 20

In certain embodiments there can be too few pick-ups. The magnitude of the contact force can be increased (to −2 nN, for instance), or the contact time can be increased (to 2 s, for instance). If these changes do not work, the fluid cell can be opened and more protein sample added to the surface.

Example 21

In certain embodiments, there can be many pick-ups but few clean fingerprints. Traces lacking a clear unfolding fingerprint can originate from several proteins tethered in parallel, a degraded protein or contaminations. The magnitude and/or duration of the contact force pulse can be reduced (~500 pN, 0.3 s for instance). If the problem persists, the experiment can be set up again with less protein. If there are still no clean fingerprints then the protein sample might be compromised. As proteins preparations age their performance in single-molecule AFM can decrease, even with no obvious changes in the behavior of the protein in SDS-PAGE or size exclusion chromatography. A new batch of protein can be purified.

Example 22

In certain embodiments cantilever calibration can change in time. Thermal drift and mechanical damage of the cantilever can lead to a change of the already calibrated parameters. Every few hours a force-extension trace can be obtained and the contact part can be checked to show the same slope as for the original calibration. If a change in the slope of the constant compliance region is measured, the cantilever can be recalibrated by moving it away from the surface and repeating steps 8-10. If a change in the total intensity of the laser takes place, the laser can be repositioned to obtain maximum intensity and the cantilever can be recalibrated. If a significant change in the value of the cantilever constant is measured, the cantilever can be changed.

Example 23

In certain embodiments there can be variation with time of the separation distance between the surface and cantilever. Mechanical drift can cause a change in the distance between the cantilever tip and the surface that is not due to the dynamics of the protein under force. This kind of drift can come from a poorly attached surface on the piezo, a poorly fixed cantilever or evaporation of the measuring solvent. The instrument described herein uses a piezo motor to adjust the separation between cantilever and surface before every attachment trial. If this kind of drift persists, the attachment of the surface to the piezo and of the cantilever can be checked and more measuring buffer can be added.

Example 24

In certain embodiments, the force dependence can show a plateau at lower rates (FIG. 37). Low values of the rates can be biased by selecting traces whose duration is short compared to the kinetics of the reaction of interest (Garcia-Manyes, S., et al., Biophys J 93, 2436-2446 (2007)). Traces should be long enough so that the vast majority of the events in the data set happen before detachment.

Example 25

In certain embodiments the force sensitivity of the studied process is not reproducible. Errors in the calibration of the cantilever can have a direct impact on the measured slope of the force sensitivity of the process (dotted lines in FIG. 37). A constant displacement of the cantilever can be expressed as $\Delta z = F_r/k_r = F_m/k_m$, where $F_r$ and $k_r$ are the real pulling force and spring constant, and $F_m$ and $k_m$ are the measured pulling force and spring constant. If Arrhenius kinetics are considered, the variation of the reaction rate with the measured force follows $$r = r_0 \cdot \exp\left(\frac{k_r}{k_m} \frac{F_m \cdot \Delta x}{k_B \cdot T}\right).$$

Hence, an error in the calibration is directly reflected in the measured distance to the transition state through $\Delta x = (k_r/k_m) \cdot \Delta x$. Therefore, overestimation of the spring constant ($k_m > k_r$) leads to smaller experimental slopes (FIG. 37). On the other hand, if the spring constant is underestimated ($k_m < k_r$), $\Delta x$ will be overestimated (FIG. 37). When using data from different miscalibrated experiments, the extrapolated rate at zero force can also be affected. To avoid this kind of calibration errors, the instrument can be configured to measure at different forces in a cyclic manner using the same cantilever. This approach can minimize any effect coming from time-dependent changes in calibration. Compare the force sensitivity measured for the same forces with different cantilevers. If the pick-up rate is too low to allow measurement of the entire force range in a single experiment, choose at least a reference force. If the calibration is correct, the rates of reaction at the reference force will be consistent for different experiments and/or cantilevers. If the results at the reference force deviate significantly from the average value, discard all data obtained for that particular experiment at any given force.

REFERENCES

The following references are incorporated by reference herein in their entireties:
Wiita et al., PNAS 103(19):7222-7227 (2006).
Wiita et al., Nature 450:124-127 (2007).
Perez-Jimenez et. al., Nat Struct Mol Biol. 16(8):890-896 (2009).
Alegre-Cebollada et. al., J Biol Chem. 285(25):18961-18966 (2010).
Beyer, M. K. & Clausen-Schaumann, H. (2005) Chem. Rev. 105, 2921-2948.
Evans, E. & Ritchie, K. (1997) Biophys. J. 72, 1541-1555.
Grandbois, M., Beyer, M., Rief, M., Clausen-Schaumann, H. & Gaub, H. E. (1999) Science 283, 1727-1730.
Marszalek, P. E., Greenleaf, W. J., Li, H., Oberhauser, A. F.&Fernandez, J. M. (2000) Proc. Natl. Acad. Sci. USA 97, 6282-6286.
Rubio-Bollinger, G., Bahn, S. R., Agrait, N., Jacobsen, K. W. & Vieira, S. (2001) Phys. Rev. Lett. 87, 026101.
Conti, M., Falini, G. & Samori, B. (2000) Angew. Chem. Int. Ed. 39, 215-218.
Sevier, C. S. & Kaiser, C. A. (2002) Nat. Rev. Mol. Cell. Biol. 3, 836-847.
Kadokura, H., Katzen, F. & Beckwith, J. (2003) Annu. Rev. Biochem. 72, 111-135.
Hogg, P. J. (2003) Trends Biochem. Sci. 28, 210-214.
Barford, D. (2004) Curr. Opin. Struct. Biol. 14, 679-686.
Yan, B. & Smith, J. W. (2001) Biochemistry 40, 8861-8867.
Chen, S. & Springer, T. A. (2001) Proc. Natl. Acad. Sci. USA 98, 950-955.
Mayans, O., Wuerges, J., Canela, S., Gautel, M. & Wilmanns, M. (2001) Structure (London) 9, 331-340.
Bustanji, Y. & Samori, B. (2002) Angew. Chem. Int. Ed. 41, 1546-1548.
Carl, P., Kwok, C. H., Manderson, G., Speicher, D. W. & Discher, D. E. (2001) Proc. Natl. Acad. Sci. USA 98, 1565-1570.
Bhasin, N., Carl, P., Harper, S., Feng, G., Lu, H., Speicher, D. W. & Discher, D. E. (2004) J. Biol. Chem. 279, 45865-45874.
Li, H. & Fernandez, J. M. (2003) J. Mol. Biol. 334, 75-86.
Oberhauser, A. F., Hansma, P. K., Carrion-Vazquez, M. & Fernandez, J. M. (2001) Proc. Natl. Acad. Sci. USA 98, 468-472.

Schlierf, M., Li, H. & Fernandez, J. M. (2004) Proc. Natl. Acad. Sci. USA 101, 7299-7304.

Fernandez, J. M. & Li, H. (2004) Science 303, 1674-1678.

Kuwajima, K., Ikeguchi, M., Sugawara, T., Hiraoka, Y. & Sugai, S. (1990) Biochemistry 29, 8240-8249.

Carrion-Vazquez, M., Oberhauser, A. F., Fowler, S. B., Marszalek, P. E., Broedel, S. E., Clarke, J. & Fernandez, J. M. (1999) Proc. Natl. Acad. Sci. USA 96, 3694-3699.

Marszalek, P. E., Lu, H., Li, H., Carrion-Vazquez, M., Oberhauser, A. F., Schulten, K. & Fernandez, J. M. (1999) Nature 402, 100-103.

Beyer, M. K. (2000) J. Chem. Phys. 112, 7307-7312.

Bell, G. I. (1978) Science 200, 618-627.

Holmgren, A. (1979) J. Biol. Chem. 254, 9627-9632.

Snyder, G. H., Cennerazzo, M. J., Karalis, A. J. & Field, D. (1981) Biochemistry 20, 6509-6519.

Fernandes, P. A. & Ramos, M. J. (2004) Chem. Eur. J. 10, 257-266.

Lide, D. R., ed. (1995) CRC Handbook of Chemistry and Physics (CRC, Cleveland).

Beyer, M. K. (2003) Angew. Chem. Int. Ed. 42, 4913-4915.

Marcus, R. A. & Sutin, N. (1985) Biochim. Biophys. Acta 811, 265-322.

Csaszar, P., Csizmadia, I. G., Viviani, W., Loos, M., Rivail, J. L. & Perczel, A. (1998) J. Mol. Struct. Theochem. 455, 107-122.

Boggon, T. J., Murray, J., Chappuis-Flament, S., Wong, E., Gumbiner, B. M. & Shapiro, L. (2002) Science 296, 1308-1313.

Graves, B. J., Crowther, R. L., Chandran, C., Rumberger, J. M., Li, S., Huang, K. S., Presky, D. H., Familletti, P. C., Wolitzky, B. A. & Burns, D. K. (1994) Nature 367, 532-538.

Wierzbicka-Patynowski, I. & Schwarzbauer, J. E. (2003) J. Cell Sci. 116, 3269-3276.

Schrijver, I., Liu, W., Brenn, T., Furthmayr, H. & Francke, U. (1999) Am. J. Hum. Genet. 65, 1007-1020.

Xie, L., Chesterman, C. N. & Hogg, P. J. (2001) J. Exp. Med. 193, 1341-1349.

Ryser, H. J. & Fluckiger, R. (2005) Drug Discov. Today 10, 1085-1094.

Matthias, L. J., Yam, P. T., Jiang, X. M., Vandegraaff, N., Li, P., Poumbourios, P., Donoghue, N. & Hogg, P. J. (2002) Nat. Immunol. 3, 727-732.

Maier, B., Koomey, M. & Sheetz, M. P. (2004) Proc. Natl. Acad. Sci. USA 101, 10961-10966.

Aktah, D. & Frank, I. (2002) J. Am. Chem. Soc. 124, 3402-3406.

Houk, J., Singh, R.&Whitesides, G. M. (1987) Methods Enzymol. 143, 129-140.

Hansen, R. E., Ostergaard, H. & Winther, J. R. (2005) Biochemistry 44, 5899-5906.

Wouters, M. A., Lau, K. K. & Hogg, P. J. (2004) BioEssays 26, 73-79.

Singh, R. & Whitesides, G. M. (1990) J. Am. Chem. Soc. 112, 6304-6309.

Holmgren, A. Thioredoxin. Annu. Rev. Biochem. 54, 237-271 (1985).

Holmgren, A. Thioredoxin structure and mechanism: conformational changes on oxidation of the active-site sulfhydryls to a disulfide. Structure 3, 239-243 (1995).

Schlierf, M., Li, H. & Fernandez, J. M. The unfolding kinetics of ubiquitin captured with single-molecule force-clamp techniques. Proc. Natl. Acad. Sci. USA 101, 7299-7304 (2004).

Wiita, A. P., Ainavarapu, S. R. K., Huang, H. H. & Fernandez, J. M. Force-dependent chemical kinetics of disulfide bond reduction observed with single-molecule techniques. Proc. Natl. Acad. Sci. USA 103, 7222-7227 (2006).

Paravicini, T. M. & Touyz, R. M. Redox signaling in hypertension. Cardiovasc. Res. 71, 247-258 (2006).

World, C. J., Yamawaki, H. & Berk, B. C. Thioredoxin in the cardiovascular system. J. Mol. Med. 84, 997-1003 (2006).

Kraut, D. A., Carroll, K. S. & Herschlag, D. Challenges in enzyme mechanism and energetics. Annu. Rev. Biochem. 72, 517-571 (2003).

Hammes-Schiffer, S. & Benkovic, S. J. Relating protein motion to catalysis. Annu. Rev. Biochem. 75, 519-541 (2006).

Carrion-Vazquez, M. et al., Mechanical and chemical unfolding of a single protein: a comparison. Proc. Natl. Acad. Sci. USA 96, 3694-3699 (1999).

Grandbois, M., Beyer, M., Rief, M., Clausen-Schaumann, H. & Gaub, H. E. How strong is a covalent bond? Science 283, 1727-1730 (1999).

Ainavarapu, S. R. et al., Contour length and refolding rate of a small protein controlled by engineered disulfide bonds. Biophys. J. 92, 225-233 (2007).

Abbondanzieri, E. A., Greenleaf, W. J., Shaevitz, J. W., Landick, R. & Block, S. M. Direct observation of base-pair stepping by RNA polymerase. Nature 438, 460-465 (2005).

Holmgren, A. Reduction of disulfides by thioredoxin. Exceptional reactivity of insulin and suggested functions of thioredoxin in mechanism of hormone action. J. Biol. Chem. 254, 9113-9119 (1979).

Krause, G., Lundstrom, J., Barea, J. L., Pueyo de la Cuesta, C. & Holmgren, A. Mimicking the active site of protein disulfide-isomerase by substitution of proline 34 in *Escherichia coli* thioredoxin. J. Biol. Chem. 266, 9494-9500 (1991).

Bell, G. I. Models for the specific adhesion of cells to cells. Science 200, 618-627 (1978).

Qin, J., Clore, G. M. & Gronenborn, A. M. The high-resolution three-dimensional solution structures of the oxidized and reduced states of human thioredoxin. Structure 2, 503-522 (1994).

Eklund, H., Gleason, F. K. & Holmgren, A. Structural and functional relations among thioredoxins of different species. Proteins 11, 13-28 (1991).

Qin, J., Clore, G. M., Kennedy, W. P., Huth, J. R. & Gronenborn, A. M. Solution structure of human thioredoxin in a mixed disulfide intermediate complex with its target peptide from the transcription factor NF B. Structure 3, 289-297 (1995).

Qin, J., Clore, G. M., Kennedy, W. P., Kuszewski, J. & Gronenborn, A. M. The solution structure of human thioredoxin complexed with its target from Ref-1 reveals peptide chain reversal. Structure 4, 613-620 (1996).

Rosenfield, R. E., Parthasarathy, R. & Dunitz, J. D. Directional preferences of nonbonded atomic contacts with divalent sulfur. 1. Electrophiles and nucleophiles. J. Am. Chem. Soc. 99, 4860-4862 (1977).

Pappas, J. A. Theoretical studies of reactions of sulfur-sulfur bond. 1. General heterolytic mechanisms. J. Am. Chem. Soc. 99, 2926-2930 (1977).

Fernandes, P. A. & Ramos, M. J. Theoretical insights into the mechanism for thiol/disulfide exchange. Chem. Eur. J. 10, 257-266 (2004).

Foloppe, N.&Nilsson, L. The glutaredoxin C P Y C motif: influence of peripheral residues. Structure 12, 289-300 (2004).

Grosberg, A. Y. & Khokhlov, A. R. Statistical Physics of Macromolecules (AIP, New York, 1994).

Tao, L. et al., Cardioprotective effects of thioredoxin in myocardial ischemia and reperfusion: role of S-nitrosation. Proc. Natl. Acad. Sci. USA 101, 11471-11476 (2004).

Kraut, D. A., Carroll, K. S. & Herschlag, D. Challenges in enzyme mechanism and energetics. Annu. Rev. Biochem. 72, 517-571 (2003).

Henzler-Wildman, K. A. et al., Intrinsic motions along an enzymatic reaction trajectory. Nature 450, 838-844 (2007).

Dai, S. et al., Structural snapshots along the reaction pathway of ferredoxin-thioredoxin reductase. Nature 448, 92-96 (2007).

Mori, T., Vale, R. D. & Tomishige, M. How kinesin waits between steps. Nature 450 750-754 (2007).

Asbury, C. L., Fehr, A. N. & Block, S. M. Kinesin moves by an asymmetric handover-hand mechanism. Science 302, 2130-2134 (2003).

Holmgren, A. Thioredoxin. Annu. Rev. Biochem. 54, 237-271 (1985).

Lillig, C. H. & Holmgren, A. Thioredoxin and related molecules—from biology to health and disease. Antioxid. Redox Signal. 9, 25-47 (2007).

Holmgren, A. Reduction of disulfides by thioredoxin. Exceptional reactivity of insulin and suggested functions of thioredoxin in mechanism of hormone action. J. Biol. Chem. 254, 9113-9119 (1979).

Holmgren, A. Thioredoxin catalyzes the reduction of insulin disulfides by dithiothreitol and dihydrolipoamide. J. Biol. Chem. 254, 9627-9632 (1979).

Holmgren, A. Tryptophan fluorescence study of conformational transitions of the oxidized and reduced form of thioredoxin. J. Biol. Chem. 247, 1992-1998 (1972).

Wiita, A. P. et al., Probing the chemistry of thioredoxin catalysis with force. Nature 450, 124-127 (2007).

Koti Ainavarapu, S. R., Wiita, A. P., Dougan, L., Uggerud, E. & Fernandez, J. M. Single molecule force spectroscopy measurements of bond elongation during a Bimolecular reaction. J. Am. Chem. Soc. 130, 6479-6487 (2008).

Wiita, A. P., Ainavarapu, S. R., Huang, H. H. & Fernandez, J. M. Force-dependent chemical kinetics of disulfide bond reduction observed with single-molecule techniques. Proc. Natl. Acad. Sci. USA 103, 7222-7227 (2006).

Damdimopoulos, A. E., Miranda-Vizuete, A., Pelto-Huikko, M., Gustafsson, J. A. & Spyrou, G. Human mitochondrial thioredoxin. Involvement in mitochondrial membrane potential and cell death. J. Biol. Chem. 277, 33249-33257 (2002).

Miranda-Vizuete, A., Damdimopoulos, A. E., Gustafsson, J. & Spyrou, G. Cloning, expression, and characterization of a novel *Escherichia coli* thioredoxin. J. Biol. Chem. 272, 30841-30847 (1997).

Spyrou, G., Enmark, E., Miranda-Vizuete, A. & Gustafsson, J. Cloning and expression of a novel mammalian thioredoxin. J. Biol. Chem. 272, 2936-2941 (1997).

Ye, J. et al., Crystal structure of an unusual thioredoxin protein with a zinc finger domain. J. Biol. Chem. 282, 34945-34951 (2007).

Boucher, I. W. et al., Structural and biochemical characterization of a mitochondrial peroxiredoxin from *Plasmodium falciparum*. Mol. Microbiol. 61, 948-959 (2006).

Powis, G. & Montfort, W. R. Properties and biological activities of thioredoxins. Annu. Rev. Biophys. Biomol. Struct. 30, 421-455 (2001).

Gelhaye, E., Rouhier, N., Navrot, N. & Jacquot, J. P. The plant thioredoxin system. Cell. Mol. Life Sci. 62, 24-35 (2005).

Meyer, Y. et al., Evolution of redoxin genes in the green lineage. Photosynth. Res. 89, 179-192 (2006).

Perez-Jimenez, R. et al., Force-clamp spectroscopy detects residue co-evolution in enzyme catalysis. J. Biol. Chem. 283, 27121-27129 (2008).

Carvalho, A. T. et al., Mechanism of thioredoxin-catalyzed disulfide reduction. Activation of the buried thiol and role of the variable active-site residues. J. Phys. Chem. B 112, 2511-2523 (2008).

Kappler, U. & Bailey, S. Molecular basis of intramolecular electron transfer in sulfiteoxidizing enzymes is revealed by high resolution structure of a heterodimeric Complex of the catalytic molybdopterin subunit and a c-type cytochrome subunit. J. Biol. Chem. 280, 24999-25007 (2005).

Costentin, C. & Saveant, J. M. Competition between SN2 and single electron transfer reactions as a function of steric hindrance illustrated by the model system alkylC1+ NO_. J. Am. Chem. Soc. 122, 2329-2338 (2000).

Holm, R. H., Kennepohl, P. & Solomon, E. I. Structural and functional aspects of metal sites in biology. Chem. Rev. 96, 2239-2314 (1996).

McLendon, G., Komar-Panicucci, S. & Hatch, S. Applying Marcus's theory to electron transfer in vivo. Electron Transfer-from Isolated Molecules to Biomolecules. In Advances in Chemical Physics Vol 107 591-600 (John Wiley & Sons, New York, N.Y., 1999). in vivo. Electron Transfer-from Isolated Molecules to Biomolecules. In Advances in Chemical Physics Vol 107 591-600 (John Wiley & Sons, New York, N.Y., 1999).

Erlandsson, M. & Hallbrink, M. Metallic zinc reduction of disulfide bonds between cysteine residues in peptides and proteins. Int. J. Pept. Res. Ther. 11, 261-265 (2005).

Aslund, F., Berndt, K. D. & Holmgren, A. Redox potentials of glutaredoxins and other thiol-disulfide oxidoreductases of the thioredoxin superfamily determined by direct protein-protein redox equilibria. J. Biol. Chem. 272, 30780-30786 (1997).

Cheng, Z., Arscott, L. D., Ballou, D. P. & Williams, C. H. Jr. The relationship of the redox potentials of thioredoxin and thioredoxin reductase from *Drosophila melanogaster* to the enzymatic mechanism: reduced thioredoxin is the reductant of glutathione in *Drosophila*. Biochemistry 46, 7875-7885 (2007).

Yasui, S., Itoh, K., Tsujimoto, M. & Ohno, A. Irreversibility of single electron transfer occurring from trivalent phosphorus compounds to Iron(III) complexes in the presence of ethanol. Bull. Chem. Soc. Jpn. 75, 1311-1318 (2002).

Hazzard, J. T., Marchesini, A., Curir, P. & Tollin, G. Direct measurement by laser flash photolysis of intramolecular electron transfer in the three-electron reduced form of ascorbate oxidase from zucchini. Biochim. Biophys. Acta 1208, 166-170 (1994).

Farver, O. & Pecht, I. Low activation barriers characterize intramolecular electron transfer in ascorbate oxidase. Proc. Natl. Acad. Sci. USA 89, 8283-8287 (1992).

Maeda, K., Hagglund, P., Finnie, C., Svensson, B. & Henriksen, A. Structural basis for target protein recognition by the protein disulfide reductase thioredoxin. Structure 14, 1701-1710 (2006).

Li, Y. et al., Conformational fluctuations coupled to the thiol-disulfide transfer between thioredoxin and arsenate reductase in *Bacillus subtilis*. J. Biol. Chem. 282, 11078-11083 (2007).

Lennon, B. W., Williams Jr., C. H., & Ludwig, M. L. Twists in catalysis: alternating conformations of *Escherichia coli* thioredoxin reductase. Science 289, 1190-1194 (2000).

Falkowski, P. G. Evolution. Tracing oxygen's imprint on earth's metabolic evolution. Science 311, 1724-1725 (2006).

Raymond, J. & Segre, D. The effect of oxygen on biochemical networks and the evolution of complex life. Science 311, 1764-1767 (2006).

Kirschvink, J. L. & Kopp, R. E. Palaeoproterozoic ice houses and the evolution of oxygen-mediating enzymes: the case for a late origin of photosystem II. Phil. Trans. R. Soc. Lond. B 363, 2755-2765 (2008).

Lemaire, S. D. et al., New thioredoxin targets in the unicellular photosynthetic eukaryote *Chlamydomonas reinhardtii*. Proc. Natl. Acad. Sci. USA 101, 7475-7480 (2004).

Sharma, A. et al., Microbial activity at gigapascal pressures. Science 295, 1514-1516 (2002).

La Duc, M. T. et al., Isolation and characterization of bacteria capable of tolerating the extreme conditions of clean room environments. Appl. Environ. Microbiol. 73, 2600-2611 (2007).

Koch, A. L. Shrinkage of growing *Escherichia coli* cells by osmotic challenge. J. Bacteriol. 159, 919-924 (1984).

Malone, A. S., Chung, Y. K. & Yousef, A. E. Genes of *Escherichia coli* O157:H7 that are involved in high-pressure resistance. Appl. Environ. Microbiol. 72, 2661-2671 (2006).

Gaucher, E. A., Govindarajan, S. & Ganesh, O. K. Palaeotemperature trend for Precambrian life inferred from resurrected proteins. Nature 451, 704-707 (2008).

Jones, P. R., Manabe, T., Awazuhara, M. & Saito, K. A new member of plant CS-lyases. A cystine lyase from *Arabidopsis thaliana*. J. Biol. Chem. 278, 10291-10296 (2003).

Beynon, R. J., Bond, J. S. & NetLibrary Inc. Proteolytic enzymes: a practical approach. in Practical Approach Series 2nd edn, xviii, 340 (Oxford University Press, Oxford; New York, 2001).

Forman-Kay, J. D., Clore, G. M., Wingfield, P. T. & Gronenborn, A. M. High-resolution three-dimensional structure of reduced recombinant human thioredoxin in solution. Biochemistry 30, 2685-2698 (1991).

Qin, J., Clore, G. M., Kennedy, W. M., Huth, J. R. & Gronenborn, A. M. Solution structure of human thioredoxin in a mixed disulfide intermediate complex with its target peptide from the transcription factor NF kappa B. Structure 3, 289-297 (1995).

Peterson, F. C. et al., Solution structure of thioredoxin h1 from *Arabidopsis thaliana*. Protein Sci. 14, 2195-2200 (2005).

Capitani, G. et al., Crystal structures of two functionally different thioredoxins in spinach chloroplasts. J. Mol. Biol. 302, 135-154 (2000).

Smeets, A. et al., Crystal structures of oxidized and reduced forms of human mitochondrial thioredoxin 2. Protein Sci. 14, 2610-2621 (2005).

Katti, S. K., LeMaster, D. M. & Eklund, H. Crystal structure of thioredoxin from *Escherichia coli* at 1.68 resolution. J. Mol. Biol. 212, 167-184 (1990).

Lancelin, J. M., Guilhaudis, L., Krimm, I., Blackledge, M. J., Marion, D. & Jacquot, J. P. NMR structures of thioredoxin m from the green alga *Chlamydomonas reinhardtii*. Proteins 41, 334-349 (2000).

Qin, J., Clore, G. M., Kennedy, W. P., Kuszewski, J. & Gronenborn, A. M. The solution structure of human thioredoxin complexed with its target from Ref-1 reveals peptide chain reversal. Structure 4, 613-620 (1996).

Kraut, D. A., Carroll, K. S., and Herschlag, D. (2003) Annu Rev Biochem 72, 517-571

Benkovic, S. J., and Hammes-Schiffer, S. (2003) Science 301, 1196-1202

Jackel, C., Kast, P., and Hilvert, D. (2008) Annu Rev Biophys 37, 153-173

Karplus, M., and McCammon, J. A. (1983) Annu Rev Biochem 52, 263-300

Benkovic, S. J., Hammes, G. G., and Hammes-Schiffer, S. (2008) Biochemistry 47, 3317-3321

Zhong, D. (2007) Curr Opin Chem Biol 11, 174-181

Schramm, V. L. (2005) Curr Opin Struct Biol 15, 604-613

Mesecar, A. D., Stoddard, B. L., and Koshland, D. E., Jr. (1997) Science 277, 202-206

Wagner, G., and Wuthrich, K. (1978) Nature 275, 247-248

Hammes-Schiffer, S., and Benkovic, S. J. (2006) Annu Rev Biochem 75, 519-541

Olsson, M. H., Parson, W. W., and Warshel, A. (2006) Chem Rev 106, 1737-1756

Yang, L. W., and Bahar, I. (2005) Structure 13, 893-904

Wang, L., Goodey, N. M., Benkovic, S. J., and Kohen, A. (2006) Proc Natl Acad Sci USA 103, 15753-15758

Perez-Jimenez, R., Wiita, A. P., Rodriguez-Larrea, D., Kosuri, P., Gavira, J. A., Sanchez-Ruiz, J. M., and Fernandez, J. M. (2008) J Biol Chem 283, 27121-27129

Boehr, D. D., McElheny, D., Dyson, H. J., and Wright, P. E. (2006) Science 313, 1638-1642

Henzler-Wildman, K. A., Lei, M., That, V., Kerns, S. J., Karplus, M., and Kern, D. (2007) Nature 450, 913-916

English, B. P., Min, W., van Oijen, A. M., Lee, K. T., Luo, G., Sun, H., Cherayil, B. J., Kou, S. C., and Xie, X. S. (2006) Nat Chem Biol 2, 87-94

Antikainen, N. M., Smiley, R. D., Benkovic, S. J., and Hammes, G. G. (2005) Biochemistry 44, 16835-16843

Palmer, A. G., 3rd. (2004) Chem Rev 104, 3623-3640

Kern, D., Eisenmesser, E. Z., and Wolf-Watz, M. (2005) Methods Enzymol 394, 507-524

Eisenmesser, E. Z., Millet, O., Labeikovsky, W., Korzhnev, D. M., Wolf-Watz, M., Bosco, D. A., Skalicky, J. J., Kay, L. E., and Kern, D. (2005) Nature 438, 117-121

Senn, H. M., and Thiel, W. (2007) Curr Opin Chem Biol 11, 182-187

Beyer, M. K., and Clausen-Schaumann, H. (2005) Chem Rev 105, 2921-2948

Lide, D. R. (1994) CRC Handbook of Chemistry and Physics, CRC Press, Boca Raton, Fla.

Asbury, C. L., Fehr, A. N., and Block, S. M. (2003) Science 302, 2130-2134

Mori, T., Vale, R. D., and Tomishige, M. (2007) Nature 450, 750-754

Wiita, A. P., Perez-Jimenez, R., Walther, K. A., Grater, F., Berne, B. J., Holmgren, A., Sanchez-Ruiz, J. M., and Fernandez, J. M. (2007) Nature 450, 124-127

Wiita, A. P., Ainavarapu, S. R., Huang, H. H., and Fernandez, J. M. (2006) Proc Natl Acad Sci USA 103, 7222-7227

Schlierf, M., Li, H., and Fernandez, J. M. (2004) Proc Natl Acad Sci USA 101, 7299-7304

Oberhauser, A. F., Hansma, P. K., Carrion-Vazquez, M., and Fernandez, J. M. (2001) Proc Natl Acad Sci USA 98, 468-472

Rief, M., Gautel, M., Oesterhelt, F., Fernandez, J. M., and Gaub, H. E. (1997) Science 276, 1109-1112

Ainavarapu, S. R., Brujic, J., Huang, H. H., Wiita, A. P., Lu, H., Li, L., Walther, K. A., Carrion-Vazquez, M., Li, H., and Fernandez, J. M. (2007) Biophys J 92, 225-233

Grandbois, M., Beyer, M., Rief, M., Clausen-Schaumann, H., and Gaub, H. E. (1999) Science 283, 1727-1730

Ainavarapu, S. R., Wiita, A. P., Huang, H. H., and Fernandez, J. M. (2008) J Am Chem Soc 130, 436-437

Garcia-Manyes, S., Brujic, J., Badilla, C. L., and Fernandez, J. M. (2007) Biophys J 93, 2436-2446

Szoszkiewicz, R., Ainavarapu, S. R., Wiita, A. P., Perez-Jimenez, R., Sanchez-Ruiz, J. M., and Fernandez, J. M. (2008) Langmuir 24, 1356-1364

Ainavarapu, S. R., Wiita, A. P., Dougan, L., Uggerud, E., and Fernandez, J. M. (2008) J Am Chem Soc 130, 6479-6487

Dougan, L., Koti, A. S., Genchev, G., Lu, H., and Fernandez, J. M. (2008) Chemphyschem 9, 2836-2847

Bell, G. I. (1978) Science 200, 618-627

Fernandes, P. A., and Ramos, M. J. (2004) Chemistry 10, 257-266

Holmgren, A. (1985) Annu Rev Biochem 54, 237-271

Lillig, C. H., and Holmgren, A. (2007) Antioxid Redox Signal 9, 25-47

Holmgren, A. (1979) J Biol Chem 254, 9627-9632

Holmgren, A. (1979) J Biol Chem 254, 9113-9119

Holmgren, A. (1972) J Biol Chem 247, 1992-1998

Krause, G., Lundstrom, J., Barea, J. L., Pueyo de la Cuesta, C., and Holmgren, A. (1991) J Biol Chem 266, 9494-9500

Rosenfield, R. E., Parthasarathy, R., and Dunitz, J. D. (1977) J Am Chem Soc 99, 4860-4862

Pappas, J. A. (1977) J Am Chem Soc 99, 2926-2930

Frey, P. A., and Hegeman, A. D. (2007) Enzymatic reaction mechanisms, Oxford University Press, Oxford Hatahet, F. et al., Protein disulfide isomerase: a critical evaluation of its function in disulfide bond formation. *Antioxid Redox Signal* 11, 2807-2850 (2009).

Heras, B. et al., DSB proteins and bacterial pathogenicity. Nat Rev Microbiol 7, 215-225 (2009).

Land, A. & Braakman, I. Folding of the human immunodeficiency virus type 1 envelope glycoprotein in the endoplasmic reticulum. Biochimie 83, 783-790 (2001).

Uehara, T. et al., S-nitrosylated protein-disulphide isomerase links protein misfolding to neurodegeneration. *Nature* 441, 513-517 (2006).

Culotta, V. C., Yang, M. & O'Halloran, T. V. Activation of superoxide dismutases: putting the metal to the pedal. Biochim Biophys Acta 1763, 747-758 (2006).

Holmgren, A. Thioredoxin. Annu Rev Biochem 54, 237-271 (1985).

Mamathambika, B. S. & Bardwell, J. C. Disulfide-linked protein folding pathways. Annu Rev Cell Dev Biol 24, 211-235 (2008).

Di Jeso, B. et al., Mixed-disulfide folding intermediates between thyroglobulin and endoplasmic reticulum resident oxidoreductases ERp57 and protein disulfide isomerase. Mol Cell Biol 25, 9793-9805 (2005).

Sevier, C. S. & Kaiser, C. A. Formation and transfer of disulphide bonds in living cells. Nat Rev Mol Cell Biol 3, 836-847 (2002).

Wickner, W. & Schekman, R. Protein translocation across biological membranes. Science 310, 1452-1456 (2005).

Bechtluft, P. et al., Direct observation of chaperone-induced changes in a protein folding pathway. Science 318, 1458-1461 (2007).

Kadokura, H., Tian, H., Zander, T., Bardwell, J. C. & Beckwith, J. Snapshots of DsbA in action: detection of proteins in the process of oxidative folding. Science 303, 534-537 (2004).

Kadokura, H. & Beckwith, J. Detecting folding intermediates of a protein as it passes through the bacterial translocation channel. Cell 138, 1164-1173 (2009).

Darby, N. J., Kemmink, J. & Creighton, T. E. Identifying and characterizing a structural domain of protein disulfide isomerase. Biochemistry 35, 10517-10528 (1996).

Wiita, A. P. et al., Probing the chemistry of thioredoxin catalysis with force. Nature 450, 124-127 (2007).

Alegre-Cebollada, J., Perez-Jimenez, R., Kosuri, P. & Fernandez, J. M. Single-molecule Force Spectroscopy Approach to Enzyme Catalysis. Journal of Biological Chemistry 285, 18961-18966 (2010).

Wiita, A. P., Ainavarapu, S. R., Huang, H. H. & Fernandez, J. M. Force-dependent chemical kinetics of disulfide bond reduction observed with single-molecule techniques. Proc Natl Acad Sci USA 103, 7222-7227 (2006).

Martin, J. L. Thioredoxin—a fold for all reasons. Structure 3, 245-250 (1995).

Lundstrom, J., Krause, G. & Holmgren, A. A Pro to His mutation in active site of thioredoxin increases its disulfide-isomerase activity 10-fold. New refolding systems for reduced or randomly oxidized ribonuclease. J Biol Chem 267, 9047-9052 (1992).

Xiao, R., Lundstrom-Ljung, J., Holmgren, A. & Gilbert, H. F. Catalysis of thiol/disulfide exchange. Glutaredoxin 1 and protein-disulfide isomerase use different mechanisms to enhance oxidase and reductase activities. J Biol Chem 280, 21099-21106 (2005).

Stewart, E. J., Aslund, F. & Beckwith, J. Disulfide bond formation in the *Escherichia coli* cytoplasm: an in vivo role reversal for the thioredoxins. EMBO J 17, 5543-5550 (1998).

Lundstrom, J. & Holmgren, A. Protein disulfide-isomerase is a substrate for thioredoxin reductase and has thioredoxin-like activity. J Biol Chem 265, 9114-9120 (1990).

Karala, A. R., Lappi, A. K. & Ruddock, L. W. Modulation of an active-site cysteine pKa allows PDI to act as a catalyst of both disulfide bond formation and isomerization. J Mol Biol 396, 883-892 (2010).

Ren, G. et al., Properties of the thioredoxin fold superfamily are modulated by a single amino acid residue. J Biol Chem 284, 10150-10159 (2009).

Ainavarapu, S. R. et al., Contour length and refolding rate of a small protein controlled by engineered disulfide bonds. Biophys J 92, 225-233 (2007).

Ren, X., Bjornstedt, M., Shen, B., Ericson, M. L. & Holmgren, A. Mutagenesis of structural half-cystine residues in human thioredoxin and effects on the regulation of activity by selenodiglutathione. Biochemistry 32, 9701-9708 (1993).

Perez-Jimenez, R. et al., Force-clamp spectroscopy detects residue co-evolution in enzyme catalysis. J Biol Chem 283, 27121-27129 (2008).

Fernandez, J. M. & Li, H. Force-clamp spectroscopy monitors the folding trajectory of a single protein. Science 303, 1674-1678 (2004).

Perez-Jimenez, R. et al., Single-molecule paleoenzymology probes the chemistry of resurrected enzymes, Nat Struct Mol Biol. 2011 May; 18(5):592-6. Epub 2011 Apr. 3.

Smith, S. B., Cui, Y. J. & Bustamante, C. *Science* 271, 795-799 (1996)

Marszalek, P. E., Oberhauser, A. F., Pang, Y. P. & Fernandez, J. M. Nature 396, 661-664 (1998).

Rief, M., Oesterhelt, F., Heymann, B. & Gaub, H. E. Science 275, 1295-1297 (1997).

Rief, M., Gautel, M., Oesterhelt, F., Fernandez, J. M. & Gaub, H. E. Science 276, 1109-1112 (1997)

Carrion-Vazquez, M. et al., Prog Biophys Mol Biol 74, 63-91 (2000)

Oberhauser, A. F., Badilla-Fernandez, C., Carrion-Vazquez, M. & Fernandez, J. M. Journal of molecular biology 319, 433-447 (2002).
Li, H. et al., Nature 418, 998-1002 (2002).
Carrion-Vazquez, M. et al., Nature Structural Biology 10, 738-743 (2003).
Brockwell, D. J. et al., Nature Structural Biology 10, 731-737 (2003).
Dietz, H. & Rief, M. P Natl Acad Sci USA 101, 16192-16197 (2004).
Ainavarapu, S. R. et al., Biophys J 92, 225-233 (2007).
Wiita, A. P., Ainavarapu, S. R., Huang, H. H. & Fernandez, J. M. Proc Natl Acad Sci USA 103, 7222-7227 (2006).
Oberhauser, A. F., Hansma, P. K., Carrion-Vazquez, M. & Fernandez, J. M. P Natl Acad Sci USA 98, 468-472 (2001).
Schlierf, M., Li, H. & Fernandez, J. M. P Natl Acad Sci USA 101, 7299-7304 (2004).
Wiita, A. P. et al., Nature 450, 124-127 (2007).
Kuo, T. L. et al., P Natl Acad Sci USA 107, 11336-11340 (2010).
Garcia-Manyes, S., Dougan, L. & Fernandez, J. M. P Natl Acad Sci USA 106, 10540-10545 (2009).
Popa, I., Fernandez, J. M. & Garcia-Manyes, S. Journal of Biological Chemistry 286, 31072-31079 (2011).
Garcia-Manyes, S., Dougan, L., Badilla, C. L., Brujic, J. & Fernandez, J. M. Proc Natl Acad Sci USA 106, 10534-10539 (2009).
Berkovich, R. et al., Proc Natl Acad Sci USA 109, 14416-14421 (2012).
Garcia-Manyes, S., Brujic, J., Badilla, C. L. & Fernandez, J. M. Biophys J 93, 2436-2446 (2007).
Walther, K. A. et al., P Natl Acad Sci USA 104, 7916-7921 (2007).
Garcia-Manyes, S., Liang, J., Szoszkiewicz, R., Kuo, T. L. & Fernandez, J. M. Nature chemistry 1, 236-242 (2009).
Ainavarapu, S. R. K., Wiita, A. P., Dougan, L., Uggerud, E. & Fernandez, J. M. Journal of the American Chemical Society 130, 6479-6487 (2008).
Liang, J. & Fernandez, J. M. Journal of the American Chemical Society 133, 3528-3534 (2011).
Perez-Jimenez, R. et al., Nature structural & molecular biology 18, 592-596 (2011).
Perez-Jimenez, R. et al., Nature structural & molecular biology 16, 890-896 (2009).
Fernandez, J. M. & Li, H. Science 303, 1674-1678 (2004).
Kosuri, P. et al., Cell 151, 794-806 (2012).
Carrion-Vazquez, M. et al., Proc Natl Acad Sci USA 96, 3694-3699 (1999).
Furuike, S., Ito, T. & Yamazaki, M. FEBS Lett 498, 72-75 (2001)
Alegre-Cebollada, J., Badilla, C. L. & Fernandez, J. M. The Journal of biological chemistry 285, 11235-11242 (2010)
Hutter, J. L. & Bechhoefer, J. Review of Scientific Instruments 64, 1868-1873 (1993)
Taniguchi, Y. & Kawakami, M. Langmuir: the ACS journal of surfaces and colloids 26, 10433-10436 (2010).
Wang, T., Arakawa, H. & Ikai, A. Biochemical and biophysical research communications 285, 9-14 (2001).
Kufer, S. K. et al., Eur. Biophys. J. Biophys. Lett. 35, 72-78 (2005)
Zakeri, B. et al., P Natl Acad Sci USA 109, E690-E697 (2012)
Brujic, J., Hermans, R. I. Z., Garcia-Manyes, S., Walther, K. A. & Fernandez, J. M. Biophys J 92, 2896-2903 (2007).
Szoszkiewicz, R. et al., Langmuir: the ACS journal of surfaces and colloids 24, 1356-1364 (2008).
Alegre-Cebollada, J., Kosuri, P., Rivas-Pardo, J. A. & Fernandez, J. M. Nature chemistry 3, 882-887 (2011).
Garcia-Manyes, S., Kuo, T. L. & Fernandez, J. M. Journal of the American Chemical Society 133, 3104-3113 (2011)
Bell, G. I. Science 200, 618-627 (1978).
Evans, E. Annu Rev Bioph Biom 30, 105-128 (2001)
Dudko, O. K., Hummer, G. & Szabo, A. Phys Rev Lett 96 (2006)
Brujic, J., Hermans, R. I., Walther, K. A. & Fernandez, J. M. Nat Phys 2, 282-286 (2006)
Berkovich, R., Garcia-Manyes, S., Urbakh, M., Klafter, J. & Fernandez, J. M. Biophys J 98, 2692-2701 (2010).
Efron, B. The Jackknife, the Bootstrap, and Other Resampling Plans (SIAM, 1982).
Li, W. J. & Grater, F. Journal of the American Chemical Society 132, 16790-16795 (2010).
Iozzi, M. F., Helgaker, T. & Uggerud, E. J Phys Chem A 115, 2308-2315 (2011). Labit, H. et al., Biotechniques 45, 649-+ (2008)
Zimmermann, J. L., Nicolaus, T., Neuert, G. & Blank, K. Nat Protoc 5, 975-985 (2010).

The invention claimed is:

1. A force-clamp spectrometer comprising:
a cantilever extending from a cantilever chip, the cantilever comprising a functionalized cantilever tip for attaching a first end of a molecular substrate;
a functionalized coverslip adjacent to the cantilever chip and mounted on a piezo-electric positioner for attaching a second end of the molecular substrate;
a laser configured to focus a laser beam on the cantilever to form a laser beam focal spot;
a split photodetector configured to detect a reflected beam;
a camera for monitoring the laser beam focal spot; and
a first movable flip mount for controlling a position of the camera, wherein the camera is positioned on the first movable flip mount, the first movable flip mount being switchable between a first camera position and a second camera position, wherein the cantilever is in focus of the camera in the second camera position; and
a second movable flip mount for controlling a position of the piezo-electric positioner, wherein the piezo-electric positioner is positioned on the second movable flip mount, the second movable flip mount being switchable between a first piezo-electric position and a second piezo-electric position, wherein in the first piezo-electric position, the cantilever is accessible for placement of a sample comprising the molecular substrate thereon and in the second piezo-electric position the cantilever is in a position for measuring the molecular substrate dynamics.

2. The force-clamp spectrometer of claim 1, wherein the molecular substrate is suspended between the cantilever and the coverslip.

3. The force-clamp spectrometer of claim 2, further comprising an electronically controlled feedback system configured to adjust the extension of the suspended molecular substrate between the functionalized cantilever tip and the functionalized coverslip.

4. The force-clamp spectrometer of claim 3, wherein the electronically controlled feedback system is further configured to allow the force-clamp spectrometer to maintain a desired force exerted on the cantilever.

5. The force-clamp spectrometer of claim 1, further comprising a magnetic-orientable prism configured to steer the reflected beam to the split photodetector, wherein the magnetic-orientable prism is mounted on magnets to eliminate mechanical drift.

* * * * *